US009775859B2

(12) United States Patent
Demetriou et al.

(10) Patent No.: US 9,775,859 B2
(45) Date of Patent: Oct. 3, 2017

(54) METHODS AND COMPOSITIONS FOR PREVENTING AND TREATING A DISEASE RELATED TO GLYCAN DYSREGULATION

(71) Applicants: Sinai Health System, Toronto (CA); The Regents of the University of California, Oakland, CA (US)

(72) Inventors: Michael Demetriou, Irvine, CA (US); James Dennis, Etobicoke (CA); Ken Siu-Kwong Lau, Toronto (CA)

(73) Assignee: SINAI HEALTH SYSTEM, Toronto, Ontario (CA)

( * ) Notice: Subject to any disclaimer, the term of this patent is extended or adjusted under 35 U.S.C. 154(b) by 464 days.

(21) Appl. No.: 14/158,221

(22) Filed: Jan. 17, 2014

(65) Prior Publication Data
US 2014/0228313 A1    Aug. 14, 2014

Related U.S. Application Data

(62) Division of application No. 11/795,183, filed as application No. PCT/US2006/001337 on Jan. 13, 2006, now Pat. No. 8,658,622.

(Continued)

(51) Int. Cl.
*A61K 31/00*    (2006.01)
*A61K 31/7072*  (2006.01)
*A01K 67/027*   (2006.01)
*A61K 31/593*   (2006.01)
*A61K 31/70*    (2006.01)
*A61K 45/06*    (2006.01)
(Continued)

(52) U.S. Cl.
CPC ...... *A61K 31/7072* (2013.01); *A01K 67/0275* (2013.01); *A61K 31/593* (2013.01); *A61K 31/70* (2013.01); *A61K 31/7008* (2013.01); *A61K 45/06* (2013.01); *G01N 33/564* (2013.01); *A01K 2227/105* (2013.01); *A01K 2267/0318* (2013.01); *G01N 2400/10* (2013.01); *G01N 2800/285* (2013.01)

(58) Field of Classification Search
CPC ............ A61K 31/7072; A61K 67/0275; A61K 31/593; A61K 31/70; A61K 31/7008; A61K 45/06; G01N 33/564
See application file for complete search history.

(56) References Cited

U.S. PATENT DOCUMENTS 4,677,061 A   6/1987 Rose
5,064,816 A   11/1991 Houlihan
(Continued)

FOREIGN PATENT DOCUMENTS

CA    2186987 A1 *  4/1998  ........... A01K 67/027

OTHER PUBLICATIONS

Dibetelogia (Jan. 1999;42(1):51-4; Abstract Only).*
(Continued)

*Primary Examiner* — Cherie M Stanfield
(74) *Attorney, Agent, or Firm* — Howson & Howson LLP

(57) ABSTRACT

Contemplated compositions and methods are directed to prevent and/or treat various autoimmune diseases that are typically associated with glycan dysregulation, and especially autoimmune demyelinating diseases. Further especially contemplated aspects include animal models and systems for screening compounds to treat and/or prevent such diseases.

13 Claims, 53 Drawing Sheets

Related U.S. Application Data

(60) Provisional application No. 60/643,962, filed on Jan. 14, 2005, provisional application No. 60/663,380, filed on Mar. 17, 2005.

(51) Int. Cl.
*G01N 33/564* (2006.01)
*A61K 31/7008* (2006.01)

(56) References Cited

U.S. PATENT DOCUMENTS

| | | | |
|---|---|---|---|
| 5,501,957 | A | 3/1996 | Dennis |
| 5,506,214 | A | 4/1996 | Beutler |
| 5,583,117 | A | 12/1996 | Von Borstel et al. |
| 5,624,938 | A | 4/1997 | Pernis |
| 5,780,453 | A | 7/1998 | Mcanalley |
| 5,883,227 | A | 3/1999 | Kline |
| 5,948,764 | A | 9/1999 | Gaur |
| 6,001,978 | A | 12/1999 | Edgington |
| 6,613,756 | B2 | 9/2003 | Duncan |
| 6,702,756 | B2 | 3/2004 | Brown |
| 6,933,119 | B2 | 8/2005 | Leppert |
| 6,936,599 | B2 | 8/2005 | Voskuhl |
| 7,396,529 | B2 | 7/2008 | Dennis |
| 2004/0082009 | A1 | 4/2004 | Dennis et al. |
| 2008/0227750 | A1 | 9/2008 | Dennis |

OTHER PUBLICATIONS

Gourmet Cookbook (shrimp bisque recipe, Reichel, Ed., Conde Nast, New York. 2004).*
Sashiwa et al., (Carbohydrate Polymers. 2003;51:391-395).*
Tabata ("Biotechnology in Functional Foods and Nutraceuticals" Chapter 9.2.5, 2010).*
Uridine reference (answers.com, last accessed Dec. 30, 2010) at p. 4 of 6.*
Dennis et al., (Biochemica et Biophysica Acta. 1999;1473:21-31, Abstract).*
Ki-Young Do, et al., J Biol Chem. Sep. 23, 1994;269(38):23456-23464).*
Cummings et al., (J Biol Chem. Nov. 25, 1982; 257(22):13421-13427).*
Palcic et al., (J Biol Chem. Apr. 25, 1990;265(12):6759-6769).*
Lemaire et al., (J Biol Chem. Mar. 18, 1994;269(11):8069-8074).*
Essentials of Glycobiology. Varki et al., Eds. Cold Spring Harbor Laboratory Press. 1999. New York. pp. 538-540.*
Andersen et al. (Curr Opin Biotech 1994 5:546-549).*
Goochee et al., (Biotechnology, Dec. 1991 9:1346-1355).*
The Gourmet Cookbook (shrimp bisque recipe), Reichel, Ed., Conde Nast, NY 2004.
Orlacchio et al, Activity levels of a beta1,6 N-acetylglucosaminyltransferase in lymphomonocytes from multiple sclerosis patients, J Neurol Sci. Oct. 22, 1997;151(2):177-83.
Tabata et al, "Biotechnology in Functional Foods and Neutraceuticals", Chapter 9.2.5, 2010.
Hayes, Vitamin D: a natural inhibitor of multiple sclerosis, Proc Nutr Soc. Nov. 2000;59(4):531-5. (abstract only).
Lowry et al, Adenosine-5-monophosphate in the treatment of multiple sclerosis, Am J Med Sci. Jul. 1953;226(1):73-83 (abstract only).
McHardle et al, Studies on Intermediate Carbohydrate Metabolism in Multiple Sclerosis, J Neurol Neurosurg Psychiatry. May 1960;23(2):127-32.
Hartstein et al, Galactose treatment of multiple sclerosis; a preliminary report, Dis Nery Syst. Jul. 1957;18(7 Part 1):255-8. (title only).
Sashiwa et al, Enzymatic production of N-acetyl-d-glucosamine from chitin. Degradation study of N-acetylchitooligosaccharide and the effect of mixing of crude enzymes, Carbohydrate Polymers, 51(4):391-5 (Mar. 1, 2003).
"Uridine", answers.com. Accessed Dec. 30, 2010.

Office action dated Jan. 5, 2011 issued in parent U.S. Appl. No. 11/795,183.
Response dated Mar. 28, 2011 to office action dated Jan. 5, 2011 issued in parent U.S. Appl. No. 11/795,183.
Office action dated Jun. 13, 2011 issued in parent U.S. Appl. No. 11/795,183.
Response dated Sep. 12, 2011 office action dated Jun. 13, 2011 issued in parent U.S. Appl. No. 11/795,183.
Andersen, "The effect of cell-culture conditions on the oligosaccharide structures of secreted glycoproteins", Curr Opin Biotech, 5(5):546-549 (Oct. 1994).
Barkai, "Robustness in simple biochemical networks", Nature, 387:913-917 (Jun. 26, 1997).
Barondes, "Galectins: A Family of Animal β-Galactoside-Binding Lectins", Cell, 76:597-598 (Feb. 25, 1994).
Bettelli et al., "Myelin oligodendrocyte glycoprotein-specific T cell receptor transgenic mice develop spontaneous autoimmune optic neuritis", J. Exp. Med., 197:1073-1081 (May 5, 2003).
Butterfield et al., "New genetic loci that control susceptibility and symptoms of experimental allergic encephalomyelitis in inbred mice", J. Immunol. 161(4):1860-1867 (Aug. 15, 1998).
Chen, H-L et al, T Cell Receptor Signaling Co-regulates Multiple Golgi Genes to Enhance N-Glycan Branching, Journal of Biological Chemistry, Nov. 20, 2009, vol. 284(47):32454-32461.
Chung, "Galectin-1 Induces Partial TCR ζ-Chain Phosphorylation and Antagonizes Processive TCR Signal Transduction", J of Immunol, 165(7):3722-3729 (Oct. 1, 2000).
Cummings, "A Mouse Lymphome Cell Line Resistant to the Leukoagglutinating Lectin from Phaseolus vulgaris is Deficient in UDP-GlcNAc: α-D-mannoside β1, 6 N-Acetylglucosaminyltransferase" J Biol Chem, 257(22):13421-13427, (Nov. 25, 1982).
Cummings, "P-Selectin and Galectin Interactions With Human Neutrophils", Proceedings of the ACS International Symposium on Recent Advances in Polyolefins, Part 1 (Mar. 29, 1998).
Cummings, "The Distribution of Repeating [Galβ1,4G1cNAcβ1,3] Sequences in Asparagine-linked Oiigosaccharides of the Mouse Lymphoma Cell Lines BW5147 and PHA$^R$ 2.1" J Biol Chem, 259(10):6253-6260 (May 25, 1984).
Demetriou et al., "Negative regulation of T-cell activation and autoimmunity by Mgat5 N-glycosylation", Nature, 409:733-739 (Feb. 8, 2001).
Dennis, "Glycoprotein Glycosylation and Cancer Progression" Biochimica Et Biophysica Acta, 1473(1):21-34 (Dec. 6, 1999).
Dennis, J et al, UDP-N-acetylglucosamine:a-6-D-mannoside h1, 6 N-acetylglucosaminyltransferase V (Mgat5) deficient mice, Biochimica et Biophysica Acta, Dec. 19, 2002; vol. 1573: pp. 414-422.
Dennis, J. et al, Genetic defects in N-glycosylation and cellular diversity in mammals, Current Opinion in Structural Biology, Sep. 1, 2001, vol. 11:pp. 601-607.
Dennis, JW et al, Adaptive regulation at the Cell Surface by N-Glycosylation, Traffic, Sep. 15, 2009, DOI:10.1111/j.1600-0854.2009.00981.x.
Dennis, JW et al, Metabolism, Cell Surface Organization, and Disease, Cell, Dec. 24, 2009, vol. 139(7): pp. 1229-1241.
Do, "Modification of glycoproteins by N-acetylglucosaminyltransferase V is greatly influenced by accessibility of the enzyme to oligosaccharide acceptors", J Biol Chem, 269(38):23456-23464 (Sep. 23, 1994).
Downward, "Stimulation of p21$^{RAS}$ upon T-cell activation", Nature, 346:719-723 (Aug. 23, 1990).
Dyment et al., "An extended genome scan in 442 Canadian multiple sclerosis-affected sibships: a report from the Canadian Collaborative Study Group", Hum. Mol. Genet., 13(10):1005-1015 (May 15, 2004) (E-pub Apr. 6, 2004).
Ebers et al., "A genetic basis for familial aggregation in multiple sclerosis. Canadian Collaborative Step Group", Nature, 377:150-151 (Sep. 14, 1995).
Ebers et al., "A population-based study of multiple sclerosis in twins", N. Engl. J. Med., 315:1638-1642 (Dec. 1986).

(56) References Cited

OTHER PUBLICATIONS

Ellies, "Core 2 Oligosaccharide Biosynthesis Distinguishes between Selectin Ligands Essential for Leukocyte Homing and Inflammation", Immunity, 9:881-890 (Dec. 1998).
Encinas et al., "Genetic analysis of susceptibility to experimental autoimmune encephalomyelitis in a cross between SJL/J and B10.S mice", J. Immunol., 157(5):2186-2192 (Sep. 1, 1996).
Goochee, "The oligosaccharides of glycoproteins: bioprocess factors affecting oligosaccharide structure and their effect on glycoprotein properties", Biotechnology, 9(12):1347-1355 (Dec. 1991).
Goverman et al., "Transgenic mice that express a myelin basic protein-specific T cell receptor develop spontaneous autoimmunity", Cell, 72(4):551-560 (Feb. 26, 1993).
Granovsky, "Mgat5 N-Glycans Regulate Integrin and T Cell Receptor Functions Affecting Cancer Development and Immune Responses In Vivo" Glycoconjugate Journal, 17:1-2, Jan. 2000, p. 26, Second International Glycosyltransferase Symposium; Toronto, Ontario, Canada; (May 12-14, 2000).
Granovsky, "Suppression of tumor growth and metastasis in Mgat5-deficient mice", Nature Medicine, 6(3):306-312 (Mar. 2000).
Grigorian, A and Demietriou, M, Manipulating Cell surface Glycoproteins by Targeting N-Glycan-Galectin Interactions, In M. Fukuda, Glycobiology, Methods in Enzymology, vol. 480, Burlington: Academic Press, 2010, Chapter 12, pp. 245-266.
Grigorian, A et al, T-cell growth, cell surface organization, and the galectin glycoprotein lattice, Immunology Review, Jul. 2009, vol. 230(1): 232-246.
Grigorian, A. et al, Control of T Cell-mediated Autoimmunity by Metabolite Flux to N-Glycan Biosynthesis, The Journal of Biological Chemistry, Jul. 6, 2007, vol. 282 (27):pp. 20027-20035 (also published May 8, 2007 by JBC Papers in Press).
Grigorian, A. et al, N-Acetylglucosamine Inhibits T-helper 1 (Th1)/T-helper 17 (Th17) Cell Responses and Treats Experimental Autoimmune Encephalomyelitis, The Journal of Biological Chemistry, Nov. 18, 2011, vol. vol. 286 (46): pp. 40133-40141 (also published Sep. 29, 2011 by JBC Papers in Press).
Gu, "Purification and Characterization of UDP-N-Acetylglucosamine: α-6-D-Mannoside β1-6N-Acetylglucosaminyltransferase (N-Acetylglucosaminyltransferase V) from a Human Lung Cancer Cell Line", J Biochem, 113(5):614-619 (May 1993).
Hadari, "Galectin-8", J Biol Chem, 270(17):3447-3453 (Feb. 1995).
Hubbard, "Glycosylation of the T-cell Antigen-Specific Receptor and Its Potential Role in Lectin-Mediated Cytotoxicity", Proc Natl Acad Sci, 83:1852-1856 (Mar. 1986).
Karsan, "Leukocyte Adhesion Deficiency Type II is a Generalized Defect of De Novo GDP-Fucose Biosynthesis", J Clin Invest, 101(11):2438-2445 (Jun. 1998).
Knibbs, "Carbohydrate-binding Protein 35. II. Analysis of the interaction of the recombinant polypeptide with saccharides", J Biol Chem, 268(20):14940-14947 (Jul. 15, 1993).
Lafaille et al., "High incidence of spontaneous autoimmune encephalomyelitis in immunodeficient anti-myelin basic protein T cell receptor transgenic mice", Cell, 78(3):399-408 (Aug. 12, 1994).
Lau, K. S. et al, Complex N-Glycan Number and Degree of Branching Cooperate to Regulate Cell Proliferation and Differentiation, Cell, Apr. 6, 2007, vol. 129:pp. 123-134.
Lee, S-U et al, N-Glycan Processing Deficiency Promotes Spontaneous Inflammatory Demyelination and Neurodegeneration, The Journal of Biological Chemistry, Nov. 16, 2007, vol. 282 (46): pp. 33725-33734 (also published by JBC Papers in Press, Sep. 13, 2007).
Lemaire, "Expression of β 1-6-branched N-linked oligosaccharides is associated with activation in human T4 and T8 cell populations", J Biol Chem, 269(11):8069-8074 (Mar. 18, 1994).
Ma, L. et al, Immunosuppressive Effects of Glucosamine, The Journal of Biological Chemistry, Oct. 18, 2002, vol. 277(42):pp. 39343-39349.
Mkhikian, H et al, Genetics and the environment converge to dysregulate N-glycosylation in multiple sclerosis, Nature Communications, May 31, 2011, vol. 2: pp. 334.
Moloney, "Fringe is a glycosyltransferase that modifies Notch", Nature, 406:369-375 (Jul. 27, 2000).
Monks, "Three-dimensional segregation of supramolecular activation clusters in T cells", Nature, 395:82-86 (Sep. 3, 1998).
Morgan, R. et al, N-Acetylglucosaminyltransferase V (Mgat5)-Mediated N-Glycosylation Negatively Regulates Th1 Cytokine Production by T Cells, The Journal of Immunology, Dec. 15, 2004, vol. 173:pp. 7200-7208.
Noseworthy, "Progress in determining the causes and treatment of multiple sclerosis", Nature, 399:A40-A47 (Jun. 24, 1999).
Offner, "Recombinant human β-galactoside binding lectin suprresses clinical and histological signs of experimental autoimmune encephalomyelitis", J of Neuroimmunology, 28(2):177-184 (Jul. 1990).
Oliveira-Dos-Santos, "CD28 Costimulation is Crucial for the Development of Spontaneous Autoimmune Encephalomyelitis", J Immunol, 162(8):4490-4495 (Apr. 15, 1999).
Pace, "Restricted Receptor Segregation into Membrane Microdomains Occurs on Human T Cells During Apoptosis Induced by Galectin-1", J Immunol, 163(7):3801-3811 (Oct. 1, 1999).
Palcic, "Regulation of N-Acetylglucosaminyltransferase V Activity", J Biol Chem, 265(12):6759-6769 (Apr. 25, 1990).
Paulson, "Glycosyltransferases", J Biol Chem, 264(30):17615-17618 (Oct. 25, 1989).
Perillo, "Apoptosis of T Cells Mediated by Galectin-1", Nature, 378(6558):736-739 (Dec. 14, 1995).
Priatel, "The ST3Gal-I Sialyltransferase Controls $CD8^+$ T Lymphocyte Homeostasis by Modulating O-Glycan Biosynthesis", Immunity, 12:273-283 (Mar. 2000).
Rabinovich, "Specific inhibition of T-cell adhesion to extracellular matrix and proinflammatory cytokine secretion by human recombinant galectin-1", Immunology, 97(1):100-106 (May 1999).
Reich, "Ligand-specific oligomerization of T-cell receptor molecules", Nature, 387:617-620 (Jun. 5, 1997).
Reif, "Networking Rho Family GTPases in Lymphocytes", Immunity, 8:395-401 (Apr. 1998).
Rudd, "Roles for Glycosylation of Cell Surface Receptors Involved in Cellular Immune Recognition", J Mol Biol, 293(2):351-366 (Oct. 22, 1999).
Saito, "cDNA cloning and chromosomal mapping of human N-acetylglucosaminyltransferase $V^*$", Biochemical and Biophysical Research Communications, 198(1):318-327 (Jan. 14, 1994).
Salvatore, S. et al, A pilot study of N-acetyl glucosamine, a nutritional substrate for glycosaminoglycan synthesis, in paediatric chronic inflammatory bowel disease, Aliment Pharmacol Ther, Dec. 2000; vol. 14:pp. 1567-1579.
Sato, "Binding Specificity of a Baby Hamster Kidney Lectin for H Type I and II Chains, Polylactosamine Glycans, and Appropriately Glycosylated Forms of Laminin and Fibronectin", J Biol Chem, 267(10):6983-6990 (Apr. 5, 1992).
Schachter, "Biosynthetic controls that determine the branching and microheterogeneity of protein-bound oligosaccharides", Biochem Cell Biol, 64(3):163-181 (Mar. 1986).
Shoreibah, "Isolation, Characterization, and Expression of a cDNA Encoding N-Acetylglucosaminyltransferase V", J Biol Chem, 268(21):15381-15385 (Jul. 25, 1993).
Steinman, "Multiple sclerosis: a coordinated immunological attack against myelin in the central nervous system", Cell, 85:299-302 (May 3, 1996).
Steinman, "Multiple sclerosis: a two-stage disease", Nat. Immunol., 2:762-764 (Sep. 2001).
Trevillyan, "Differential Inhibition of T Cell Receptor Signal Transduction and Early Activation Events by a Selective Inhibitor of Protein-Tyrosine Kinase", J Immunol, 145(10):3223-3230 (Nov. 15, 1990).
Valitutti, "Serial triggering of many T-cell receptors by a few peptide-MHC complexes", Nature, 375:148-151 (May 11, 1995).
Varki, "Essentials of Glycobiology", Eds. Cold Spring Harbor Laboratory Press. New York., pp. 2-3 and 538-540 (1999).

(56) References Cited

OTHER PUBLICATIONS

Vespa, "Galectin-1 Specifically Modulates TCR Signals to Enhance TCR Apoptosis but Inhibit IL-2 Production and Proliferation", J Immunol, 162(2):799-806 (Jan. 15, 1999).

Viola, "T Cell Activation Determined by T Cell Receptor Number and Tunable Thresholds", Science, 273(5271):104-106 (Jul. 5, 1996).

Viola, "T Lymphocyte Costimulation Mediated by Reorganization of Membrane Microdomains", Science, 283(5402):680 (Jan. 29, 1999).

Waldner et al., "Fulminant spontaneous autoimmunity of the central nervous system in mice transgenic for the myelin proteolipid protein-specific T cell receptor", Proc. Natl. Acad. Sci USA, 97(7):3412-3417 (Mar. 28, 2000).

Wall, "Inhibitors of glycoprotein processing alter T-cell proliferative responses to antigen and to interleukin 2", Proc Natl Acad Sci, 85:5644-5648 (Aug. 1988).

Wang, "Atomic structure of an αβ T cell receptor (TCR) heterodimer in complex with an anti-TCR Fab fragment derived form a mitogenic antibody", The EMBO Journal, 17(1):10-26 (Jan. 2, 1998).

Wulfing, "A Receptor/Cytoskeletal Movement Triggered by Costimulation During T Cell Activation", Science, 282:2266 (Dec. 18, 1998).

Zhang, G-X, et al, Glucosamine Abrogates the Acute Phase of Experimental Autoimmune Encephalomyelitis by Induction of Th2 Response, Dec. 1, 2005, Journal of Immunology, vol. 175:pp. 7202-7208.

PCT International Search Report and Written Opinion of the International Searching Authority for PCT/US06/01337, dated Dec. 8, 2009.

\* cited by examiner

A) GCS1 SNP I (Exon1)

B) GANAB SNP III (Exon11)

C) GANAB SNP IV (Intron 21)

Figure 11

D) GANAB SNP V (Intron 23)

E) MAN1A1 SNP IX and X (Exon 13 3' UTR)

F) MGAT1 SNP VI (Exon 2 3' UTR)

SEQUENCE LISTING

<160> NUMBER OF SEQ ID NOS: 110

<210> SEQ ID NO 1
<211> LENGTH: 21
<212> TYPE: DNA
<213> ORGANISM: Homo sapiens

<400> SEQUENCE: 1
ggaaatggcc ttgaaaacac a                                              21

<210> SEQ ID NO 2
<211> LENGTH: 19
<212> TYPE: DNA
<213> ORGANISM: Artificial
<220> FEATURE:
<223> OTHER INFORMATION: chemically synthesized

<400> SEQUENCE: 2
caagcacacc tgggatcca                                                 19

<210> SEQ ID NO 3
<211> LENGTH: 20
<212> TYPE: DNA
<213> ORGANISM: Homo sapiens

<400> SEQUENCE: 3
ccagcagatg tggatcagca                                                20

<210> SEQ ID NO 4
<211> LENGTH: 16
<212> TYPE: DNA
<213> ORGANISM: Artificial
<220> FEATURE:
<223> OTHER INFORMATION: chemically synthesized

<400> SEQUENCE: 4
ttgcggtgca cgatgg                                                    16

<210> SEQ ID NO 5
<211> LENGTH: 41
<212> TYPE: DNA
<213> ORGANISM: Homo sapiens
<220> FEATURE:
<221> NAME/KEY: misc_feature
<223> OTHER INFORMATION: R = G OR A

<400> SEQUENCE: 5
tgggtatgtc ggggcgctgg rtgctggcgt ggtaccgtgc g                        41

<210> SEQ ID NO 6
<211> LENGTH: 40
<212> TYPE: DNA
<213> ORGANISM: Homo sapiens
<220> FEATURE:
<221> NAME/KEY: misc_feature
<223> OTHER INFORMATION: R = G OR A

<400> SEQUENCE: 6
gaaatagtac aacttaatgr attagctttt gggtttaact                          40

<210> SEQ ID NO 7
<211> LENGTH: 41
<212> TYPE: DNA
<213> ORGANISM: Homo sapiens
<220> FEATURE:
<221> NAME/KEY: misc_feature

<223> OTHER INFORMATION: R = G OR A

<400> SEQUENCE: 7
ggtggagttg gtgggtcatc rgggctcact gcctcctgcc c          41

<210> SEQ ID NO 8
<211> LENGTH: 41
<212> TYPE: DNA
<213> ORGANISM: Homo sapiens
<220> FEATURE:
<221> NAME/KEY: misc_feature
<223> OTHER INFORMATION: S = C OR G

<400> SEQUENCE: 8
ccactttctt gctcacctca scagttgcat gttctagtcc t          41

<210> SEQ ID NO 9
<211> LENGTH: 41
<212> TYPE: DNA
<213> ORGANISM: Homo sapiens
<220> FEATURE:
<221> NAME/KEY: misc_feature
<223> OTHER INFORMATION: R = G OR A

<400> SEQUENCE: 9
ggaatcttct agaaatgcca rctataacct gaaatagtgt t          41

<210> SEQ ID NO 10
<211> LENGTH: 20
<212> TYPE: DNA
<213> ORGANISM: Artificial
<220> FEATURE:
<223> OTHER INFORMATION: chemically synthesized

<400> SEQUENCE: 10
cgttgttggg agatggaaag          20

<210> SEQ ID NO 11
<211> LENGTH: 20
<212> TYPE: DNA
<213> ORGANISM: Artificial
<220> FEATURE:
<223> OTHER INFORMATION: chemically synthesized

<400> SEQUENCE: 11
tcaggcaaca aacaaggaca          20

<210> SEQ ID NO 12
<211> LENGTH: 20
<212> TYPE: DNA
<213> ORGANISM: Homo sapiens

<400> SEQUENCE: 12
agtagcaatg ggcgacaaag          20

<210> SEQ ID NO 13
<211> LENGTH: 20
<212> TYPE: DNA
<213> ORGANISM: Artificial
<220> FEATURE:
<223> OTHER INFORMATION: chemically synthesized

<400> SEQUENCE: 13
gctttgcgaa gcgagtctat          20

-continued

```
<210> SEQ ID NO 14
<211> LENGTH: 19
<212> TYPE: DNA
<213> ORGANISM: Artificial
<220> FEATURE:
<223> OTHER INFORMATION: chemically synthesized

<400> SEQUENCE: 14
ccccggactt cttcgagta                                                   19

<210> SEQ ID NO 15
<211> LENGTH: 20
<212> TYPE: DNA
<213> ORGANISM: Artificial
<220> FEATURE:
<223> OTHER INFORMATION: chemically synthesized

<400> SEQUENCE: 15
cgaacgttgc caaactctct                                                  20

<210> SEQ ID NO 16
<211> LENGTH: 20
<212> TYPE: DNA
<213> ORGANISM: Artificial
<220> FEATURE:
<223> OTHER INFORMATION: chemically synthesized

<400> SEQUENCE: 16
cccccatttc ctctacctgt                                                  20

<210> SEQ ID NO 17
<211> LENGTH: 21
<212> TYPE: DNA
<213> ORGANISM: Artificial
<220> FEATURE:
<223> OTHER INFORMATION: chemically synthesized

<400> SEQUENCE: 17
ccctcccact catctgcttt c                                                21

<210> SEQ ID NO 18
<211> LENGTH: 2890
<212> TYPE: DNA
<213> ORGANISM: Homo sapiens
<300> PUBLICATION INFORMATION:
<308> DATABASE ACCESSION NUMBER: NM_006302
<309> DATABASE ENTRY DATE: 2005-10-16
<313> RELEVANT RESIDUES IN SEQ ID NO: (1)..(2890)

<400> SEQUENCE: 18
ggcgctggct ggcaggtgtc gctaaccgga cggtggtcgc cagggcgaga ggcgggagcc       60
ggagaggtga ggcaggaccc gggctccact gccgcctctc cgagctcttg tgacgcggac      120
ctcagtgcca ggatggctcg gggcgagcgg cggcgccgcg cagtgccggc agagggagtg      180
cggacagccg agagggcggc tcggggaggc cccgggcgac gggacggccg gggcggcggg      240
ccgcgtagca cggctggagg agtggctctg gccgtcgtgg tcctgtcttt ggccctgggt      300 atgtcgggc gctgggtgct ggcgtggtac cgtgcgcggc gggcggtcac gctgcactcc      360
gcgcctcctg tgttgcctgc cgactcctcc agccccgccg tggccccgga cctcttctgg      420
ggaacctacc gccctcacgt ctacttcggc atgaagaccc gcagcccgaa acccctcctc      480
accggactga tgtgggcgca gcagggcacc accccgggga ctcctaagct caggcacacg      540
tgtgagcagg gggacggtgt gggtccctat ggctgggagt ccacgacgg cctctccttc      600
```

-continued

```
gggcgccaac acatccagga tggggcctta aggctcacca ctgagttcgt caagaggcct      660
gggggtcagc acggagggga ctggagctgg agagtgactg tagagcctca ggactcaggt      720
acttctgccc tcccttggt ctccctgttc ttctatgtgg tgacagatgg caaggaagtc       780
ctactaccag aggttgggc caaggggcag ttgaagttta tcagtgggca caccagtcaa       840
cttggtaact tccgctttac acttttgcca ccaaccagtc caggggatac agccccaag       900 tatggcagct acaatgtctt ctggacctcc aacccaggac tgcccctgct gacagagatg      960
gtaaagagtc gcctaaatag ctggtttcag catcggcccc caggggcctc ccctgaacgc     1020
tacctcggct tgccaggatc cctgaagtgg gaggacagag gtccaagtgg gcaagggcag    1080
gggcagttct tgatacagca ggtgaccctg aaaattccat tttccataga gtttgtgttt    1140
gaatcaggca gtgcccaggc aggaggaaat caagccctgc caagactggc aggcagtcta    1200
ctgacccagg ccctggagag ccatgctgaa ggctttagag agcgctttga aagaccttc     1260 cagctgaagg agaagggcct gagctctggc gagcaggctt tgggtcaggc tgccctcagc    1320
ggcctccttg gtggaattgg ctacttctac ggacaagggc tggtattgcc agacatcggg    1380
gtggaagggt ctgagcagaa ggtggaccca gccctctttc cacccgtacc tcttttaca    1440 gcagtgccct cccggtcatt cttcccacga ggcttccttt gggatgaagg ctttcaccag    1500
ctggtggttc agcggtggga tccctccctc acccgggaag cccttggcca ctggctgggg    1560
ctgctaaatg ctgatggctg gattgggagg gagcagatac tggggatga ggcccgagcc    1620 cgggtgcctc cagaattcct agtacaacga gcagtccacg ccaaccccc aaccctactt    1680 ttgcctgtag cccatatgct agaggttggt gaccctgacg acttggcttt cctccgaaag    1740
gccttgcccc gcctgcatgc ctggttttcc tggctccatc agagccaggc aggcccactg    1800
ccactatctt accgctggcg gggacgggac cctgccttac caaccttact gaaccccaag    1860
accctaccct ctgggctgga tgactacccc cgggcttcac accttcagt aaccgagcgg    1920 cacctggacc tgcgatgttg ggtgggactg ggtgcccgtg tgctgacgcg gctggcagag    1980
catctgggtg aggctgaggt agctgctgag ctgggcccac tggctgcctc actggaggca    2040
gcagagagcc tggatgagct gcactgggcc ccagagctag gagtctttgc agactttggg    2100
aaccacacaa aagcagtaca gctgaagccc aggcccctc aggggctcgt tcgggtggtg    2160
ggtcggcccc aacctcaact gcagtatgta gatgctcttg gctatgtcag tcttttccc    2220 ttgctgctgc gactgctgga ccccacctca tcccgccttg ggcccctgct ggacattcta    2280
gccgacagcc gccatctctg gagccccttt ggtttacgct cccttgcagc ctccagctcc    2340
ttttatggcc agcgcaattc agagcatgat ccccccctact ggcgggtgc tgtgtggctc    2400 aatgtcaact acctggcttt gggagcactc caccactatg gcatctgga gggtcctcac    2460 caggctcggg ctgccaaact ccacggtgag ctccgtgcca acgtggtagg caatgtatgg    2520
cgccagtacc aggccacagg cttttctttgg gagcagtaca gtgaccgcga tgggcgaggc    2580
atgtgccgcc ctttccacgg ctggaccagc cttgtcttac tggccatggc tgaagactac    2640
tgaagggagg gagaggaggg gagccaagac actcatgcca ctctggctct gaaggacaag    2700
ggacaaaggc ttctggcttt tgcccccagc cccttggata ccagtaattc aaaccttcct    2760
cattcattct caggtgtctc cttgctgtca tcccacatag ccctggggtg aatgtgaatc    2820
cagagtctat ttttctaaat aaattggaaa aacaaaaaa aaaaaaaaaa aaaaaaaaaa    2880
aaaaaaaaaa                                                             2890
```

-continued

```
<210> SEQ ID NO 19
<211> LENGTH: 836
<212> TYPE: PRT
<213> ORGANISM: Homo sapiens
<300> PUBLICATION INFORMATION:
<308> DATABASE ACCESSION NUMBER: NP_006293
<309> DATABASE ENTRY DATE: 2005-10-16
<313> RELEVANT RESIDUES IN SEQ ID NO: (1)..(836)

<400> SEQUENCE: 19

Met Ala Arg Gly Glu Arg Arg Arg Ala Val Pro Ala Glu Gly Val
1               5                   10                  15

Arg Thr Ala Glu Arg Ala Ala Arg Gly Gly Pro Gly Arg Arg Asp Gly
            20                  25                  30

Arg Gly Gly Gly Pro Arg Ser Thr Ala Gly Val Ala Leu Ala Val
        35                  40                  45

Val Val Leu Ser Leu Ala Leu Gly Met Ser Gly Arg Trp Val Leu Ala
    50                  55                  60

Trp Tyr Arg Ala Arg Arg Ala Val Thr Leu His Ser Ala Pro Pro Val
65                  70                  75                  80

Leu Pro Ala Asp Ser Ser Pro Ala Val Ala Pro Asp Leu Phe Trp
                85                  90                  95

Gly Thr Tyr Arg Pro His Val Tyr Phe Gly Met Lys Thr Arg Ser Pro
                100                 105                 110

Lys Pro Leu Leu Thr Gly Leu Met Trp Ala Gln Gln Gly Thr Thr Pro
            115                 120                 125

Gly Thr Pro Lys Leu Arg His Thr Cys Glu Gln Gly Asp Gly Val Gly
        130                 135                 140

Pro Tyr Gly Trp Glu Phe His Asp Gly Leu Ser Phe Gly Arg Gln His
145                 150                 155                 160

Ile Gln Asp Gly Ala Leu Arg Leu Thr Thr Glu Phe Val Lys Arg Pro
                165                 170                 175

Gly Gly Gln His Gly Gly Asp Trp Ser Trp Arg Val Thr Val Glu Pro
            180                 185                 190

Gln Asp Ser Gly Thr Ser Ala Leu Pro Leu Val Ser Leu Phe Phe Tyr
        195                 200                 205

Val Val Thr Asp Gly Lys Glu Val Leu Leu Pro Glu Val Gly Ala Lys
    210                 215                 220

Gly Gln Leu Lys Phe Ile Ser Gly His Thr Ser Gln Leu Gly Asn Phe
225                 230                 235                 240

Arg Phe Thr Leu Leu Pro Pro Thr Ser Pro Gly Asp Thr Ala Pro Lys
                245                 250                 255

Tyr Gly Ser Tyr Asn Val Phe Trp Thr Ser Asn Pro Gly Leu Pro Leu
            260                 265                 270

Leu Thr Glu Met Val Lys Ser Arg Leu Asn Ser Trp Phe Gln His Arg
        275                 280                 285

Pro Pro Gly Ala Ser Pro Glu Arg Tyr Leu Gly Leu Pro Gly Ser Leu
    290                 295                 300

Lys Trp Glu Asp Arg Gly Pro Ser Gly Gln Gly Gln Gly Gln Phe Leu
305                 310                 315                 320

Ile Gln Gln Val Thr Leu Lys Ile Pro Phe Ser Ile Glu Phe Val Phe
                325                 330                 335

Glu Ser Gly Ser Ala Gln Ala Gly Asn Gln Ala Leu Pro Arg Leu
            340                 345                 350

Ala Gly Ser Leu Leu Thr Gln Ala Leu Glu Ser His Ala Glu Gly Phe
        355                 360                 365
```

```
Arg Glu Arg Phe Glu Lys Thr Phe Gln Leu Lys Glu Lys Gly Leu Ser
        370                 375                 380

Ser Gly Glu Gln Ala Leu Gly Gln Ala Ala Leu Ser Gly Leu Leu Gly
385                 390                 395                 400

Gly Ile Gly Tyr Phe Tyr Gly Gln Gly Leu Val Leu Pro Asp Ile Gly
                405                 410                 415

Val Glu Gly Ser Glu Gln Lys Val Asp Pro Ala Leu Phe Pro Pro Val
                420                 425                 430

Pro Leu Phe Thr Ala Val Pro Ser Arg Ser Phe Phe Pro Arg Gly Phe
                435                 440                 445

Leu Trp Asp Glu Gly Phe His Gln Leu Val Val Gln Arg Trp Asp Pro
    450                 455                 460

Ser Leu Thr Arg Glu Ala Leu Gly His Trp Leu Gly Leu Leu Asn Ala
465                 470                 475                 480

Asp Gly Trp Ile Gly Arg Glu Gln Ile Leu Gly Asp Glu Ala Arg Ala
                485                 490                 495

Arg Val Pro Pro Glu Phe Leu Val Gln Arg Ala Val His Ala Asn Pro
                500                 505                 510

Pro Thr Leu Leu Leu Pro Val Ala His Met Leu Glu Val Gly Asp Pro
    515                 520                 525

Asp Asp Leu Ala Phe Leu Arg Lys Ala Leu Pro Arg Leu His Ala Trp
530                 535                 540

Phe Ser Trp Leu His Gln Ser Gln Ala Gly Pro Leu Pro Leu Ser Tyr
545                 550                 555                 560

Arg Trp Arg Gly Arg Asp Pro Ala Leu Pro Thr Leu Leu Asn Pro Lys
                565                 570                 575

Thr Leu Pro Ser Gly Leu Asp Asp Tyr Pro Arg Ala Ser His Pro Ser
                580                 585                 590

Val Thr Glu Arg His Leu Asp Leu Arg Cys Trp Val Gly Leu Gly Ala
            595                 600                 605

Arg Val Leu Thr Arg Leu Ala Glu His Leu Gly Glu Ala Glu Val Ala
    610                 615                 620

Ala Glu Leu Gly Pro Leu Ala Ala Ser Leu Glu Ala Ala Glu Ser Leu
625                 630                 635                 640

Asp Glu Leu His Trp Ala Pro Glu Leu Gly Val Phe Ala Asp Phe Gly
                645                 650                 655

Asn His Thr Lys Ala Val Gln Leu Lys Pro Arg Pro Pro Gln Gly Leu
                660                 665                 670

Val Arg Val Val Gly Arg Pro Gln Pro Leu Gln Tyr Val Asp Ala
        675                 680                 685

Leu Gly Tyr Val Ser Leu Phe Pro Leu Leu Arg Leu Leu Asp Pro
    690                 695                 700

Thr Ser Ser Arg Leu Gly Pro Leu Leu Asp Ile Leu Ala Asp Ser Arg
705                 710                 715                 720

His Leu Trp Ser Pro Phe Gly Leu Arg Ser Leu Ala Ala Ser Ser Ser
                725                 730                 735

Phe Tyr Gly Gln Arg Asn Ser Glu His Asp Pro Pro Tyr Trp Arg Gly
                740                 745                 750

Ala Val Trp Leu Asn Val Asn Tyr Leu Ala Leu Gly Ala Leu His His
            755                 760                 765

Tyr Gly His Leu Glu Gly Pro His Gln Ala Arg Ala Ala Lys Leu His
    770                 775                 780
```

```
Gly Glu Leu Arg Ala Asn Val Val Gly Asn Val Trp Arg Gln Tyr Gln
785                 790                 795                 800

Ala Thr Gly Phe Leu Trp Glu Gln Tyr Ser Asp Arg Asp Gly Arg Gly
            805                 810                 815

Met Cys Arg Pro Phe His Gly Trp Thr Ser Leu Val Leu Leu Ala Met
        820                 825                 830

Ala Glu Asp Tyr
        835

<210> SEQ ID NO 20
<211> LENGTH: 3952
<212> TYPE: DNA
<213> ORGANISM: Homo sapiens
<300> PUBLICATION INFORMATION:
<308> DATABASE ACCESSION NUMBER: NM_014610
<309> DATABASE ENTRY DATE: 2005-09-24
<313> RELEVANT RESIDUES IN SEQ ID NO: (1)..(3952)

<400> SEQUENCE: 20
aggtttgggg tcaaggagca aactctgcac aagatggcgg cggtagcggc agtggcggcg      60
cgtaggaggc ggtcttgggc gtctttggta ctggcttttt tagggggtctg cctggggatt    120
acccttgctg tggatagaag caactttaag acctgtgaag agagttcttt ctgcaagcga    180
cagagaagca tacggccagg cctctctcca taccgagcct tgctggactc tctacagctt    240
ggtcctgatt ccctcacggt ccatctgatc catgaggtca ccaaggtgtt gctggtgcta    300
gagcttcagg ggcttcaaaa gaacatgact cggttcagga ttgatgagct ggagcctcgg    360
cgaccccgat accgtgtacc agatgttttg gtggctgatc caccaatagc ccggctttct    420
gtctctggtc gtgatgagaa cagtgtggag ttaaccatgg ctgagggacc ctacaagatc    480
atcttgacag cacggccatt ccgccttgac ctactagagg accgaagtct tttgcttagt    540
gtcaatgccc gaggactctt ggagtttgag catcagaggg cccctagggt ctctttctcg    600
gataaggtta atctcacgct tggtagcata tgggataaga tcaagaacct tttctctagg    660
caaggatcaa agacccagc tgagggcgat ggggcccagc ctgaggaaac acccagggat    720
ggcgacaagc cagaggagac tcaggggaag gcagagaaag atgagccagg agcctgggag    780
gagacattca aaactcactc tgacagcaag ccgtatggcc ccatgtctgt gggtttggac    840
ttctctctgc caggcatgga gcatgtctat gggatccctg agcatgcaga caacctgagg    900
ctgaaggtca ctgagggtgg ggagccatat cgcctctaca atttggatgt gttccagtat    960
gagctgtaca acccaatggc cttgtatggg tctgtgcctg tgctcctggc acacaaccct   1020
catcgcgact tgggcatctt ctggctcaat gctgcagaga cctgggttga tatatcttcc   1080
aacactgccg ggaagaccct gtttgggaag atgattggact acctgcaggg ctctggggag   1140
acccacagaa cagatgttcg ctggatgtca gagactggca tcattgacgt cttcctgctg   1200
ctggggccct ccatctctga tgttttccgg caatatgcta gtctcacagg aacccaggcg   1260
ttgcccccac tcttctccct cggctaccac cagagccgtt ggaactaccg ggacgaggct   1320
gatgtgctgg aagtggatca gggctttgat gatcacaacc tgccctgtga tgtcatctgg   1380
ctagacattg aacatgctga tgcaagcgcg tatttcacct gggacccag tcgcttccct   1440
cagccccgca ccatgcttga gcgcttggct tctaagaggc ggaagctggt ggccatcgta   1500
gaccccaca tcaaggtgga ctccggctac cgagttcacg aggagctgcg gaacctgggg   1560
ctgtatgtta aacccgggga tggctctgac tatgagggct ggtgctggcc aggctcagct   1620
ggttaccctg acttcactaa tcccacgatg agggcctggt gggctaacat gttcagctat   1680
```

```
gacaattatg agggctcagc tcccaacctc tttgtctgga atgacatgaa cgaaccatct      1740
gtgttcaatg gtcctgaggt caccatgctc aaggatgccc agcattatgg gggctgggag      1800
caccgggatg tgcataacat ctatggcctt tatgtgcaca tggcgactgc tgatgggctg      1860
agacagcgct ctgggggcat ggaacgcccc tttgtcctgg ccagggcctt cttcgctggc      1920
tcccagcgct ttggagccgt gtggacaggg gacaacactg ccgagtggga ccatttgaag      1980
atctctattc ctatgtgtct cagcttgggg ctggtgggac tttccttctg tggggcggat      2040
gtgggtggct tcttcaaaaa cccagagcca gagctgcttg tgcgctggta ccagatgggt      2100
gcttaccagc cattcttccg ggcacatgcc cacttggaca ctgggcgacg agagccatgg      2160
ctgttaccat ctcagcacaa tgatataatc cgagatgcct gggccagcg atattctttg       2220 ctgcccttct ggtacaccct cttatatcag gcccatcggg aaggcattcc tgtcatgagg      2280
tgcagtaccc tcaggatgtg actaccttca atatagatga tcagtacttg cttggggatg      2340
cgttgctggt tcaccctgta tcagactctg gagcccatgg tgtccaggtc tatctgcctg      2400
gccaagggga ggtgtggtat gacattcaaa gctaccagaa gcatcatggt ccccagaccc      2460
tgtacctgcc tgtaactcta agcagtatcc ctgtgttcca gcgtggaggg acaatcgtgc      2520
ctcgatggat gcgagtgcgg cggtcttcag aatgtatgaa ggatgacccc atcactctct      2580
ttgttgcact tagccctcag ggtacagctc aaggagagct ctttctggat gatgggcaca      2640
cgttcaacta tcagactcgc caagagttcc tgctgcgtcg attctcattc tctggcaaca      2700
cccttgtctc cagctcagca gaccctgaag gacactttga gacaccaatc tggattgagc      2760
gggtggtgat aatagggggct ggaaagccag cagctgtggt actccagaca aaaggatctc      2820
cagaaagccg cctgtccttc cagcatgacc ctgagacctc tgtgttggtc ctgcgcaagc      2880
ctggcatcaa tgtggcatct gattggagta ttcacctgcg ataacccaag ggatgttctg      2940
ggttaggggg agggaagggg agcattagtg ctgagagata ttctttcttc tgccttggag      3000
ttcggccctc cccagacttc acttatgcta gtctaagacc cagattctgc caacatttgg      3060
gcaggatgag agggctgacc ctgggctcca aattcctctt gtgatctcct cacctctccc      3120
actccattga taccaactct ttcccttcat tcccccaaca tcctgttgct ctaactggag      3180
cacattcact tacgaacacc aggaaaccac agggcccttg tcgcccctc tctttccctt       3240 atttaggagc cctgaactcc cccagagtct atccattcat gcctcttgta tgttgatgcc      3300
acttcttgga agaagatgag ggcaatgagt tagggctcct tttccccttc cctcccacca      3360
gattgctctc ccacctttca tttcttcctc caggctttac tcccctttt atgccccacc       3420 gatacactgg gaccacccct taccccggac aggatgaatg gatcaaagga gtgaggttgc      3480
taaagaacat cctttttccct ctcattctac ccttttcctc tccccgattc cttgtagagc      3540
tgctgcaatt cttagagggg cagttctacc tcctctgtcc ctcggcagaa agacgtttcc      3600
acacctctta ggggatgcgc attaaacttc ttttgccccc ttcttgtccc ctttgagggg      3660
cacttaagat ggagaaatca gttgtggttt cagtgaatca tggtcacctg tatttattgc      3720
taggagaagc ctgagggtgg ggggagatga tcatgtgtgc tcgggggttgg ctggaagccc     3780 tgggtggggg gttgggggag gactaatggg gagtcgggga atatttgtgg gtatttttttt     3840 tacttcctct tggttcccag ctgtgacacg ttttgatcaa aggagaaaca ataaagggat      3900
aacccataaa aaccataaat aaaaaaaaaa aaaaaaaaaa aaaaaaaaaa aa              3952

<210> SEQ ID NO 21
```

<211> LENGTH: 3887
<212> TYPE: DNA
<213> ORGANISM: Homo sapiens
<300> PUBLICATION INFORMATION:
<308> DATABASE ACCESSION NUMBER: NM_198334
<309> DATABASE ENTRY DATE: 2005-09-24
<313> RELEVANT RESIDUES IN SEQ ID NO: (1)..(3887)

<400> SEQUENCE: 21

| | | | | | |
|---|---|---|---|---|---|
| aggtttgggg | tcaaggagca | aactctgcac | aagatggcgg | cggtagcggc | agtggcggcg | 60 |
| cgtaggaggc | ggtcttgggc | gtctttggta | ctggcttttt | tagggggtctg | cctggggatt | 120 |
| accccttgctg | tggatagaag | caactttaag | acctgtgaag | agagttctttt | ctgcaagcga | 180 |
| cagagaagca | tacggccagg | cctctctcca | taccgagcct | tgctggactc | tctacagctt | 240 |
| ggtcctgatt | ccctcacggt | ccatctgatc | catgaggtca | ccaaggtgtt | gctggtgcta | 300 |
| gagcttcagg | ggcttcaaaa | gaacatgact | cggttcagga | ttgatgagct | ggagcctcgg | 360 |
| cgaccccgat | accgtgtacc | agatgttttg | gtggctgatc | caccaatagc | ccggcttttct | 420 |
| gtctctggtc | gtgatgagaa | cagtgtggag | ttaaccatgg | ctgagggacc | ctacaagatc | 480 |
| atcttgacag | cacggccatt | ccgccttgac | ctactagagg | accgaagtct | tttgcttagt | 540 |
| gtcaatgccc | gaggactctt | ggagtttgag | catcagaggg | cccctagggt | ctcgcaagga | 600 |
| tcaaaagacc | cagctgaggg | cgatgggggcc | cagcctgagg | aaacacccag | ggatggcgac | 660 |
| aagccagagg | agactcaggg | gaaggcagag | aaagatgagc | caggagcctg | ggaggagaca | 720 |
| ttcaaaactc | actctgacag | caagccgtat | ggccccatgt | ctgtgggttt | ggacttctct | 780 |
| ctgccaggca | tggagcatgt | ctatgggatc | cctgagcatg | cagacaacct | gaggctgaag | 840 |
| gtcactgagg | gtggggagcc | atatcgcctc | tacaatttgg | atgtgttcca | gtatgagctg | 900 |
| tacaacccaa | tggccttgta | tgggtctgtg | cctgtgctcc | tggcacacaa | ccctcatcgc | 960 |
| gacttgggca | tcttctggct | caatgctgca | gagacctggg | ttgatatatc | ttccaacact | 1020 |
| gccgggaaga | ccctgtttgg | gaagatgatg | gactacctgc | agggctctgg | ggagacccca | 1080 |
| cagacagatg | ttcgctggat | gtcagagact | ggcatcattg | acgtcttcct | gctgctgggg | 1140 |
| ccctccatct | ctgatgtttt | ccggcaatat | gctagtctca | caggaaccca | ggcgttgccc | 1200 |
| ccactcttct | ccctcggcta | ccaccagagc | cgttggaact | accgggacga | ggctgatgtg | 1260 |
| ctggaagtgg | atcagggctt | tgatgatcac | aacctgccct | gtgatgtcat | ctggctagac | 1320 |
| attgaacatg | ctgatggcaa | gcggtatttc | acctgggacc | ccagtcgctt | ccctcagccc | 1380 |
| cgcaccatgc | ttgagcgctt | ggcttctaag | aggcggaagc | tggtgccat | cgtagacccc | 1440 |
| cacatcaagg | tggactccgg | ctaccgagtt | cacgaggagc | tgcggaacct | ggggctgtat | 1500 |
| gttaaaaccc | gggatggctc | tgactatgag | ggctggtgct | ggccaggctc | agctggttac | 1560 |
| cctgacttca | ctaatcccac | gatgagggcc | tggtgggcta | acatgttcag | ctatgacaat | 1620 |
| tatgagggct | cagctcccaa | cctctttgtc | tggaatgaca | tgaacgaacc | atctgtgttc | 1680 |
| aatggtcctg | aggtcaccat | gctcaaggat | gcccagcatt | atggggggctg | ggagcaccgg | 1740 |
| gatgtgcata | acatctatgg | cctttatgtg | cacatggcga | ctgctgatgg | gctgagacag | 1800 |
| cgctctgggg | gcatggaacg | ccccctttgtc | ctggccaggg | ccttcttcgc | tggctcccag | 1860 |
| cgctttggag | ccgtgtggac | agggggacaac | actgccgagt | gggaccattt | gaagatctct | 1920 |
| attcctatgt | gtctcagctt | ggggctggtg | ggacttttcct | tctgtggggc | ggatgtgggt | 1980 |
| ggcttcttca | aaaacccaga | gccagagctg | cttgtgcgct | ggtaccagat | gggtgcttac | 2040 |
| cagccattct | tccgggcaca | tgcccacttg | gacactgggc | gacgagagcc | atggctgtta | 2100 |

-continued

```
ccatctcagc acaatgatat aatccgagat gccttgggcc agcgatattc tttgctgccc    2160
ttctggtaca ccctcttata tcaggcccat cgggaaggca ttcctgtcat gaggcccctg    2220
tgggtgcagt accctcagga tgtgactacc ttcaatatag atgatcagta cttgcttggg    2280
gatgcgttgc tggttcaccc tgtatcagac tctggagccc atggtgtcca ggtctatctg    2340
cctggccaag ggaggtgtg gtatgacatt caaagctacc agaagcatca tggtccccag     2400
accctgtacc tgcctgtaac tctaagcagt atccctgtgt tccagcgtgg agggacaatc    2460
gtgcctcgat ggatgcgagt gcggcggtct tcagaatgta tgaaggatga ccccatcact    2520
ctctttgttg cacttagccc tcagggtaca gctcaaggag agctctttct ggatgatggg    2580
cacacgttca actatcagac tcgccaagag ttcctgctgc gtcgattctc attctctggc    2640
aacacccttg tctccagctc agcagaccct gaaggacact tgagacacc aatctggatt     2700 gagcgggtgg tgataatagg ggctggaaag ccagcagctg tggtactcca gacaaaagga    2760
tctccagaaa gccgcctgtc cttccagcat gaccctgaga cctctgtgtt ggtcctgcgc    2820
aagcctggca tcaatgtggc atctgattgg agtattcacc tgcgataacc caagggatgt    2880
tctgggttag ggggagggaa ggggagcatt agtgctgaga gatattcttt cttctgcctt    2940
ggagttcggc cctccccaga cttcacttat gctagtctaa gacccagatt ctgccaacat    3000
ttgggcagga tgagagggct gaccctgggc tccaaattcc tcttgtgatc tcctcacctc    3060
tcccactcca ttgataccaa ctctttccct tcattccccc aacatcctgt tgctctaact    3120
ggagcacatt cacttacgaa caccaggaaa ccacagggcc cttgtcgccc cttctctttc    3180
ccttatttag gagccctgaa ctcccccaga gtctatccat tcatgcctct tgtatgttga    3240
tgccacttct tggaagaaga tgagggcaat gagttagggc tccttttccc cttccctccc    3300
accagattgc tctcccacct ttcatttctt cctccaggct ttactcccct ttttatgccc    3360
caccgataca ctgggaccac cccttacccc ggacaggatg aatggatcaa aggagtgagg    3420
ttgctaaaga acatcctttt ccctctcatt ctaccctttt cctctccccg attccttgta    3480
gagctgctgc aattcttaga ggggcagttc tacctcctct gtccctcggc agaaagacgt    3540
ttccacacct cttagggat gcgcattaaa cttcttttgc ccccttcttg tcccctttga     3600
ggggcactta agatggagaa atcagttgtg gtttcagtga atcatggtca cctgtattta    3660
ttgctaggag aagcctgagg gtgggggag atgatcatgt gtgctcgggg ttggctggaa     3720
gccctgggtg gggggttggg ggaggactaa tggggagtcg gggaatattt gtgggtattt    3780
tttttacttc ctcttggttc ccagctgtga cacgttttga tcaaggagaa acaataaag     3840 ggataaacca taaataaaaa aaaaaaaaa aaaaaaaaa aaaaaa                     3887
```

<210> SEQ ID NO 22
<211> LENGTH: 3953
<212> TYPE: DNA
<213> ORGANISM: Homo sapiens
<300> PUBLICATION INFORMATION:
<308> DATABASE ACCESSION NUMBER: NM_198335
<309> DATABASE ENTRY DATE: 2005-09-24
<313> RELEVANT RESIDUES IN SEQ ID NO: (1)..(3953)

<400> SEQUENCE: 22

```
aggtttgggg tcaaggagca aactctgcac aagatggcgg cggtagcggc agtggcggcg      60
cgtaggaggc ggtcttgggc gtcttttggta ctggcttttt tagggtctg cctggggatt     120 acccttgctg tggatagaag caactttaag acctgtgaag agagttcttt ctgcaagcga    180
```

| | |
|---|---|
| cagagaagca tacggccagg cctctctcca taccgagcct tgctggactc tctacagctt | 240 |
| ggtcctgatt ccctcacggt ccatctgatc catgaggtca ccaaggtgtt gctggtgcta | 300 |
| gagcttcagg ggcttcaaaa gaacatgact cggttcagga ttgatgagct ggagcctcgg | 360 |
| cgaccccgat accgtgtacc agatgttttg gtggctgatc caccaatagc ccggctttct | 420 |
| gtctctggtc gtgatgagaa cagtgtggag ttaaccatgg ctgagggacc ctacaagatc | 480 |
| atcttgacag cacggccatt ccgccttgac ctactagagg accgaagtct tttgcttagt | 540 |
| gtcaatgccc gaggactctt ggagtttgag catcagaggg cccctagggt ctctttctcg | 600 |
| gataaggtta atctcacgct tggtagcata tgggataaga tcaagaacct tttctctagg | 660 |
| caaggatcaa aagacccagc tgagggcgat ggggcccagc ctgaggaaac acccagggat | 720 |
| ggcgacaagc cagaggagac tcaggggaag gcagagaaag atgagccagg agcctgggag | 780 |
| gagacattca aaactcactc tgacagcaag ccgtatggcc ccatgtctgt gggtttggac | 840 |
| ttctctctgc caggcatgga gcatgtctat gggatccctg agcatgcaga caacctgagg | 900 |
| ctgaaggtca ctgagggtgg ggagccatat cgcctctaca atttggatgt gttccagtat | 960 |
| gagctgtaca acccaatggc cttgtatggg tctgtgcctg tgctcctggc acacaaccct | 1020 |
| catcgcgact tgggcatctt ctggctcaat gctgcagaga cctgggttga tatatcttcc | 1080 |
| aacactgccg ggaagaccct gtttgggaag atgatggact acctgcaggg ctctggggag | 1140 |
| accccacaga cagatgttcg ctggatgtca gagactggca tcattgacgt cttcctgctg | 1200 |
| ctggggccct ccatctctga tgttttccgg caatatgcta gtctcacagg aacccaggcg | 1260 |
| ttgccccac tcttctccct cggctaccac cagagccgtt ggaactaccg ggacgaggct | 1320 |
| gatgtgctgg aagtggatca gggctttgat gatcacaacc tgccctgtga tgtcatctgg | 1380 |
| ctagacattg aacatgctga tggcaagcgg tatttcacct gggaccccag tcgcttccct | 1440 |
| cagccccgca ccatgcttga gcgcttggct tctaagaggc ggaagctggt ggccatcgta | 1500 |
| gacccccaca tcaaggtgga ctccggctac cgagttcacg aggagctgcg gaacctgggg | 1560 |
| ctgtatgtta aaacccggga tggctctgac tatgagggct ggtgctggcc aggctcagct | 1620 |
| ggttaccctg acttcactaa tcccacgatg agggcctggt gggctaacat gttcagctat | 1680 |
| gacaattatg agggctcagc tcccaacctc tttgtctgga atgacatgaa cgaaccatct | 1740 |
| gtgttcaatg tcctgaggt caccatgctc aaggatgccc agcattatgg gggctgggag | 1800 |
| caccgggatg tgcataacat ctatggcctt tatgtgcaca tggcgactgc tgatgggctg | 1860 |
| agacagcgct ctgggggcat ggaacgcccc tttgtcctgg ccagggcctt cttcgctggc | 1920 |
| tcccagcgct ttggagccgt gtggacaggg gacaacactg ccgagtggga ccatttgaag | 1980 |
| atctctattc ctatgtgtct cagcttgggg ctggtgggac tttccttctg tggggcggat | 2040 |
| gtgggtggct tcttcaaaaa cccagagcca gagctgcttg tgcgctggta ccagatgggt | 2100 |
| gcttaccagc cattcttccg ggcacatgcc cacttggaca ctgggcgacg agagccatgg | 2160 |
| ctgttaccat ctcagcacaa tgatataatc cgagatgcct gggccagcg atattctttg | 2220 |
| ctgcccttct ggtacaccct cttatatcag gcccatcggg aaggcattcc tgtcatgagg | 2280 |
| gtgcagtacc ctcaggatgt gactaccttc aatatagatg atcagtactt gcttggggat | 2340 |
| gcgttgctgg ttcaccctgt atcagactct ggagcccatg gtgtccaggt ctatctgcct | 2400 |
| ggccaagggg aggtgtggta tgacattcaa agctaccaga agcatcatgg tcccagacc | 2460 |
| ctgtacctgc tgtaactct aagcagtatc cctgtgttcc agcgtggagg gacaatcgtg | 2520 |
| cctcgatgga tgcgagtgcg gcggtcttca gaatgtatga aggatgaccc catcactctc | 2580 |

-continued

```
tttgttgcac ttagccctca gggtacagct caaggagagc tctttctgga tgatgggcac    2640
acgttcaact atcagactcg ccaagagttc ctgctgcgtc gattctcatt ctctggcaac    2700
acccttgtct ccagctcagc agaccctgaa ggacactttg agacaccaat ctggattgag    2760
cgggtggtga taatagggggc tggaaagcca gcagctgtgg tactccagac aaaaggatct    2820
ccagaaagcc gcctgtcctt ccagcatgac cctgagacct ctgtgttggt cctgcgcaag    2880
cctggcatca atgtggcatc tgattggagt attcacctgc gataacccaa gggatgttct    2940
gggttagggg gagggaaggg gagcattagt gctgagagat attctttctt ctgccttgga    3000
gttcggccct ccccagactt cacttatgct agtctaagac ccagattctg ccaacatttg    3060
ggcaggatga gagggctgac cctgggctcc aaattcctct tgtgatctcc tcacctctcc    3120
cactccattg ataccaactc tttcccttca ttcccccaac atcctgttgc tctaactgga    3180
gcacattcac ttacgaacac caggaaacca cagggccctt gtcgccccct ctctttccct    3240
tatttaggag ccctgaactc ccccagagtc tatccattca tgcctcttgt atgttgatgc    3300
cacttcttgg aagaagatga gggcaatgag ttagggctcc ttttcccctt ccctcccacc    3360
agattgctct cccacctttc atttcttcct ccaggcttta ctccccttttt tatgccccac    3420 cgatacactg ggaccacccc ttaccccgga caggatgaat ggatcaaagg agtgaggttg    3480
ctaaagaaca tccttttccc tctcattcta ccctttttcct ctcccccgatt ccttgtagag    3540 ctgctgcaat tcttagaggg gcagttctac ctcctctgtc cctcggcaga agacgtttc    3600 cacacctctt aggggatgcg cattaaactt cttttgcccc cttcttgtcc cctttgaggg    3660
gcacttaaga tggagaaatc agttgtggtt tcagtgaatc atggtcacct gtatttattg    3720
ctaggagaag cctgagggtg gggggagatg atcatgtgtg ctcggggttg gctggaagcc    3780
ctgggtgggg ggttggggga ggactaatgg ggagtcgggg aatatttgtg ggtattttt    3840 ttacttcctc ttggttccca gctgtgcacc gttttgatca aaggagaaac aataaaggga    3900
taacccataa aaaccataaa taaaaaaaaaa aaaaaaaaa aaaaaaaaa aaa    3953
```

<210> SEQ ID NO 23
<211> LENGTH: 755
<212> TYPE: PRT
<213> ORGANISM: Homo sapiens
<300> PUBLICATION INFORMATION:
<308> DATABASE ACCESSION NUMBER: NP_055425
<309> DATABASE ENTRY DATE: 2005-09-24
<313> RELEVANT RESIDUES IN SEQ ID NO: (1)..(755)

<400> SEQUENCE: 23

```
Met Ala Ala Val Ala Ala Val Ala Ala Arg Arg Arg Ser Trp Ala
1               5                   10                  15

Ser Leu Val Leu Ala Phe Leu Gly Val Cys Leu Gly Ile Thr Leu Ala
                20                  25                  30

Val Asp Arg Ser Asn Phe Lys Thr Cys Glu Glu Ser Ser Phe Cys Lys
            35                  40                  45

Arg Gln Arg Ser Ile Arg Pro Gly Leu Ser Pro Tyr Arg Ala Leu Leu
        50                  55                  60

Asp Ser Leu Gln Leu Gly Pro Asp Ser Leu Thr Val His Leu Ile His
65                  70                  75                  80

Glu Val Thr Lys Val Leu Leu Val Leu Glu Leu Gln Gly Leu Gln Lys
                85                  90                  95

Asn Met Thr Arg Phe Arg Ile Asp Glu Leu Glu Pro Arg Pro Arg
            100                 105                 110
```

```
Tyr Arg Val Pro Asp Val Leu Val Ala Asp Pro Pro Ile Ala Arg Leu
            115                 120                 125

Ser Val Ser Gly Arg Asp Glu Asn Ser Val Glu Leu Thr Met Ala Glu
130                 135                 140

Gly Pro Tyr Lys Ile Ile Leu Thr Ala Arg Pro Phe Arg Leu Asp Leu
145                 150                 155                 160

Leu Glu Asp Arg Ser Leu Leu Ser Val Asn Ala Arg Gly Leu Leu
            165                 170                 175

Glu Phe Glu His Gln Arg Ala Pro Arg Val Ser Phe Ser Asp Lys Val
            180                 185                 190

Asn Leu Thr Leu Gly Ser Ile Trp Asp Lys Ile Lys Asn Leu Phe Ser
            195                 200                 205

Arg Gln Gly Ser Lys Asp Pro Ala Glu Gly Asp Gly Ala Gln Pro Glu
            210                 215                 220

Glu Thr Pro Arg Asp Gly Asp Lys Pro Glu Glu Thr Gln Gly Lys Ala
225                 230                 235                 240

Glu Lys Asp Glu Pro Gly Ala Trp Glu Glu Thr Phe Lys Thr His Ser
                245                 250                 255

Asp Ser Lys Pro Tyr Gly Pro Met Ser Val Gly Leu Asp Phe Ser Leu
            260                 265                 270

Pro Gly Met Glu His Val Tyr Gly Ile Pro Glu His Ala Asp Asn Leu
            275                 280                 285

Arg Leu Lys Val Thr Glu Gly Glu Pro Tyr Arg Leu Tyr Asn Leu
            290                 295                 300

Asp Val Phe Gln Tyr Glu Leu Tyr Asn Pro Met Ala Leu Tyr Gly Ser
305                 310                 315                 320

Val Pro Val Leu Leu Ala His Asn Pro His Arg Asp Leu Gly Ile Phe
                325                 330                 335

Trp Leu Asn Ala Ala Glu Thr Trp Val Asp Ile Ser Ser Asn Thr Ala
            340                 345                 350

Gly Lys Thr Leu Phe Gly Lys Met Met Asp Tyr Leu Gln Gly Ser Gly
            355                 360                 365

Glu Thr Pro Gln Thr Asp Val Arg Trp Met Ser Glu Thr Gly Ile Ile
            370                 375                 380

Asp Val Phe Leu Leu Leu Gly Pro Ser Ile Ser Asp Val Phe Arg Gln
385                 390                 395                 400

Tyr Ala Ser Leu Thr Gly Thr Gln Ala Leu Pro Pro Leu Phe Ser Leu
            405                 410                 415

Gly Tyr His Gln Ser Arg Trp Asn Tyr Arg Asp Glu Ala Asp Val Leu
            420                 425                 430

Glu Val Asp Gln Gly Phe Asp Asp His Asn Leu Pro Cys Asp Val Ile
            435                 440                 445

Trp Leu Asp Ile Glu His Ala Asp Gly Lys Arg Tyr Phe Thr Trp Asp
450                 455                 460

Pro Ser Arg Phe Pro Gln Pro Arg Thr Met Leu Glu Arg Leu Ala Ser
465                 470                 475                 480

Lys Arg Arg Lys Leu Val Ala Ile Val Asp Pro His Ile Lys Val Asp
                485                 490                 495

Ser Gly Tyr Arg Val His Glu Glu Leu Arg Asn Leu Gly Leu Tyr Val
            500                 505                 510

Lys Thr Arg Asp Gly Ser Asp Tyr Glu Gly Trp Cys Trp Pro Gly Ser
            515                 520                 525
```

```
Ala Gly Tyr Pro Asp Phe Thr Asn Pro Thr Met Arg Ala Trp Trp Ala
        530                 535                 540

Asn Met Phe Ser Tyr Asp Asn Tyr Glu Gly Ser Ala Pro Asn Leu Phe
545                 550                 555                 560

Val Trp Asn Asp Met Asn Glu Pro Ser Val Phe Asn Gly Pro Glu Val
                565                 570                 575

Thr Met Leu Lys Asp Ala Gln His Tyr Gly Gly Trp Glu His Arg Asp
            580                 585                 590

Val His Asn Ile Tyr Gly Leu Tyr Val His Met Ala Thr Ala Asp Gly
        595                 600                 605

Leu Arg Gln Arg Ser Gly Gly Met Glu Arg Pro Phe Val Leu Ala Arg
610                 615                 620

Ala Phe Phe Ala Gly Ser Gln Arg Phe Gly Ala Val Trp Thr Gly Asp
625                 630                 635                 640

Asn Thr Ala Glu Trp Asp His Leu Lys Ile Ser Ile Pro Met Cys Leu
                645                 650                 655

Ser Leu Gly Leu Val Gly Leu Ser Phe Cys Gly Ala Asp Val Gly Gly
                660                 665                 670

Phe Phe Lys Asn Pro Glu Pro Glu Leu Leu Val Arg Trp Tyr Gln Met
        675                 680                 685

Gly Ala Tyr Gln Pro Phe Phe Arg Ala His Ala His Leu Asp Thr Gly
690                 695                 700

Arg Arg Glu Pro Trp Leu Leu Pro Ser Gln His Asn Asp Ile Ile Arg
705                 710                 715                 720

Asp Ala Leu Gly Gln Arg Tyr Ser Leu Leu Pro Phe Trp Tyr Thr Leu
                725                 730                 735

Leu Tyr Gln Ala His Arg Glu Gly Ile Pro Val Met Arg Cys Ser Thr
            740                 745                 750

Leu Arg Met
        755

<210> SEQ ID NO 24
<211> LENGTH: 944
<212> TYPE: PRT
<213> ORGANISM: Homo sapiens
<300> PUBLICATION INFORMATION:
<308> DATABASE ACCESSION NUMBER: NP_938148
<309> DATABASE ENTRY DATE: 2005-09-24
<313> RELEVANT RESIDUES IN SEQ ID NO: (1)..(944)

<400> SEQUENCE: 24

Met Ala Ala Val Ala Val Ala Ala Arg Arg Arg Ser Trp Ala
1               5                   10                  15

Ser Leu Val Leu Ala Phe Leu Gly Val Cys Leu Gly Ile Thr Leu Ala
                20                  25                  30

Val Asp Arg Ser Asn Phe Lys Thr Cys Glu Glu Ser Phe Cys Lys
            35                  40                  45

Arg Gln Arg Ser Ile Arg Pro Gly Leu Ser Pro Tyr Arg Ala Leu Leu
        50                  55                  60

Asp Ser Leu Gln Leu Gly Pro Asp Ser Leu Thr Val His Leu Ile His
65                  70                  75                  80

Glu Val Thr Lys Val Leu Leu Val Leu Glu Leu Gln Gly Leu Gln Lys
                85                  90                  95

Asn Met Thr Arg Phe Arg Ile Asp Glu Leu Glu Pro Arg Arg Pro Arg
            100                 105                 110

Tyr Arg Val Pro Asp Val Leu Val Ala Asp Pro Pro Ile Ala Arg Leu
```

```
            115                 120                 125
Ser Val Ser Gly Arg Asp Glu Asn Ser Val Glu Leu Thr Met Ala Glu
130                 135                 140
Gly Pro Tyr Lys Ile Ile Leu Thr Ala Arg Pro Phe Arg Leu Asp Leu
145                 150                 155                 160
Leu Glu Asp Arg Ser Leu Leu Leu Ser Val Asn Ala Arg Gly Leu Leu
                165                 170                 175
Glu Phe Glu His Gln Arg Ala Pro Arg Val Ser Gln Gly Ser Lys Asp
                180                 185                 190
Pro Ala Glu Gly Asp Gly Ala Gln Pro Glu Glu Thr Pro Arg Asp Gly
                195                 200                 205
Asp Lys Pro Glu Glu Thr Gln Gly Lys Ala Glu Lys Asp Glu Pro Gly
210                 215                 220
Ala Trp Glu Glu Thr Phe Lys Thr His Ser Asp Ser Lys Pro Tyr Gly
225                 230                 235                 240
Pro Met Ser Val Gly Leu Asp Phe Ser Leu Pro Gly Met Glu His Val
                245                 250                 255
Tyr Gly Ile Pro Glu His Ala Asp Asn Leu Arg Leu Lys Val Thr Glu
                260                 265                 270
Gly Gly Glu Pro Tyr Arg Leu Tyr Asn Leu Asp Val Phe Gln Tyr Glu
                275                 280                 285
Leu Tyr Asn Pro Met Ala Leu Tyr Gly Ser Val Pro Val Leu Leu Ala
                290                 295                 300
His Asn Pro His Arg Asp Leu Gly Ile Phe Trp Leu Asn Ala Ala Glu
305                 310                 315                 320
Thr Trp Val Asp Ile Ser Ser Asn Thr Ala Gly Lys Thr Leu Phe Gly
                325                 330                 335
Lys Met Met Asp Tyr Leu Gln Gly Ser Gly Glu Thr Pro Gln Thr Asp
                340                 345                 350
Val Arg Trp Met Ser Glu Thr Gly Ile Ile Asp Val Phe Leu Leu Leu
                355                 360                 365
Gly Pro Ser Ile Ser Asp Val Phe Arg Gln Tyr Ala Ser Leu Thr Gly
                370                 375                 380
Thr Gln Ala Leu Pro Pro Leu Phe Ser Leu Gly Tyr His Gln Ser Arg
385                 390                 395                 400
Trp Asn Tyr Arg Asp Glu Ala Asp Val Leu Glu Val Asp Gln Gly Phe
                405                 410                 415
Asp Asp His Asn Leu Pro Cys Asp Val Ile Trp Leu Asp Ile Glu His
                420                 425                 430
Ala Asp Gly Lys Arg Tyr Phe Thr Trp Asp Pro Ser Arg Phe Pro Gln
                435                 440                 445
Pro Arg Thr Met Leu Glu Arg Leu Ala Ser Lys Arg Arg Lys Leu Val
                450                 455                 460
Ala Ile Val Asp Pro His Ile Lys Val Asp Ser Gly Tyr Arg Val His
465                 470                 475                 480
Glu Glu Leu Arg Asn Leu Gly Leu Tyr Val Lys Thr Arg Asp Gly Ser
                485                 490                 495
Asp Tyr Glu Gly Trp Cys Trp Pro Gly Ser Ala Gly Tyr Pro Asp Phe
                500                 505                 510
Thr Asn Pro Thr Met Arg Ala Trp Trp Ala Asn Met Phe Ser Tyr Asp
                515                 520                 525
Asn Tyr Glu Gly Ser Ala Pro Asn Leu Phe Val Trp Asn Asp Met Asn
                530                 535                 540
```

Glu Pro Ser Val Phe Asn Gly Pro Glu Val Thr Met Leu Lys Asp Ala
545                 550                 555                 560

Gln His Tyr Gly Gly Trp Glu His Arg Asp Val His Asn Ile Tyr Gly
            565                 570                 575

Leu Tyr Val His Met Ala Thr Ala Asp Gly Leu Arg Gln Arg Ser Gly
            580                 585                 590

Gly Met Glu Arg Pro Phe Val Leu Ala Arg Ala Phe Phe Ala Gly Ser
        595                 600                 605

Gln Arg Phe Gly Ala Val Trp Thr Gly Asp Asn Thr Ala Glu Trp Asp
    610                 615                 620

His Leu Lys Ile Ser Ile Pro Met Cys Leu Ser Leu Gly Leu Val Gly
625                 630                 635                 640

Leu Ser Phe Cys Gly Ala Asp Val Gly Gly Phe Phe Lys Asn Pro Glu
            645                 650                 655

Pro Glu Leu Leu Val Arg Trp Tyr Gln Met Gly Ala Tyr Gln Pro Phe
            660                 665                 670

Phe Arg Ala His Ala His Leu Asp Thr Gly Arg Arg Glu Pro Trp Leu
    675                 680                 685

Leu Pro Ser Gln His Asn Asp Ile Ile Arg Asp Ala Leu Gly Gln Arg
690                 695                 700

Tyr Ser Leu Leu Pro Phe Trp Tyr Thr Leu Leu Tyr Gln Ala His Arg
705                 710                 715                 720

Glu Gly Ile Pro Val Met Arg Pro Leu Trp Val Gln Tyr Pro Gln Asp
            725                 730                 735

Val Thr Thr Phe Asn Ile Asp Asp Gln Tyr Leu Leu Gly Asp Ala Leu
            740                 745                 750

Leu Val His Pro Val Ser Asp Ser Gly Ala His Gly Val Gln Val Tyr
            755                 760                 765

Leu Pro Gly Gln Gly Glu Val Trp Tyr Asp Ile Gln Ser Tyr Gln Lys
770                 775                 780

His His Gly Pro Gln Thr Leu Tyr Leu Pro Val Thr Leu Ser Ser Ile
785                 790                 795                 800

Pro Val Phe Gln Arg Gly Gly Thr Ile Val Pro Arg Trp Met Arg Val
            805                 810                 815

Arg Arg Ser Ser Glu Cys Met Lys Asp Asp Pro Ile Thr Leu Phe Val
            820                 825                 830

Ala Leu Ser Pro Gln Gly Thr Ala Gln Gly Glu Leu Phe Leu Asp Asp
            835                 840                 845

Gly His Thr Phe Asn Tyr Gln Thr Arg Gln Glu Phe Leu Leu Arg Arg
        850                 855                 860

Phe Ser Phe Ser Gly Asn Thr Leu Val Ser Ser Ala Asp Pro Glu
865                 870                 875                 880

Gly His Phe Glu Thr Pro Ile Trp Ile Glu Arg Val Val Ile Ile Gly
            885                 890                 895

Ala Gly Lys Pro Ala Ala Val Val Leu Gln Thr Lys Gly Ser Pro Glu
        900                 905                 910

Ser Arg Leu Ser Phe Gln His Asp Pro Glu Thr Ser Val Leu Val Leu
        915                 920                 925

Arg Lys Pro Gly Ile Asn Val Ala Ser Asp Trp Ser Ile His Leu Arg
        930                 935                 940

<210> SEQ ID NO 25
<211> LENGTH: 963

-continued

<212> TYPE: PRT
<213> ORGANISM: Homo sapiens
<300> PUBLICATION INFORMATION:
<308> DATABASE ACCESSION NUMBER: NP_938149
<309> DATABASE ENTRY DATE: 2005-09-24
<313> RELEVANT RESIDUES IN SEQ ID NO: (1)..(963)

<400> SEQUENCE: 25

Met Ala Ala Val Ala Val Ala Ala Arg Arg Arg Ser Trp Ala
1               5                   10                  15

Ser Leu Val Leu Ala Phe Leu Gly Val Cys Leu Gly Ile Thr Leu Ala
            20                  25                  30

Val Asp Arg Ser Asn Phe Lys Thr Cys Glu Glu Ser Ser Phe Cys Lys
        35                  40                  45

Arg Gln Arg Ser Ile Arg Pro Gly Leu Ser Pro Tyr Arg Ala Leu Leu
    50                  55                  60

Asp Ser Leu Gln Leu Gly Pro Asp Ser Leu Thr Val His Leu Ile His
65                  70                  75                  80

Glu Val Thr Lys Val Leu Leu Val Leu Glu Leu Gln Gly Leu Gln Lys
                85                  90                  95

Asn Met Thr Arg Phe Arg Ile Asp Glu Leu Glu Pro Arg Arg Pro Arg
            100                 105                 110

Tyr Arg Val Pro Asp Val Leu Val Ala Asp Pro Pro Ile Ala Arg Leu
        115                 120                 125

Ser Val Ser Gly Arg Asp Glu Asn Ser Val Glu Leu Thr Met Ala Glu
    130                 135                 140

Gly Pro Tyr Lys Ile Ile Leu Thr Ala Arg Pro Phe Arg Leu Asp Leu
145                 150                 155                 160

Leu Glu Asp Arg Ser Leu Leu Leu Ser Val Asn Ala Arg Gly Leu Leu
                165                 170                 175

Glu Phe Glu His Gln Arg Ala Pro Arg Val Ser Phe Ser Asp Lys Val
            180                 185                 190

Asn Leu Thr Leu Gly Ser Ile Trp Asp Lys Ile Lys Asn Leu Phe Ser
        195                 200                 205

Arg Gln Gly Ser Lys Asp Pro Ala Glu Gly Asp Gly Ala Gln Pro Glu
    210                 215                 220

Glu Thr Pro Arg Asp Gly Asp Lys Pro Glu Glu Thr Gln Gly Lys Ala
225                 230                 235                 240

Glu Lys Asp Glu Pro Gly Ala Trp Glu Glu Thr Phe Lys Thr His Ser
                245                 250                 255

Asp Ser Lys Pro Tyr Gly Pro Met Ser Val Gly Leu Asp Phe Ser Leu
            260                 265                 270

Pro Gly Met Glu His Val Tyr Gly Ile Pro Glu His Ala Asp Asn Leu
        275                 280                 285

Arg Leu Lys Val Thr Glu Gly Gly Glu Pro Tyr Arg Leu Tyr Asn Leu
    290                 295                 300

Asp Val Phe Gln Tyr Glu Leu Tyr Asn Pro Met Ala Leu Tyr Gly Ser
305                 310                 315                 320

Val Pro Val Leu Leu Ala His Asn Pro His Arg Asp Leu Gly Ile Phe
                325                 330                 335

Trp Leu Asn Ala Ala Glu Thr Trp Val Asp Ile Ser Ser Asn Thr Ala
            340                 345                 350

Gly Lys Thr Leu Phe Gly Lys Met Met Asp Tyr Leu Gln Gly Ser Gly
        355                 360                 365

Glu Thr Pro Gln Thr Asp Val Arg Trp Met Ser Glu Thr Gly Ile Ile

```
                370                 375                 380
Asp Val Phe Leu Leu Leu Gly Pro Ser Ile Ser Asp Val Phe Arg Gln
385                 390                 395                 400

Tyr Ala Ser Leu Thr Gly Thr Gln Ala Leu Pro Pro Leu Phe Ser Leu
                405                 410                 415

Gly Tyr His Gln Ser Arg Trp Asn Tyr Arg Asp Glu Ala Asp Val Leu
                420                 425                 430

Glu Val Asp Gln Gly Phe Asp Asp His Asn Leu Pro Cys Asp Val Ile
                435                 440                 445

Trp Leu Asp Ile Glu His Ala Asp Gly Lys Arg Tyr Phe Thr Trp Asp
                450                 455                 460

Pro Ser Arg Phe Pro Gln Pro Arg Thr Met Leu Glu Arg Leu Ala Ser
465                 470                 475                 480

Lys Arg Arg Lys Leu Val Ala Ile Val Asp Pro His Ile Lys Val Asp
                485                 490                 495

Ser Gly Tyr Arg Val His Glu Glu Leu Arg Asn Leu Gly Leu Tyr Val
                500                 505                 510

Lys Thr Arg Asp Gly Ser Asp Tyr Glu Gly Trp Cys Trp Pro Gly Ser
                515                 520                 525

Ala Gly Tyr Pro Asp Phe Thr Asn Pro Thr Met Arg Ala Trp Trp Ala
                530                 535                 540

Asn Met Phe Ser Tyr Asp Asn Tyr Glu Gly Ser Ala Pro Asn Leu Phe
545                 550                 555                 560

Val Trp Asn Asp Met Asn Glu Pro Ser Val Phe Asn Gly Pro Glu Val
                565                 570                 575

Thr Met Leu Lys Asp Ala Gln His Tyr Gly Gly Trp Glu His Arg Asp
                580                 585                 590

Val His Asn Ile Tyr Gly Leu Tyr Val His Met Ala Thr Ala Asp Gly
                595                 600                 605

Leu Arg Gln Arg Ser Gly Gly Met Glu Arg Pro Phe Val Leu Ala Arg
                610                 615                 620

Ala Phe Phe Ala Gly Ser Gln Arg Phe Gly Ala Val Trp Thr Gly Asp
625                 630                 635                 640

Asn Thr Ala Glu Trp Asp His Leu Lys Ile Ser Ile Pro Met Cys Leu
                645                 650                 655

Ser Leu Gly Leu Val Gly Leu Ser Phe Cys Gly Ala Asp Val Gly Gly
                660                 665                 670

Phe Phe Lys Asn Pro Glu Pro Glu Leu Leu Val Arg Trp Tyr Gln Met
                675                 680                 685

Gly Ala Tyr Gln Pro Phe Phe Arg Ala His Ala His Leu Asp Thr Gly
                690                 695                 700

Arg Arg Glu Pro Trp Leu Leu Pro Ser Gln His Asn Asp Ile Ile Arg
705                 710                 715                 720

Asp Ala Leu Gly Gln Arg Tyr Ser Leu Leu Pro Phe Trp Tyr Thr Leu
                725                 730                 735

Leu Tyr Gln Ala His Arg Glu Gly Ile Pro Val Met Arg Val Gln Tyr
                740                 745                 750

Pro Gln Asp Val Thr Thr Phe Asn Ile Asp Asp Gln Tyr Leu Leu Gly
                755                 760                 765

Asp Ala Leu Leu Val His Pro Val Ser Asp Ser Gly Ala His Gly Val
                770                 775                 780

Gln Val Tyr Leu Pro Gly Gln Gly Glu Val Trp Tyr Asp Ile Gln Ser
785                 790                 795                 800
```

-continued

```
Tyr Gln Lys His His Gly Pro Gln Thr Leu Tyr Leu Pro Val Thr Leu
            805                 810                 815

Ser Ser Ile Pro Val Phe Gln Arg Gly Thr Ile Val Pro Arg Trp
        820                 825                 830

Met Arg Val Arg Arg Ser Ser Glu Cys Met Lys Asp Asp Pro Ile Thr
            835                 840                 845

Leu Phe Val Ala Leu Ser Pro Gln Gly Thr Ala Gln Gly Glu Leu Phe
        850                 855                 860

Leu Asp Asp Gly His Thr Phe Asn Tyr Gln Thr Arg Gln Glu Phe Leu
865                 870                 875                 880

Leu Arg Arg Phe Ser Phe Ser Gly Asn Thr Leu Val Ser Ser Ala
            885                 890                 895

Asp Pro Glu Gly His Phe Glu Thr Pro Ile Trp Ile Glu Arg Val Val
        900                 905                 910

Ile Ile Gly Ala Gly Lys Pro Ala Ala Val Val Leu Gln Thr Lys Gly
        915                 920                 925

Ser Pro Glu Ser Arg Leu Ser Phe Gln His Asp Pro Glu Thr Ser Val
        930                 935                 940

Leu Val Leu Arg Lys Pro Gly Ile Asn Val Ala Ser Asp Trp Ser Ile
945                 950                 955                 960

His Leu Arg
```

<210> SEQ ID NO 26
<211> LENGTH: 4139
<212> TYPE: DNA
<213> ORGANISM: Homo sapiens
<300> PUBLICATION INFORMATION:
<308> DATABASE ACCESSION NUMBER: NM_005907
<309> DATABASE ENTRY DATE: 2005-09-23
<313> RELEVANT RESIDUES IN SEQ ID NO: (1)..(4139)

<400> SEQUENCE: 26

```
agtgctcgcg gggccgcggc ggagtgtacc gtgctgctct actcgctgcc attcgcccgc    60
aggtcggcgc gctcgcccac ctgagccgcg ccggggctgc gggaccgtgg gacagcgcgc   120
tcagcccagc ctaggaaaga ggcagcagtc tcagcgcgga gatggggagc gggcgaagtt   180
gacgagtctc ccgcccacgc tgcgcccctc ctgcccagag gggctgcagc cagcggtctg   240
tcgcgcgtgc ctgtgtgccc gaggagccgc cccggggaga agaccggcg cggagttgtt    300
cccccaggga ggatccgcag cccagccgag ggggtcgggc ggcctggcta cgcaggaccc   360
agccccgcag ccgcggactc ccagcggcgg cgaagtttgg ctgctgagcg gcgcggcgcc   420
ggaccactgg acagcgggag cgatgcccgt ggggggcctg ttgccgctct tcagcagccc   480
cgcgggcggc gtcctgggcg gggggctcgg cggcggcgt gcaggaagg ggtcgggccc    540
cgccgccctc cgcctgacgg agaagttcgt gctgctgctg gtattcagcg ccttcatcac   600
gctctgcttc ggggcgatct tcttcctgcc agactcctcc aagctgctca gcgggtcct    660
gttccactcc agccccgcct tgcagccggc cgccgaccac aagcccgggc cggggcgcg    720
cgccgaggac gcggccgagg ggcgagcccg gcgccgcgag gaggggcac ccggggaccc    780
ggaggccgcc ctggaggaca acttggccag gatccgcgaa aaccacgagc gggctctcag   840
ggaagccaag gagaccctgc agaagctgcc cgaggagatc caaagagaca tcctactgga   900
gaagaagaag gtgcccagg accagctgcg tgacaaggcg ccgttcagag gcctgccccc   960
ggtggacttc gtgccccaa tcggggtgga gagccgggag cccgccgacg ccgccatccg  1020
```

```
cgagaaaagg gcaaagatca aagagatgat gaaacatgct tggaataatt ataaaggtta    1080
tgcctgggga ttaaatgaac tcaaacctat atcaaaagga ggccattcaa gcagtttgtt    1140
tggtaacatc aaaggagcaa ctatagtaga tgccctggat acactttta ttatggaaat     1200 gaaacatgaa tttgaagaag caaaatcatg ggttgaagaa aatttagatt ttaatgtgaa    1260
tgctgaaatt tctgtctttg aagtaaatat acgctttgtt ggtggactac tctcagccta    1320
ctatctgtct ggagaagaga tttttcgaaa gaaagcagtg gaactggggg taaaattgct    1380
acctgcattt catactccct ctggaatacc ttgggcattg ctgaatatga aaagtggtat    1440
tggaaggaac tggccctggg cctctggagg cagcagtatt ctggcagaat ttggaaccct    1500
gcatttggag tttatgcact tgagccactt atcaggaaac cccatctttg ctgaaaaggt    1560
aatgaatatt cgaacagtac tgaacaaact ggaaaaacca caaggccttt atcctaacta    1620
tctgaatccc agtagtggac agtggggtca acatcatgta tcagttggag gacttggaga    1680
cagcttctat gagtatttgc tgaaggcctg gttaatgtct gacaagacag atctggaagc    1740
taagaagatg tattttgatg ctgttcaggc tatcgagact catttgatcc gcaagtctag    1800
cagcggacta acttatatcg cagagtggaa agggggcctc ctggagcaca agatgggcca    1860
cctgacctgc ttcgcggggg gcatgttcgc actcgggggct gatgcagctc ccgaaggcat    1920
ggcccaacac taccttgaac tcggggctga aattgcccgt acttgtcatg aatcatataa    1980
tcgaacattt atgaaactgg gaccagaagc tttcagattt gatggtggtg ttgaagccat    2040
cgctacaaga caaaatgaaa aatactacat cttacggcca gaagttatgg agacttacat    2100
gtatatgtgg agactgactc atgatccaaa gtacaggaaa tgggcctggg aagccgtaga    2160
ggccttggaa aaccattgca gagtgaatgg aggctattca ggcctaaggg atgtttacct    2220
tcttcatgag agttatgatg atgtgcagca gagtttcttc ctggcagaga cattgaaata    2280
tttgtaccta atattttctg acgacgatct tcttccactg gagcattgga tcttcaatag    2340
cgaggcacat cttctcccta tcctcccctaa agataaaaag gaagttgaaa tcagagagga    2400
ataaaaagac attttatatt ttattctgct ccattccctt cactgtatac cttaataatt    2460
ccttttctgg taatcaggca catgatgaac tttgattagt aggtctgtga ttaagttctt    2520
aaattgtttt gcagtctttt atgtttatta tcataggtat aggtggacct aaattcctta    2580
tcatatcctt tattaattca gccagtgtat ccaccagttt tttgtttatg tttttaagta    2640
acctattatc tctggatttc atgaaggtgt aatatcgttt ttgttaaact gaatagaatt    2700
gtatagcgat gacctcttaa ttataatttg atttgactgc aaaactttt cctcctctaa     2760 gaggagatga tgtctgcttt aagctgtaat gttttgccat gttgcaaaaa gccataataa    2820
taagtataaa aaagcttttt cctttacaat ttcatgttaa tctggtttgt ctgtccacca    2880
gagacagatc ttctgtgaca gcctccttat gcaggtctat cattatttga tagaatgtct    2940
tctaaaatac ttcactcaca ttgtaattca aattagaaag tcattccaaa aggatcatgt    3000
catgttgacc tcatttcatc ggaactgcag tatattttg ttggttaatt atattagtgt     3060
tttctatttt gtaaatgtgt cctttaattt tactttaaat gccctgtgtc atttctggat    3120
tatatactag ttaatttctt ccattcccta ctacacagag aggtgagctt tcaaattttg    3180
cagagctctg ctatcactga attacattta tctgaagaaa atagtacaac ttaatggatt    3240
agcttttggg tttaactgaa tatatgaaga aattgggtct gtctaaagag agggtatttc    3300
atatggcttt tagttcactt gtttgtattt catcttgatt ttttttctttg gaaaataaag    3360 cattctatttt ggttcagatt tctcagattt gaaaaaggct ctatctcaga tgtagtaaat    3420
```

```
tatttcctt  cagtttgtga  aagcaggatt  tgactctgaa  agaagctttg  ccaattttac      3480
ttattcgtga  tcaatcaagg  aaaatctaat  aaatttagg  ccaaataaga  atatagcata      3540
tttagtatgg  ttatagtcaa  cacagagatc  acaacttaga  agaaatataa  agaaatggcc     3600 actcccatc   ccccacagtc  ctggagtaaa  tcaaaatcaa  tatatgattc  ttttaaacat    3660
taagtttgaa  ataggaatgg  ttttctcaag  aatagatttg  gtgtgatacc  ttgtgtttgc    3720
ttacattggc  ccactatata  tacatatata  tttatgtaga  tatacttcca  tgaaagggct    3780
aatacgatgc  atatactgaa  gggcaaggac  tttgaccatg  tcaattttca  gccgagaatg    3840
gtcagaaaga  tcagtacaac  cccatggatt  aggctgaaac  atatgaaatt  gctgcatttg    3900
tagtttaaaa  actgtcagca  gtttcatatg  gttccaccta  atattattga  agacaattat    3960
tttcttagct  atcaataggc  ttaatagttt  tagttatttt  agcttttgaa  agtgttttaa    4020
aagatttcct  ttatcggaca  ggaccatctt  tatgacctgc  tttctgtttt  tcaatatcat    4080
acattggtgt  atgtcaaaga  ataaattagt  aaaattagta  aaaaaaaaaa  aaaaaaaaa     4139
```

<210> SEQ ID NO 27
<211> LENGTH: 653
<212> TYPE: PRT
<213> ORGANISM: Homo sapiens
<300> PUBLICATION INFORMATION:
<308> DATABASE ACCESSION NUMBER: NP_005898
<309> DATABASE ENTRY DATE: 2005-09-23
<313> RELEVANT RESIDUES IN SEQ ID NO: (1)..(653)

<400> SEQUENCE: 27

```
Met Pro Val Gly Gly Leu Leu Pro Leu Phe Ser Ser Pro Ala Gly Gly
 1               5                  10                  15

Val Leu Gly Gly Gly Leu Gly Gly Gly Gly Arg Lys Gly Ser Gly
            20                  25                  30

Pro Ala Ala Leu Arg Leu Thr Glu Lys Phe Val Leu Leu Val Phe
        35                  40                  45

Ser Ala Phe Ile Thr Leu Cys Phe Gly Ala Ile Phe Phe Leu Pro Asp
50                  55                  60

Ser Ser Lys Leu Leu Ser Gly Val Leu Phe His Ser Ser Pro Ala Leu
65                  70                  75                  80

Gln Pro Ala Ala Asp His Lys Pro Gly Pro Gly Ala Arg Ala Glu Asp
                85                  90                  95

Ala Ala Glu Gly Arg Ala Arg Arg Glu Glu Gly Ala Pro Gly Asp
            100                 105                 110

Pro Glu Ala Ala Leu Glu Asp Asn Leu Ala Arg Ile Arg Glu Asn His
        115                 120                 125

Glu Arg Ala Leu Arg Glu Ala Lys Glu Thr Leu Gln Lys Leu Pro Glu
    130                 135                 140

Glu Ile Gln Arg Asp Ile Leu Leu Glu Lys Lys Val Ala Gln Asp
145                 150                 155                 160

Gln Leu Arg Asp Lys Ala Pro Phe Arg Gly Leu Pro Val Asp Phe
                165                 170                 175

Val Pro Pro Ile Gly Val Glu Ser Arg Glu Pro Ala Asp Ala Ala Ile
            180                 185                 190

Arg Glu Lys Arg Ala Lys Ile Lys Glu Met Met Lys His Ala Trp Asn
        195                 200                 205

Asn Tyr Lys Gly Tyr Ala Trp Gly Leu Asn Glu Leu Lys Pro Ile Ser
    210                 215                 220
```

```
Lys Gly Gly His Ser Ser Ser Leu Phe Gly Asn Ile Lys Gly Ala Thr
225                 230                 235                 240

Ile Val Asp Ala Leu Asp Thr Leu Phe Ile Met Glu Met Lys His Glu
            245                 250                 255

Phe Glu Glu Ala Lys Ser Trp Val Glu Glu Asn Leu Asp Phe Asn Val
            260                 265                 270

Asn Ala Glu Ile Ser Val Phe Glu Val Asn Ile Arg Phe Val Gly Gly
            275                 280                 285

Leu Leu Ser Ala Tyr Tyr Leu Ser Gly Glu Glu Ile Phe Arg Lys Lys
            290                 295                 300

Ala Val Glu Leu Gly Val Lys Leu Leu Pro Ala Phe His Thr Pro Ser
305                 310                 315                 320

Gly Ile Pro Trp Ala Leu Leu Asn Met Lys Ser Gly Ile Gly Arg Asn
            325                 330                 335

Trp Pro Trp Ala Ser Gly Gly Ser Ser Ile Leu Ala Glu Phe Gly Thr
            340                 345                 350

Leu His Leu Glu Phe Met His Leu Ser His Leu Ser Gly Asn Pro Ile
            355                 360                 365

Phe Ala Glu Lys Val Met Asn Ile Arg Thr Val Leu Asn Lys Leu Glu
            370                 375                 380

Lys Pro Gln Gly Leu Tyr Pro Asn Tyr Leu Asn Pro Ser Ser Gly Gln
385                 390                 395                 400

Trp Gly Gln His His Val Ser Val Gly Gly Leu Gly Asp Ser Phe Tyr
            405                 410                 415

Glu Tyr Leu Leu Lys Ala Trp Leu Met Ser Asp Lys Thr Asp Leu Glu
            420                 425                 430

Ala Lys Lys Met Tyr Phe Asp Ala Val Gln Ala Ile Glu Thr His Leu
            435                 440                 445

Ile Arg Lys Ser Ser Ser Gly Leu Thr Tyr Ile Ala Glu Trp Lys Gly
            450                 455                 460

Gly Leu Leu Glu His Lys Met Gly His Leu Thr Cys Phe Ala Gly Gly
465                 470                 475                 480

Met Phe Ala Leu Gly Ala Asp Ala Ala Pro Glu Gly Met Ala Gln His
            485                 490                 495

Tyr Leu Glu Leu Gly Ala Glu Ile Ala Arg Thr Cys His Glu Ser Tyr
            500                 505                 510

Asn Arg Thr Phe Met Lys Leu Gly Pro Glu Ala Phe Arg Phe Asp Gly
            515                 520                 525

Gly Val Glu Ala Ile Ala Thr Arg Gln Asn Glu Lys Tyr Tyr Ile Leu
            530                 535                 540

Arg Pro Glu Val Met Glu Thr Tyr Met Tyr Met Trp Arg Leu Thr His
545                 550                 555                 560

Asp Pro Lys Tyr Arg Lys Trp Ala Trp Glu Ala Val Glu Ala Leu Glu
            565                 570                 575

Asn His Cys Arg Val Asn Gly Gly Tyr Ser Gly Leu Arg Asp Val Tyr
            580                 585                 590

Leu Leu His Glu Ser Tyr Asp Asp Val Gln Gln Ser Phe Phe Leu Ala
            595                 600                 605

Glu Thr Leu Lys Tyr Leu Tyr Leu Ile Phe Ser Asp Asp Leu Leu
            610                 615                 620

Pro Leu Glu His Trp Ile Phe Asn Ser Glu Ala His Leu Leu Pro Ile
625                 630                 635                 640

Leu Pro Lys Asp Lys Lys Glu Val Glu Ile Arg Glu Glu
```

<210> SEQ ID NO 28
<211> LENGTH: 2937
<212> TYPE: DNA
<213> ORGANISM: Homo sapiens
<300> PUBLICATION INFORMATION:
<308> DATABASE ACCESSION NUMBER: NM_002406
<309> DATABASE ENTRY DATE: 2005-09-23
<313> RELEVANT RESIDUES IN SEQ ID NO: (1)..(2937)

<400> SEQUENCE: 28

```
gggttgcgcc agggagccgg aaagccgact cccgaagttg gggtcctggg aaaacttggg      60
tcctggggttg actgagaagc ggcggggaaa ggaggcgggc caggaggagg gggcctggcg    120
gacgccggcc gggggcggg gcgcggcggg gctgtcggtc acgcccctca gtccgccccg      180
ccccgccccg cctgccgggg aagggccacg ttgcccggcc cggccgtccg gccccggcgc    240
gccgcagaaa gggctggcga gtcgaaaggc gaggcggccg cggcagcgct tgggacgcgc    300
ctgggcaccg ggctcgctcc ctgcgccccg gagcaggcca agttcggggc caggacgtcg    360
ggaggacctg gtgcatggct gcctcctaat cccatagtcc agaggaggca tccctaggac    420
tgcgggcaag ggagccgggc aagcccaggg cagccttgaa ccgtcccctg gcctgccctc    480
cccggtgggg gccaggatgc tgaagaagca gtctgcaggg cttgtgctgt ggggcgctat    540
cctctttgtg gcctggaatg ccctgctgct cctcttcttc tggacgcgcc cagcacctgg    600
caggccaccc tcagtcagcg ctctcgatgg cgaccccgcc agcctcaccc gggaagtgat    660
tcgcctggcc caagacgccg aggtggagct ggagcggcag cgtgggctgc tgcagcagat    720
cggggatgcc ctgtcgagcc agcggggggag ggtgcccacc gcggccccctc ccgcccagcc    780
gcgtgtgcct gtgaccccg cgccggcggt gattcccatc ctggtcatcg cctgtgaccg    840
cagcactgtt cggcgctgcc tggacaagct gctgcattat cggccctcgg ctgagctctt    900
ccccatcatc gttagccagg actgcgggca cgaggagacg gcccaggcca tcgcctccta    960
cggcagcgcg gtcacgcaca tccggcagcc cgacctgagc agcattgcgg tgccgccgga   1020
ccaccgcaag ttccagggct actacaagat cgcgcgccac taccgctggg cgctgggcca   1080
ggtcttccgg cagtttcgct tccccgcggc cgtggtggtg gaggatgacc tggaggtggc   1140
cccggacttc ttcgagtact tcggggccac ctatccgctg ctgaaggccg acccctccct   1200
gtggtgcgtc tcggcctgga atgacaacgg caaggagcag atggtggacg ccagcaggcc   1260
tgagctgctc taccgcaccg acttttttccc tggcctgggc tggctgctgt tggccgagct   1320
ctgggctgag ctggagccca gtggccaaa ggccttctgg gacgactgga tgcggcggcc   1380
ggagcagcgg caggggcggg cctgcatacg ccctgagatc tcaagaacga tgacctttgg   1440
ccgcaagggt gtgagccacg ggcagttctt tgaccagcac ctcaagttta tcaagctgaa   1500
ccagcagttt gtgcacttca cccagctgga cctgtcttac ctgcagcggg aggcctatga   1560
ccgagatttc ctcgcccgcg tctacggtgc tccccagctg caggtggaga agtgaggac   1620
caatgaccgg aaggagctgg gggaggtgcg ggtgcagtat acgggcaggg acagcttcaa   1680
ggctttcgcc aaggctctgg gtgtcatgga tgaccttaag tcggggggttc cgagagctgg   1740
ctaccggggt attgtcacct tccagttccg gggccgccgt gtccacctgg cgcccccacc   1800
gacgtgggag ggctatgatc ctagctgaa ttagcacctg cctgtcctc ctgggcccct   1860
ccttgccaca tcatgagctg aggtgggacc acagtcccca ggctgcatcg gcctgcctgt   1920
gtttccctct taggtgcatt tatctttttg attttttccga gtggcattta agtgcacaaa   1980
```

```
tgataacaag aggattattc tcccgttctc aagggagtca gatcagggga actattctag   2040
ggtatgttgc ggggtattaa gcaggaaacc actgtgtggt gggggggcact gggcttgttg   2100 gggccagaaa tgtccacgtc ctgagctttc tcctggagca tgtgcagaga gtttggcaac   2160
gttcgctctc ttgaccagac cccttctccc tgacctggct cttccagcca gggcacgagc   2220
cctccttcta tacctgctcc ccttccccca gtggggactg agttatggga aaggggaca    2280 tatttgtggc caaatgata ctaaccaaag gggcttcctt gtcagggcct ggtggagttg     2340
gtgggtcatc ggggctcact gcctcctgcc cttctctcct gtctgacccc cacttagccc   2400
ttctctcctt gcagcctagc agtttatagt tctgagatgg aaagttgaag ggggcaagca   2460
agacctctcc tcagcccatg cccagctgtc aggagagagg tgcagggagg aaggccttgt   2520
gctgggacaa cctctctctt gccttacctc agagagggac tatgccctga cccctccttt   2580
ctgaaaatca gtgccctccc tgttgctcta ggaggctcct gctggcttgg tagaagacag   2640
aattcgatct gcctgtccct tttccccctg gggtttgaca cacaggctcc tctcagcatg   2700
aggtggagca gtgaccaggt ggagcagtga ccaggacgcc tctggcccag tgctgcccag   2760
cctccccgcc cgctcccagg cgccccatgt cctcacaggc caggacgcca tggcaggatg   2820
gagaggactt ggtggatttt tgtttcttgc ctgacctcag tttcatgaaa gaaagtggaa   2880
gctacagaat tattttctaa aataaaggct gaattgtctg aaaaaaaaaa aaaaaaa       2937
```

<210> SEQ ID NO 29
<211> LENGTH: 445
<212> TYPE: PRT
<213> ORGANISM: Homo sapiens
<300> PUBLICATION INFORMATION:
<308> DATABASE ACCESSION NUMBER: NP_002397
<309> DATABASE ENTRY DATE: 2005-09-23
<313> RELEVANT RESIDUES IN SEQ ID NO: (1)..(445)

<400> SEQUENCE: 29

```
Met Leu Lys Lys Gln Ser Ala Gly Leu Val Leu Trp Gly Ala Ile Leu
  1               5                  10                  15

Phe Val Ala Trp Asn Ala Leu Leu Leu Leu Phe Phe Trp Thr Arg Pro
                 20                  25                  30

Ala Pro Gly Arg Pro Pro Ser Val Ser Ala Leu Asp Gly Asp Pro Ala
             35                  40                  45

Ser Leu Thr Arg Glu Val Ile Arg Leu Ala Gln Asp Ala Glu Val Glu
         50                  55                  60

Leu Glu Arg Gln Arg Gly Leu Leu Gln Gln Ile Gly Asp Ala Leu Ser
 65                  70                  75                  80

Ser Gln Arg Gly Arg Val Pro Thr Ala Ala Pro Ala Gln Pro Arg Val
                 85                  90                  95

Val Pro Val Thr Pro Ala Pro Ala Val Ile Pro Ile Leu Val Ile Ala
                100                 105                 110

Cys Asp Arg Ser Thr Val Arg Arg Cys Leu Asp Lys Leu Leu His Tyr
            115                 120                 125

Arg Pro Ser Ala Glu Leu Phe Pro Ile Ile Val Ser Gln Asp Cys Gly
        130                 135                 140

His Glu Glu Thr Ala Gln Ala Ile Ala Ser Tyr Gly Ser Ala Val Thr
145                 150                 155                 160

His Ile Arg Gln Pro Asp Leu Ser Ser Ile Ala Val Pro Pro Asp His
                165                 170                 175

Arg Lys Phe Gln Gly Tyr Tyr Lys Ile Ala Arg His Tyr Arg Trp Ala
```

```
            180                 185                 190
Leu Gly Gln Val Phe Arg Gln Phe Arg Phe Pro Ala Val Val Val
        195                 200                 205
Glu Asp Asp Leu Glu Val Ala Pro Asp Phe Glu Tyr Phe Arg Ala
210                 215                 220
Thr Tyr Pro Leu Leu Lys Ala Asp Pro Ser Leu Trp Cys Val Ser Ala
225                 230                 235                 240
Trp Asn Asp Asn Gly Lys Glu Gln Met Val Asp Ala Ser Arg Pro Glu
                245                 250                 255
Leu Leu Tyr Arg Thr Asp Phe Phe Pro Gly Leu Gly Trp Leu Leu Leu
            260                 265                 270
Ala Glu Leu Trp Ala Glu Leu Glu Pro Lys Trp Pro Lys Ala Phe Trp
        275                 280                 285
Asp Asp Trp Met Arg Arg Pro Glu Gln Arg Gln Gly Arg Ala Cys Ile
290                 295                 300
Arg Pro Glu Ile Ser Arg Thr Met Thr Phe Gly Arg Lys Gly Val Ser
305                 310                 315                 320
His Gly Gln Phe Phe Asp Gln His Leu Lys Phe Ile Lys Leu Asn Gln
                325                 330                 335
Gln Phe Val His Phe Thr Gln Leu Asp Leu Ser Tyr Leu Gln Arg Glu
            340                 345                 350
Ala Tyr Asp Arg Asp Phe Leu Ala Arg Val Tyr Gly Ala Pro Gln Leu
        355                 360                 365
Gln Val Glu Lys Val Arg Thr Asn Asp Arg Lys Glu Leu Gly Glu Val
    370                 375                 380
Arg Val Gln Tyr Thr Gly Arg Asp Ser Phe Lys Ala Phe Ala Lys Ala
385                 390                 395                 400
Leu Gly Val Met Asp Asp Leu Lys Ser Gly Val Pro Arg Ala Gly Tyr
                405                 410                 415
Arg Gly Ile Val Thr Phe Gln Phe Arg Gly Arg Val His Leu Ala
            420                 425                 430
Pro Pro Pro Thr Trp Glu Gly Tyr Asp Pro Ser Trp Asn
        435                 440                 445

<210> SEQ ID NO 30
<211> LENGTH: 5078
<212> TYPE: DNA
<213> ORGANISM: Homo sapiens
<300> PUBLICATION INFORMATION:
<308> DATABASE ACCESSION NUMBER: NM_002410
<309> DATABASE ENTRY DATE: 2005-10-16
<313> RELEVANT RESIDUES IN SEQ ID NO: (1)..(5078)

<400> SEQUENCE: 30
taatactcct ttattccctg ttttaaaaat ttttttaaat ttgatacaat aattatacat      60
aataatggag taccatgtga gattcaatcc acatatacat tgtgaaatga tcaaattagg     120
atagttagca tgcacatcac ccccaaataa ttattacttt tgtggtgaga acacttaaaa     180
ttgtctcttt tagaaatata cgttattatt aaccatagtc acctcgctgt gcaatagaac     240
accagaactt attcctccta aatgtaactt tttaccattg accactccc tcctcacccc      300 cctctctcct ccccacccct ggtaaccact gttctgttat ctcctatgat agcaactttt     360
tagcttctgc atgtgagatt gtacggtagt tgccttctg tgcctggatt atttcattta      420
gcataatgtc cttcgggtat atccctgttg ctgcaaaaga caggatttct ctctcttttt     480
ctggttgaat agtattccat tgtcagagaa tgttgtaaga ctaggaaagg aacactgcag     540
```

```
gctggagccc tggggaaatg gtctgaggca ggtggtggga ctagagctgg ggtctggcaa    600
acaggctggg tttgattgtc agcataatag agagcactca tgtgccagct gggtgggagg    660
agcagccgag tgaagaaggg gaagcctctc aggaagcatg tgcagggttt atggtaatga    720
gcagaccagc aggtacgtag tgggagaggg gtgtgatggg gcagaggaac ttacgttatg    780
atagtacaag acagaggttg agcctcattt taataggcat tgtggtgggt gttgaatagt    840 gatgaatgt atgggtctgg aatcaggctg cctggtcaag ggctctgaaa catgagtgtg    900
catcagaatc acctcgaggc ttgttaaagg ataggctgtg gaccacatct cctcagttgc    960
tgattcagtg ggtgtgggtg gggcctgaga attcacattt cccactggtg atgctgctgt   1020
tactgattgg gaccacattt ggggaacact ggtctagaat tgagaggttg gcaaaccttc   1080
tctgttaaga ggtagatagt aaatattta ggccttctgg gctacaaaga gtatctgtta   1140
catatttttt attgcttttc atgacccatt aagcatatat atatcattct ctgccatata   1200
caaacaggct gttgggggag tgaggatgat gtagggaagg tggggcatgg tttaataacc   1260
cctgggccat gcctagatga tcagtcctct gccacatagc tggctgacct ttgccaagtt   1320
aatcaccttt tacctttatt ttctcatgtt tctaataaaa cagagacgat aatattcata   1380
cttcttacca tatagaactt ctgaggattc agtgagcaaa gccacaaaag atggtatgtc   1440
acaatatctg ggatatagct agaatttata atttatttt actctgttga taggcaatgg   1500
gaaaacagta agaggcagac caacagtgat ccagggctct gaaagctaat tgcttcaaga   1560
tcctgctacc atttctttt gggccgcttg caaagaagaa tcctttgact gaagcatgta   1620
tgtacactct gaagtacagc ctgggttagt ctcttataag ggatcggatc attgctcagc   1680
tctcccttga gtggcactta gaaaatggcg ctattcgtaa gctgactggt attgggccca   1740
ggactctggc tgaaggggtg ggcatgctgg taaccatttg caacctatgc tcaggtccta   1800
cttgttggga agccctgatt gagaagagtg gcctggtctg tgctggcatt agataggatc   1860
tggctgcatt aatattgaaa ctactctgcc ttttaatgtc tcatttgcc tcatggtggg   1920 agtgaaagtg agaaccacag aaaatctgcc tgccaggtgt tccacatttc ttgtgctaca   1980
gcatgcaagt gagcagtgag gtgtaccttt tcctcatgta gctgggaaag caatacccct   2040
gcttgtacct ctggcatatc ttctctgtgc tggtgcacct agagaggttg cctggtggcc   2100
ctgagagagc catctcatca ctaaacactg atggtgaaaa gctggccatg ctcaaataag   2160
atgtagcaat ctacctcttc tttgtctagt tacccccaag ggggcatcca ctttcttgct   2220
cacctcacca gttgcatgtt ctagtccttg ccagaagcac ataataatga ctttgtaagc   2280
ttaagttaca ggcacacaaa agggcctgat ggtgatatga ctccaccctc cccgttttg    2340 ctgacattcc gccaaatatc cttctgtctc ctccccacct tgcaaaacaa acttcctgtt   2400
ttgaatttgg tccaggctgg aacagcccca ccacacctgt taacacacgc agacgcacac   2460 ttccccctttc ataattgctt agcttcttgt tgcctagcca gatttcccct cagcttacag   2520
ttcctgaatc ataagatatt gaaccagcaa atttaagagt tgacattta cttagaggta   2580 ttcaagtgaa aacatggctt ctggtttatt ttgctgtatt gtgccatgac cacttggcta   2640
attcttctcc tccttcacat cagaatggaa gtgaggaaag gcaaccagct gacacaggag   2700
ccagagtgag accagcagac tctcacactc aacctacacc atgaatttgt gtctatcttc   2760
tacgcgttaa gagccaagga caggtgaagt tgccagagag caatggctct cttcactccg   2820
tggaagttgt cctctcagaa gctgggcttt ttcctggtga cttttggctt catttgggt    2880
```

```
atgatgcttc tgcactttac catccagcag cgaactcagc ctgaaagcag ctccatgctg   2940
cgcgagcaga tcctggacct cagcaaaagg tacatcaagg cactggcaga agaaaacagg   3000
aatgtggtgg atgggccata cgctggagtc atgacagctt atgatctgaa gaaaacccct   3060
gctgtgttat tagataacat tttgcagcgc attggcaagt tggagtcgaa ggtggacaat   3120
cttgttgtca atggcaccgg aacaaactca accaactcca ctacagctgt tcccagcttg   3180
gttgcacttg agaaaattaa tgtggcagat atcattaacg gagctcaaga aaaatgtgta   3240
ttgcctccta tggacggcta ccctcactgt gagggaaaga tcaagtggat gaaagacatg   3300
tggcgttcag atccctgcta cgcagactat ggagtggatg gatccaccctg ctctttttt    3360 atttacctca gtgaggttga aaattggtgt cctcatttac cttggagagc aaaaaatccc   3420
tacgaagaag ctgatcataa ttcattggcg gaaattcgta cagattttaa tattctctac   3480
agtatgatga aaaagcatga agaattccgg tggatgagac tacggatccg gcgaatggct   3540
gacgcatgga tccaagcaat caagtccctg gcagaaaagc agaaccttga aaagagaaag   3600
cggaagaaag tcctcgttca cctgggactc ctgaccaagg aatctggatt taagattgca   3660
gagacagctt tcagtggtgg ccctcttggt gaattagttc aatggagtga tttaattaca   3720
tctctgtact tactgggcca tgacattagg atttcagctt cactggctga gctcaaggaa   3780
atcatgaaga aggttgtagg aaaccgatct ggctgcccaa ctgtaggaga cagaattgtt   3840
gagctcattt acattgatat tgtaggactt gctcaattca agaaaactct tggaccatcc   3900
tgggttcatt accagtgcat gctccgagtc cttgattcat ttggtactga acccgaattt   3960
aatcatgcaa attatgccca atcgaaaggc cacaagaccc cttggggaaa atggaatctg   4020
aaccctcagc agttttatac catgttccct cataccccag acaacagctt tctggggttt   4080
gtggttgagc agcacctgaa ctccagtgat atccaccaca ttaatgaaat caaaaggcag   4140
aaccagtccc ttgtgtatgg caaagtggat agcttctgga agaataagaa gatctacttg   4200
gacattattc acacatacat ggaagtgcat gcaactgttt atggctccag cacaaagaat   4260
attcccagtt acgtgaaaaa ccatggtatc ctcagtggac gggacctgca gttccttctt   4320
cgagaaacca agttgtttgt tggacttggg ttcccttacg agggcccagc tcccctggaa   4380
gctatcgcaa atggatgtgc ttttctgaat cccaagttca acccacccaa aagcagcaaa   4440
aacacagact ttttcattgg caagccaact ctgagagagc tgacatccca gcatccttac   4500
gctgaagttt tcatcgggcg gccacatgtg tggactgttg acctcaacaa tcaggaggaa   4560
gtagaggatg cagtgaaagc aatttttaaat cagaagattg agccatacat gccatatgaa   4620
tttacgtgcg aggggatgct acagagaatc aatgctttca ttgaaaaaca ggacttctgc   4680
catgggcaag tgatgtggcc acccctcagc gccctacagg tcaagcttgc tgagcccggg   4740
cagtcctgca agcaggtgtg ccaggagagc cagctcatct gcgagccttc tttcttccag   4800
cacctcaaca aggacaagga catgctgaag tacaaggtga cctgccaaag ctcagagctg   4860
gccaaggaca tcctggtgcc ctcctttgac cctaagaata gcactgtgt gtttcaaggt   4920 gacctcctgc tcttcagctg tgcaggcgcc caccccaggc accagagggt ctgcccctgc   4980
cgggacttca tcaagggcca ggtggctctc tgcaaagact gcctatagca gctacctgct   5040
cagccctgca ccatgctgct ggggaagaca gtggcccc                          5078
```

<210> SEQ ID NO 31
<211> LENGTH: 741
<212> TYPE: PRT
<213> ORGANISM: Homo sapiens

```
<300> PUBLICATION INFORMATION:
<308> DATABASE ACCESSION NUMBER: NP_002401
<309> DATABASE ENTRY DATE: 2005-10-16
<313> RELEVANT RESIDUES IN SEQ ID NO: (1)..(741)

<400> SEQUENCE: 31

Met Ala Leu Phe Thr Pro Trp Lys Leu Ser Ser Gln Lys Leu Gly Phe
1               5                   10                  15

Phe Leu Val Thr Phe Gly Phe Ile Trp Gly Met Met Leu Leu His Phe
            20                  25                  30

Thr Ile Gln Gln Arg Thr Gln Pro Glu Ser Ser Ser Met Leu Arg Glu
        35                  40                  45

Gln Ile Leu Asp Leu Ser Lys Arg Tyr Ile Lys Ala Leu Ala Glu Glu
    50                  55                  60

Asn Arg Asn Val Val Asp Gly Pro Tyr Ala Gly Val Met Thr Ala Tyr
65                  70                  75                  80

Asp Leu Lys Lys Thr Leu Ala Val Leu Leu Asp Asn Ile Leu Gln Arg
                85                  90                  95

Ile Gly Lys Leu Glu Ser Lys Val Asp Asn Leu Val Val Asn Gly Thr
            100                 105                 110

Gly Thr Asn Ser Thr Asn Ser Thr Thr Ala Val Pro Ser Leu Val Ala
        115                 120                 125

Leu Glu Lys Ile Asn Val Ala Asp Ile Ile Asn Gly Ala Gln Glu Lys
    130                 135                 140

Cys Val Leu Pro Pro Met Asp Gly Tyr Pro His Cys Glu Gly Lys Ile
145                 150                 155                 160

Lys Trp Met Lys Asp Met Trp Arg Ser Asp Pro Cys Tyr Ala Asp Tyr
                165                 170                 175

Gly Val Asp Gly Ser Thr Cys Ser Phe Phe Ile Tyr Leu Ser Glu Val
            180                 185                 190

Glu Asn Trp Cys Pro His Leu Pro Trp Arg Ala Lys Asn Pro Tyr Glu
        195                 200                 205

Glu Ala Asp His Asn Ser Leu Ala Glu Ile Arg Thr Asp Phe Asn Ile
    210                 215                 220

Leu Tyr Ser Met Met Lys Lys His Glu Glu Phe Arg Trp Met Arg Leu
225                 230                 235                 240

Arg Ile Arg Arg Met Ala Asp Ala Trp Ile Gln Ala Ile Lys Ser Leu
                245                 250                 255

Ala Glu Lys Gln Asn Leu Glu Lys Arg Lys Arg Lys Lys Val Leu Val
            260                 265                 270

His Leu Gly Leu Leu Thr Lys Glu Ser Gly Phe Lys Ile Ala Glu Thr
        275                 280                 285

Ala Phe Ser Gly Gly Pro Leu Gly Glu Leu Val Gln Trp Ser Asp Leu
    290                 295                 300

Ile Thr Ser Leu Tyr Leu Leu Gly His Asp Ile Arg Ile Ser Ala Ser
305                 310                 315                 320

Leu Ala Glu Leu Lys Glu Ile Met Lys Lys Val Val Gly Asn Arg Ser
                325                 330                 335

Gly Cys Pro Thr Val Gly Asp Arg Ile Val Glu Leu Ile Tyr Ile Asp
            340                 345                 350

Ile Val Gly Leu Ala Gln Phe Lys Lys Thr Leu Gly Pro Ser Trp Val
        355                 360                 365

His Tyr Gln Cys Met Leu Arg Val Leu Asp Ser Phe Gly Thr Glu Pro
    370                 375                 380
```

```
Glu Phe Asn His Ala Asn Tyr Ala Gln Ser Lys Gly His Lys Thr Pro
385                 390                 395                 400

Trp Gly Lys Trp Asn Leu Asn Pro Gln Gln Phe Tyr Thr Met Phe Pro
            405                 410                 415

His Thr Pro Asp Asn Ser Phe Leu Gly Phe Val Val Glu Gln His Leu
        420                 425                 430

Asn Ser Ser Asp Ile His His Ile Asn Glu Ile Lys Arg Gln Asn Gln
        435                 440                 445

Ser Leu Val Tyr Gly Lys Val Asp Ser Phe Trp Lys Asn Lys Lys Ile
    450                 455                 460

Tyr Leu Asp Ile Ile His Thr Tyr Met Glu Val His Ala Thr Val Tyr
465                 470                 475                 480

Gly Ser Ser Thr Lys Asn Ile Pro Ser Tyr Val Lys Asn His Gly Ile
                485                 490                 495

Leu Ser Gly Arg Asp Leu Gln Phe Leu Leu Arg Glu Thr Lys Leu Phe
            500                 505                 510

Val Gly Leu Gly Phe Pro Tyr Glu Gly Pro Ala Pro Leu Glu Ala Ile
        515                 520                 525

Ala Asn Gly Cys Ala Phe Leu Asn Pro Lys Phe Asn Pro Pro Lys Ser
530                 535                 540

Ser Lys Asn Thr Asp Phe Phe Ile Gly Lys Pro Thr Leu Arg Glu Leu
545                 550                 555                 560

Thr Ser Gln His Pro Tyr Ala Glu Val Phe Ile Gly Arg Pro His Val
                565                 570                 575

Trp Thr Val Asp Leu Asn Asn Gly Glu Glu Val Glu Asp Ala Val Lys
            580                 585                 590

Ala Ile Leu Asn Gln Lys Ile Glu Pro Tyr Met Pro Tyr Glu Phe Thr
    595                 600                 605

Cys Glu Gly Met Leu Gln Arg Ile Asn Ala Phe Ile Glu Lys Gln Asp
610                 615                 620

Phe Cys His Gly Gln Val Met Trp Pro Pro Leu Ser Ala Leu Gln Val
625                 630                 635                 640

Lys Leu Ala Glu Pro Gly Gln Ser Cys Lys Gln Val Cys Gln Glu Ser
                645                 650                 655

Gln Leu Ile Cys Glu Pro Ser Phe Phe Gln His Leu Asn Lys Asp Lys
            660                 665                 670

Asp Met Leu Lys Tyr Lys Val Thr Cys Gln Ser Ser Glu Leu Ala Lys
        675                 680                 685

Asp Ile Leu Val Pro Ser Phe Asp Pro Lys Asn Lys His Cys Val Phe
        690                 695                 700

Gln Gly Asp Leu Leu Leu Phe Ser Cys Ala Gly Ala His Pro Arg His
705                 710                 715                 720

Gln Arg Val Cys Pro Cys Arg Asp Phe Ile Lys Gly Gln Val Ala Leu
                725                 730                 735

Cys Lys Asp Cys Leu
            740

<210> SEQ ID NO 32
<211> LENGTH: 2531
<212> TYPE: DNA
<213> ORGANISM: Homo sapiens
<300> PUBLICATION INFORMATION:
<308> DATABASE ACCESSION NUMBER: NM_001015883
<309> DATABASE ENTRY DATE: 2005-10-18
<313> RELEVANT RESIDUES IN SEQ ID NO: (1)..(2531)
```

```
<400> SEQUENCE: 32
gggccggagg gccgcggtgt gccgcggggc agttgcgggt tgtcataacg gtccccgccg      60
gagtgaggcg aggccgcgtc gctcagttct ggccgtctag ggcccctgta aggatgagag     120
cgcagaggac gcagggccgc tggaggcgca ggtaacgaag ctagggtgcg gttgggaccg     180
cggctgagct ttttccggga cccgtggtgc tgaatggaga ggacggagac gaagccgagc     240
cgcggctcct agcggcggcg ccgatgctcg agctgtagct gcgctcccgg ccctggagac     300
catgaggttc cgcatctaca aacggaaggt gctaatcctg acgctcgtgg tggccgcctg     360
cggcttcgtc ctctggagca gcaatgggcg acaaaggaag aacgaggccc tcgccccacc     420
gttgctggac gccgaacccg cgcggggtgc cggcggccgc ggtgtgggacc accctctgt     480 ggctgtgggc atccgcaggg tctccaacgt gtcggcggct tccctggtcc cggcggtccc     540
ccagcccgag gcggacaacc tgacgctgcg gtaccggtcc ctggtgtacc agctgaactt     600
tgatcagacc ctgaggaatg tagataaggc tggcacctgg gccccccggg agctggtgct     660
ggtggtccag gtgcataacc ggcccgaata cctcagactg ctgctggact cacttcgaaa     720
agcccaggga attgacaacg tcctcgtcat cttagccat gacttctggt cgaccgagat     780
caatcagctg atcgccgggg tgaatttctg tccggttctg caggtgttct ttcctttcag     840
cattcagttg taccctaacg agtttccagg tagtgaccct agagattgtc ccagagacct     900
gccgaagaat gccgctttga aattggggtg catcaatgct gagtatcccg actccttcgg     960
ccattataga gaggccaaat tctcccagac caaacatcac tggtggtgga agctgcattt    1020
tgtgtgggaa agagtgaaaa ttcttcgaga ttatgctggc cttatacttt tcctagaaga    1080
ggatcactac ttagccccag acttttacca tgtcttcaaa aagatgtgga aactgaagca    1140
gcaagagtgc cctgaatgtg atgttctctc cctggggacc tatagtgcca gtcgcagttt    1200
ctatggcatg gctgacaagg tagatgtgaa aacttggaaa tccacagagc acaatatggg    1260
tctagccttg acccggaatg cctatcgaaa gctgatcgag tgcacagaca ctttctgtac    1320
ttatgatgat tataactggg actggactct tcaatacttg actgtatctt gtcttccaaa    1380
attctggaaa gtgctggttc ctcaaattcc taggatcttt catgctggag actgtggtat    1440
gcatcacaag aaaacctgta gaccatccac tcagagtgcc caaattgagt cactcttaaa    1500
taataacaaa caatacatgt ttccagaaac tctaactatc agtgaaaagt ttactgtggt    1560
agccatttcc ccacctagaa aaatggaggg tggggagat attagggacc atgaactctg    1620
taaaagttat agaagactgc agtgaaaatc acagttacaa aagcgacagt cttctatttt    1680
tgatatttgt ccaaacagga catacaattg aataaaagag tttaggaact ggtttctgct    1740
ttaatacaaa aacaaaatct tgtaaaaggt gtccaaatac atagtaatct tttccagtta    1800
tgtctgatta agatttaaaa ctgaaggttt cattttggga gtagggtttt aaagctcaat    1860
ctgttatctg ctaaaattga ttattgttga tatgagagaa gagggaaat tttatttaaa    1920 ttgcatttat taatctttttt atctgaaact ttgtacactt ttccactttc aaaacctatt    1980
ttaagtacag caaaatttat ttaaaactgt catagcagta aaaagtatta cgatgaaatt    2040
gttagggtat taatggaaca aacccagttt cactctcttg acacacttat taggaaggga    2100
ttgcttcact ggtttaataa tttaaaagtt atgtttgtta aacaccctgt cagaacagtc    2160
attttcagta ttagattcct gtactattgt gttttgagtg tgttttggaa ccttcataga    2220
acacactttc ttttgaatg tatttgattg ataagaaagt ttaaacattg ttttcacctc    2280
aatgtagaaa tacagtggtt ttgtttttttt ttttctttta gtgctgacaa aataaaatac    2340
```

| | |
|---|---|
| tcattttttgc ataaaaaggt tcctaatcct tttgcagaat aagttttgtt tactctttat | 2400 |
| accaaaattc agtgaaggca ttctacaagt tttgagttag cattacattt taatatttac | 2460 |
| tattgctaca ttgtataatt gagtttgaaa taaaacccag cttatgacaa tgcaaaaaaa | 2520 |
| aaaaaaaaaa a | 2531 |

<210> SEQ ID NO 33
<211> LENGTH: 2728
<212> TYPE: DNA
<213> ORGANISM: Homo sapiens
<300> PUBLICATION INFORMATION:
<308> DATABASE ACCESSION NUMBER: NM_002408
<309> DATABASE ENTRY DATE: 2005-01-08
<313> RELEVANT RESIDUES IN SEQ ID NO: (1)..(2728)

<400> SEQUENCE: 33

| | |
|---|---|
| gggccggagg gccgcggtgt gccgcggggc agttgcgggt tgtcataacg gtccccgccg | 60 |
| gagtgaggcg aggccgcgtc gctcagttct ggccgtctag ggcccctgta aggatgagag | 120 |
| cgcagaggac gcagggccgc tggaggcgca ggtaacgaag ctagggtgcg gttgggaccg | 180 |
| cggctgagct ttttccggga cccgtggtgc tgaatggaga ggacgagac gaagccgagc | 240 |
| cgcggctcct agcggcggcg ccgatgctcg agctgtagct gccaggcgag gatgtgtgga | 300 |
| gcgcaggcgg cgcggggtaa atgagaggtc tcggcccca ggaccccgg ggcccgggat | 360 |
| gagttagcga gggcagccgc gggggccagt tccgaccgtg acaggccaag gcgacggccg | 420 |
| ccgcccgccc gccccttccg tgcagaagca gctgctcctt ccgcgcccg cccgcctgcg | 480 |
| ctcccggccc tggagaccat gaggttccgc atctacaaac ggaaggtgct aatcctgacg | 540 |
| ctcgtggtgg ccgcctgcgg cttcgtcctc tggagcagca atgggcgaca aaggaagaac | 600 |
| gaggccctcg ccccaccgtt gctggacgcc gaacccgcgc ggggtgccgg cggccgcggt | 660 |
| ggggaccacc cctctgtggc tgtgggcatc cgcagggtct ccaacgtgtc ggcggcttcc | 720 |
| ctggtcccgg cggtccccca gcccgaggcg gacaacctga cgctgcggta ccggtccctg | 780 |
| gtgtaccagc tgaactttga tcagaccctg aggaatgtag ataaggctgg cacctgggcc | 840 |
| ccccgggagc tggtgctggt ggtccaggtg cataaccggc ccgaataccct cagactgctg | 900 |
| ctggactcac ttcgaaaagc ccagggaatt gacaacgtcc tcgtcatctt tagccatgac | 960 |
| ttctggtcga ccgagatcaa tcagctgatc gccggggtga atttctgtcc ggttctgcag | 1020 |
| gtgttctttc ctttcagcat tcagttgtac cctaacgagt ttccaggtag tgaccctaga | 1080 |
| gattgtccca gagacctgcc gaagaatgcc gctttgaaat tggggtgcat caatgctgag | 1140 |
| tatcccgact ccttcggcca ttatagagag gccaaattct cccagaccaa acatcactgg | 1200 |
| tggtggaagc tgcattttgt gtgggaaaga gtgaaaattc ttcgagatta tgctggcctt | 1260 |
| atacttttcc tagaagagga tcactactta gccccagact tttaccatgt cttcaaaaag | 1320 |
| atgtggaaac tgaagcagca agagtgccct gaatgtgatg ttctctccct ggggacctat | 1380 |
| agtgccagtc gcagtttcta tggcatggct gacaaggtag atgtgaaaac ttggaaatcc | 1440 |
| acagagcaca atatgggtct agccttgacc cggaatgcct atcagaagct gatcgagtgc | 1500 |
| acagacactt tctgtactta tgatgattat aactgggact ggactcttca atacttgact | 1560 |
| gtatcttgtc ttccaaaatt ctggaaagtg ctggttcctc aaattcctag gatctttcat | 1620 |
| gctggagact gtggtatgca tcacaagaaa acctgtagac catccactca gagtgcccaa | 1680 |
| attgagtcac tcttaaataa taacaaacaa tacatgtttc cagaaactct aactatcagt | 1740 |

-continued

```
gaaaagttta ctgtggtagc catttcccca cctagaaaaa atggagggtg gggagatatt   1800
agggaccatg aactctgtaa aagttataga agactgcagt gaaaatcaca gttacaaaag   1860
cgacagtctt ctattttga tatttgtcca aacaggacat acaattgaat aaaagagttt    1920
aggaactggt ttctgcttta atacaaaaac aaaatcttgt aaaaggtgtc caaatacata   1980
gtaatctttt ccagttatgt ctgattaaga tttaaaactg aaggtttcat tttgggagta   2040
gggttttaaa gctcaatctg ttatctgcta aaattgatta ttgttgatat gagagaagag   2100
gggaaatttt atttaaattg catttattaa tcttttatc tgaaactttg tacacttttc    2160
cactttcaaa acctatttta agtacagcaa aatttattta aaactgtcat agcagtaaaa   2220
agtattacga tgaaattgtt agggtattaa tggaacaaac ccagtttcac tctcttgaca   2280
cacttattag gaagggattg cttcactggt ttaataattt aaaagttatg tttgttaaac   2340
accctgtcag aacagtcatt ttcagtatta gattcctgta ctattgtgtt ttgagtgtgt   2400
tttggaacct tcatagaaca cactttcttt tggaatgtat ttgattgata agaaagttta   2460
aacattgttt tcacctcaat gtagaaatac agtggttttg tttttttttt tcttttagtg   2520
ctgacaaaat aaaatactca ttttgcata aaaaggttcc taatcctttt gcagaataag    2580
ttttgtttac tctttatacc aaaattcagt gaaggcattc tacaagtttt gagttagcat   2640
tacattttaa tatttactat tgctacattg tataattgag tttgaaataa aacccagctt   2700
atgacaatgc aaaaaaaaaa aaaaaaaa                                      2728
```

<210> SEQ ID NO 34
<211> LENGTH: 447
<212> TYPE: PRT
<213> ORGANISM: Homo sapiens
<300> PUBLICATION INFORMATION:
<308> DATABASE ACCESSION NUMBER: NP_001015883
<309> DATABASE ENTRY DATE: 2005-10-18
<313> RELEVANT RESIDUES IN SEQ ID NO: (1)..(447)

<400> SEQUENCE: 34

```
Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
            20                  25                  30

Lys Asn Glu Ala Leu Ala Pro Pro Leu Leu Asp Ala Glu Pro Ala Arg
        35                  40                  45

Gly Ala Gly Gly Arg Gly Gly Asp His Pro Ser Val Ala Val Gly Ile
    50                  55                  60

Arg Arg Val Ser Asn Val Ser Ala Ala Ser Leu Val Pro Ala Val Pro
65                  70                  75                  80

Gln Pro Glu Ala Asp Asn Leu Thr Leu Arg Tyr Arg Ser Leu Val Tyr
                85                  90                  95

Gln Leu Asn Phe Asp Gln Thr Leu Arg Asn Val Asp Lys Ala Gly Thr
            100                 105                 110

Trp Ala Pro Arg Glu Leu Val Leu Val Val Gln Val His Asn Arg Pro
        115                 120                 125

Glu Tyr Leu Arg Leu Leu Leu Asp Ser Leu Arg Lys Ala Gln Gly Ile
    130                 135                 140

Asp Asn Val Leu Val Ile Phe Ser His Asp Phe Trp Ser Thr Glu Ile
145                 150                 155                 160

Asn Gln Leu Ile Ala Gly Val Asn Phe Cys Pro Val Leu Gln Val Phe
                165                 170                 175
```

Phe Pro Phe Ser Ile Gln Leu Tyr Pro Asn Glu Phe Pro Gly Ser Asp
            180                 185                 190

Pro Arg Asp Cys Pro Arg Asp Leu Pro Lys Asn Ala Ala Leu Lys Leu
        195                 200                 205

Gly Cys Ile Asn Ala Glu Tyr Pro Asp Ser Phe Gly His Tyr Arg Glu
    210                 215                 220

Ala Lys Phe Ser Gln Thr Lys His His Trp Trp Lys Leu His Phe
225                 230                 235                 240

Val Trp Glu Arg Val Lys Ile Leu Arg Asp Tyr Ala Gly Leu Ile Leu
                245                 250                 255

Phe Leu Glu Glu Asp His Tyr Leu Ala Pro Asp Phe Tyr His Val Phe
            260                 265                 270

Lys Lys Met Trp Lys Leu Lys Gln Gln Glu Cys Pro Glu Cys Asp Val
        275                 280                 285

Leu Ser Leu Gly Thr Tyr Ser Ala Ser Arg Ser Phe Tyr Gly Met Ala
    290                 295                 300

Asp Lys Val Asp Val Lys Thr Trp Lys Ser Thr Glu His Asn Met Gly
305                 310                 315                 320

Leu Ala Leu Thr Arg Asn Ala Tyr Gln Lys Leu Ile Glu Cys Thr Asp
                325                 330                 335

Thr Phe Cys Thr Tyr Asp Asp Tyr Asn Trp Asp Trp Thr Leu Gln Tyr
            340                 345                 350

Leu Thr Val Ser Cys Leu Pro Lys Phe Trp Lys Val Leu Val Pro Gln
        355                 360                 365

Ile Pro Arg Ile Phe His Ala Gly Asp Cys Gly Met His His Lys Lys
    370                 375                 380

Thr Cys Arg Pro Ser Thr Gln Ser Ala Gln Ile Glu Ser Leu Leu Asn
385                 390                 395                 400

Asn Asn Lys Gln Tyr Met Phe Pro Glu Thr Leu Thr Ile Ser Glu Lys
                405                 410                 415

Phe Thr Val Val Ala Ile Ser Pro Pro Arg Lys Asn Gly Gly Trp Gly
            420                 425                 430

Asp Ile Arg Asp His Glu Leu Cys Lys Ser Tyr Arg Arg Leu Gln
        435                 440                 445

<210> SEQ ID NO 35
<211> LENGTH: 41
<212> TYPE: DNA
<213> ORGANISM: Homo sapiens
<220> FEATURE:
<221> NAME/KEY: misc_feature
<223> OTHER INFORMATION: Y = T OR C

<400> SEQUENCE: 35
ctgaggccca gggagagcac ytggggccag aatctctcag t                41

<210> SEQ ID NO 36
<211> LENGTH: 41
<212> TYPE: DNA
<213> ORGANISM: Homo sapiens
<220> FEATURE:
<221> NAME/KEY: misc_feature
<223> OTHER INFORMATION: K - G OR T

<400> SEQUENCE: 36
gggaagatga tggactacct kcagggctct ggggagaccc c                41

<210> SEQ ID NO 37

```
<211> LENGTH: 41
<212> TYPE: DNA
<213> ORGANISM: Homo sapiens
<220> FEATURE:
<221> NAME/KEY: misc_feature
<223> OTHER INFORMATION: S = C OR G

<400> SEQUENCE: 37
tctggctgcc ggttccatct scctgtaaat ttccagaagg g              41

<210> SEQ ID NO 38
<211> LENGTH: 41
<212> TYPE: DNA
<213> ORGANISM: Homo sapiens
<220> FEATURE:
<221> NAME/KEY: misc_feature
<223> OTHER INFORMATION: Y = C OR T

<400> SEQUENCE: 38
gtctcctcct tccttctgtt ytgttatttt tccccctgat g              41

<210> SEQ ID NO 39
<211> LENGTH: 41
<212> TYPE: DNA
<213> ORGANISM: Homo sapiens
<220> FEATURE:
<221> NAME/KEY: misc_feature
<223> OTHER INFORMATION: R = G OR A

<400> SEQUENCE: 39
ttagtgctcg cggggccgcg rcggagtgta ccgtgctgct c              41

<210> SEQ ID NO 40
<211> LENGTH: 41
<212> TYPE: DNA
<213> ORGANISM: Homo sapiens
<220> FEATURE:
<221> NAME/KEY: misc_feature
<223> OTHER INFORMATION: R = A OR G

<400> SEQUENCE: 40
ttcccccagg gaggatccgc rgcccagccg aggggggtcgg g             41

<210> SEQ ID NO 41
<211> LENGTH: 41
<212> TYPE: DNA
<213> ORGANISM: Homo sapiens
<220> FEATURE:
<221> NAME/KEY: misc_feature
<223> OTHER INFORMATION: R = G OR A

<400> SEQUENCE: 41
gaaaatagta caacttaatg rattagcttt tgggtttaac t              41

<210> SEQ ID NO 42
<211> LENGTH: 206
<212> TYPE: DNA
<213> ORGANISM: Homo sapiens
<220> FEATURE:
<221> NAME/KEY: misc_feature
<223> OTHER INFORMATION: M = C OR A
<220> FEATURE:
<221> NAME/KEY: misc_feature
<223> OTHER INFORMATION: Y = T OR C
<220> FEATURE:
<221> NAME/KEY: misc_feature
<223> OTHER INFORMATION: S = G OR C
<220> FEATURE:
<221> NAME/KEY: misc_feature
```

```
<222> LOCATION: (182)..(182)
<223> OTHER INFORMATION: n is a, c, g, t or u

<400> SEQUENCE: 42
gcgcggctcc aggmtgggca gctgcgctgg agggccgagg gcaggggtgg ggtcgggcgt      60
ccaccctcag ggttgcgcca gggagccgga aagccgactc ccgaagttgg ggtcctggga    120
aaacttgggt cctgggttga ctgagaagcg gygsggaaag gaggcggscc aggaggaggg    180
gncctggcgg acgccggccg ggggggc                                         206

<210> SEQ ID NO 43
<211> LENGTH: 41
<212> TYPE: DNA
<213> ORGANISM: Homo sapiens
<220> FEATURE:
<221> NAME/KEY: misc_feature
<223> OTHER INFORMATION: Y = T OR C

<400> SEQUENCE: 43
gaggagacgg cccaggccat ygcctcctac ggcagcgcgg t                          41

<210> SEQ ID NO 44
<211> LENGTH: 40
<212> TYPE: DNA
<213> ORGANISM: Homo sapiens
<220> FEATURE:
<221> NAME/KEY: misc_feature
<223> OTHER INFORMATION: R = G OR A

<400> SEQUENCE: 44
ggtggagttg gtggtcatcr gggctcactg cctcctgccc                            40

<210> SEQ ID NO 45
<211> LENGTH: 41
<212> TYPE: DNA
<213> ORGANISM: Homo sapiens
<220> FEATURE:
<221> NAME/KEY: misc_feature
<223> OTHER INFORMATION: S = C OR G

<400> SEQUENCE: 45
ccactttctt gctcacctca scagttgcat gttctagtcc t                          41

<210> SEQ ID NO 46
<211> LENGTH: 41
<212> TYPE: DNA
<213> ORGANISM: Homo sapiens
<220> FEATURE:
<221> NAME/KEY: misc_feature
<223> OTHER INFORMATION: K = G OR T

<400> SEQUENCE: 46
ctttgctgtg tactgcttcc kgtgacgcca tagggctctc a                          41

<210> SEQ ID NO 47
<211> LENGTH: 205
<212> TYPE: DNA
<213> ORGANISM: Homo sapiens
<220> FEATURE:
<221> NAME/KEY: misc_feature
<223> OTHER INFORMATION: M = C or A
<220> FEATURE:
<221> NAME/KEY: misc_feature
<223> OTHER INFORMATION: Y = T OR C
<220> FEATURE:
<221> NAME/KEY: misc_feature
<223> OTHER INFORMATION: S = G OR C
```

<400> SEQUENCE: 47

```
gcgcggctcc aggmtgggca gctgcgctgg agggccgagg gcaggggtgg ggtcggcgt      60
ccaccctcag ggttgcgcca gggagccgga aagccgactc ccgaagttgg ggtcctggga    120
aaacttgggt cctgggttga ctgagaagcg gygsggaaag gaggcggscc aggaggaggg    180
gcctggcgga cgccggccgg ggggc                                           205
```

<210> SEQ ID NO 48
<211> LENGTH: 240
<212> TYPE: DNA
<213> ORGANISM: Homo sapiens

<400> SEQUENCE: 48

```
cgagctcttg tgacgcggac ctcagtgcca ggatggctcg gggcgagcgg cggcgccgcg     60
cagtgccggc agagggagtg cggacagccg agagggcggc tcggggaggc cccgggcgac   120
gggacggccg gggcggcggg ccgcgtagca cggctggagg agtggctctg gccgtcgtgg   180
tcctgtcttt ggccctgggt atgtcggggc gctgggtgct ggcgtggtac cgtgcgcggc   240
```

<210> SEQ ID NO 49
<211> LENGTH: 69
<212> TYPE: PRT
<213> ORGANISM: Homo sapiens

<400> SEQUENCE: 49

Met Ala Arg Gly Glu Arg Arg Arg Ala Val Pro Ala Glu Gly Val
1               5                   10                  15

Arg Thr Ala Glu Arg Ala Ala Arg Gly Gly Pro Gly Arg Arg Asp Gly
                20                  25                  30

Arg Gly Gly Gly Pro Arg Ser Thr Ala Gly Gly Val Ala Leu Ala Val
            35                  40                  45

Val Val Leu Ser Leu Ala Leu Gly Met Ser Gly Arg Trp Val Leu Ala
        50                  55                  60

Trp Tyr Arg Ala Arg
65

<210> SEQ ID NO 50
<211> LENGTH: 240
<212> TYPE: DNA
<213> ORGANISM: Homo sapiens

<400> SEQUENCE: 50

```
cgagctcttg tgacgcggac ctcagtgcca ggatggctcg gggcgagcgg cggcgccgcg     60
cagtgccggc agagggagtg cggacagccg agagggcggc tcggggaggc cccgggcgac   120
gggacggccg gggcggcggg ccgcgtagca cggctggagg agtggctctg gccgtcgtgg   180
tcctgtcttt ggccctgggt atgtcggggc gctggatgct ggcgtggtac cgtgcgcggc   240
```

<210> SEQ ID NO 51
<211> LENGTH: 69
<212> TYPE: PRT
<213> ORGANISM: Homo sapiens

<400> SEQUENCE: 51

Met Ala Arg Gly Glu Arg Arg Arg Ala Val Pro Ala Glu Gly Val
1               5                   10                  15

Arg Thr Ala Glu Arg Ala Ala Arg Gly Gly Pro Gly Arg Arg Asp Gly
                20                  25                  30

```
Arg Gly Gly Gly Pro Arg Ser Thr Ala Gly Gly Val Ala Leu Ala Val
        35                  40                  45

Val Val Leu Ser Leu Ala Leu Gly Met Ser Gly Arg Trp Met Leu Ala
 50                  55                  60

Trp Tyr Arg Ala Arg
 65

<210> SEQ ID NO 52
<211> LENGTH: 153
<212> TYPE: DNA
<213> ORGANISM: Homo sapiens

<400> SEQUENCE: 52
accctgtttg ggaagatgat ggactacctg cagggctctg gggagacccc acagacagat      60
gttcgctgga tgtcagagac tggcatcatt gacgtcttcc tgctgctggg gccctccatc    120
tctgatgttt tccggcaata tgctagtctc aca                                  153

<210> SEQ ID NO 53
<211> LENGTH: 51
<212> TYPE: PRT
<213> ORGANISM: Homo sapiens

<400> SEQUENCE: 53

Thr Leu Phe Gly Lys Met Met Asp Tyr Leu Gln Gly Ser Gly Glu Thr
 1               5                  10                  15

Pro Gln Thr Asp Val Arg Trp Met Ser Glu Thr Gly Ile Ile Asp Val
            20                  25                  30

Phe Leu Leu Leu Gly Pro Ser Ile Ser Asp Val Phe Arg Gln Tyr Ala
        35                  40                  45

Ser Leu Thr
    50

<210> SEQ ID NO 54
<211> LENGTH: 153
<212> TYPE: DNA
<213> ORGANISM: Homo sapiens

<400> SEQUENCE: 54
accctgtttg ggaagatgat ggactacctt cagggctctg gggagacccc acagacagat      60
gttcgctgga tgtcagagac tggcatcatt gacgtcttcc tgctgctggg gccctccatc    120
tctgatgttt tccggcaata tgctagtctc aca                                  153

<210> SEQ ID NO 55
<211> LENGTH: 177
<212> TYPE: DNA
<213> ORGANISM: Homo sapiens

<400> SEQUENCE: 55
tgatccggta tcttacctct tttgtcactc acaggtgtgg tatgacattc aaagctacca      60
gaagcatcat ggtccccaga ccctgtacct gcctgtaact ctaagcagtg tgagtaagcc    120
tggtctggct gccggttcca tctccctgta aatttccaga aggggaggga atgtgtg        177

<210> SEQ ID NO 56
<211> LENGTH: 177
<212> TYPE: DNA
<213> ORGANISM: Homo sapiens

<400> SEQUENCE: 56
```

```
tgatccggta tcttacctct tttgtcactc acaggtgtgg tatgacattc aaagctacca    60
gaagcatcat ggtccccaga ccctgtacct gcctgtaact ctaagcagtg tgagtaagcc   120
tggtctggct gccggttcca tctgcctgta aatttccaga aggggaggga atgtgtg      177
```

<210> SEQ ID NO 57
<211> LENGTH: 360
<212> TYPE: DNA
<213> ORGANISM: Homo sapiens

<400> SEQUENCE: 57

```
ctcagggtac agctcaagga gagctctttc tggatgatgg gcacacgttc aactatcaga    60
ctcgccaaga gttcctgctg cgtcgattct cattctctgg caacacccct gtctccaggt   120
aatgggtcac ccactcttcc ttggctgcct tgctggggc ctgatccttg tgggggctcc    180
cagttcactg tgctcttttc tcacattctg accttgcttt gggtctcctc cttccttctg   240
ttctgttatt tttcccccctg atggacatct gcttttacca tctccagctc agcagaccct   300
gaaggacact ttgagacacc aatctggatt gagcgggtgg tgataatagg ggctggaaag   360
```

<210> SEQ ID NO 58
<211> LENGTH: 360
<212> TYPE: DNA
<213> ORGANISM: Homo sapiens

<400> SEQUENCE: 58

```
ctcagggtac agctcaagga gagctctttc tggatgatgg gcacacgttc aactatcaga    60
ctcgccaaga gttcctgctg cgtcgattct cattctctgg caacacccct gtctccaggt   120
aatgggtcac ccactcttcc ttggctgcct tgctggggc ctgatccttg tgggggctcc    180
cagttcactg tgctcttttc tcacattctg accttgcttt gggtctcctc cttccttctg   240
ttttgttatt tttcccccctg atggacatct gcttttacca tctccagctc agcagaccct   300
gaaggacact ttgagacacc aatctggatt gagcgggtgg tgataatagg ggctggaaag   360
```

<210> SEQ ID NO 59
<211> LENGTH: 180
<212> TYPE: DNA
<213> ORGANISM: Homo sapiens

<400> SEQUENCE: 59

```
tatactagtt aatttcttcc attccctact acacagagag gtgagctttc aaattttgca    60
gagctctgct atcactgaat tacatttatc tgaagaaaat agtacaactt aatggattag   120
cttttgggtt taactgaata tatgaagaaa ttgggtctgt ctaaagagag ggtatttcat   180
```

<210> SEQ ID NO 60
<211> LENGTH: 180
<212> TYPE: DNA
<213> ORGANISM: Homo sapiens

<400> SEQUENCE: 60

```
tatactagtt aatttcttcc attccctact acacagagag gtgagctttc aaattttttca    60 gagctctgct atcactgaat tacatttatc tgaagaaaat agtacaactt aatgaattag   120
cttttgggtt taactgaata tatgaagaaa ttgggtctgt ctaaagagag ggtatttcat   180
```

<210> SEQ ID NO 61
<211> LENGTH: 180
<212> TYPE: DNA

<213> ORGANISM: Homo sapiens

<400> SEQUENCE: 61

| ttatgggaga agggggacata tttgtggcca aaatgatact aaccaaaggg gcttccttgt | 60 |
| cagggcctgg tggagttggt gggtcatcgg ggctcactgc ctcctgccct tctctcctgt | 120 |
| ctgaccccca cttagccctt ctctccttgc agcctagcag tttatagttc tgagatggaa | 180 |

<210> SEQ ID NO 62
<211> LENGTH: 180
<212> TYPE: DNA
<213> ORGANISM: Homo sapiens

<400> SEQUENCE: 62

| ttatgggaga agggggacata tttgtggcca aaatgatact aaccaaaggg gcttccttgt | 60 |
| cagggcctgg tggagttggt gggtcatcag ggctcactgc ctcctgccct tctctcctgt | 120 |
| ctgaccccca cttagccctt ctctccttgc agcctagcag tttatagttc tgagatggaa | 180 |

<210> SEQ ID NO 63
<211> LENGTH: 179
<212> TYPE: DNA
<213> ORGANISM: Homo sapiens

<400> SEQUENCE: 63

| tggccatgct caaataagat gtagcaatct acctcttctt tgtctagtta cccccaaggg | 60 |
| ggcatccact ttcttgctca cctcaccagt tgcatgttct agtccttgcc agaagcacat | 120 |
| aataatgact ttgtaagctt aagttacagg cacacaaaag ggcctgatgg tgatatgac | 179 |

<210> SEQ ID NO 64
<211> LENGTH: 179
<212> TYPE: DNA
<213> ORGANISM: Homo sapiens

<400> SEQUENCE: 64

| tggccatgct caaataagat gtagcaatct acctcttctt tgtctagtta cccccaaggg | 60 |
| ggcatccact ttcttgctca cctcagcagt tgcatgttct agtccttgcc agaagcacat | 120 |
| aataatgact ttgtaagctt aagttacagg cacacaaaag ggcctgatgg tgatatgac | 179 |

<210> SEQ ID NO 65
<211> LENGTH: 240
<212> TYPE: DNA
<213> ORGANISM: Homo sapiens

<400> SEQUENCE: 65

| ctgcatattt agtgtcactg atgctttta ggttgaaaat tggtgtcctc atttaccttg | 60 |
| gagagcaaaa aatccctacg aagaagctga tcataattca ttggtaagtg attttggaaa | 120 |
| actctttcta gacttgtgca tttaggtcag atgccaagtg atacatgtgg aatcttctag | 180 |
| aaatgccaac tataacctga aatagtgtta cactgaaaaa cttctgtatt cgtctctgtg | 240 |

<210> SEQ ID NO 66
<211> LENGTH: 240
<212> TYPE: DNA
<213> ORGANISM: Homo sapiens
<220> FEATURE:
<221> NAME/KEY: misc_feature
<222> LOCATION: (15)..(15)
<223> OTHER INFORMATION: n is a, c, g, or t

<400> SEQUENCE: 66

```
ctgcatattt agtgncactg atgctttta ggttgaaaat tggtgtcctc atttaccttg    60
gagagcaaaa atccctacg aagaagctga tcataattca ttggtaagtg attttggaaa   120
actctttcta gacttgtgca tttaggtcag atgccaagtg atacatgtgg aatcttctag  180
aaatgccagc tataacctga atagtgtta cactgaaaaa cttctgtatt cgtctctgtg   240
```

<210> SEQ ID NO 67
<211> LENGTH: 240
<212> TYPE: DNA
<213> ORGANISM: Homo sapiens

<400> SEQUENCE: 67

```
attgcttgtg agactgaggt gttcggttct tttccagctg acatcccagc atccttacgc    60
tgaagttttc atcgggcggc cacatgtgtg gactgttgac ctcaacaatc aggaggaagt   120
agaggatgca gtgaaagcaa ttttaaatca gaaggttggt tcattttatt ccactttccc   180
tcctttctaa tgtgacctga aatgtgtata aaacacatca taggtccttg tttttagcaa   240
```

<210> SEQ ID NO 68
<211> LENGTH: 240
<212> TYPE: DNA
<213> ORGANISM: Homo sapiens

<400> SEQUENCE: 68

```
attgcttgtg agactgaggt gttcggttct tttccagctg acatcccagc atccttacgc    60
tgaagttttc atcgggcggc cacatgtgtg gactgttgac ctcaacaatc aggaggaagt   120
agaggatgca gtgaaagcaa ttttaaatca gaaggttggt tcattttatt ccactttccc   180
tcctctctaa tgtgacctga aatgtgtata aaacacatca taggtccttg tttttagcaa   240
```

<210> SEQ ID NO 69
<211> LENGTH: 240
<212> TYPE: DNA
<213> ORGANISM: Homo sapiens

<400> SEQUENCE: 69

```
cgagctcttg tgacgcggac ctcagtgcca ggatggctcg gggcgagcgg cggcgccgcg    60
cagtgccggc agagggagtg cggacagccg agagggcggc tcggggaggc cccgggcgac   120
gggacggccg gggcggcggg ccgcgtagca cggctggagg agtggctctg gccgtcgtgg   180
tcctgtcttt ggccctgggt atgtcggggc gctgggtgct ggcgtggtac cgtgcgcggc   240
```

<210> SEQ ID NO 70
<211> LENGTH: 69
<212> TYPE: PRT
<213> ORGANISM: Homo sapiens

<400> SEQUENCE: 70

Met Ala Arg Gly Glu Arg Arg Arg Ala Val Pro Ala Glu Gly Val
1               5                   10                  15

Arg Thr Ala Glu Arg Ala Ala Arg Gly Gly Pro Gly Arg Arg Asp Gly
            20                  25                  30

Arg Gly Gly Gly Pro Arg Ser Thr Ala Gly Gly Val Ala Leu Ala Val
        35                  40                  45

Val Val Leu Ser Leu Ala Leu Gly Met Ser Gly Arg Trp Val Leu Ala
    50                  55                  60

Trp Tyr Arg Ala Arg
65

<210> SEQ ID NO 71
<211> LENGTH: 240
<212> TYPE: DNA
<213> ORGANISM: Homo sapiens

<400> SEQUENCE: 71

```
cgagctcttg tgacgcggac ctcagtgcca ggatggctcg gggcgagcgg cggcgccgcg        60
cagtgccggc agagggagtg cggacagccg agagggcggc tcggggaggc cccgggcgac       120
gggacggccg gggcggcggg ccgcgtagca cggctggagg agtggctctg gccgtcgtgg       180
tcctgtcttt ggccctgggt atgtcggggc gctggatgct ggcgtggtac cgtgcgcggc       240
```

<210> SEQ ID NO 72
<211> LENGTH: 69
<212> TYPE: PRT
<213> ORGANISM: Homo sapiens

<400> SEQUENCE: 72

```
Met Ala Arg Gly Glu Arg Arg Arg Ala Val Pro Ala Glu Gly Val
1               5                   10                  15
Arg Thr Ala Glu Arg Ala Ala Arg Gly Gly Pro Gly Arg Arg Asp Gly
            20                  25                  30
Arg Gly Gly Gly Pro Arg Ser Thr Ala Gly Gly Val Ala Leu Ala Val
        35                  40                  45
Val Val Leu Ser Leu Ala Leu Gly Met Ser Gly Arg Trp Met Leu Ala
    50                  55                  60
Trp Tyr Arg Ala Arg
65
```

<210> SEQ ID NO 73
<211> LENGTH: 240
<212> TYPE: DNA
<213> ORGANISM: Homo sapiens

<400> SEQUENCE: 73

```
tggcagaatc tcttgaagtc cctatgtatg tctgtagagg cttggtatag tatgacccac        60
atgcctttgc aaagccattg tgtcaggcca ggaggctgag gcccagggag agcacttggg       120
gccagaatct ctcagtagag gcaacagagc caggattggc attcataacc caggcccctg       180
aatcattctg cctttctctt ctgggatgtt gacagaggct ggtgttcagg cctgtgcctc       240
```

<210> SEQ ID NO 74
<211> LENGTH: 240
<212> TYPE: DNA
<213> ORGANISM: Homo sapiens

<400> SEQUENCE: 74

```
tggcagaatc tcttgaagtc cctatgtatg tctgtagagg cttggtatag tatgacccac        60
atgcctttgc aaagccattg tgtcaggcca ggaggctgag gcccagggag agcacctggg       120
gccagaatct ctcagtagag gcaacagagc caggattggc attcataacc caggcccctg       180
aatcattctg cctttctctt ctgggatgtt gacagaggct ggtgttcagg cctgtgcctc       240
```

<210> SEQ ID NO 75
<211> LENGTH: 180
<212> TYPE: DNA
<213> ORGANISM: Homo sapiens

<400> SEQUENCE: 75

```
tatgggtctg tgcctgtgct cctggcacac aaccctcatc gcgacttggg catcttctgg      60
ctcaatgctg cagagacctg ggttgatata tcttccaaca ctgccgggaa ggtgagagca     120
caggcacggg gaaaaggag ggagtgaagc ttccaggcct tgaggcaaat aggtatacta     180
```

<210> SEQ ID NO 76
<211> LENGTH: 180
<212> TYPE: DNA
<213> ORGANISM: Homo sapiens

<400> SEQUENCE: 76

```
tatgggtctg tgcctgtgct cctggcacac aaccctcatc gcgacttggg catcttctgg      60
ctcaatgctg cagagacctg ggttgatata tcttccaaca ctgccgggaa ggtgagagca     120
caggcacggg ggaaaaggag ggagtgaagc ttccaggcct tgaggcaaat aggtatacta     180
```

<210> SEQ ID NO 77
<211> LENGTH: 180
<212> TYPE: DNA
<213> ORGANISM: Homo sapiens

<400> SEQUENCE: 77

```
tatgggtctg tgcctgtgct cctggcacac aaccctcatt gcgacttggg catcttctgg      60
ctcaatgctg cagagacctg ggttgatata tcttccaaca ctgccgggaa ggtgagagca     120
caggcacggg ggaaaaggag ggagtgaagc ttccaggcct tgaggcaaat aggtatacta     180
```

<210> SEQ ID NO 78
<211> LENGTH: 120
<212> TYPE: DNA
<213> ORGANISM: Homo sapiens

<400> SEQUENCE: 78

```
accctgtttg ggaagatgat ggactacctg cagggctctg gggagacccc acagacagat      60
gttcgctgga tgtcagagac tggcatcatt gacgtcttcc tgctgctggg gccctccatc     120
```

<210> SEQ ID NO 79
<211> LENGTH: 39
<212> TYPE: PRT
<213> ORGANISM: Homo sapiens

<400> SEQUENCE: 79

Thr Leu Phe Gly Lys Met Met Asp Tyr Leu Gln Gly Ser Gly Glu Thr
1               5                   10                  15

Pro Gln Thr Asp Val Arg Trp Met Ser Glu Thr Gly Ile Asp Val Phe
            20                  25                  30

Leu Leu Leu Gly Pro Ser Ile
        35

<210> SEQ ID NO 80
<211> LENGTH: 120
<212> TYPE: DNA
<213> ORGANISM: Homo sapiens

<400> SEQUENCE: 80

```
accctgtttg ggaagatgat ggactacctg cagggctctg gggagacccc acagacagat      60
gttcgctgga tgtcagagac tggcatcatt gacgtcttcc tgctgctggg gccctccatc     120
```

<210> SEQ ID NO 81
<211> LENGTH: 280

```
<212> TYPE: DNA
<213> ORGANISM: Homo sapiens

<400> SEQUENCE: 81
atggtgtcca ggtctatctg cctggccaag gggaggtgag ttaaggaagg gcatggtggg      60
gaaagatggt ggaagccaaa ggaggcaaac aggacgggac ccctgtgcac tgagtgatcc     120
ggtatcttac ctcttttgtc actcacaggt gtggtatgac attcaaagct accagaagca     180
tcatggtccc cagaccctgt acctgcctgt aactctaagc agtgtgagta agcctggtct     240
ggctgccggt tccatctccc tgtaaatttc cagaagggga                            280

<210> SEQ ID NO 82
<211> LENGTH: 280
<212> TYPE: DNA
<213> ORGANISM: Homo sapiens

<400> SEQUENCE: 82
atggtgtcca ggtctatctg cctggccaag gggaggtgag ttaaggaagg gcatggtggg      60
gaaagatggt ggaagccaaa ggaggcaaac aggacgggac ccctgtgcat tgagtgatcc     120
ggtatcttac ctcttttgtc actcacaggt gtggtatgac attcaaagct accagaagca     180
tcatggtccc cagaccctgt acctgcctgt aactctaagc agtgtgagta agcctggtct     240
ggctgccggt tccatctccc tgtaaatttc cagaagggga                            280

<210> SEQ ID NO 83
<211> LENGTH: 280
<212> TYPE: DNA
<213> ORGANISM: Homo sapiens

<400> SEQUENCE: 83
atggtgtcca ggtctatctg cctggccaag gggaggtgag ttaaggaagg gcatggtggg      60
gaaagatggt ggaagccaaa ggaggcaaac aggacgggac ccctgtgcac tgagtgatcc     120
ggtatcttac ctcttttgtc actcacaggt gtggtatgac attcaaagct accagaagca     180
tcatggtccc cagaccctgt acctgcctgt aactctaagc agtgtgagta agcctggtct     240
ggctgccggt tccatctgcc tgtaaatttc cagaagggga                            280

<210> SEQ ID NO 84
<211> LENGTH: 240
<212> TYPE: DNA
<213> ORGANISM: Homo sapiens

<400> SEQUENCE: 84
ctcgccaaga gttcctgctg cgtcgattct cattctctgg caacaccctt gtctccaggt      60
aatgggtcac ccactcttcc ttggctgcct ttgctggggc ctgatccttg tggggctcc     120 cagttcactg tgctcttttc tcacattctg accttgcttt gggtctcctc cttccttctg     180
ttctgttatt tttcccctg atggacatct gcttttacca tctccagctc agcagaccct      240

<210> SEQ ID NO 85
<211> LENGTH: 240
<212> TYPE: DNA
<213> ORGANISM: Homo sapiens

<400> SEQUENCE: 85
ctcgccaaga gttcctgctg cgtcgattct cattctctgg caacacccct gtctccaggt      60
aatgggtcac ccactcttcc ttggctgcct ttgctggggc ctgatccttg tggggctcc     120
```

```
cagttcactg tgctcttttc tcacattctg accttgcttt gggtctcctc cttccttctg    180
ttttgttatt tttcccctg atggacatct gcttttacca tctccagctc agcagaccct     240
```

<210> SEQ ID NO 86
<211> LENGTH: 282
<212> TYPE: DNA
<213> ORGANISM: Homo sapiens

<400> SEQUENCE: 86

```
agtgctcgcg gggccgcggc ggagtgtacc gtgctgctct actcgctgcc attcgcccgc    60
aggtcggcgc gctcgcccac ctgagccgcg ccggggctgc gggaccgtgg dacagcgcgc   120
tcagcccagc ctaggaaaga ggcagcagtc tcagcgcgga gatggggagc gggcgaagtt   180
gacgagtctc ccgcccacgc tgcgcccctc ctgcccagag gtgcgctgcc cctccccgag   240
gtgctcgcgc gctgccctga ccccctcctg cgcgggacac cc                      282
```

<210> SEQ ID NO 87
<211> LENGTH: 294
<212> TYPE: DNA
<213> ORGANISM: Homo sapiens

<400> SEQUENCE: 87

```
ggcagtgaga ttagtgctcg cggggccgcg acggagtgta ccgtgctgct ctactcgctg    60
ccattcgccc gcaggtcggc gcgctcgccc acctgagccg cgccggggct gcgggaccgt   120
gggacagcgc gctcagccca gcctaggaaa gaggcagcag tctcagcgcg gagatgggga   180
gcgggcgaag ttgacgagtc tcccgcccac gctgcgcccc tcctgcccag aggtgcgctg   240
cccctccccg aggtgctcgc gcgctgccct gccccctcc tgcgcgggac accc          294
```

<210> SEQ ID NO 88
<211> LENGTH: 160
<212> TYPE: DNA
<213> ORGANISM: Homo sapiens

<400> SEQUENCE: 88

```
caggggctgc agccagcggt ctgtcgcgcg tgcctgtgtg cccgaggagc cgccccgggg    60
agaagacccg gcgcggagtt gttccccag ggaggatccg cagcccagcc gagggggtcg    120
ggcggcctgg ctacgcagga cccagccccg cagccgcgga                         160
```

<210> SEQ ID NO 89
<211> LENGTH: 160
<212> TYPE: DNA
<213> ORGANISM: Homo sapiens

<400> SEQUENCE: 89

```
caggggctgc agccagcggt ctgtcgcgcg tgcctgtgtg cccgaggagc cgccccgggg    60
agaagacccg gcgcggagtt gttccccag ggaggatccg cggcccagcc gagggggtcg   120
ggcggcctgg ctacgcagga cccagccccg cagccgcgga                         160
```

<210> SEQ ID NO 90
<211> LENGTH: 180
<212> TYPE: DNA
<213> ORGANISM: Homo sapiens

<400> SEQUENCE: 90

```
tatactagtt aatttcttcc attccctact acacagagag gtgagctttc aaattttgca    60
gagctctgct atcactgaat tacatttatc tgaagaaaat agtacaactt aatggattag   120
```
cttttgggtt taactgaata tatgaagaaa ttgggtctgt ctaaagagag ggtatttcat    180

<210> SEQ ID NO 91
<211> LENGTH: 180
<212> TYPE: DNA
<213> ORGANISM: Homo sapiens

<400> SEQUENCE: 91
tatactagtt aatttcttcc attccctact acacagagag gtgagctttc aaattttcca    60
gagctctgct atcactgaat tacatttatc tgaagaaaat agtacaactt aatgaattag    120
cttttgggtt taactgaata tatgaagaaa ttgggtctgt ctaaagagag ggtatttcat    180

<210> SEQ ID NO 92
<211> LENGTH: 206
<212> TYPE: DNA
<213> ORGANISM: Homo sapiens

<400> SEQUENCE: 92
gcgcggctcc aggctgggca gctgcgctgg agggccgagg gcaggggtgg ggtcgggcgt    60
ccaccctcag ggttgcgcca gggagccgga aagccgactc ccgaagttgg ggtcctggga    120
aaacttgggt cctgggttga ctgagaagcg gcggggaaag gaggcgggcc aggaggaggg    180
ggcctggcgg acgccggccg gggggc                                         206

<210> SEQ ID NO 93
<211> LENGTH: 206
<212> TYPE: DNA
<213> ORGANISM: Homo sapiens

<400> SEQUENCE: 93
gcgcggctcc aggctgggca gctgcgctgg agggccgagg gcaggggtgg ggtcgggcgt    60
ccaccctcag ggttgcgcca gggagccgga aagccgactc ccgaagttgg ggtcctggga    120
aaacttgggt cctgggttga ctgagaagcg gcggggaaag gaggcgggcc aggaggaggg    180
ggcctggcgg acgccggccg gggggc                                         206

<210> SEQ ID NO 94
<211> LENGTH: 205
<212> TYPE: DNA
<213> ORGANISM: Homo sapiens

<400> SEQUENCE: 94
gcgcggctcc aggatgggca gctgcgctgg agggccgagg gcaggggtgg ggtcgggcgt    60
ccaccctcag ggttgcgcca gggagccgga aagccgactc ccgaagttgg ggtcctggga    120
aaacttgggt cctgggttga ctgagaagcg gtgcggaaag gaggcggccc aggaggaggg    180
gcctggcgga cgccggccgg gggc                                           205

<210> SEQ ID NO 95
<211> LENGTH: 660
<212> TYPE: DNA
<213> ORGANISM: Homo sapiens

<400> SEQUENCE: 95
ttctctctcc tgtctttagg tgcatggctg cctcctaatc ccatagtcca gaggaggcat    60
ccctaggact gcgggcaagg gagccgggca agcccagggc agccttgaac cgtcccctgg    120
cctgccctcc ccggtgggg ccaggatgct gaagaagcag tctgcagggc ttgtgctgtg    180

```
gggcgctatc ctctttgtgg cctggaatgc cctgctgctc ctcttcttct ggacgcgccc    240
agcacctggc aggccaccct cagtcagcgc tctcgatggc gaccccgcca gcctcacccg    300
ggaagtgatt cgcctggccc aagacgccga ggtggagctg gagcggcagc gtgggctgct    360
gcagcagatc ggggatgccc tgtcgagcca gcggggagg gtgcccaccg cggcccctcc     420
cgcccagccg cgtgtgcctg tgaccccgc gccggcggtg attcccatcc tggtcatcgc     480
ctgtgaccgc agcactgttc ggcgctgcct ggacaagctg ctgcattatc ggccctcggc    540
tgagctcttc cccatcatcg ttagccagga ctgcgggcac gaggagacgg cccaggccat    600
cgcctcctac ggcagcgcgg tcacgcacat ccggcagccc gacctgagca gcattgcggt    660
```

<210> SEQ ID NO 96
<211> LENGTH: 660
<212> TYPE: DNA
<213> ORGANISM: Homo sapiens

<400> SEQUENCE: 96

```
ttctctctcc tgtctttagg tgcatggctg cctcctaatc ccatagtcca gaggaggcat     60
ccctaggact gcgggcaagg gagccgggca agcccagggc agccttgaac cgtcccctgg    120
cctgccctcc ctggtggggg ccaggatgct gaagaagcag tctgcagggc ttgtgctgtg    180
gggcgctatc ctctttgtgg cctggaatgc cctgctgctc ctcttcttct ggacgcgccc    240
agcacctggc aggccaccct cagtcagcgc tctcgatggc gaccccgcca gcctcacccg    300
ggaagtgatt cgcctggccc aagacgccga ggtggagctg gagcggcagc gtgggctgct    360
gcagcagatc ggggatgccc tgtcgagcca gcggggagg gtgcccaccg cggcccctcc     420
cgcccagccg cgtgtgcctg tgaccccgc gccggcggtg attcccatcc tggtcatcgc     480
ctgtgaccgc agcactgttc ggcgctgcct ggacaagctg ctgcattatc ggccctcggc    540
tgagctcttc cccatcatcg ttagccagga ctgcgggcac gaggagacgg cccaggccat    600
cgcctcctac ggcagcgcgg tcacgcacat ccggcagccc gacctgagca gcattgcggt    660
```

<210> SEQ ID NO 97
<211> LENGTH: 660
<212> TYPE: DNA
<213> ORGANISM: Homo sapiens

<400> SEQUENCE: 97

```
ttctctctcc tgtctttagg tgcatggctg cctcctaatc ccatagtcca gaggaggcat     60
ccctaggact gcgggcaagg gagccgggca agcccagggc agccttgaac cgtcccctgg    120
cctgccctcc ccggtggggg ccaggatgct gaagaagcag tctgcagggc ttgtgctgtg    180
gggcgctatc ctctttgtgg cctggaatgc cctgctgctc ctcttcttct ggacgcgccc    240
agcacctggc aggccaccct cagtcagcgc tctcgatggc gaccccgcca gcctcacccg    300
ggaagtgatt cgcctggccc aagacgccga ggtggagctg gagcggcagc gtgggctgct    360
gcagcagatc ggggatgccc tgtcgagcca gcggggagg gtgcccaccg cggcccctcc     420
cgcccagccg cgtgtgcctg tgaccccgc gccggcggtg attcccatcc tggtcatcgc     480
ctgtgaccgc agcactgttc ggcgctgcct ggacaagctg ctgcattatc ggccctcggc    540
tgagctcttc cccatcatcg ttagccagga ctgcgggcac gaggagacgg cccaggccat    600
tgcctcctac ggcagcgcgg tcacgcacat ccggcagccc gacctgagca gcattgcggt    660
```

<210> SEQ ID NO 98
<211> LENGTH: 180

```
<212> TYPE: DNA
<213> ORGANISM: Homo sapiens

<400> SEQUENCE: 98
gcctatgacc gagatttcct cgcccgcgtc tacggtgctc cccagctgca ggtggagaaa    60
gtgaggacca atgaccggaa ggagctgggg gaggtgcggg tgcagtatac gggcagggac   120
agcttcaagg ctttcgccaa ggctctgggt gtcatggatg accttaagtc gggggttccg   180

<210> SEQ ID NO 99
<211> LENGTH: 60
<212> TYPE: PRT
<213> ORGANISM: Homo sapiens

<400> SEQUENCE: 99

Ala Tyr Asp Arg Asp Phe Leu Ala Arg Val Tyr Gly Ala Pro Gln Leu
  1               5                  10                  15

Gln Val Glu Lys Val Arg Thr Asn Asp Arg Lys Glu Leu Gly Glu Val
             20                  25                  30

Arg Val Gln Tyr Thr Gly Arg Asp Ser Phe Lys Ala Phe Ala Lys Ala
         35                  40                  45

Leu Gly Val Met Asp Asp Leu Lys Ser Gly Val Pro
     50                  55                  60

<210> SEQ ID NO 100
<211> LENGTH: 180
<212> TYPE: DNA
<213> ORGANISM: Homo sapiens

<400> SEQUENCE: 100
gcctatgacc gagatttcct cgcccgcgtc tacggtgctc cccagctgca ggtggagaaa    60
gtgaggacca atgaccggaa ggagttgggg gaggttcggg tgcagtatac gggcagggac   120
agcttcaagg ctttcgccaa ggctctgggt gtcatggatg accttaagtc gggggttccg   180

<210> SEQ ID NO 101
<211> LENGTH: 120
<212> TYPE: DNA
<213> ORGANISM: Homo sapiens

<400> SEQUENCE: 101
ttatgggaga aggggacata tttgtggcca aaatgatact aaccaaaggg gcttccttgt    60
cagggcctgg tggagttggt gggtcatcgg ggctcactgc ctcctgccct tctctcctgt   120

<210> SEQ ID NO 102
<211> LENGTH: 120
<212> TYPE: DNA
<213> ORGANISM: Homo sapiens

<400> SEQUENCE: 102
ttatgggaga aggggacata tttgtggcca aaatgatact aaccaaaggg gcttccttgt    60
cagggcctgg tggagttggt gggtcatcag ggctcactgc ctcctgccct tctctcctgt   120

<210> SEQ ID NO 103
<211> LENGTH: 120
<212> TYPE: DNA
<213> ORGANISM: Homo sapiens

<400> SEQUENCE: 103
tggccatgct caaataagat gtagcaatct acctcttctt tgtctagtta cccccaaggg    60
```

```
ggcatccact ttcttgctca cctcaccagt tgcatgttct agtccttgcc agaagcacat    120

<210> SEQ ID NO 104
<211> LENGTH: 120
<212> TYPE: DNA
<213> ORGANISM: Homo sapiens

<400> SEQUENCE: 104
tggccatgct caaataagat gtagcaatct acctcttctt tgtctagtta cccccaaggg     60
ggcatccact ttcttgctca cctcagcagt tgcatgttct agtccttgcc agaagcacat    120

<210> SEQ ID NO 105
<211> LENGTH: 240
<212> TYPE: DNA
<213> ORGANISM: Homo sapiens

<400> SEQUENCE: 105
ctgcatattt agtgtcactg atgcttttta ggttgaaaat tggtgtcctc atttaccttg     60
gagagcaaaa aatccctacg aagaagctga tcataattca ttggtaagtg attttggaaa    120
actctttcta gacttgtgca tttaggtcag atgccaagtg atacatgtgg aatcttctag    180
aaatgccaac tataacctga aatagtgtta cactgaaaaa cttctgtatt cgtctctgtg    240

<210> SEQ ID NO 106
<211> LENGTH: 240
<212> TYPE: DNA
<213> ORGANISM: Homo sapiens

<400> SEQUENCE: 106
ctgcatattt agtgtcactg atgcttttta ggttgaaaat tggtgtcctc atttaccttg     60
gagagcaaaa aatccctacg aagaagctga tcataattca ttggtaagtg attttggaaa    120
actctttcta gacttgtgca tttaggtcag atgccaagtg atacatgtgg aatcttctag    180
aaatgccagc tataacctga aatagtgtta cactgaaaaa cttctgtatt cgtctctgtg    240

<210> SEQ ID NO 107
<211> LENGTH: 240
<212> TYPE: DNA
<213> ORGANISM: Homo sapiens

<400> SEQUENCE: 107
attgcttgtg agactgaggt gttcggttct tttccagctg acatcccagc atccttacgc     60
tgaagttttc atcgggcggc cacatgtgtg gactgttgac ctcaacaatc aggaggaagt    120
agaggatgca gtgaaagcaa ttttaaatca gaaggttggt tcatttttatt ccactttccc    180 tcctttctaa tgtgacctga aatgtgtata aacacatca taggtccttg ttttttagcaa    240

<210> SEQ ID NO 108
<211> LENGTH: 240
<212> TYPE: DNA
<213> ORGANISM: Homo sapiens

<400> SEQUENCE: 108
attgcttgtg agactgaggt gttcggttct tttccagctg acatcccagc atccttacgc     60
tgaagttttc atcgggcggc cacatgtgtg gactgttgac ctcaacaatc aggaggaagt    120
agaggatgca gtgaaagcaa ttttaaatca gaaggttggt tcatttttatt ccactttccc    180 tcctctctaa tgtgacctga aatgtgtata aacacatca taggtccttg ttttttagcaa    240
```

```
<210> SEQ ID NO 109
<211> LENGTH: 180
<212> TYPE: DNA
<213> ORGANISM: Homo sapiens

<400> SEQUENCE: 109
gttctctgtc cttctccttc atggtatcat gctctgtttc cacagattga gccatacatg        60
ccatatgaat ttacgtgcga ggggatgcta cagagaatca atgctttcat tgaaaaacag       120
gtaaggctta tcagaagtca gtctgtcttt gctgtgtact gcttcctgtg acgccatagg       180

<210> SEQ ID NO 110
<211> LENGTH: 180
<212> TYPE: DNA
<213> ORGANISM: Homo sapiens

<400> SEQUENCE: 110
gttctctgtc cttctccttc atggtatcat gctctgtttc cacagattga gccatacatg        60
ccatatgaat ttacgtgcga ggggatgcta cagagaatca atgctttcat tgaaaaacag       120
gtaaggctta tcagaagtca gtctgtcttt gctgtgtact gcttccggtg acgccatagg       180
```

METHODS AND COMPOSITIONS FOR PREVENTING AND TREATING A DISEASE RELATED TO GLYCAN DYSREGULATION

This application is a divisional of U.S. patent application Ser. No. 11/795,183, filed Oct. 3, 2008, which is a US national phase of International Patent Application No. PCT/US2006/001337, filed Jan. 13, 2006, which claims the benefit of the priorities of U.S. Provisional Patent Application No. 60/663,380, filed Mar. 17, 2005, and U.S. Provisional Patent Application No. 60/643,962, filed Jan. 14, 2005. Each of these applications is hereby incorporated by reference.

FIELD OF THE INVENTION

The field of the invention is compositions and methods of diagnosis, prevention, and treatment of diseases associated with glycan dysregulation, and especially as they relate to autoimmune diseases. Further aspects are directed to compositions and methods of animal models and systems for screening compounds to diagnose, treat and/or prevent such diseases.

BACKGROUND OF THE INVENTION

Multiple Sclerosis (MS) is a T-cell mediated autoimmune demyelinating disease of the central nervous system (CNS) of unknown etiology (1-3), and often presents in several clinically distinct forms. For example, relapsing remitting multiple sclerosis (MS) is characterized by T-cell induced autoimmune destruction of the myelin sheath and produces relapsing and remitting attacks of neurological dysfunction (RRMS) (1-3), which is typically followed by a secondary progressive neurodegenerative phase (SPMS), distinguished by axonal damage and neuronal loss (2). Primary progressive MS (PPMS) is similar to SPMS but lacks the initial relapsing-remitting phase.

With adult onset and partially familial relationships, causality is thought to result from complex interactions between environmental and genetic factors (1,6,7). Whole genome screens have identified a number of candidate loci associated with MS (8) and the animal model EAE (9, 10), which are typically MHC-related genes. However, non-MHC genes with strong association to MS have yet to be identified as such genes may correlate to the suspected environmental component of the MS etiology.

Golgi β1-6 N-acetylglucosaminyltransferase V (Mgat5) is a potent negative regulator of TCR signaling, T-cell proliferation, TH1 differentiation and autoimmunity (e.g., involved in EAE, a murine model of MS) (4,5). Mgat5-modified N-glycans are extended with poly-N-acetyllactosamine sequences, which are preferred ligands for galectins. Mgat5 N-glycans on T cell receptor (TCR) hind multivalent galectins, thus restricting TCR recruitment into the immune synapse (4). It should be noted that myelin-specific transgenic mice develop spontaneous CNS autoimmune demyelinating disease (11-14), but spontaneous disease secondary to physiologically-relevant gene dysfunction has not been reported.

Diagnosis of MS is often based on several individual potential markers, and most commonly focus on identification of specific nucleic acids as described in U.S. Pat. No. 6,933,119 to Leppert et al. or U.S. Pat. No. 6,001,978 to Perron. Other known diagnostic assays involve detection of specific polypeptides as described by Kline in U.S. Pat. No. 5,883,227, or on T-cell subpopulation measurement as taught in U.S. Pat. No. 4,677,061. Still further known diagnostic tests are based on tests of human motor function as described in U.S. Pat. No. 6,702,756.

Similarly, numerous chemically distinct treatment modalities for MS have been proposed. Among many other compounds, modified adenine derivatives were employed as described in U.S. Pat. No. 5,506,214, while heterocyclic phospholipids were proposed as therapeutic agents in U.S. Pat. No. 5,064,816. In yet other examples of pharmaceutical active compounds for treatment of MS, chloroquine was presented in U.S. Pat. No. 5,624,938, and aloe vera products were described as therapeutic agents in U.S. Pat. No. 5,780,453. Still further known compositions for treatment of MS include peptide analogues as taught in U.S. Pat. No. 5,948,764, estriol as described in U.S. Pat. No. 6,936,599, and various tetracycline derivatives as taught in U.S. Pat. No. 6,613,756.

As will be readily apparent to the person of ordinary skill in the art, such vast disparity in proposed active ingredients for treatment of MS and disparate markers strongly suggest a multi-factorial etiology, a potentially complex underlying metabolic system, and/or a general lack in the interplay of environmental factors and underlying genetic disposition.

Thus, while numerous compositions and methods for diagnosis, prevention, and treatment of MS and other autoimmune diseases are known in the art, all or almost all of them, suffer from one or more disadvantages. Therefore, there is still a need for improved pharmaceutical agents for treatment and chemoprevention of MS and other autoimmune diseases.

SUMMARY OF THE INVENTION

Applicants using forward and reverse genetic methods have demonstrated that a biochemical deficiency of the Golgi processing pathway leading to β1,6GlcNAc branched tetrantennary N-glycan predisposes to autoimmune diseases. A nonhuman animal model of autoimmune demyelinating diseases, more particularly multiple sclerosis (MS), was developed. Defective N-glycan processing induces spontaneous demyelinating disease in the animal model and metabolically supplementing the hexosamine pathway rescues this phenotype and inhibits disease by increasing supply of UDP-GlcNAc to MGAT5.

The invention also revealed that the PL/J mouse strain background is naturally hypomorphic for production of β1,6GlcNAc branched tetrantennary N-glycan, and is an aspect of the disease model that is additive with mutation of Mgat5.

In an aspect, the invention provides a nonhuman animal characterized by lacking one or both Mgat5 gene alleles at least in its somatic cells and displaying pathology of an autoimmune demyelinating disease, in particular a CNS demyelinating disease, more particularly MS. In aspects of the invention the incidence, severity, and/or mortality of disease in the nonhuman animal are characterized by an inverse correlation with Mgat5 N-glycan products.

In another aspect, the invention relates to methods for generating nonhuman animals of the invention. In addition, the invention relates to methods of using a nonhuman or transgenic animal of the invention as a model animal of an autoimmune demyelinating disease, in particular multiple sclerosis, comprising measuring the extent of presentation of characteristics similar to an autoimmune demyelinating disease, in particular multiple sclerosis, more particularly PPMS and SPMS.

The invention further relates to a transgenic nonhuman animal assay system which provides a model system for testing a compound that reduces or inhibits pathology associated with a condition or disease described herein. Therefore, in an aspect the present invention provides methods of screening a test compound comprising exposing a nonhuman animal of the invention to the test compound; and determining a response of the animal to the test compound. In yet another aspect, the present invention provides a method of conducting a drug discovery business using the methods for screening compounds as described herein.

Compounds identified using methods of the invention may be useful in the treatment and prophylaxis of diseases discussed herein. The compounds may also be incorporated in pharmaceutical compositions.

Applicants have also demonstrated that an autoimmune disease such as MS is associated with inherent genetic deficiencies in the N-glycan pathway that reduce β1, 6 GlcNAc branching and promote autoimmunity conditional to metabolite flux through the hexosamine pathway. N-glycan and hexosamine pathway genes are over represented at putative MS loci. Glycomic analysis led to the identification of rare MS associated single nucleotide polymorphisms (SNPs) within the N-glycan pathway.

In one aspect of the inventive subject matter, Applicants found that Mgat5 glycan expression in cells obtained from MS patients was significantly lowered as compared to normal control cells obtained from healthy patients, and that such reduction in Mgat5 glycans is correlated in a gradual manner with T-cell receptor sensitivity and susceptibility to spontaneous and induced demyelinating disease. Contrary to traditional approaches, Applicants then investigated all genes known to influence and/or regulate N-glycan biosynthesis leading to β1,6GlcNAc branched tetrantennary N-glycan, that is Mgat5-modified N-glycans, and determined if such genes indeed correlate with linkage mapping for MS. In a further step, they probed the structural glycan products of associated pathways to identify abnormal accumulation and/or depletion of the components (and their substrates and products). Based on such analysis, genes were sequenced to detect defects that would be associated with the disease, and the findings were then correlated with functional assays to identify mutations and/or polymorphisms that at least in part contribute to the disease.

Broadly stated, the invention contemplates a method comprising two, three, or more, preferably all, of the following steps:
  a) Identify one or more defective biochemical pathway using model systems and validate with human tissue.
  b) Bioinformaticly identify all potential human genes that may regulate the pathway(s) and determine whether they map to loci associated with the disease identified by traditional gene mapping techniques.
  c) Obtain relevant patient tissue and use mass spectroscopy to identify abnormal accumulation of pathway intermediates.
  d) Sequence all genes that regulate identified defects in the pathway(s) starting with genes that map disease.
  e) Validate identified mutations/polymorphisms with functional assays and determine frequency in control and patient populations.

More specifically, it was found that Mgat5 glycans are reduced on resting T cells and display reduced up-regulation following TCR stimulation. Thus, a dysregulation of Mgat5 in which Mgat5 quantity and/or activity is reduced promotes an undesirable reduction in GlcNAc branched N-glycans. Natural genetic variations that reduce expression of Mgat5-modified glycan increase sensitivity to autoimmune disease. Using the broad method as outlined above it was found that a number of genes in the N-glycan pathway required for Mgat5 glycan expression disproportionately mapped to known MS associated loci, and that limited enzymatic inhibition of these genes phenocopy MS T cells. Subsequent MALDI-TOF mass spectroscopy of glycans from patients with MS showed that patients with MS frequently have blocks at various steps in the N-glycan processing pathway. Based on these and other facts, numerous single nucleotide polymorphisms were discovered in the relevant genes that are blocked in the N-glycan pathway as defined by MALDI-TOF. Taken together, these data identify biochemical and genetic defects in the N-glycan processing pathway as significant susceptibility factors in MS and suggest that these genes are likely to be defective in other autoimmune diseases.

It is therefore contemplated that numerous diseases, and especially autoimmune diseases (e.g., MS and rheumatoid arthritis) may be diagnosed (in some cases even before first manifestation of signs and symptoms) by analyzing one or more component of implicated pathways with a gene known to be associated with a disease.

For example, genetic testing may be employed to identify mutations that functionally affect (in terms of control or level of expression as well as in terms of coding for a dysfunctional mutant protein) at least one, and more typically most or all of the components in a pathway known to include a gene that is relevant to a disease. Such testing may be done using solid-phase based testing (e.g., gene chip) for SNPs, deletions, and/or other mutations. Alternatively, genetic testing may also include rtPCR and/or quantitative PCR to determine the level of expression of the genes that are part of the pathway.

Additionally, or alternatively, testing may also include all factors that are known to regulate directly or indirectly expression of a gene in a suspect pathway. For example, vitamin D is known to affect expression of one or more genes in the Mgat5 pathway. Similarly, substrate concentrations of enzymes may be determined in a patient sample, where that enzyme is known to catalyze a rate-limiting step in the pathway.

While testing may be performed on the protein, carbohydrate, or cellular level, all analytical methods well known to the art may be employed. For example, expression levels may be quantitated using antibodies or their fragments (e.g., via ELISA, western blot, FACS, etc.), by determination of enzymatic kinetics of the polypeptides (e.g., $K_M$, kcat, etc.) or by mass spectroscopy analysis of the proteins or glycans in biological samples. Similarly, it is also contemplated that a patient sample may be analyzed for the presence or quantity of a substrate, product, and/or cofactor that is required by an enzyme that is part of the pathway under investigation. For example, the quantity of Mgat5 glycan product may be determined in patients that are diagnosed for MS.

Based on the diagnostic outcome, suitable treatment options may then be devised. For example, where diagnostic testing has revealed a low concentration of a substrate for a rate-limiting step in an enzymatic cascade, supplementation (dietary or otherwise) may be useful in treatment of a disease. Similarly, where diagnostic testing has revealed a low concentration of a compound that induces expression of a key enzyme (e.g., Vitamin D in Mgat5), supplementation (dietary or otherwise) may be useful in treatment of a disease.

Alternatively, genetic defects may also be overcome by somatic gene therapy in which a delivery vehicle (e.g., viral, or liposomal) provides one or more genes to counterbalance or correct the underlying genetic defect. Of course, where possible, the underlying genetic defect may also be treated by targeting the element that corresponds to the defect. For example, where a lack of the product of Mgat5 triggers T-cell activation, products and/or metabolites that raise Mgat5 enzyme or Mgat5 modified glycans may be employed as therapeutic agents.

Specific embodiments and applications of compositions and methods related to glycan dysregulation and associated conditions are disclosed herein.

In an aspect, the invention provides methods and compositions for treating or preventing a disease discussed herein, in particular an autoimmune disease, more particularly and rheumatoid arthritis or an autoimmune demyelinating disease, most particularly multiple sclerosis, in a subject comprising increasing in the subject expression or amount of N-glycans, in particular Mgat5 modified glycans and/or polylactosamine modified glycans. The expression or amount of N-glycans, in particular Mgat5 modified glycans or polylactosamine modified glycans, can be increased by administering N-glycans (e.g., Mgat5 modified glycans or polylactosamine modified glycans) to the subject or an agonist of a component of the N-glycan or hexosamine pathways (e.g., an agonist of an enzyme of the N-glycan pathway, especially Mgat5), or increasing expression or synthesis of a component of the N-glycan or hexosamine pathways (e.g., an enzyme of the N-glycan pathway, especially Mgat5), an acceptor for an enzyme of the N-glycan pathway (e.g., an acceptor for Mgat5), or a donor for an enzyme of the N-glycan pathway (e.g., a donor for Mgat5) or metabolites thereof.

In another aspect, the invention provides a method of treating an autoimmune disease in a subject comprising modulating one or more of N-glycan processing, an N-glycan pathway, a hexosamine pathway, and/or N-glycans (e.g., expression or levels), in particular Mgat5 glycans or polylactosamine modified glycans. In an aspect, N-glycan processing, an N-glycan pathway, a hexosamine pathway, and/or N-glycans (e.g., expression or levels), in particular Mgat5 glycans or polylactosamine modified glycans, are modulated by modulating one or more of glucosidase I (GCS1), glucosidase, alpha, neutral AB (GANAB), glucosidase II, mannosidase I (MI), Mannosidase, alpha, class 1A, member 1 (MAN1A1), mannosidase II (MII/MIIx), MGAT1, and MGAT5. In a particular embodiment, N-glycan processing, the N-glycan pathway, the hexosamine pathway, and/or N-glycans (in particular Mgat5 modified glycans), are modulated by administering a substance that raises N-glycan levels or up-regulates MGAT5 expression. In an embodiment, the method comprises increasing Mgat5 modified glycan levels by administering an agonist of Mgat5, a sugar donor for Mgat5, a metabolite of pathways for synthesis of the sugar donor or precursors thereof (e.g., a hexosamine pathway metabolite), or regulators of agonists of a sugar donor or pathway for synthesis of a sugar donor.

In another aspect, the invention provides a composition, in particular a pharmaceutical composition, comprising (a) an agonist of one or more of the following enzymes: glucosidase I (GCS1), glucosidase, alpha, neutral AB (GANAB), glucosidase II, mannosidase I (MI), Mannosidase, alpha, class 1A, member 1 (MAN1A1), mannosidase II (MII/MIIx), Mgat1, Mgat2, and Mgat5; or (b) a sugar donor for one of the enzymes in (a) or a metabolite of pathways for synthesis of the sugar donor or precursors thereof, or regulators of agonists of a sugar donor or pathway for synthesis of a sugar donor.

In an embodiment, the invention provides a composition, in particular a pharmaceutical composition, comprising an agonist of Mgat5, a sugar donor for Mgat5, a metabolite of pathways for synthesis of the sugar donor or precursors thereof, or regulators of agonists of a sugar donor or pathway for synthesis of a sugar donor.

A pharmaceutical pack or kit is provided comprising one or more containers filled with one or more of the ingredients of a composition of the invention to provide a therapeutic effect. Associated with such container(s) can be various written materials such as labels, instructions for use, or a notice in the form prescribed by a governmental agency regulating the manufacture, use or sale of pharmaceuticals, dietary supplements, or biological products, which notice reflects approval by the agency of manufacture, use, or sale for human administration.

The invention provides a method of treatment or prophylaxis of a disease disclosed herein (e.g., an autoimmune disease) based on the presence of a polymorphism in a gene of the N-glycan pathway or hexosamine pathway.

The invention also provides a method for treating a disease disclosed herein (e.g., an autoimmune disease) comprising obtaining a sample of biological material containing at least one polynucleotide from the subject; analyzing the polynucleotide to detect the presence of at least one polymorphism in a gene of the N-glycan pathway or hexosamine pathway associated with the disease; and treating the subject in such a way as to counteract the effect of any such polymorphism detected.

In an aspect of the invention, a method is provided for the prophylactic prevention of a subject with a genetic predisposition to a disease disclosed herein, (e.g., an autoimmune disease) comprising obtaining a sample of biological material containing at least one polynucleotide from the subject; analyzing the polynucleotide to detect the presence of at least one polymorphism in a gene of the N-glycan pathway or hexosamine pathway associated with the disease; and treating the subject.

The invention provides methods, reagents and kits for detecting an individual's increased or decreased risk for a disease disclosed herein, in particular autoimmune and related diseases. Therefore, the invention contemplates methods of, and products for, diagnosing and monitoring of a disease disclosed herein (e.g, an autoimmune disease, in particular an autoimmune demyelinating disease, more particularly multiple sclerosis) in a sample from a subject, comprising assaying for an alteration or change in an N-glycan (e.g., Mgat5 modified glycans or polylactosamine modified glycans), and/or in polypeptides or genes of a N-glycan pathway or hexosamine pathway (e.g, Mgat5), in a sample from the subject compared to a standard.

The invention provides a method of analyzing a polynucleotide from an individual to determine which nucleotides are present at polymorphic sites within a gene of the N-glycan pathway or hexosamine pathway. The analysis can be performed on a plurality of individuals who are tested for the presence of the disease phenotype. The presence or absence of a disease phenotype or propensity for developing a disease state can then be correlated with a base or set of bases present at the polymorphic sites in the individual tested. Alternatively, this determination step is performed in such a way as to determine the identity of the polymorphisms.

The invention relates to methods for using polymorphisms associated with a gene of the glycan pathway or hexosamine pathway to diagnose a disease disclosed herein (e.g, an autoimmune disease).

In an aspect the invention provides a method for diagnosing or aiding in the diagnosis of a disease disclosed herein (e.g., an autoimmune disease) in a subject comprising the steps of determining in the subject the genetic profile of genes of an N-glycan pathway or a hexosamine pathway (in particular genes co-localized in chromosomal regions associated with the disease), thereby diagnosing or aiding in the diagnosis of the disease.

In an aspect the invention provides a method for diagnosing a genetic susceptibility for a disease disclosed herein (e.g., an autoimmune disease) in a subject comprising obtaining a biological sample containing polynucleotides from the subject; and analyzing the polynucleotides to detect the presence or absence of a polymorphism in a gene of a N-glycan pathway or hexosamine pathway of the subject wherein a polymorphism is associated with a genetic predisposition for the disease.

The invention provides a method for screening patients comprising obtaining sequence information for one or more genes of the N-glycan pathway or hexosamine pathway from the patient and determining the identity of one or more polymorphisms in the gene(s) that is indicative of a disease disclosed herein (e.g., an autoimmune disease). The patient may be at risk of developing the disease or have the disease.

The invention also provides a method for determining the efficacy of a treatment for a particular patient with a disease disclosed herein (e.g., an autoimmune disease) based on genotype comprising (a) determining the genotype for one or more polymorphism sites in a gene of the N-glycan pathway or hexosamine pathway for a group of patients receiving a treatment; (b) sorting patients into subgroups based on their genotype; (c) identifying correlations between the subgroups and the efficacy of the treatment in the patients, (d) determining the genotype for the same polymorphism sites in the gene(s) of the particular patient and determining the efficacy of the treatment for the particular patient based on a comparison of the genotype with the correlations identified in (c).

The invention further provides a method for classifying a subject who is or is not at risk for developing a disease disclosed herein (e.g., an autoimmune disease) as a candidate for a particular course of therapy or a particular diagnostic evaluation. The invention still further provides a method for selecting a clinical course of therapy or a diagnostic evaluation to treat a subject who is or is not at risk for developing a disease disclosed herein (e.g., an autoimmune disease).

The invention also relates to a kit for carrying out a method of the invention.

These and other aspects, features, and advantages of the present invention should be apparent to those skilled in the art from the following drawings and detailed description.

DESCRIPTION OF THE DRAWINGS

The invention will now be described in relation to the drawings in which.

DETAILED DESCRIPTION OF THE INVENTION

Glossary

Figure 1:
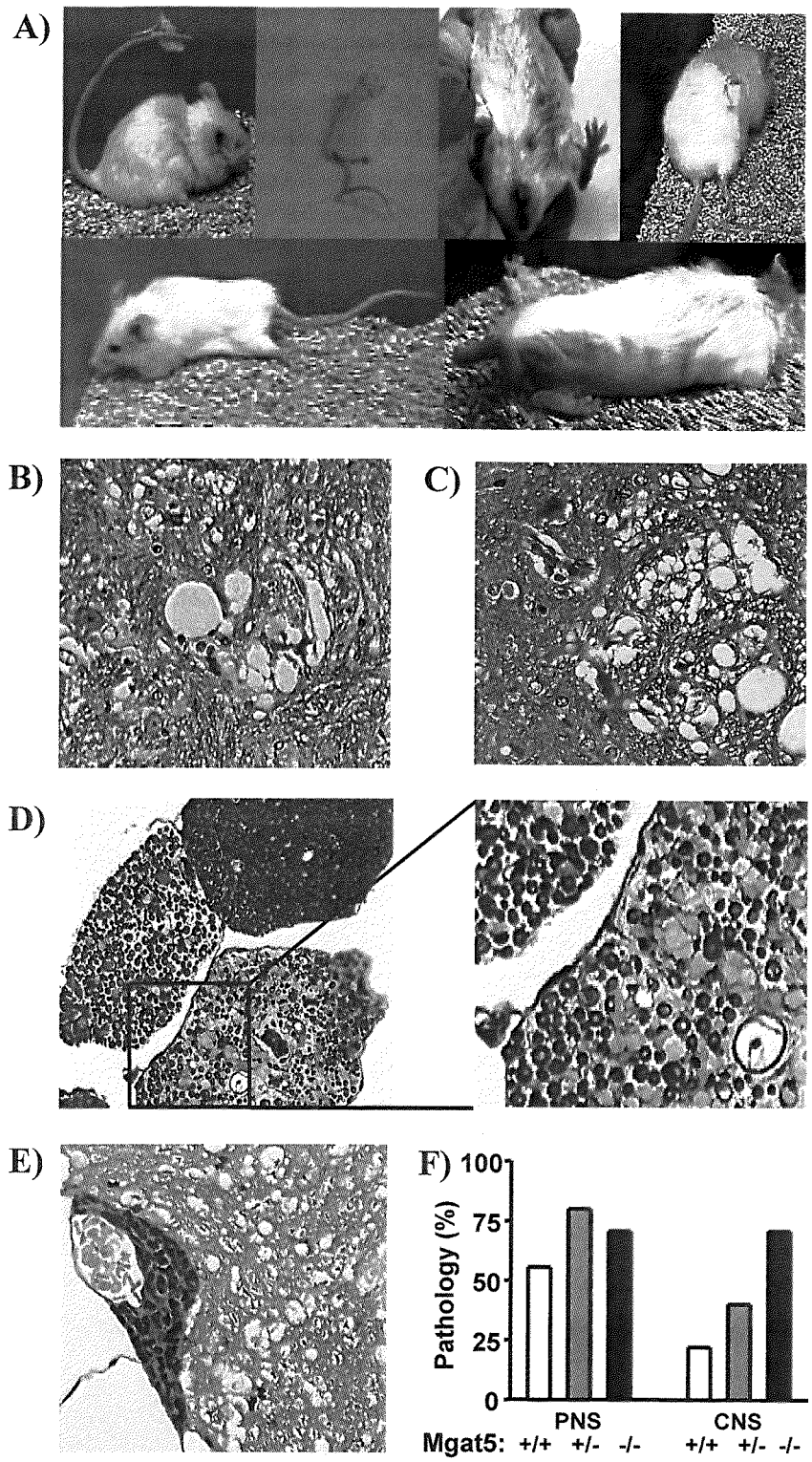
FIG. 1. Dystonic posturing and CNS/PNS Demyelinating Pathology in PL/J mice. A) Clinically affected mice were observed to have dystonic posturing of the tail, hind limbs and/or axial skeleton. B-E) Paraffin embedded sections from brainstem (B), spinal cord (C,E) and spinal roots (D) from clinically affected PL/J mice were stained with Haematoxylin & Eosin (E) or Luxol Fast Blue (B-D). Arrows point to large naked axons. F) Frequency of spinal root (PNS) and CNS pathology in Mgat5$^{+/+}$ (n=9), Mgat5$^{+/-}$ (n=10) and Mgat5$^{-/-}$ (n=17) PL/J mice (p=0.048, chi square for CNS).

In accordance with the present invention there may be employed conventional techniques of molecular biology and polynucleotide chemistry within the skill of the art. Such techniques are explained fully in the literature. See for example, Sambrook et al, Molecular Cloning: A Laboratory Manual, Third Edition (2001) Cold Spring Harbor Laboratory Press, Cold Spring Harbor, N.Y.); DNA Cloning: A Practical Approach, Volumes I and II (D. N. Glover ed. 1985); Oligonucleotide Synthesis (M. J. Gait ed. 1984); Polynucleotide Hybridization B. D. Hames & S. J. Higgins eds. (1985); Transcription and Translation B. D. Hames & S. J. Higgins eds (1984); Oligonucleotide Synthesis (M. J. Gait, ed., 1984); the series, Methods in Enzymology (Academic Press, Inc.); the series Current Protocols in Human Genetics (Dracopoli et al., eds., 1984 with quarterly updates, John Wiley & Sons, Inc.); Berger and Kimmel, Guide to Molecular Cloning Techniques, Methods in Enzymology volume 152 Academic Press, Inc., San Diego, Calif.; Current Protocols in Molecular Biology, F. M. Ausubel et al., eds., Current Protocols, a joint venture between Greene Publishing Associates, Inc. and John Wiley & Sons, Inc., (supplemented through 2004); Freshney (1994) Culture of Animal Cells, a Manual of Basic Technique, third edition, Wiley-Liss, New York and the references cited therein; Fundamental Methods Springer Lab Manual, Springer-Verlag (Berlin Heidelberg New York); and Atlas and Parks (Eds.), The Handbook of Microbiological Media (1993) CRC Press, Boca Raton, Fla., all of which are incorporated herein by reference.

Unless defined otherwise, all technical and scientific terms used herein have the same meaning as commonly understood by one of ordinary skill in the art to which this invention belongs. The following definitions supplement those in the art and are directed to the present application and are not to be imputed to any related or unrelated case. Although any methods and materials similar or equivalent to those described herein can be used in the practice for testing of the invention, particular materials and methods are described herein.

Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." The term "about" means plus or minus 0.1 to 50%, 5-50%, or 10-40%, preferably 10-20%, more preferably 10% or 15%, of the number to which reference is being made.

The terms "administering" or "administration" refers to the process by which a therapeutically effective amount of compounds or a composition contemplated herein are delivered to a patient for preventive or treatment purposes. Compounds and compositions are administered in accordance with good medical practices taking into account the patient's clinical condition, the site and method of administration, dosage, patient age, sex, body weight, and other factors known to physicians.

An "agonist" is used in its broadest sense. Agonist can include any agent that results in activation, enhancement or alteration of the presence or expression of a component of an N-glycan or hexosamine pathway (e.g., Mgat5), including polynucleotides encoding the component, in particular mRNA or DNA, or results in activation, enhancement or alteration of the presence or expression of N-glycans (e.g. Mgat5 modified glycans and/or polylactosamine modified glycans). Agonists may include proteins, peptides, polynucleotides, carbohydrates, or any other molecules that provide the desired activation, enhancement, or alteration. An agonist may activate, enhance or alter a pathway for synthesis of a sugar donor. The stimulation may be direct, or indirect, or by a competitive or non-competitive mechanism.

"Allele" refers to different sequence variants found at different polymorphic regions. The sequence variants may be single or multiple base changes, including without limitation insertions, deletions, or substitutions, or may be a variable number of sequence repeats.

"Allele frequency" refers to the frequency that a given allele appears in a population.

An "antibody" is a multi-subunit protein produced by a mammalian organism in response to an antigen challenge. Antibodies include but are not limited to monoclonal antibodies, polyclonal antibodies, antibody fragments (e.g. a Fab or (Fab)$_2$ fragments), antibody heavy chains, humanized antibodies, antibody light chains, genetically engineered single chain $F_v$ molecules (Ladner et al, U.S. Pat. No. 4,946,778), recombinantly produced binding partners, chimeric antibodies, for example, antibodies which contain the binding specificity of murine antibodies, but in which the remaining portions are of human origin, or derivatives, such as enzyme conjugates or labeled derivatives.

Antibodies including monoclonal and polyclonal antibodies, fragments and chimeras, may be prepared using methods known to those skilled in the art. Isolated native or recombinant polypeptides may be utilized to prepare antibodies. See, for example, Kohler et al. (1975) Nature 256:495-497; Kozbor et al. (1985) J. Immunol Methods 81:31-42; Cote et al. (1983) Proc Natl Acad Sci 80:2026-2030; and Cole et al. (1984) Mol Cell Biol 62:109-120 for the preparation of monoclonal antibodies; Huse et al. (1989) Science 246: 1275-1281 for the preparation of monoclonal Fab fragments; and, Pound (1998) Immunochemical Protocols, Humana Press, Totowa, N.J. for the preparation of phagemid or B-lymphocyte immunoglobulin libraries to identify antibodies.

Antibodies specific for a polypeptide may also be obtained from scientific or commercial sources. In an embodiment of the invention, antibodies are reactive against a polypeptide if they bind with a $K_a$ of greater than or equal to $10^{-7}$ M. Binding partners may be constructed utilizing recombinant DNA techniques to incorporate the variable regions of a gene which encodes a specifically binding antibody (See Bird et al., Science 242:423-426, 1988).

"Arrays", "micro arrays" or "DNA chips" refer to an array of distinct polynucleotides or oligonucleotides synthesized on a substrate, such as paper, nylon or other type of membrane, filter, chip, glass slide, or any other suitable solid support. A microarray may be prepared and used according to the methods described in U.S. Pat. No. 5,837,832, Chee et al., PCT application WO95/11995 (Chee et al.), Lockhart, D. J. et al. (1996; Nat. Biotech. 14: 1675-1680) and Schena, M. et al. (1996; Proc. Natl. Acad. Sci. 93: 10614-10619) or produced by the methods described by Brown et al., U.S. Pat. No. 5,807,522. Any number of probes, such as allele-specific oligonucleotides, may be used in an array, wherein each probe or pair of probes corresponds to a different polymorphism (e.g., SNP position). Oligonucleotides can be synthesized at designated areas on a substrate using a light-directed chemical process. Hybridization assays based on arrays rely on differences in hybridization stability of oligonucleotide probes to perfectly matched and mismatched target sequence variants. Each array can contain thousands to millions of individual synthetic DNA probes arranged in a grid-like pattern, each corresponding to a particular SNP position or allelic variant.

A "disease" refers to any disease which can be treated by the preventive and therapeutic methods and compositions of the invention including without limitation conditions or diseases associated or related to glycan dysregulation. In aspects of the invention the disease is associated or related to alterations (e.g. decrease or reduction) in a component of a N-glycan pathway or hexosamine pathway (e.g., Mgat5) or N-glycans (e.g., Mgat5 modified glycans and/or polylactosamine modified glycans). Examples of such diseases include autoimmune diseases such as insulin-dependent diabetes mellitus, autoimmune demyelinating diseases (e.g., multiple sclerosis, chronic inflammatory demyelinating polyneuropathy), rheumatoid arthritis, myasthenia gravis, systemic lupus erythematosus, autoimmune hemolytic anemia, glomerulonephritis, enhanced delayed type hypersensitivity, scleroderma, Sjogren's syndrome, Wegener's granulomatosis, polymyalgia rheumatica, temporal arteritis/giant cell arteritis, allergic conditions, hypersensitivity, Hashimoto's thyroiditis (underactive thyroid), Graves' disease (overactive thyroid), psoriasis, Celiac disease, Crohn's disease, ulcerative colitis, Guillain-Barre syndrome, Addison's disease, primary biliary sclerosis, Sclerosing cholangitis, autoimmune hepatitis, and Raynaud's phenomenon.

Autoimmune demyelinating diseases may be categorized into the diseases wherein the demyelination occurs in the central nervous system (CNS) and the diseases wherein the demyelination occurs in the peripheral nervous system (PNS). Examples of diseases associated with the demyelination in the central nervous system are acute disseminated encephalomyelitis including idiopathic acute disseminated encephalomyelitis, post infectious acute disseminated encephalomyelitis, post vaccinal acute disseminated encephalomyelitis and the like, multiple sclerosis including concentric sclerosis, neuromyelitis optica (Devic's disease), and the like. These diseases, and in particular multiple sclerosis, can undergo recurring remission and relapse and both the disease in the remission phase and the relapse phase are to be diagnosed, and treated by the methods and compositions of the invention acting as a preventive agent and a therapeutic agent, respectively. Diseases associated with demyelination in the peripheral nerve system include without limitation chronic, inflammatory demyelinating polyradiculitis/polyneuropathy (CIDP) and the like, and acute, inflammatory, demyelinating polyradiculitis/polyneuropathy (i.e., Gullian Barre Syndrome) and the like.

In certain aspects of the invention the methods and compositions are used in the treatment and prevention of diseases wherein the demyelination occurs in the central nervous system.

In aspects of the invention the disease is a Th1-mediated (cell-mediated) autoimmune diseases including: multiple sclerosis (MS), rheumatoid arthritis (RA), autoimmune thyroiditis, and uveitis, in particular MS.

The term "dysregulation" as used herein in conjunction with a component of a cell refers to any effect that alters at least one of the activity and quantity of the component in the cell as compared to a cell not affected by that dysregulation. For example, a dysregulation of Mgat5 refers to a reduction in the amount of properly expressed Mgat5 glycans in a cell (e.g., less than 70% are expressed as compared to normal), a reduction in expression or catalytic activity of Mgat5 and other enzymes in the N-glycan or hexosamine pathways upstream of Mgat5 (e.g., $K_M$ increased by 20% or $V_{MAX}$ decreased by 25%), and/or presence of Mgat5 or upstream N-glycan or hexosamine pathway enzymes in an environment that is depleted in at least one substrate, or altered in pH.

"GANAB" refers to an AB isozyme of neutral alpha-glucosidase AB that hydrolyzes the terminal 1,3-alpha-D-glucosidic links in 1,3-alpha-D-glucans, preferably the mammalian enzyme. Examples of GANAB enzymes include human GANAB (GeneID 23193; Treml Ket al, Glycobiology. 2000 May 10(5):493-502; SEQ ID NOs. 20-25), and mouse GNAB (Accession No. NM_008060; Arendt, C. W. and Ostergaard, H. L, J. Biol. Chem. 272 (20), 13117-13125 (1997)). "GANAB" includes the wild type enzyme, or part thereof, or a mutant, variant or homolog of such an enzyme. Where the context admits, the term refers to a polynucleotide or gene encoding a GANB enzyme including the coding region, non-coding region preceding (leader) and following coding regions, introns, and exons of a GANAB sequence. In particular, the GANAB gene includes the promoter.

"Genetic predisposition", "genetic susceptibility" and "susceptibility" all refer to the likelihood that a subject will develop a disease (e.g. an autoimmune disease). A subject with an increased susceptibility or predisposition will be more likely than average to develop a disease while a subject with a decreased predisposition will be less likely than average to develop the disease. A genetic variant is associated with an altered susceptibility or predisposition if the allele frequency of the genetic variant in a population with a disease or disorder varies from its allele frequency in a control population without the disease of disorder or a wild type sequence by at least about 5%, 10%, 15%, 20%, 25%, 30%, 35%, 40%, 50%, 55%, 60% or 65%.

"Genetic variant" or "variant" refers to a specific genetic variant which is present at a particular genetic locus in at least one individual in a population and that differs from the wild type.

"GCS1" refers to glucosidase I, which is the first enzyme in the N-linked oligosaccharide processing pathway. GCS1 cleaves the distal alpha-1,2-linked glucose residue from the Glc(3)-Man(9)-GlcNAc(2) oligosaccharide precursor. The term preferably refers to the mammalian enzyme. Examples of GCS1 enzymes include human GCS1 (Gene ID: 7841; Accession NO. NM_006302; Kalz-Fuller B, et al, Eur J Biochem. 1995 Jul. 15; 231(2):344-51. Erratum in: Eur J Biochem 1997 Nov. 1; 249(3):912; SEQ ID NOs. 18 and 19), and rat GCS1 (GeneID: 78947; Accession NM_031749). "GCS1" includes the wild type enzyme, or part thereof, or a mutant, variant or homolog of such an enzyme. Where the context admits, the term refers to a gene or polynucleotide encoding a GCS1 enzyme including the coding region, non-coding region preceding (leader) and following coding regions, introns, and exons of a GCS1sequence. In particular, the GCS1 gene includes the promoter.

The term "genotype" refers to the identity of alleles present in an individual or a sample. In the context of the present invention the term particularly refers to the description of the polymorphic alleles present in an individual or a sample. "Genotyping" a sample or an individual for a polymorphic marker involves determining the specific allele or the specific nucleotide carried by an individual at a polymorphic marker.

The term "haplotype" refers to the combination of alleles on one chromosome. In the context of the present invention it may refer to a combination of polymorphisms found in an individual which may be associated with a phenotype.

Figure 7:
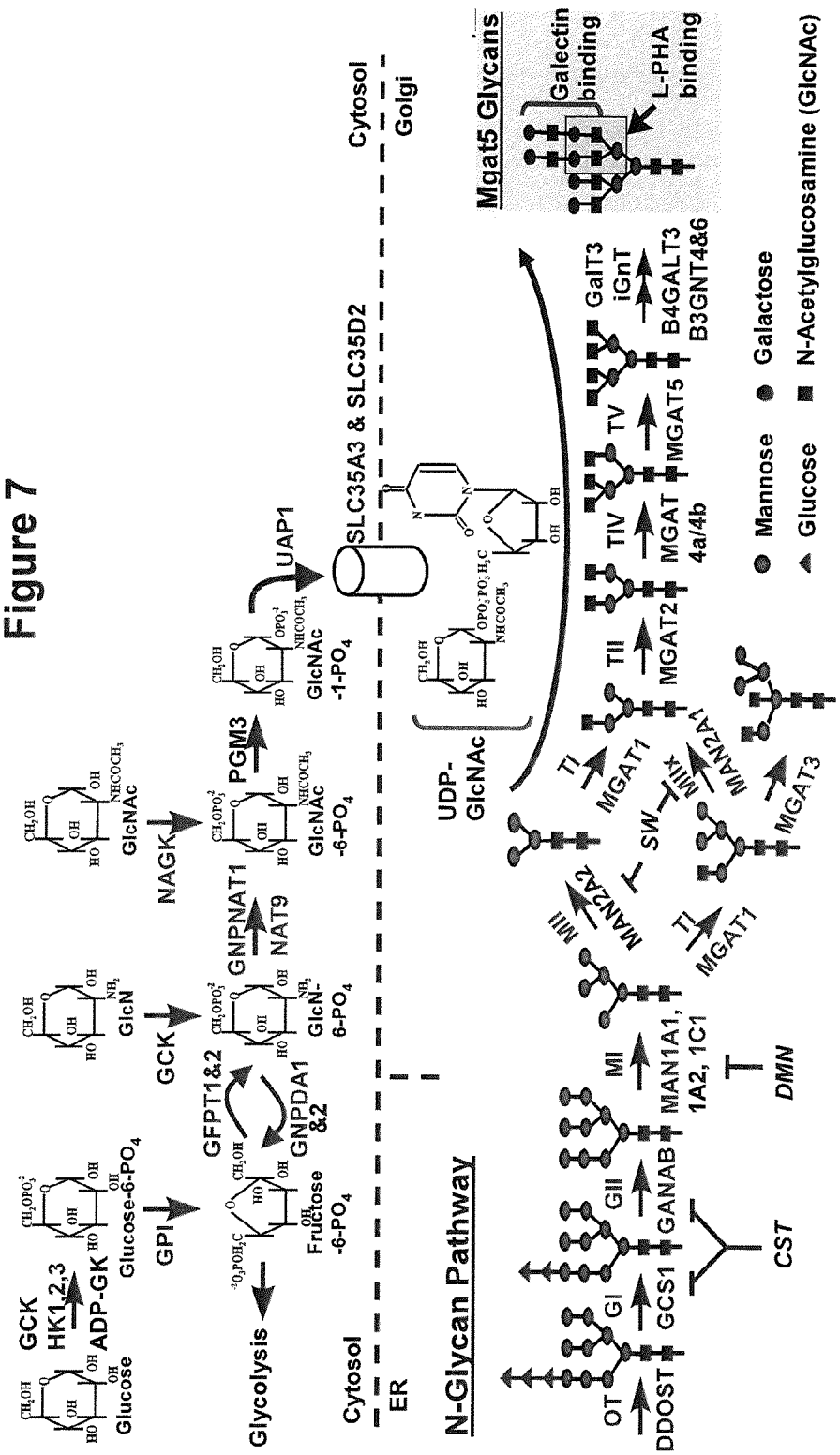
FIG. 7. Regulation of Mgat5 glycan synthesis by the N-glycan and hexosamine pathways. A) Regulation of β1, 6GlcNAc-branched N-glycan biosynthesis by the Hexosamine and N-glycan pathways. Genes shown are involved in the production and Golgi transport of UDP-GlcNAc as well as N-glycan biosynthesis to β1, 6GlcNAc-branched N-glycans with poly-N-acetyllactosamine. Those in blue localize to 18 putative MS loci (Table 4, 5). UDP-GlcNAc is required by the N-acetylglucosaminyltransferases MGAT1, 2, 3, 4 & 5 and B3GNT4 & 6. β1, 6 GlcNAc branching by MGAT5 promotes poly-N-acetyllactosamine production by B3GNT4 & 6 and the galactosyltransferase B4GALT3, forming a high affinity ligand for galectins. MGAT3 negatively regulates β1, 6GlcNAc-branched N-glycan levels by producing a bisecting GlcNAc that inhibits MII (MAN2A1), MGAT2 and MGAT5 activity (59). All enzymes are monomeric except GII (two subunits) and OT (multiple subunits), where at least one subunit, GCS1, GANAB and DDOST respectively, map to one of the 18 MS regions. B,C) mRNA isolated from Jurkat T cells at rest and stimulated with anti-CD3 antibody for the indicated doses and times was reverse transcribed into cDNA and analyzed by Taqman quantitative RT-PCR. B) Relative expression of the indicated genes at rest, normalized to MAN2A1. C) Change in mRNA expression of the indicated genes following TCR stimulation normalized to the resting state. D) Jurkat T cells were incubated with the alkaloids castanospermine (CST), deoxymannojirimycin (DMN) or swainsonine (SW) for 3 days to inhibit various steps in N-glycan processing (see A) and stained with L-PHA-FITC and analyzed by FACS. Shown is the relative change in staining compared to untreated. Error bars are S.E.M for triplicate staining.
Figure 7:
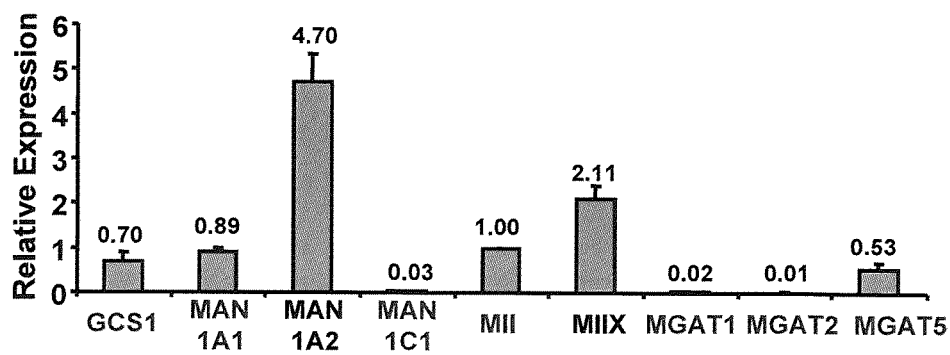
Figure 7:
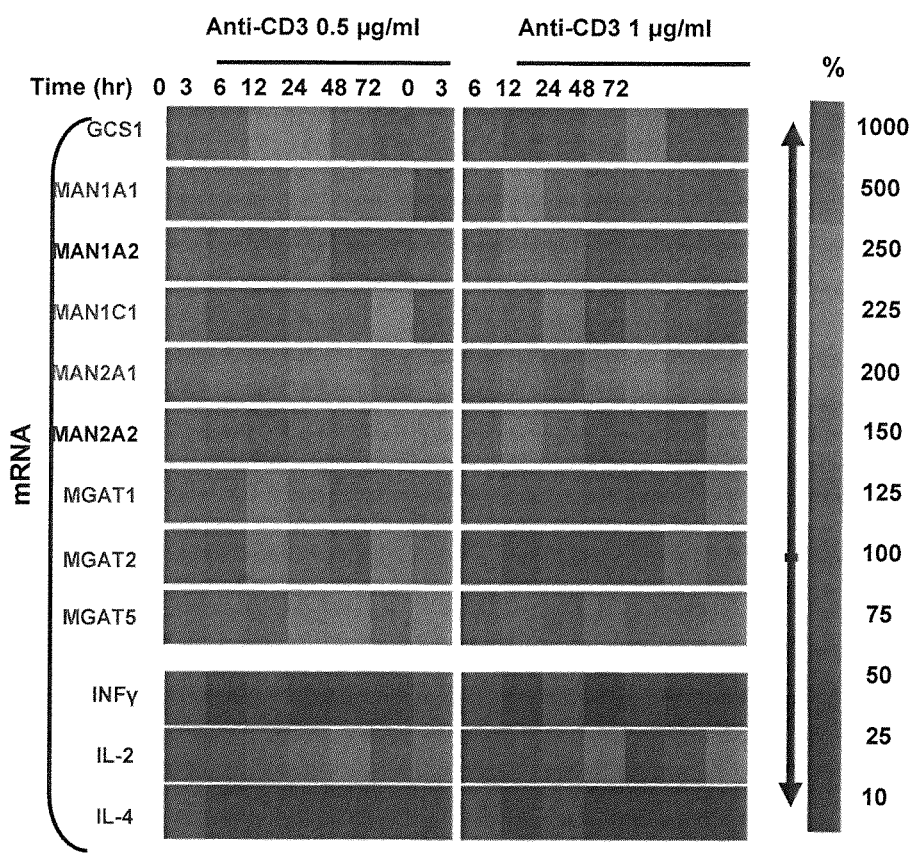
Figure 7:
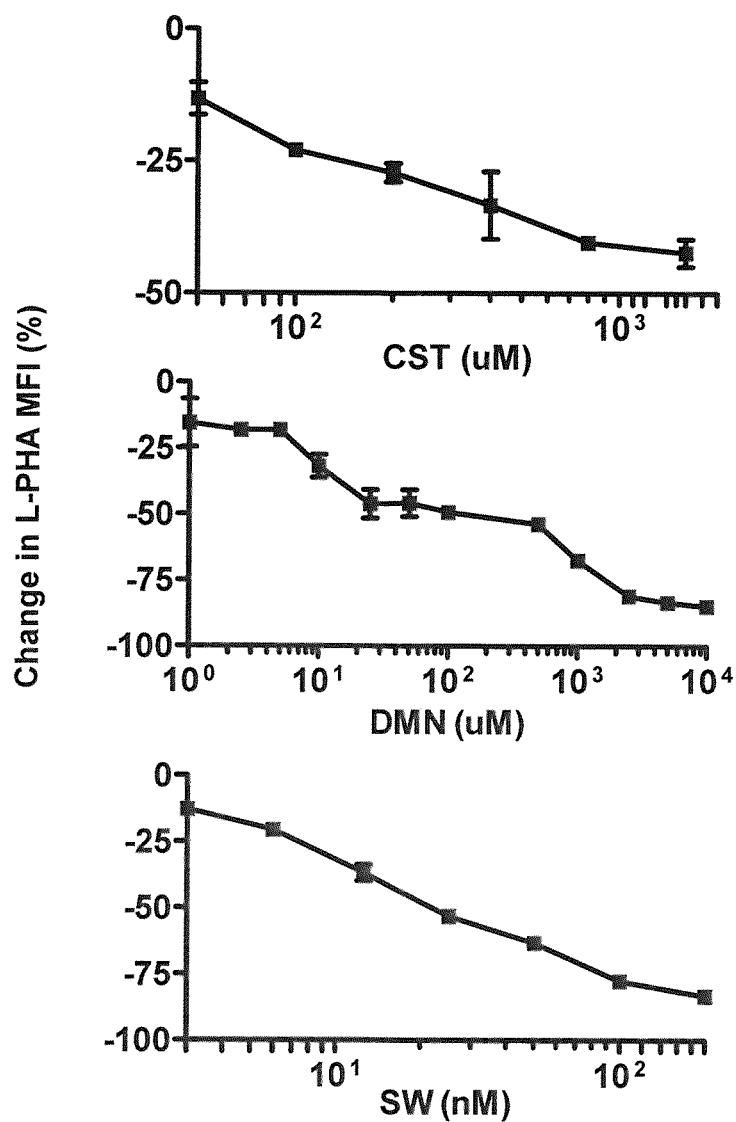

The "hexosamine pathway" refers to the pathway leading to the formation of UDP-N-acetylglucosamine (UDP-Glc-NAc) from glucose. FIG. 7A shows a schematic diagram of the hexosamine pathway.

"MAN1A1" refers to a mannosidase, alpha, class 1A, member which is a type II transmembrane protein. This protein catalyzes the removal of 3 distinct mannose residues from peptide-bound Man(9)-GlcNAc(2) oligosaccharides and belongs to family 47 of glycosyl hydrolases. The term preferably refers to the mammalian enzyme. Examples of GANAB enzymes include human MAN1A11 (Gene ID: 4121; Accession No. NM_005907; Tremblay L O and Herscovics A Glycobiology. 1999 October; 9(10):1073-8; SEQ ID NOs. 26 and 27), and canine MAN1A1 (GeneID: 431698; Accession No. AY514736). "MAN1A1" includes the wild type enzyme, or part thereof, or a mutant, variant or homolog of such an enzyme. Where the context admits, the term refers to a polynucleotide or gene encoding a MAN1A1 enzyme including the coding region, non-coding region preceding (leader) and following coding regions, introns, and exons of a MAN1A1 sequence. In particular, the MAN1A1 gene includes the promoter.

"Mgat1" refers to UDP-N-acetylglucosamine: alpha-3-D-mannoside beta-1,2-N-acetyl glucose aminyltransferase I which is a medial-Golgi enzyme essential for the synthesis of hybrid and complex N-glycans. The protein shows typical features of a type II transmembrane protein. The term preferably refers to the mammalian enzyme. Examples of Mgat1 enzymes include human Mgat1 (Gene ID: 4245; Accession NO. NM_002406; Kumar et al. Proc Natl Acad Sci USA. 1990 December; 87(24):9948-52; SEQ ID NOs. 28 and 29), and rat Mgat1 (GeneID: 81519; Accession No. NM_030861). "Mgat1" includes the wild type enzyme, or part thereof, or a mutant, variant or homolog of such an enzyme. The term "MGAT1" refers to a gene or polynucleotide encoding an Mgat1 enzyme, including the coding region, non-coding region preceding (leader) and following coding regions, introns, and exons of a MGAT1 sequence. In particular, the MGAT1 gene includes the promoter.

"Mgat2" refers to mannosyl (alpha-1,6-)-glycoprotein beta-1,2-N-acetylglucosaminyltransferase. The protein is a Golgi enzyme catalyzing an essential step in the conversion of oligomannose to complex N-glycans. The enzyme has the typical glycosyltransferase domains: a short N-terminal cytoplasmic domain, a hydrophobic non-cleavable signal-anchor domain, and a C-terminal catalytic domain. The term preferably refers to the mammalian enzyme. Examples of Mgat2 enzymes include human Mgat2 (Gene ID: 4247; Accession Nos. NM_001015883, NM_002408, NP_001015883 and NP_002399; SEQ ID NOs.32, 33, and 34), and rat Mgat2 (GeneID: 94273 Accession Nos. NM_053604 and NP_446056). "Mgat2" includes the wild type enzyme, or part thereof, or a mutant, variant or homolog of such an enzyme. The term "MGAT2" refers to a gene or polynucleotide encoding an Mgat2 enzyme, including the coding region, non-coding region preceding (leader) and following coding regions, introns, and exons of a MGAT2 sequence. In particular, the MGAT2 gene includes the promoter.

"Mgat5" refers to β1,6N-acetylglucosaminyltransferase V enzymes, preferably mammalian enzymes that catalyze the addition of N-acetylglucosamine in beta 1-6 linkage to the alpha-linked mannose of biantennary N-linked oligosaccharides. Examples of Mgat5 enzymes are found on the ExPASy proteomics server as Enzyme: 2.4.1.155, and include human Mgat5 (Saito et al, 1994; gb:d17716, sw:q09328; SEQ. ID. Nos. 30 and 31), and rat Mgat5 (Shoreibah et al 1993, J. Biol. Chem. 268: 15381-15385; gb114284, sw:q08834;). "Mgat5" includes the wild type enzyme, or part thereof, or a mutant, variant or homolog of such an enzyme. The term "MGAT5" refers to a gene or polynucleotide encoding an Mgat5 enzyme, including the coding region, non-coding region preceding (leader) and following coding regions, introns, and exons of a MGAT5 sequence. In particular, the MGAT5 gene includes the promoter. A "promoter" is a regulatory sequence of DNA that is involved in the binding of RNA polymerase to initiate transcription of a gene and is considered part of the corresponding gene.

"Mgat5 modified glycan" refers to a GlcNAβ1,6Manα1,6-branched N-glycan structure. The glycans are produced by Mgat5 which catalyzes the addition of β1,6GlcNAc to N-glycan intermediates found on newly synthesized glycoproteins transiting the medial Golgi (Cummings, R. D., et al., J. Biol. Chem., 257: 13421-13427 (1982). The glycans are elongated in trans-Golgi to produce tri (2, 2, 6) and tetra (2, 4, 2, 6) antennary N-glycans. A Mgat5 modified glycan may be substituted with for example polylactosamine (i.e. it may be a polylactosamine modified glycan). A Mgat5 modified glycan may be part of or covalently linked to a cell surface glycoprotein, including a glycoprotein of the T cell receptor complex.

"N-glycans" refers to asparagine (N)-linked oligosaccharides. All N-linked oligosaccharides are linked to the amide N in the sidechain of asparagine in the consensus sequence Asn-Xaa-Ser/Thr, where Xaa can be any amino acid besides Pro and Asp. N-glycans can be subdivided into three distinct groups called 'high mannose type', 'hybrid type', and 'complex type', with the common pentasaccharide core—Manp (alpha1,6)-(Manp(alpha1,3))-Manp(beta1,4)-GlcpNAc (beta1,4)-GlcpNAc(beta1,N)-Asn—occuring in all three groups. N-glycans include Mgat5 modified glycans and polylactosamine modified glycans.

"N-glycan pathway" refers to the pathway by which N-glycans are processed or synthesized. FIG. 7A shows a schematic diagram of the N-glycan pathway.

As used herein "nutraceutically acceptable derivative" refers to a derivative or substitute for the stated chemical species that operates in a similar manner to produce the intended effect, and is structurally similar and physiologically compatible. Examples of substitutes include without limitation salts, esters, hydrates, or complexes of the stated chemical. The substitute could also be a precursor or prodrug to the stated chemical, which subsequently undergoes a reaction in vivo to yield the stated chemical or a substitute thereof.

The term "pharmaceutically acceptable carrier, excipient, or vehicle" refers to a medium which does not interfere with the effectiveness or activity of an active ingredient and which is not toxic to the hosts to which it is administered. A carrier, excipient, or vehicle includes diluents, binders, adhesives, lubricants, disintegrates, bulking agents, wetting or emulsifying agents, pH buffering agents, and miscellaneous materials such as absorhants that may be needed in order to prepare a particular composition. Examples of carriers etc. include but are not limited to saline, buffered saline, dextrose, water, glycerol, ethanol, and combinations thereof. The use of such media and agents for an active substance is well known in the art.

"Polylactosamine modified glycan" refers to specific glycan structures comprising N-acetyllactosamine (Galβ1,4Gl-cNAc) and polymeric forms of N-acetyllactosamine, also known as poly N-acetyllactosamine or polylactosamine (Cummings, R. D. and Kornfeld, S. J. Biol. Chem., 259: 6253-6260 (19840). Preferably the polylactosamine modified glycan is an Mgat5 modified glycan substituted with poly N-acetyllactosamine. A polylactosamine modified glycan may be part of or covalently linked to a cell surface glycoprotein, including a glycoprotein of the T cell receptor complex.

"Polymorphism" or "polymorphism site" refers to a set of genetic variants at a particular genetic locus among individuals in a population. A "single nucleotide polymorphism" (SNP) occurs at a polymorphic site occupied by a single nucleotide which is the site of variation between allelic sequences. The site is usually preceded by and followed by highly conserved sequences of the allele. In the context of the present invention the term refers to a set of genetic variants in genetic loci associated with the N-glycan pathway or hexosamine pathway co-localized in chromosomal regions associated with a disease disclosed herein (e.g., an autoimmune disease, in particular MS or rheumatoid arthritis), or genetic loci associated with a disease disclosed herein or a predisposition to a disease disclosed herein. In aspects of the invention the term refers to genetic variants of a gene of the N-glycan pathway or hexosamine pathway, in particular a GCS1, GANAB, MAN1A1, MGAT1, MGAT2, and/or MGAT5 gene.

Polymorphism sites may correspond to one or more polymorphisms within or outside the promoter region of a gene of the N-glycan pathway or hexosamine pathway, in particular a GCS1, GANAB, MAN1A1, MGAT1, MGAT2, and MGAT5 gene. Other polymorphism sites, including polymorphisms linked to these polymorphisms, may be determined using methods known in the art and/or disclosed herein. It will be noted that the numerical designations of the positions of the polymorphisms within a sequence are sequence specific and the same numerical positions may be assigned different numerical designations depending on the way in which the sequence is numbered and the sequence selected. In addition, sequence variations within a population, including insertions or deletions may change the relative position of the polymorphism and subsequently the numerical designations of particular nucleotides at and around a polymorphism. Sequences for specific polymorphisms are in FIGS. 11, 22, and 23, and SEQ. ID NOs.:5, 6, 7, 8, 9 and 35-47.

The terms "polynucleotide" and "oligonucleotide" refer to single-stranded or double-stranded nucleotide polymers comprised of more than two nucleotide subunits covalently joined together. The nucleotides may comprise ribonucleotides, deoxyribonucleotides, and/or any other N-glycoside of a purine or pyrimidine base, or modified purine or pyrimidine bases, non-standard or derivatized base moieties (see for example, U.S. Pat. Nos. 6,001,611, 5,955,589, 5,844,063, 5,789,562, 5,750,3343, 5,728,525, and 5,679,785), or any combination thereof. The sugar groups of the nucleotide subunits may also comprise modified derivatives of ribose or deoxyribose, (e.g. o-methyl ribose). Subunits may be joined by phosphodiester linkages, phosphorothioate linkages, methyl phosphonate linkages or by other linkages, including rare or non-naturally occurring linkages that do not interfere with hybridization. An oligonucleotide may have uncommon nucleotides or non-nucleotide subunits.

The term "primer" refers to an oligonucleotide that has a hybridization specificity sufficient for the initiation of an enzymatic polymerization under predetermined conditions in an amplification reaction, a sequencing method, a reverse transcription method, and similar reactions and methods. For example, a primer can be a single-stranded oligonucleotide capable of acting as a point of initiation of template-directed DNA synthesis under suitable conditions (e.g., in the presence of four different nucleoside triphosphates and an agent for polymerization, such as DNA or RNA polymerase or reverse transcriptase) in an appropriate buffer and at a suitable temperature. The length of a primer will depend on its intended use but typically ranges from 15 to 30 nucleotides. A primer need not reflect the exact sequence of the template but it must be sufficiently complementary to hybridize with a template.

A "probe" refers to a polynucleotide capable of binding in a base-specific manner to a complementary strand of polynucleotide, such as a complementary strand of polynucleotide to be identified in a sample under predetermined conditions, for example in an amplification technique such as a 5'-nuclease reaction, a hybridization-dependent detection method (e.g. Southern or Northern blot), and the like.

Hybridizations with nucleic acids or probes can be generally performed under "stringent conditions". Stringent conditions are known to those skilled in the art and can be found in Current Protocols in Molecular Biology, John Wiley & Sons, N.Y. (1989), 6.3.1-6.3.6. For example, hybridizations may be performed at a salt concentration of no more than 1M and a temperature of at least 25° C. In methods of the invention for allele-specific probe hybridizations, conditions of 5×SPPE (750 mM NaCL, 50 mM NaPhosphate, 5 mM EDTA, pH 7.4) and a temperature of 25-30° C. can be used. Another example of stringent hybridization conditions are hybridization in 6× sodium chloride/sodium citrate (SSC) at about 45° C., followed by one or more washes in 0.2×SSC, 0.1% SDS at 50-65° C. However, one skilled in the art could readily substitute other compositions of equal suitability. Examples of moderate to low stringency hybridization conditions are also well known in the art.

Probes may be immobilized on a solid support by covalent bonding, absorption, hydrophobic and/or electrostatic interaction, direct synthesis on a solid support, and the like. The probes may be labeled with labels such as radioactive isotopes, enzymes, in particular enzymes capable of acting on a chromogenic, fluorescent or luminescent substrate (e.g. peroxidase or alkaline phosphatase), chromophoric chemical compounds, acridinium esters (see U.S. Pat. No. 5,185, 439), substrates, cofactors, inhibitors, magnetic particles, chromogenic, fluorigenic or luminescent compounds, analogues of nucleotide bases, and ligands (e.g., biotin). Examples of fluorescent compounds include fluorescein, carboxyfluorescein, tetrachloro fluorescein, hexachlorofluorescein, Cy3, Cy3.5, Cy5, tetramethylrhodamine, rhodamine and its derivatives (e.g. carboxy-X-rhodamine), and Texas Red. Examples of luminescent compounds include luciferin, and 2,3-dihydrophthalazinediones (e.g. luminol). Examples of radioactive isotopes include $^{3}H$, $^{35}S$, $^{32}P$ $^{125}I$, $^{57}Co$, and $^{14}C$. Many labels are commercially available and can be used in the context of the present invention.

Probes and primers can be modified with chemical groups to enhance their performance or facilitate the characterization of hybridization or amplification products. In an aspect of the invention, the probes or primers have modified backbones (e.g., phosphorothioate or methylphosphonate groups) which render the oligonucleotides resistant to the nucleolytic activity of certain polymerases or to nucleases. Non-nucleotide linkers (e.g. EP No. 0313219) that do not interfere with hybridization or elongation of the primer can also be incorporated in the polynucleotide chain. A 3' end of an amplification primer or probe may be blocked to prevent initiation of DNA synthesis (see WO 94/03472), or the 5' end may be modified so that it is resistant to the 5'exonuclease activity present in some polymerases.

Oligonucleotides that are primer or probe sequences may comprise DNA, RNA, or polynucleotide analogs including uncharged polynucleotide analogs such as peptide polynucleotides (PNAs) (see PCT Published Application No. WO92/20702; Nielsen et al, Science 254, 1497-1500, 1991), morpholino analogs (see U.S. Pat. Nos. 5,185,444, 5,034, 506, and 5,142,047), and N3'-P5'-phosphoamidate (PA) analogs (see for example, U.S. Pat. No. 6,169,170).

Polynucleotides and oligonucleotides may be prepared using methods known in the art, including synthetic, recombinant, ex vivo generation, or a combination thereof, as well as conventional purification methods. For example, polynucleotides and oligonucleotides can be synthesized using nucleotide phosphoramidite chemistry, in particular using instruments available from Applied Biosystems, Inc (Foster City, Calif.), DuPont (Wilmington, Det) or Milligen (Bedford, Mass.).

When desirable, polynucleotides and oligonucleotides may be labeled using methods known in the art (see U.S. Pat. Nos. 5,464,746; 5,424,414; and 4,948,882). Polynucleotides and oligonucleotides, including labeled or modified polynucleotides and oligonucleotides, can also be obtained from commercial sources. For example, polynucleotides and oligonucleotides can be ordered from QIAGEN (http://oligos.qiagen.com), The Midland Certified Reagent Company (www.mcrc.com), and ExpressGen Inc (Chicago, Ill.).

The term "sample" and the like mean a material known or suspected of expressing or containing a component of a N-glycan or hexosamine pathway (in particular, an enzyme of a N-glycan or hexosamine pathway such as Mgat5), N-glycans (e.g., Mgat5 modified glycans or polylactosamine modified glycans), a polynucleotide comprising a disease-associated polymorphism (e.g., SNP-containing polynucleotide of the invention), a polypeptide variant of the invention, or a gene of the N-glycan pathway or hexosamine pathway, in particular a GCS1, GANAB, MAN1A1, MGAT1, MGAT2, and/or MGAT5 gene.

A test sample can be used directly as obtained from the source or following a pretreatment to modify the character of the sample. The sample can be derived from any biological source, such as tissues, extracts, or cell cultures, including cells, cell lysates, and physiological fluids, such as, for example, whole blood, plasma, serum, saliva, ocular lens fluid, cerebral spinal fluid, sweat, urine, milk, ascites fluid, synovial fluid, peritoneal fluid and the like. The sample can be treated prior to use, such as preparing plasma from blood, diluting viscous fluids, and the like. Methods of treatment can involve filtration, distillation, extraction, concentration, inactivation of interfering components, the addition of reagents, and the like. Polynucleotides may be isolated from samples and utilized in the methods of the invention. Thus a test sample may be a polynucleotide sequence corresponding to the sequence in the test sample, that is all or part of the region in the sample polynucleotide may first be amplified using a conventional technique such as PCR, before being analyzed for sequence variation. A polynucleotide sample may comprise RNA, mRNA, DNA, cDNA, genomic DNA, and oligonucleotides, and may be double-stranded or single-stranded. The polynucleotides may be sense strand, the non-coding regions, and/or the antisense strand, and can include all or a portion of the coding sequence of the gene, and may further comprise additional non-coding regions such as introns, and non-coding sequences including regulatory sequences (e.g. a promoter). A polynucleotide can be fused to a marker sequence, for example, a sequence that is used to purify the polynucleotide.

In embodiments of the invention the sample is a mammalian sample, preferably human sample. In another embodiment the sample is a physiological fluid.

The term "sequencing" refers to a method for determining the order of nucleotides in a polynucleotide. Methods for sequencing polynucleotides are well known in the art and include the Sanger method of dideoxy-mediated chain termination (for example, see. Sanger et al., Proc. Natl. Acad. Sci. 74:5463, 1977; "DNA Sequencing" in Sambrook et al. (eds), Molecular Cloning: A Laboratory Manual (Second Edition), Plainview, N.Y.: Cold Spring Harbor Laboratory Press (1989)); the Maxam-Gilbert chemical degradation of DNA (Maxam and Gilbert, Methods Enzymol. 65:499 (1980); and "DNA Sequencing" in Sambrook et al., supra, 1989); and automated methods, for example, mass spectrometry methods.

The terms "subject", "individual", or "patient" refer to an animal including a warm-blooded animal such as a mammal, which is afflicted with or suspected of having or being pre-disposed to, or at risk of developing as disease disclosed herein especially an autoimmune disease, in particular MS or rheumatoid arthritis. Mammal includes without limitation any members of the Mammalia. In general, the terms refer to a human. The terms also include animals bred for food, pets, or sports, including domestic animals such as horses, cows, sheep, poultry, fish, pigs, and goats, cats, dogs, zoo animals, apes (e.g. gorilla or chimpanzee), and rodents such as rats and mice. The methods herein for use on subjects/individuals/patients contemplate prophylactic as well as curative use. Typical subjects for treatment include persons susceptible to, suffering from or that have suffered a disease discussed herein especially an autoimmune disease or related disease, in particular MS or rheumatoid arthritis.

"Synergistic" means a greater pharmacological or therapeutic effect with the use of a multi-component composition or combination therapy (e.g. GlcNAc and uridine or uracil) than with the use of one of the compounds alone. This synergistic effect can work through either similar or different mechanisms or pathways of action. One advantage of a combination therapy with a synergistic effect is that standard dosages can be used for a greater therapeutic effect than expected from the addition of the effect of one or two compounds as the case may be administered alone; or alternatively lower dosages or reduced frequency of administration of the therapeutic compound(s) may be used to achieve a better therapeutic effect.

"Therapeutically effective amount" relates to the amount or dose of an active compound, composition, or combination therapy of the invention that will lead to one or more desired beneficial effects. A therapeutically effective amount of a compound, composition, or preparation can vary according to factors such as the disease state, age, sex, and weight of the individual, and the ability of the substance to elicit a desired response in the individual. Dosage regime may be adjusted to provide the optimum therapeutic response (e.g. beneficial effects). For example, several divided doses may be administered daily or the dose may be proportionally reduced as indicated by the exigencies of the therapeutic situation.

The terms "trait" and "phenotype", used interchangeably herein, refer to any visible, detectable, or otherwise measurable property of an organism such as symptoms of, or susceptibility to a disease disclosed herein (e.g., an autoimmune disease). Generally, the terms are used herein to refer to symptoms, or susceptibility to a disease disclosed herein (e.g., an autoimmune disease), or to an individual's response to an agent acting on a disease, or to symptoms of, or susceptibility to side effects to an agent acting on a disease.

The term "treating" refers to reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a compound or composition of the present invention to a subject that is not at the time of administration afflicted with the disease. "Preventing" also refers to preventing the recurrence of a disease, the relapse of a disease after remission, or of one or more symptoms associated with such disease. The terms "treatment" and "therapeutically," refer to the act of treating, as "treating" is defined above.

DESCRIPTION OF EMBODIMENTS

Animal Model

The invention provides a nonhuman animal characterized by lacking one or both Mgat5 gene alleles at least in its somatic cells and displaying pathology of an autoimmune demyelinating disease, in particular a CNS demyelinating disease, more particularly MS. In aspects of the invention the incidence, severity, and/or mortality of disease in the nonhuman animal are characterized by an inverse correlation with Mgat5 products.

The invention also provides a nonhuman animal that is usable as an animal model presenting CNS pathology or PNS pathology similar to chronic MS plaques or CIDP. In an aspect, the invention provides a nonhuman animal that is usable as an animal model presenting a clinical condition typical of primary progressive multiple sclerosis (PPMS) and secondary progressive multiple sclerosis (SPMS) in screening a remedy for demyelinating autoimmune diseases, more particularly multiple sclerosis. In an aspect, the invention provides a nonhuman animal that is usable as an animal model presenting a clinical condition typical of primary progressive multiple sclerosis (PPMS) and secondary progressive multiple sclerosis (SPMS) in screening a remedy to prevent the neurodegeneration in MS.

Another aspect of the invention provides a nonhuman animal presenting pathological conditions of human Chronic Inflammatory Demyelinating Polyneuropathy (CIDP).

In a further aspect, the present invention provides a transgenic knockout rodent, in particular a mouse or rat, lacking one or both Mgat5 gene alleles at least in its somatic cells and displaying pathology of a CNS autoimmune demyelinating disease.

In an embodiment a transgenic knockout rodent is provided (e.g. PL/J mice) which are hypomophic for Mgat5-modified N-glycans).

In embodiments of the present invention, nonhuman animals are provided with somatic and germ cells having a functional disruption of one, or preferably both, alleles of an endogenous Mgat5 gene. Accordingly, the invention provides viable nonhuman animals having a mutated or deleted Mgat5 gene and thus lacking or substantially lacking Mgat5 activity. Animals of the invention can display a chronic and slowly progressive clinical course without relapses or recovery and involuntary movements in a Mgat5 gene dose dependent manner. The involuntary movements can include tremor and/or focal dystonic posturing of the tail, hindlimbs and/or spine, and/or paroxysmal episodes of dystonia common in patients with MS.

In some embodiments, the nonhuman animals display pathology similar to chronic MS plaques which can be characterized by mononuclear cells admixed with myelin debris centered around blood vessels, gliosis, neuronophagia, axonal swelling (spheroids) and axonal degeneration. Axonal pathology may also be observed in otherwise normal appearing CNS white matter. PNS pathology can be characterized by multi-focal spinal root demyelination with naked and swollen axons. Neuronal bodies with prominent central chromatolysis may be observed in the spinal cord, consistent with anterograde reaction to peripheral damage. Myokymia, positive sharp waves and delayed spinal root nerve condition velocity may be typical of physiologic spinal root demeylination and the human PNS autoimmune demyelinating disease Chronic Inflammatory Demyelinating Polyneuropathy (CIDP).

A nonhuman animal of the invention is exemplified by mice lacking one or both alleles of Mgat5 as more particularly described in the Examples herein.

The present invention further relates to a method for generating nonhuman animals of the invention. Any method for generating knockout animals is contemplated by the present invention. Such methods include pronuclear microinjection, retrovirus mediated gene transfer into germ lines, gene targeting in embryonic stem cells, electroporation of embryos, and sperm-mediated gene transfer. In certain embodiments, the present invention provides methods for generating a transgenic animal comprising crossing a first Mgat5 knockout EAE resistant animal and a second EAE sensitive animal. In some rodent embodiments (e.g. mice) the first animal is a 129/Sv knockout animal and the second animal is a PL/J animal strain. A method for generating a knockout animal can further comprise backcrossing the progeny onto an EAE sensitive animal.

The invention provides a method of using a nonhuman or transgenic animal of the invention as a model animal of an autoimmune demyelinating disease, in particular multiple sclerosis, comprising measuring the extent of presentation of characteristics similar to an autoimmune demyelinating disease, in particular multiple sclerosis, more particularly PPMS and SPMS. The characteristics may include the display of clinical condition and pathology described herein, and/or the amount of Mgat5 modified glycans on T cells obtained from the animals.

The invention provides a transgenic nonhuman animal assay system which provides a model system for testing a compound that reduces or inhibits pathology associated with a condition or disease described herein, comprising:
(a) administering the compound to a transgenic nonhuman animal of the invention; and
(b) determining whether said compound reduces or inhibits the pathology in the transgenic non-human animal relative to a transgenic non-human animal of step (a) which has not been administered the agent.

The compound may be useful in the treatment and prophylaxis of diseases discussed herein. The compounds may also be incorporated in a pharmaceutical composition, and may optionally comprise a pharmaceutically acceptable carrier, vehicle or excipient.

The present invention also provides methods of screening a test compound comprising exposing a nonhuman animal of the invention to the test compound; and determining a response of the animal to the test compound. In certain embodiments, a change in response compared to an animal not exposed to the test compound indicates a response to the compound. In other embodiments, the animals (cells, tissues, or organs) are examined directly and compared to a wild-type animal or animal not exposed to the test compound.

In embodiments of the invention, the compound tested is a candidate compound for treatment or prevention of a condition described herein, in particular an autoimmune demyelinating disease, in particular multiple sclerosis. In other embodiments, the compound is a known compound for the treatment or prevention of a condition described herein, in particular an autoimmune demyelinating disease, in particular multiple sclerosis.

The present invention provides a method of conducting a drug discovery business comprising:
(a) providing methods for screening compounds as described herein;
(b) conducting therapeutic profiling of compounds identified in step (a), or further analogs thereof, for efficacy and toxicity in animals; and
(c) formulating a pharmaceutical preparation including one or more compounds identified in step (b) as having an acceptable therapeutic profile.

In certain embodiments, the subject method can also include a step of establishing a distribution system for distributing the pharmaceutical preparation for sale, and may optionally include establishing a sales group for marketing the pharmaceutical preparation.

Yet another aspect of the invention provides a method of conducting a drug discovery business comprising:
(a) providing methods for screening compounds described herein;
(b) (optionally) conducting therapeutic profiling of compounds identified in step (a) for efficacy and toxicity in animals; and
(c) licensing, to a third party, the rights for further drug development and/or sales for agents identified in step (a), or analogs thereof.

The method may further comprise the steps of preparing a quantity of a compound and/or preparing a pharmaceutical composition comprising the compound.

Polynucleotides

The present invention relates to isolated polynucleotides or oligonucleotides that contain one or more SNPs of a gene of a N-glycan or hexosamine pathway. The present invention further provides isolated polynucleotides that encode the variant protein. Such polynucleotides or oligonucleotides will consist of, consist essentially of, or comprise one or more SNPs of the present invention. The polynucleotides can have additional nucleic acid residues, such as nucleic acid residues that are naturally associated with it or heterologous nucleotide sequences.

An isolated SNP-containing polynucleotide comprises a SNP of the present invention separated from other nucleic acid present in the natural source of the nucleic acid. Generally, the isolated SNP-containing polynucleotide, as used herein, will be comprised of one or more SNP positions disclosed by the present invention with flanking nucleotide sequence on either side of the SNP positions. A flanking sequence may comprise about 300 bases, 100 bases, 50 bases, 30 bases, 15 bases, 10 bases, or 4 bases on either side of a SNP position for detection reagents or as long as the entire protein encoding sequence if it is to be used to produce a protein containing a coding variants. A polynucleotide or oligonucleotide is generally isolated from remote and unimportant flanking sequences and is of appropriate length such that it can be subjected to the specific manipulations or uses described herein, including recombinant expression, preparation of probes and primers for the SNP position, and other uses specific to the SNP-containing polynucleotides or oligonucleotides.

An isolated polynucleotide, such as a cDNA comprising a SNP of the present invention is generally substantially free of other cellular material, or culture medium when produced by recombinant techniques, or chemical precursors or other chemicals when chemically synthesized. A polynucleotide comprising a SNP can be fused to other coding or regulatory sequences and still be considered isolated. For example, a recombinant DNA contained in a vector or maintained in heterologous host cells is considered isolated. In vivo or in vitro RNA transcripts of an isolated SNP-containing DNA molecules is considered an isolated RNA. An isolated SNP-containing polynucleotide can be in the form of RNA, such as mRNA, or in the form of DNA, including cDNA and genomic DNA obtained by cloning or produced by chemical synthetic procedures or by a combination thereof. Isolated SNP-containing polynucleotides can be double-stranded or single-stranded; single-stranded polynucleotides can be the coding strand (sense strand) or the non-coding strand (antisense strand).

Polynucleotides that hybridize under stringent conditions to the isolated SNP-containing polynucleotides are also contemplated. For example, hybridization conditions may be selected so that nucleotide sequences encoding a peptide at least 60-70%, 80%, 90% or more homologous to each other typically remain hybridized to each other.

An aspect of the invention provides polynucleotides, for example, polynucleotides comprising one or more novel polymorphisms in a gene associated with a disease disclosed herein (e.g. an autoimmune disease, in particular) and/or oligonucleotides useful for detecting such polymorphisms. Accordingly, one embodiment of the invention is an isolated polynucleotide molecule comprising a portion of a gene, its complement, and/or a variant thereof. In particular aspects, the variant comprises a polymorphism identified herein. More particularly, the variant comprises at least one of the polymorphisms identified herein to be associated with a disease disclosed herein (e.g. an autoimmune disease, in particular MS). In a further embodiment, the polynucleotide molecule comprises or consists of a primer and/or a probe specific to at least one of the polymorphisms identified in a gene of the N-glycan pathway or hexosamine pathway, in particular a GCS1, GANAB, MAN1A1, MGAT1, MGAT2, and/or MGAT5 gene (e.g., those identified herein to be associated with disease disclosed herein, in particular an autoimmune disease, more particularly MS).

Figure 11:
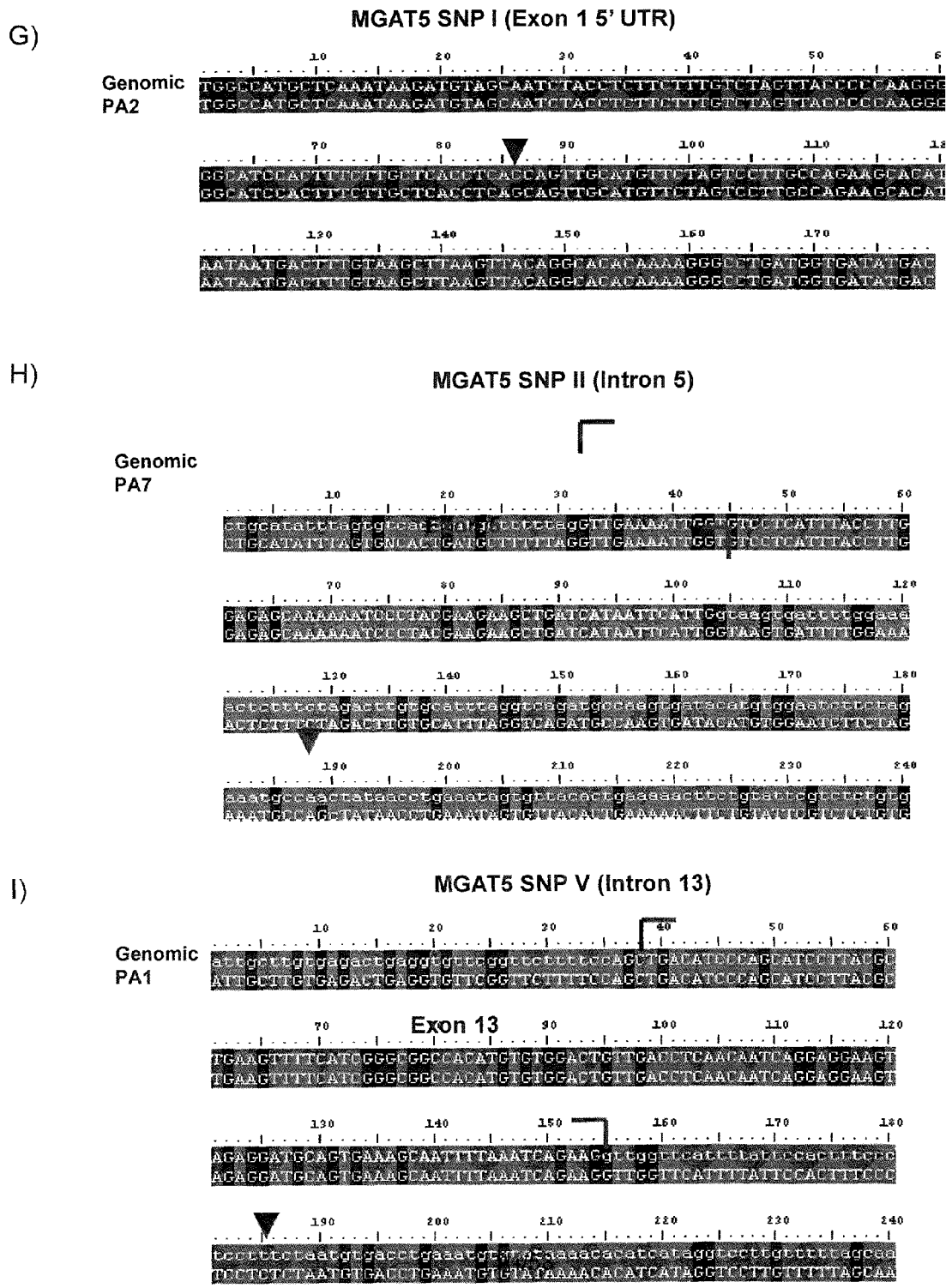
FIG. 11. Rare SNPs in GCS1, GCS1, GANAB, MAN1A1, MGAT1 and MGAT5 associated with MALDI-TOF Glycan profile. A-I) Sequences are shown for the indicated SNPs with small, unlabeled boxes defining coding SNPs, arrow heads defining UTR and intronic SNPs and exon/intron junctions as indicated. A) GCS1 SNP 1 (Exon 1): The DNA sequence for the genomic sequence of GCS1 Exon I is shown in SEQ ID NO: 48. The corresponding amino acid sequence is shown in SEQ ID NO: 49. The DNA sequence for multiple sclerosis patient PA3 GCS1 Exon I (containing SNP I) is shown in SEQ ID NO: 50. The corresponding amino acid sequence is shown in SEQ ID NO: 51. B) GANAB SNP III (Exon 11): The DNA sequence for the genomic sequence of GANAB Exon 11 is shown in SEQ ID NO: 52. The corresponding amino acid sequence is shown in SEQ ID NO: 53. The DNA sequence for patient PA3 GANAB Exon 11 (containing SNP III) is shown in SEQ ID NO: 54. The corresponding amino acid sequence is unchanged and is shown in SEQ ID NO: 53. C) GANAB SNP IV (Intron 21): The DNA sequence for the genomic sequence of GANAB Intron 21 is shown in SEQ ID NO: 55. The DNA sequence for patient PA1 GANAB Intron 21 (containing SNP IV) is shown in SEQ ID NO: 56. D) GANAB SNP V (Intron 23): The DNA sequence for the genomic sequence of GANAB Intron 23 is shown in SEQ ID NO: 57. The DNA sequence for patient PA3 GANAB Intron 23 (containing SNP V) is shown in SEQ ID NO: 58. E) MAN1A1 SNP IX and X (Exon 13 3' UTR): The DNA sequence for the genomic sequence of MAN1A1 Exon 13 3' UTR is shown in SEQ ID NO: 59. The DNA sequence for patient PAJ MAN1A1 Exon 13 3' UTR (containing SNP IX and X) is shown in SEQ ID NO: 60. F) MGAT1 SNP VI (Exon 2 3' UTR): The DNA sequence for the genomic sequence of MGAT1 Exon 2 3' UTR is shown in SEQ ID NO: 61. The DNA sequence for patient PA7 MGAT1 Exon 2 3' UTR (containing SNP VI) is shown in SEQ ID NO: 62. G) MGAT5 SNP I (Exon 1 5' UTR): The DNA sequence for the genomic sequence of MGAT5 Exon I 5' UTR is shown in SEQ ID NO: 63. The DNA sequence for patient PA2 MGAT5 Exon 1 5' UTR (containing SNP I) is shown in SEQ ID NO: 64. H) MGAT5 SNP II (Intron 5): The DNA sequence for the genomic sequence of MGAT5 Intron 5 is shown in SEQ ID NO: 65. The DNA sequence for patient PA7 MGAT5 Intron 5 (containing SNP II) is shown in SEQ ID NO: 66. I) MGAT5 SNP V (Intron 13): The DNA sequence for the genomic sequence of MGAT5 Intron 13 is shown in SEQ ID NO: 67. The DNA sequence for patient PA1 MGAT5 Intron 13 (containing SNP V) is shown in SEQ ID NO: 68. The sequences referred to above as "exon" or "intron" are used for convenience and may refer to more or less than the full length exon or intron sequences.
Figure 22:
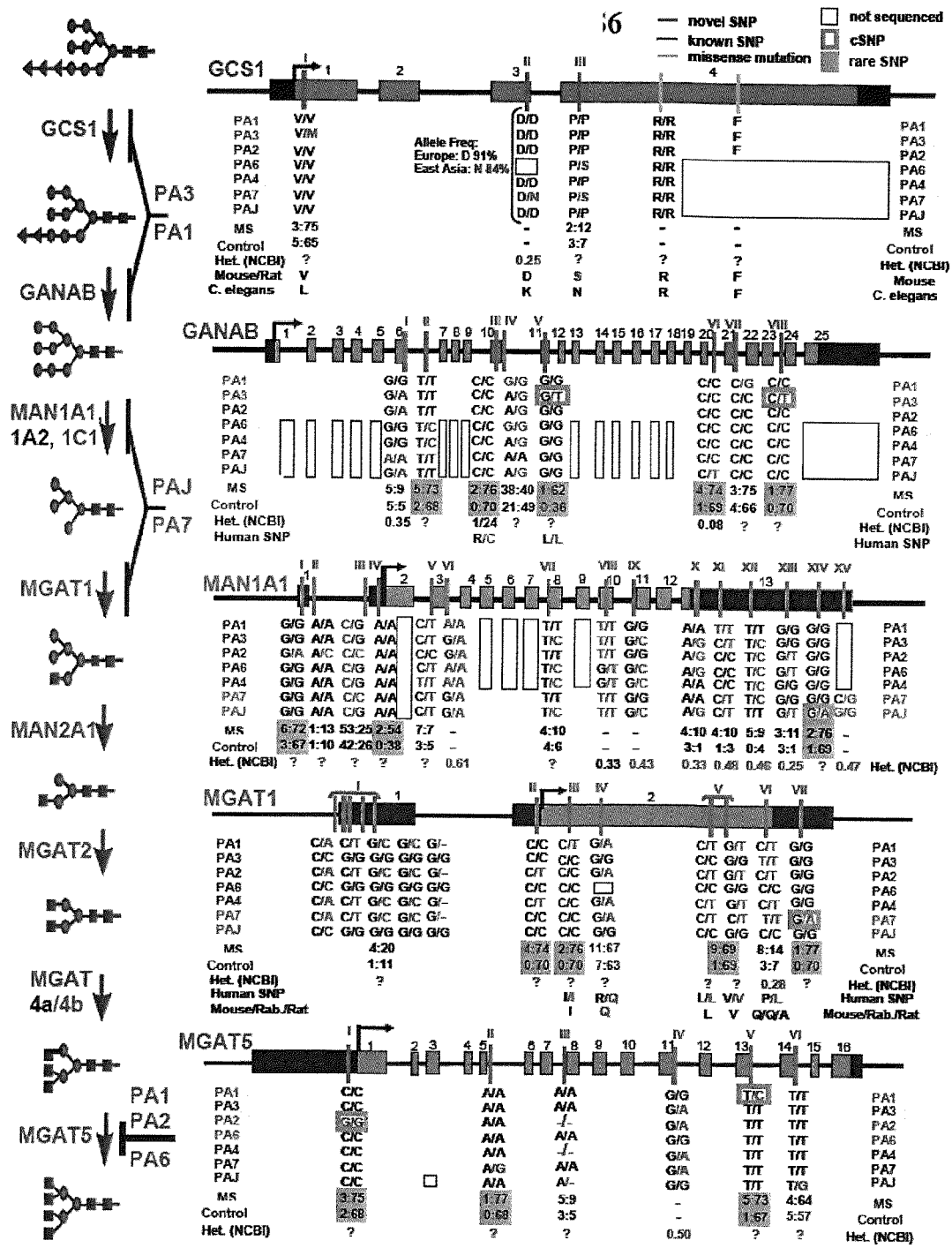
FIG. 22. Single nucleotide polymorphisms in genes controlling N-glycan processing in MS patients and controls. MS patients with altered N-glycan processing are shown in red next to the genes controlling the steps with accumulated N-glycan intermediates by MALDI-TOF. Sequencing of genomic DNA on PCR products from PA1-7,J for each exon identified 14 previously unknown SNPs (red), which were confirmed by sequencing in both directions in at least two separate PCR amplifications, as well as 24 previously known SNPs (blue, NCBI SNP database). Exon and introns are not to scale. MS and Control refer to the ratio of chromosomes +SNP and −SNP as determined by sequencing and/or allelic discrimination. Genotyping of GCS1, GANAB SNP IV and MAN1A1 SNP III by sequencing identified GCS1, GANAB SNP III and MAN1A1 SNP IV. Green boxes refer to correlation (cSNP) with the MALDI-TOF profile in FIG. 21 and allelic frequency ≤5% in control samples. Grey background defines all SNPs with allelic frequency ≤5% in control samples, which were confirmed by an allelic discrimination assay that is independent of Taq error (excluding MAN1A1 IV and GCS1, GANAB SNP V which required sequencing to genotype). Het. refers to predicted heterozygosity as defined in the NCBI SNP database. SNPs that appeared linked are grouped together except MGAT1 SNP I and SNP IV, which were observed together in a small sample size. MAN1A2 and MAN1C1 were not targeted for sequencing as the former does not map to the 18 MS chromosomal regions defined in Table 4 and the latter is not significantly expressed in T cells. Sequences for the previously unknown SNPs (red) are in FIG. 23. The known SNPs (blue) are GCS1: II-rs1063588, IIIrs2268416; GCS1, GANAB: I-rs2957121, III-rs1063445, IV-rs10897289, VI-rs11231166; MAN1A1: II-rs4946409, 111-1295388, V-rs6915947, VI-rs195092, VII-rs9481891, VIII-rs2072890, IX-rs2142887, X-rs3756943, XI-rs18513744, XII-rs3798602, XIIIrs1042800, XV-rs1046226. MGAT1: II-rs3733751, IV-rs7726357, V-rs2070924 and rs2070925, VI-rs634501. MGAT5: III-rs3214771, IV-rs3748900, V-rs2289465.
Figure 23:
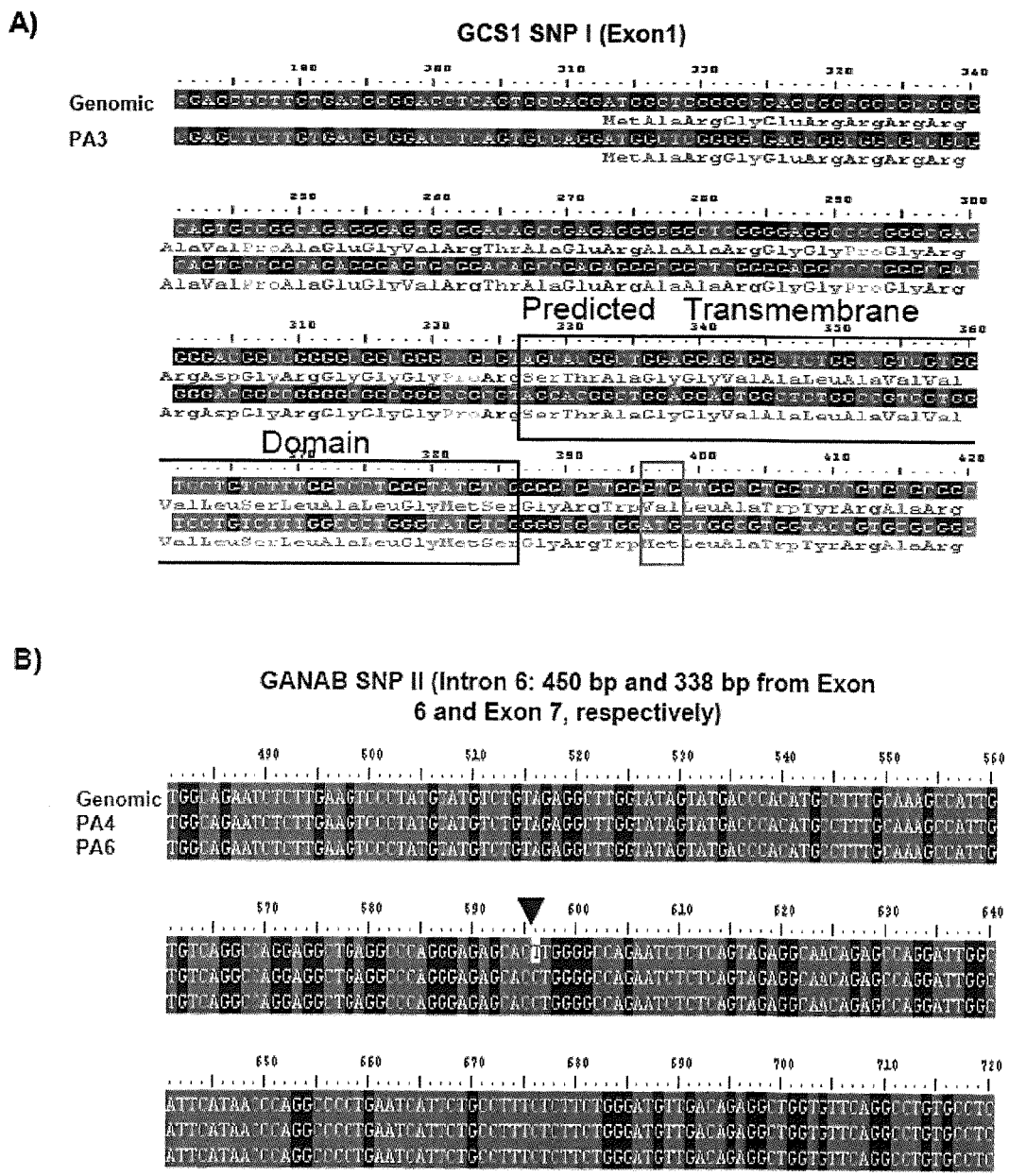
FIG. 23. Rare SNPs in GCS1, GCS1, GANAB, MAN1A1, MGAT1 and MGAT5 associated with MALDI-TOF Glycan profile. A-Q). Sequences are shown for the indicated SNPs with small, unlabeled boxes defining coding SNPs, arrow heads defining UTR and intronic SNPs and exon/intron junctions as indicated. A) GCS1 SNP 1 (Exon 1): The DNA sequence for the genomic sequence of GCS1 Exon I is shown in SEQ ID NO: 69. The corresponding amino acid sequence is shown in SEQ ID NO: 70. The DNA sequence for patient PA3 GCS1 Exon 1 (containing SNP I) is shown in SEQ ID NO: 71. The corresponding amino acid sequence is shown in SEQ ID NO: 72. B) GANAB SNP II (Intron 6): The DNA sequence for the genomic sequence of GANAB Intron 6 is shown in SEQ ID NO: 73. The DNA sequence for patients PA4 and PA6 GANAB Intron 6 (containing SNP II) is shown in SEQ ID NO: 74. C) GANAB SNP III & V (Exon 10 and Intron 10): The DNA sequence for the genomic sequence of GANAB Exon 10 and Intron 10 (first line) is shown in SEQ ID NO: 75. The DNA sequence corresponding to the second line containing the [A/G] SNP IV is shown in SEQ ID NO: 76. The DNA sequence corresponding to the third and fourth lines containing the Arg→Cys SNPIII (Exon 10) is shown in SEQ ID NO: 77. D) GANAB SNP V (Exon 11): The DNA sequence for the genomic sequence of GANAB Exon 11 is shown in SEQ ID NO: 78. The corresponding amino acid sequence is shown in SEQ ID NO: 79. The DNA sequence for patient PA3 GANAB Exon 11 (containing SNP V) is shown in SEQ ID NO: 80. The corresponding amino acid sequence is unchanged and is shown in SEQ ID NO: 79. E) GANAB SNP VI and VII (Exons 20 and 21): The DNA sequence for the genomic sequence of GANAB Exons 20 and 21 is shown in SEQ ID NO: 81. The DNA sequence for patient PAJ GANAB Exons 20 and 21 (containing SNP VI) is shown in SEQ ID NO: 82. The DNA sequence for patient PA1 GANAB Exons 20 and 21 (containing SNP VII) is shown in SEQ ID NO: 83. F) GANAB SNP VIII (Intron 23): The DNA sequence for the genomic sequence of GANAB Intron 23 is shown in SEQ ID NO: 84. The DNA sequence for patient PA3 GANAB Intron 23 (containing SNP VIII) is shown in SEQ ID NO: 85. G) MAN1A1 SNP I (Exon 1 5' UTR) and SNP II (Intron I): The DNA sequence for the genomic sequence of MAN1A1 Exon 1 and Intron 1 is shown in SEQ ID NO: 86. The DNA sequence for patient PA2 MAN1A1 Exon 1 (containing SNP I) and Intron 1 (containing SNP II) is shown in SEQ ID NO: 87. H) MAN1A1 SNP IV (Exon 2 5' UTR): The DNA sequence for the genomic sequence of MAN1A1 Exon 2 5' UTR is shown in SEQ ID NO: 88. The DNA sequence containing SNP IV in MAN1A1 Exon 2 5'UTR is shown in SEQ ID NO: 89. I) MAN1A1 SNP XIII and XIV (Exon 13 3' UTR): The DNA sequence for the genomic sequence of MAN1A1 Exon 13 3' UTR is shown in SEQ ID NO: 90. The DNA sequence for patient PAJ MAN1A1 Exon 13 3' UTR (containing SNP XIII and XIV) is shown in SEQ ID NO: 91. J) MGAT1 SNP I (Promoter and Exon 1 5' UTR): The DNA sequence for the genomic sequence of MGAT1 Promoter and Exon 1 5' UTR is shown in SEQ ID NO: 92. The DNA sequence for patient PAJ MGAT1 Promoter and Exon 1 5' UTR (containing SNP I) is shown in SEQ ID NO: 93. The DNA sequence for patient PA7 MGAT1 Promoter and Exon 1 5' UTR (containing SNP I) is shown in SEQ ID NO: 94. K) MGAT1 SNP II (Exon 2 5' UTR) and SNP III (Exon 2-synonymous): The DNA sequence for the genomic sequence of MGAT1 Exon 2 5' UTR and Exon 2 is shown in SEQ ID NO: 95. The DNA sequence for patients PA2 and PA4 MGAT1 Exon 2 5' UTR and Exon 2 (containing SNP II) is shown in SEQ ID NO: 96. The DNA sequence for patient PA1 MGAT1 Exon 2 5' UTR and Exon 2 (containing SNP III) is shown in SEQ ID NO: 97. L) MGAT1 SNP V (Exon 2): The DNA sequence for the genomic sequence of MGAT1 Exon 2 is shown in SEQ ID NO: 98. The corresponding amino acid sequence is shown in SEQ ID NO: 99. The DNA sequence for patients PA1, PA2, PA4 and PA7 MGAT1 Exon 2 (containing SNP V) is shown in SEQ ID NO: 100. The corresponding amino acid sequence is unchanged and is shown in SEQ ID NO: 99. M) MGAT1 SNP VII (Exon 2 3' UTR): The DNA sequence for the genomic sequence of MGAT1 Exon 2 3' UTR is shown in SEQ ID NO: 101. The DNA sequence for patient PA7 MGAT1 Exon 2 3' UTR (containing SNP VII) is shown in SEQ ID NO: 102. N) MGAT5 SNP 1 (Exon 1 5' UTR): The DNA sequence for the genomic sequence of MGAT5 Exon 1 5' UTR is shown in SEQ ID NO: 103. The DNA sequence for patient PA2 MGAT5 Exon 1 5' UTR (containing SNP I) is shown in SEQ ID NO: 104. O) MGAT5 SNP II (Intron 5): The DNA sequence for the genomic sequence of MGAT5 Intron 5 is shown in SEQ ID NO: 105. The DNA sequence for patient PA7 MGAT5 Intron 5 (containing SNP II) is shown in SEQ ID NO: 106. P) MGAT5 SNP V (Intron 13): The DNA sequence for the genomic sequence of MGAT5 Intron 13 is shown in SEQ ID NO: 107. The DNA sequence for patient PA1 MGAT5 Intron 13 (containing SNP V) is shown in SEQ ID NO: 108. Q) MGAT5 SNP VI (Intron 14): The DNA sequence for the genomic sequence of MGAT5 Intron 14 is shown in SEQ ID NO: 109. The DNA sequence for patient PAJ MGAT5 Intron 14 (containing SNP VI) is shown in SEQ ID NO: 110. The sequences referred to above as "exon" or "intron" are used for convenience and may refer to more or less than the full length exon or intron sequences.
Figure 23:
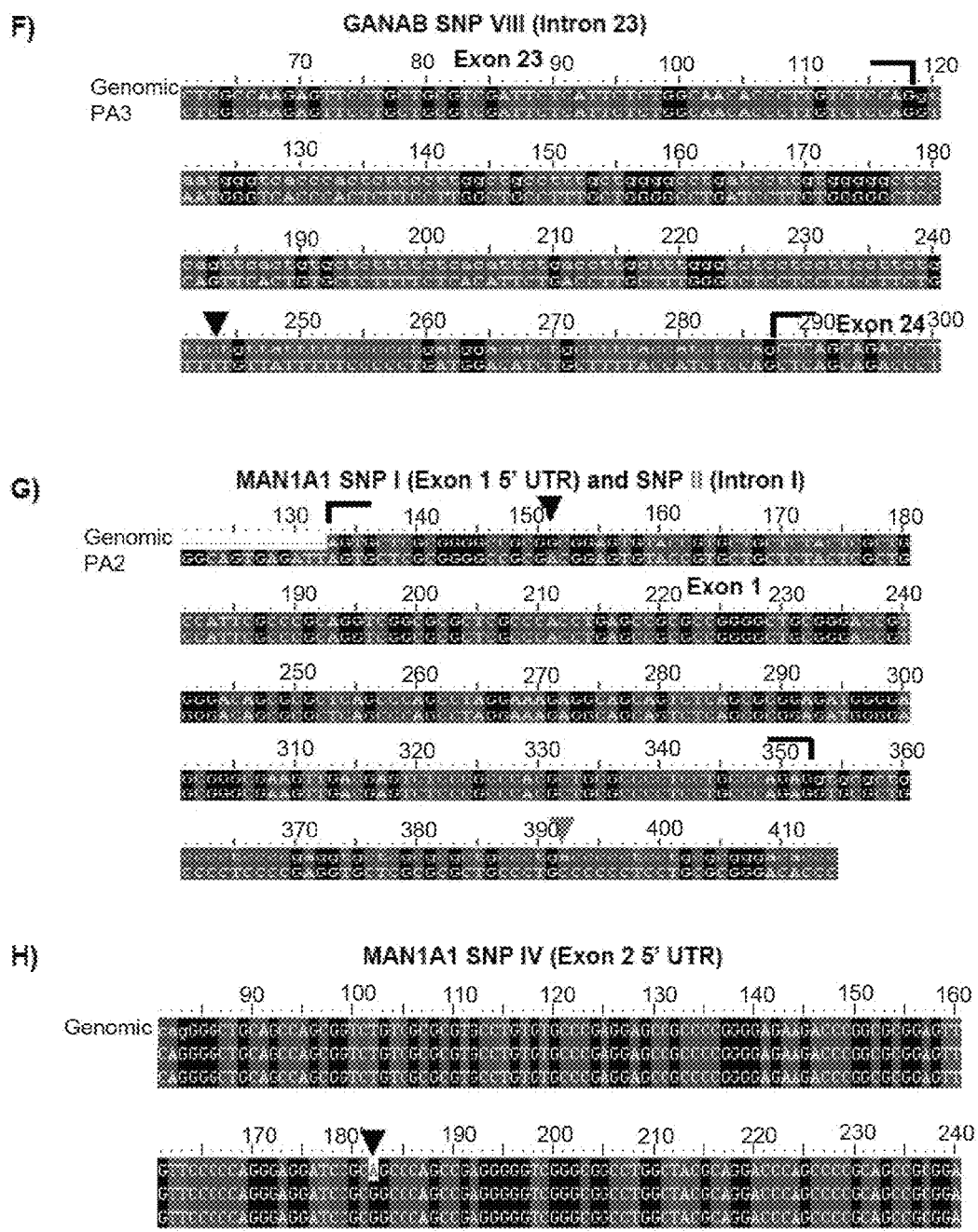
Figure 23:
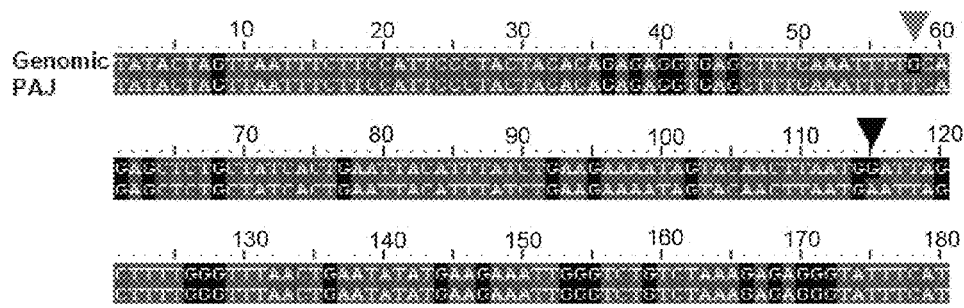
Figure 23:
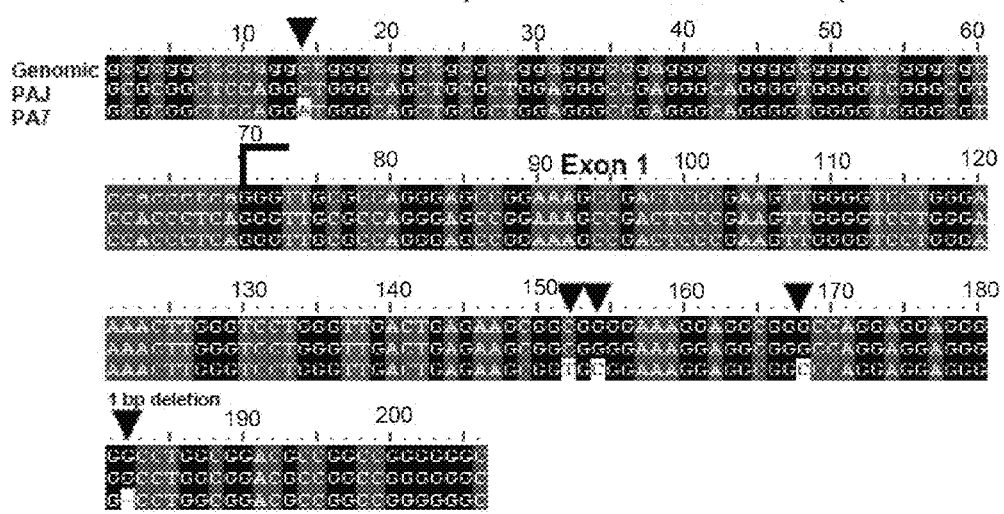
Figure 23:
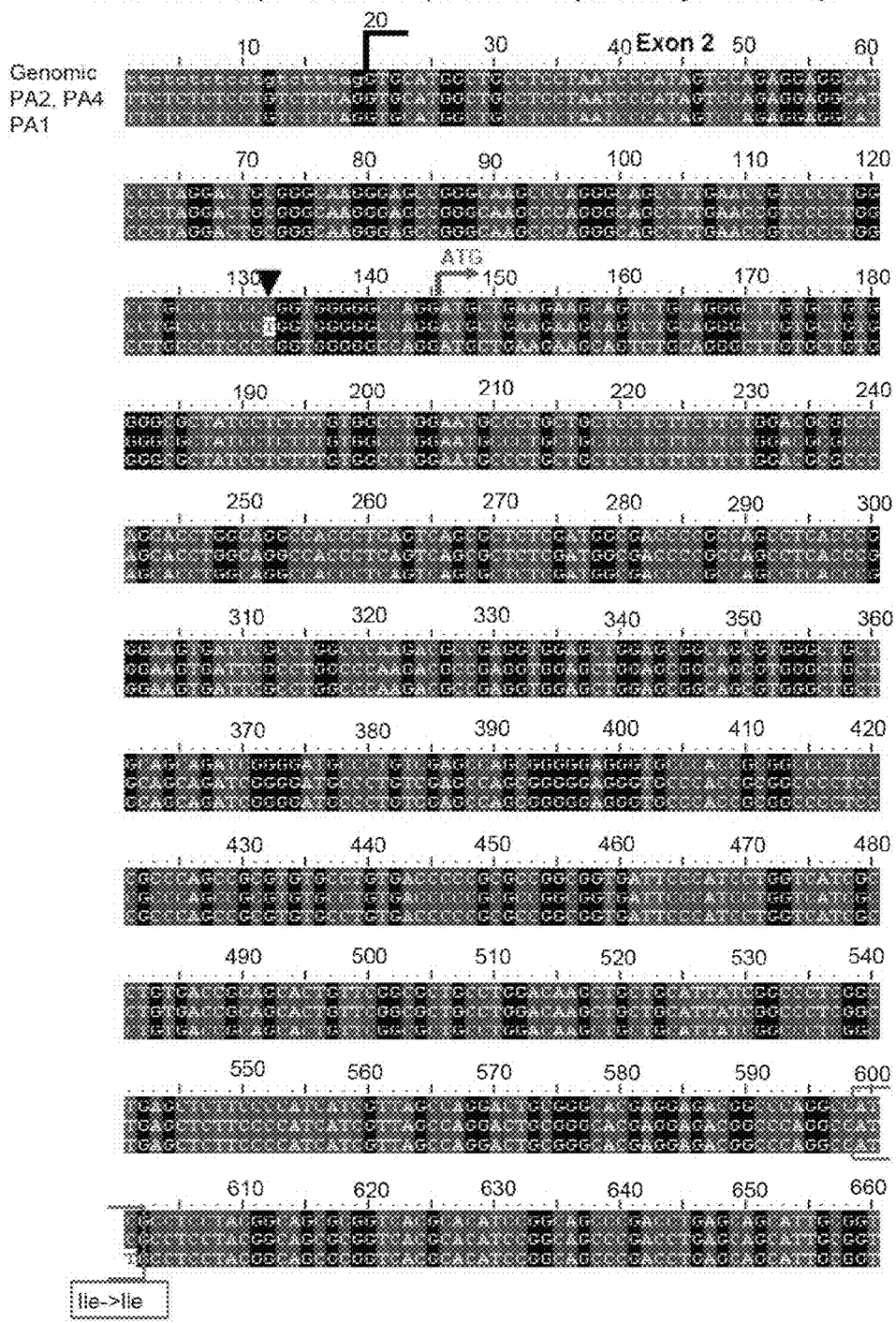
Figure 23:
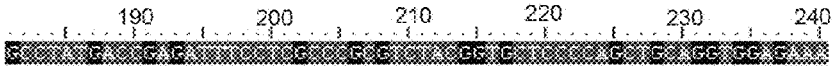
Figure 23:
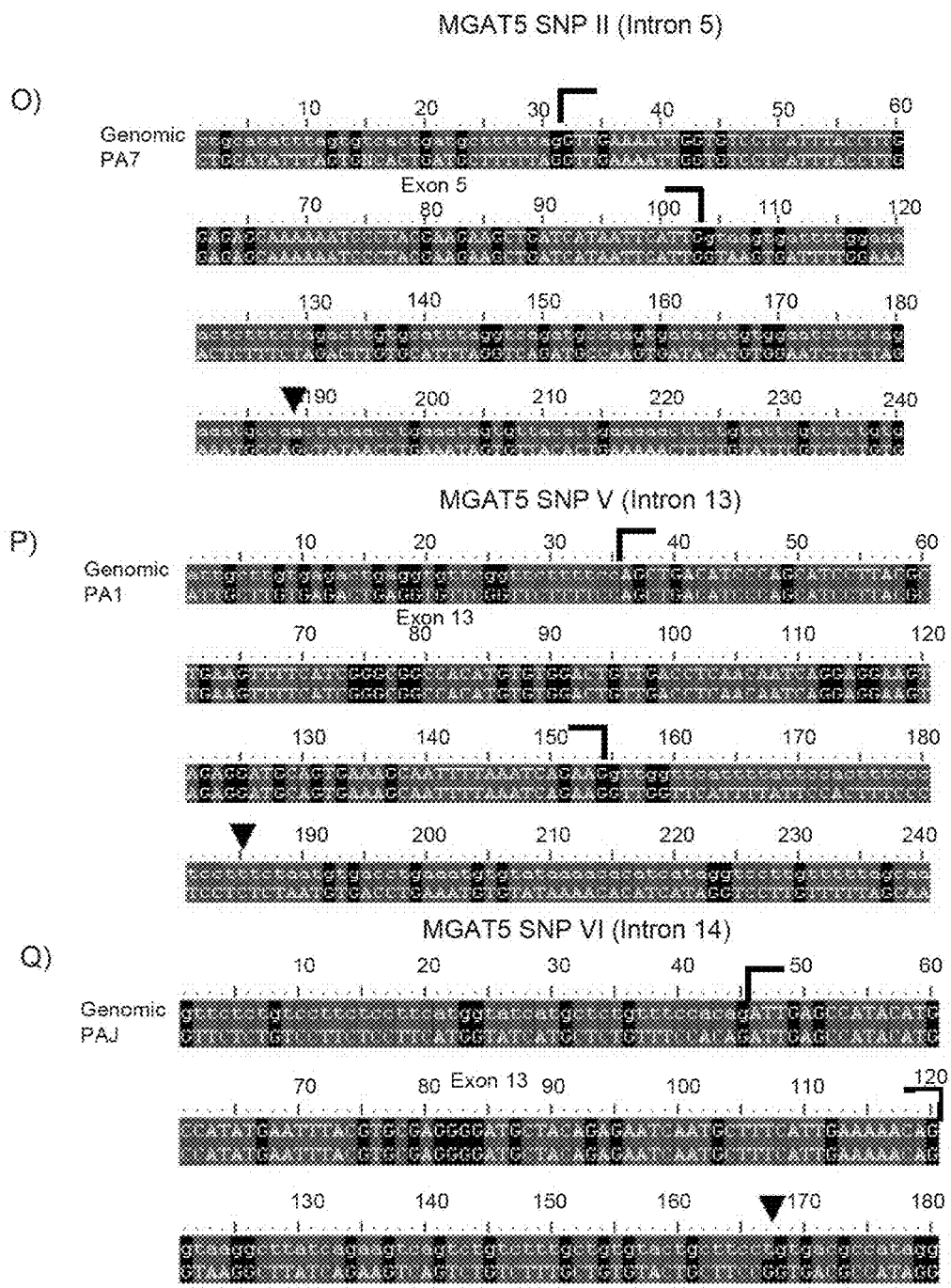

In embodiments of the invention a SNP-containing polynucleotide is a polynucleotide shown in FIGS. 11, 22, and 23, and SEQ ID NOs.:5, 6, 7, 8, 9, and 35-47.

The invention also provides a vector comprising a SNP-containing polynucleotide. Vectors can be for maintenance (cloning vectors) or for expression (expression vectors) of the SNP-containing polynucleotides The term "vector" refers to a vehicle, preferably a nucleic acid molecule that can transport a SNP-containing polynucleotide. When the vector is a polynucleotide, the SNP-containing nucleic acid polynucleotides are covalently linked to the vector nucleic acid. Such vectors include plasmids, single or double stranded phages, single or double stranded RNA or DNA viral vectors, or artificial chromosomes, such as a BAC, PAC, YAC, OR MAC. A vector can function in procaryotic or eukaryotic host cells or in both (shuttle vectors).

A vector can be introduced into an appropriate host cell for propagation or expression using well-known techniques. Therefore, the invention also relates to recombinant host cells containing the vectors described herein. Recombinant host cells are prepared by introducing the vectors into the cells by techniques know to a person of ordinary skill in the art. These include, but are not limited to, calcium phosphate transfection, DEAE-dextran-mediated transfection, cationic lipid-mediated transfection, electroporation, transduction infection, lipofection, and other techniques such as those found in Sambrook, et al. (Molecular Cloning: A Laboratory Manual. 2nd, ed., Cold Spring Harbor Laboratory, Cold Spring Harbor Laboratory Press, Cold Spring Harbor, N.Y., 1989). Host cells can include prokaryotic cells, lower eukaryotic cells such as yeast, other eukaryotic cells such as insect cells, and higher eukaryotic cells such as mammalian cells.

Polypeptide Variants/Antibodies

A polymorphic SNP-containing polynucleotide may encode a variant of a gene product (polypeptide). Therefore, the present invention provides isolated variant polypeptides that comprise, consist of or consist essentially of one or more variant amino acids encoded by a nonsynonymous nucleotide substitution at one or more of the SNP positions disclosed herein; also referred to as variant amino acids, polypeptides, or proteins encoded by SNPs disclosed herein. A variant polypeptide includes, but is not limited to deletions, additions and substitutions in the amino acid sequence of the polypeptide caused by SNPs of the present invention. One class of substitutions is conserved amino acid substitutions where a given amino acid is substituted for another amino acid of like characteristics. Examples of conservative substitutions are replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. [See Bowie et al., *Science* 247:1306-1310 (1990) concerning amino acid changes are likely to be phenotypically silent.]

A variant polypeptide may be fully functional or can lack function in one or more activities, e.g. enzymatic activity. A fully functional variant generally contains only a conservative variation or a variation in non-critical residues or in non-critical regions. A functional variant may also contain a substitution of similar amino acids that results in no change or an insignificant change in function. Alternatively, substitutions may affect function to some degree. A non-functional variant generally contains one or more non-conservative amino acid substitution, deletion, insertion, inversion, or truncation in a critical residue or critical region.

A variant polypeptide is typically "isolated" or "purified", that is, it substantially free of cellular material or free of chemical precursors or other chemicals. A variant polypeptide can be purified to homogeneity or other degrees of purity. The level of purification will be based on the intended use and should allow for the desired function of the variant polypeptide, even if in the presence of considerable amounts of other components.

An isolated variant polypeptide can be purified from cells that naturally express it or from cells that have been altered to express it (recombinant). An isolated variant polypeptide can also be synthesized using known protein synthesis methods. By way of example, a polynucleotide containing SNP encoding a variant polypeptide can be cloned into an expression vector, the expression vector introduced into a host cell and the variant polypeptide expressed in the host cell. The variant polypeptide can then be isolated from the cells using standard protein purification techniques.

Accordingly, the present invention provides variant polypeptides that consist of amino acid sequences that contain one or more of the amino acid polymorphisms encoded by a SNP of the invention. A polypeptide consists of an amino acid sequence when the amino acid sequence is the final amino acid sequence of the polypeptide.

The present invention further provides variant polypeptides that consist essentially of amino acid sequences that contain one or more of the amino acid polymorphisms encoded by a SNP of the invention. A polypeptide consists essentially of an amino acid sequence when such an amino acid sequence is present with only a few additional amino acid residues in the final polypeptide.

The present invention further provides variant polypeptides that are comprised of amino acid sequences that contain one or more of the amino acid polymorphisms encoded by a SNP of the invention. A polypeptide comprises an amino acid sequence when the amino acid sequence is at least part of the final amino acid sequence of the polypeptide. A polypeptide can be only the variant polypeptide or have additional amino acid molecules, such as amino acid residues (contiguous encoded sequence) that, are naturally associated with it or heterologous amino acid residues/peptide sequences. Such a variant polypeptides can have a few additional amino acid residues or can comprise several hundred or more additional amino acids.

Variant polypeptides can be attached to heterologous sequences to form chimeric or fusion proteins. Such chimeric and fusion proteins comprise a variant polypeptide operatively linked to a heterologous polypeptide having an amino acid sequence not substantially homologous to the variant polypeptide. "Operatively linked" means that the variant polypeptide and the heterologous protein are fused in-frame. A heterologous polypeptide can be fused to the N-terminus or C-terminus of the variant polypeptide. A chimeric or fusion protein may be produced by standard recombinant DNA techniques. For example, DNA fragments coding for the different protein sequences can be ligated together in-frame using conventional techniques, or a fusion gene can be synthesized by conventional techniques including automated DNA synthesizers. PCR amplification of gene fragments can also be carried out using anchor primers which provide complementary overhangs between two consecutive gene fragments which can subsequently be annealed and re-amplified to generate a chimeric gene sequence (see Ausubel et al., *Current Protocols in Molecular Biology*, 1992). In addition, expression vectors that encode a fusion moiety (e.g., a GST protein) are commercially available. A polynucleotide encoding a variant polypeptide can be cloned into such an expression vector such that the fusion moiety is linked in-frame to the variant polypeptide.

A variant polypeptides may contain amino acids other than the 20 naturally occurring amino acids. In addition, many amino acids, including the terminal amino acids, in a variant polypeptide may be modified by natural processes, such as processing and other post-translational modifications, or by chemical modification techniques well known in the art. Common modifications that occur naturally in polypeptides are well known to those of skill in the art. Thus, a variant polypeptide includes derivatives or analogs in which a substituted amino acid residue is not one encoded by the genetic code. A variant polypeptide may also comprise an amino acid with a substituent group fused with another compound, such as a compound to increase the half-life of the polypeptide (for example, polyethylene glycol), or fused with a leader or secretory sequence or a sequence for purification of the mature polypeptide or a pro-protein sequence.

Known polypeptide modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Fragments of a variant polypeptide containing one or more amino acid polymorphisms and polypeptides and peptides that comprise and consist of such fragments are also with the scope of the present invention. The fragments of the invention are not to be construed as encompassing fragments that maybe disclosed publicly prior to the present invention. A fragment may comprise at least 8 or more contiguous amino acid residues from a variant protein, wherein at least one residue is a variant amino acid encoded by a nonsynonymous nucleotide substitution at a SNP position provided by the present invention. A fragment can be chosen based on the ability to retain one or more of the biological activities of the variant polypeptide or on the ability to perform a function, e.g. catalytic activity. Preferably the fragments are biologically active fragments.

The invention also provides antibodies that selectively bind to the variant polypeptides of the present invention as well as fragments thereof. Such antibodies may be used to quantitatively or qualitatively detect the variant polypeptides. Generally, an antibody selectively binds a target variant polypeptide when it binds the variant polypeptide and does not significantly bind to non-variant polypeptides, i.e., the antibody does not bind to wild-type, or previously disclosed polypeptides that do not contain a variant amino acid encoded by a nonsynonymous nucleotide substitution at a SNP position disclosed herein.

Antibodies of variant polypeptides can be prepared from any region of the variant polypeptide provided that the region contains a variant amino acid encoded by a nonsynonymous nucleotide substitution at a SNP position. However, preferred regions will also include those involved in function/activity and/or protein/binding partner interaction.

An antibody that binds a variant polypeptide can be detected by coupling the antibody to a detectable substance. Examples of detectable substances include various enzymes, prosthetic groups, fluorescent materials, luminescent materials, bioluminescent materials, and radioactive materials.

Diagnostic Applications

The invention contemplates methods of, and products for, diagnosing and monitoring a disease disclosed herein, in particular an autoimmune disease, more particularly rheumatoid arthritis or an autoimmune demyelinating disease such as multiple sclerosis, in a sample from a subject, comprising assaying for an alteration or change in N-glycans (e.g., Mgat5 modified glycans, or polylactosamine modified glycans), and/or in components (in particular polypeptides (e.g., enzymes) and genes encoding the polypeptides, enzyme substrates, cofactors, and products) of a N-glycan pathway or hexosamine pathway, in a sample from the subject compared to a standard.

N-glycans (e.g., Mgat5 modified glycans, or polylactosamine modified glycans) and components (in particular polypeptides (e.g., enzymes) and genes encoding the polypeptides, enzyme substrates, cofactors, and products) of an N-glycan pathway or hexosamine pathway can be assayed using a variety of methods known to the skilled artisan. For example, enzyme assays can be used to assay for glucosidase I (GCS1), glucosidase, alpha, neutral AB (GANAB), glucosidase II, mannosidase I (MI), Mannosidase, alpha, class 1A, member 1 (MAN1A1), mannosidase II (MII/MIIx), MGAT1, MGAT2, and MGAT5 activity or expression. Mgat5 modified glycans and polylactosamine modified glycans may be assayed using substances that hind to the glycans. Substances that bind to the glycans may be antibodies or lectins. For example, leukoagglutinin (L-PHA) is a tetravalent plant lectin that binds specifically to Mgat5 modified glycans and tomato lectin (LEA), which is a plant lectin that hinds N-acetylpolylactosamine. In an aspect, expression levels of a component of an N-glycan or hexosamine pathway are quantitated using binding agents such as antibodies or their fragments (e.g., via ELISA, western blot, Flourescent Activated Cell Sorting (FACS), etc.) or lectins (L-PHA and LEA binding assays). Components of an N-glycan or hexosamine pathway may also be quantitated by determination of enzymatic kinetics of the polypeptides (e.g., $K_M$, kcat, etc.) or by mass spectroscopy. In particular, MALDI-TOF mass spectrometry can be used to profile the N-glycans present in patient sample for diagnosis of defective N-glycan processing leading to Mgat5 modified N-glycans. Similarly, it is also contemplated that a patient sample may be analyzed for the presence or quantity of a substrate, product, and/or cofactor that is required in an enzyme that is part of the pathway under investigation. For example, the quantity of Mgat5 product or its sugar nucleotide substrate UDP-GlcNAc and upstream metabolites may be determined in patients that are diagnosed for MS.

Accordingly in aspects of the invention, processes and kits for determining the identity of target N-glycans by mass spectrometry are provided. The processes include the steps of determining the molecular mass of target N-glycans by mass spectrometry, and then comparing the mass to a standard, whereby the identity of the N-glycans can be ascertained. Identity includes, but is not limited to, identifying the type of N-glycans or identifying a change in N-glycans. Selection of the standard will be determined as a function of the information desired.

One process for determining the identity of a target N-glycan includes the steps of a) obtaining a target N-glycan; b) determining the molecular mass of the target N-glycan by mass spectrometry, and c) comparing the molecular mass of the target N-glycan with the molecular mass of a corresponding known N-glylcan. By comparing the molecular mass of the target with a known N-glycan, the identity of the target N-glycan can be ascertained. As disclosed herein, N-glycans can be isolated from a cell or tissue obtained from a subject such as a human. N-glycans can be isolated from PBMC's of a subject by methods known in the art, for example, by digestion with an enzyme such as trypsin followed by treatment with PNGaseF.

In an aspect of the invention, a method is provided for screening for or identifying a subject having or predisposed to a disease disclosed herein comprising:
  a) obtaining a sample containing N-glycans from the subject;

b) determining the molecular mass of the N-glycans by mass spectrometry;

c) comparing the molecular mass of the N-glycans with the molecular mass of corresponding known N-glycans, thereby determining the identity of the N-glycans wherein the N-glycans are markers for the disease.

The process is performed using a mass spectrometric analysis, including for example, matrix assisted laser desorption ionization (MALDI), continuous or pulsed electrospray ionization, ionspray, thermospray, or massive cluster impact mass spectrometry and a detection format such as linear time-of-flight (TOF), reflectron time-of-flight, single quadruple, multiple quadruple, single magnetic sector, multiple magnetic sector, Fourier transform ion cyclotron resonance, ion trap, and combinations thereof such as MALDI-TOF spectrometry, preferably MALDI-TOF.

In an embodiment, the invention features a method of diagnosing, or assessing the prognosis of multiple sclerosis in a subject. The method includes providing a test sample from a subject and detecting in the test sample Mgat5 and/or N-glycans (e.g., Mgat5 modified glycans and/or polylactosamine modified glycans). The levels of Mgat5 and N-glycans in the test sample are compared to a standard or control sample, which is derived from one or more individuals who have multiple sclerosis symptoms and have a known multiple sclerosis status, or from an individual or individuals who do not show multiple sclerosis symptoms. MS status can include, for example, exacerbations, attacks, remissions, benign, moderate, malignant and stable stages of the disease.

In an embodiment, the invention features a method of diagnosing, or assessing the prognosis of rheumatoid arthritis in a subject. The method includes providing a test sample from a subject and detecting in the test sample Mgat2 and/or N-glycans. The levels of Mgat2 and N-glycans in the test sample are compared to a standard or control sample, which is derived from one or more individuals who have rheumatoid arthritis symptoms, or from an individual or individuals who do not show rheumatoid arthritis symptoms.

A standard may correspond to levels quantitated for another sample or an earlier sample from the subject, or levels quantitated for a control sample. Levels for control samples from healthy subjects, different stages or types of condition, may be established by prospective and/or retrospective statistical studies. Diagnosis may be made by a finding of statistically different levels of detected N-glycans (e.g., Mgat5 modified glycans, or polylactosamine modified glycans) and components (e.g., polypeptides or genes) of a N-glycan pathway or hexosamine pathway associated with a disease disclosed herein (e.g, an autoimmune disease, in particular autoimmune demyelinating disease, more particularly multiple sclerosis), compared to a control sample or previous levels quantitated for the same subject. In certain diagnostic and monitoring applications of the invention, incidence, severity, and mortality of the condition are inversely correlated with Mgat5.

Certain aspects of the invention stem from the observation that at least one polymorphism [e.g. single nucleotide polymorphism (SNP)] in a gene of a N-glycan pathway or hexosamine pathway, which gene co-localized in chromosomal regions associated with a disease disclosed herein (e.g. autoimmune disease), is correlated with an individual's risk for the disease. The contribution or association of particular polymorphisms with disease phenotypes enables the polymorphisms to be used to develop superior diagnostic tests that are capable of identifying individuals who express a detectable trait (e.g., a disease disclosed herein) as the result of a specific genotype, or individuals whose genotype places them at risk of developing a detectable trait at a subsequent time.

Therefore, aspects of the invention provide methods for detecting an individual's increased or decreased risk for a disease disclosed herein (e.g., an autoimmune disease). Still further embodiments provide methods, kits, reagents and arrays useful for detecting an individual's risk for a disease disclosed herein (e.g., an autoimmune disease). The methods of the invention may be useful to assess the predisposition and/or susceptibility of an individual to a disease disclosed herein (e.g., an autoimmune disease). A polymorphism may be particularly relevant in the development of a disease disclosed herein (e.g., an autoimmune disease), and thus the present invention may be used to recognize individuals who are particularly at risk of developing these conditions.

In other aspects, the invention provides a method for screening patients comprising obtaining from the patient sequence information for one or more genes of the N-glycan pathway or hexosamine pathway, in particular GCS1, GANAB, MAN1A1, MGAT1, MGAT2, and MGAT5 gene sequence information, and determining the identity of one or more polymorphisms in the gene(s) that is indicative of a disease disclosed herein (e.g., an autoimmune disease, in particular MS or rheumatoid arthritis). The patient may be at risk of developing a disease or have a disease.

A polymorphism may contribute to a phenotype (e.g. disease condition) of an individual in different ways. Some polymorphisms occur within the coding sequence of a polypeptide and contribute to the phenotype by affecting the structure of the polypeptide or by influencing replication, transcription, mRNA splicing, mRNA stability and/or translation. Other polymorphisms occur within noncoding regions and may indirectly affect phenotype by influencing replication, transcription, mRNA splicing, mRNA stability, and/or translation. In addition, a single polymorphism may affect more than one trait, and a single polymorphism trait may be affected by polymorphisms in different genes.

The diagnostic methods, reagents and kits of the invention may be based on a single polymorphism or a group of polymorphisms. Combined detection of a plurality of polymorphisms (e.g. 2, 3, 4, 5, 6, 7, 8, 9, 10, 15, 20, 25 or more) generally will increase the probability of an accurate diagnosis. To further increase the accuracy of a diagnostic method of the invention, the polymorphism analysis may be combined with that of other polymorphisms or other risk factors of a disease disclosed herein, including without limitation family history, diet, or environmental factors. Therefore, diagnostic methods of the invention are optionally combined with known clinical methods, to diagnose a disease disclosed herein, in particular an autoimmune disease. Thus, the methods optionally include performing at least one clinical test for a disease disclosed herein, in particular an autoimmune disease, such as Magnetic Resonance Imaging of the brain.

A polymorphism detected using a method of the invention can be any predisposing or protective polymorphism in a gene of the N-glycan pathway or hexosamine pathway, in particular a GCS1, GANAB, MAN1A1, MGAT1, MGAT2, and/or MGAT5 gene. In an embodiment of the invention, the polymorphism can be any polymorphism identified as predisposing or protective by methods taught herein. In another embodiment, the polymorphism can be a single nucleotide polymorphism (SNP) in a gene of the N-glycan pathway or hexosamine pathway, in particular a GCS1, GANAB, MAN1A1, MGAT1, MGAT2, and/or MGAT5 gene. In a further embodiment, specific haplotypes in a N-glycan or hexosamine gene locus, in particular a GCS1, GANAB, MAN1A1, MGAT1, MGAT2, and/or MGAT5 gene locus as well as specific combinations of, and interactions between SNPs at these and other loci can be indicative of an increased or a decreased risk of a disease disclosed herein, (e.g., an autoimmune disease, in particular MS or rheumatoid arthritis).

The invention provides a method of analyzing a polynucleotide from an individual to determine which nucleotides are present at polymorphic sites within a gene of the N-glycan pathway or hexosamine pathway to identify polymorphisms within the gene, wherein the gene is co-localized in chromosomal regions associated with a disease disclosed herein (in particular an autoimmune disease, more particularly MS or rheumatoid arthritis). The analysis can be performed on a plurality of individuals who are tested for the presence of the disease phenotype. The presence or absence of a disease phenotype or propensity for developing a disease state can then be correlated with a base or set of bases present at the polymorphic sites in the individual tested. Alternatively, this determination step is performed in such a way as to determine the identity of the polymorphisms.

In an aspect, the invention provides a method for detecting an individual's increased or decreased risk for a disease disclosed herein (e.g., an autoimmune disease, in particular MS or rheumatoid arthritis) by detecting in a polynucleotide sample of the individual the presence of at least one disease-associated polymorphism in a gene of a N-glycan pathway or hexosamine pathway co-localized in chromosomal regions associated with the disease, in particular a GCS1, GANAB, MAN1A1, MGAT1, MGAT2, and/or MGAT5 gene, wherein the presence of the at least one polymorphism indicates the individual's increased or decreased risk for the disease.

In a particular aspect of the invention, methods are used to determine an individual's risk for an autoimmune disease and related diseases. In the methods, the presence of at least one autoimmune disease-associated polymorphism in a polynucleotide sample of the individual is detected. In particular aspects, the autoimmune disease-associated polymorphism is a polymorphism in a gene of the N-glycan pathway or hexosamine pathway co-localized in chromosomal regions associated with the disease, more particularly a polymorphism in a GCS1, GANAB, MAN1A1, MGAT1, MGAT2, and MGAT5 gene. The presence of at least one polymorphism provides an indication of the individual's risk for an autoimmune disease. The individual's risk for an autoimmune disease can be either an increased risk or a decreased risk as compared to an individual without the at least one polymorphism (e.g., an individual with a different allele at that polymorphic site). Accordingly, the at least one polymorphism can comprise a predisposing or a protective polymorphism in a gene of the N-glycan pathway or hexosamine pathway co-localized in chromosomal regions associated with the disease, in particular the polymorphism is in a GCS1, GANAB, MAN1A1, MGAT1, MGAT2, and/or MGAT5 gene.

In an embodiment, the invention provides a method for identifying a polymorphism in a gene sequence of a gene of the N-glycan pathway or hexosamine pathway, in particular a GCS1, GANAB, MAN1A1, MGAT1, MGAT2, and MGAT5 gene sequence, that correlates with a disease disclosed herein, in particular an autoimmune disease, more particularly MS or rheumatoid arthritis. The method may comprise obtaining gene sequence information in respect to gene(s) of the N-glycan pathway or hexosamine pathway co-localized in chromosomal regions associated with the disease from a group of patients with the disease, identifying a site of at least one polymorphism in the gene(s), and determining genotypes at the site for individual patients in the group. The genotypes may be correlated with the disease severity, prognosis of the patient, or treatments. In particular, the method is performed on a sufficient population size to obtain a statistically significant correlation.

The invention provides a method for diagnosing or aiding in the diagnosis of disease disclosed herein (e.g., an autoimmune disease, in particular MS or rheumatoid arthritis) in a subject comprising the steps of determining the genetic profile of genes of N-glycan pathway or hexosamine pathway of the subject, in particular the genetic profile of GCS1, GANAB, MAN1A1, MGAT1, MGAT2, and/or MGAT5 genes, thereby diagnosing or aiding in the diagnosis of the disease.

In an aspect the invention provides a method for diagnosing a genetic susceptibility for a disease disclosed herein (e.g., an autoimmune disease, in particular MS or rheumatoid arthritis) in a subject comprising obtaining a biological sample containing polynucleotides from the subject; and analyzing the polynucleotides to detect the presence or absence of one or more polymorphism in a gene of a N-glycan pathway or hexosamine pathway of the subject, in particular polymorphisms in a GCS1, GANAB, MAN1A1, MGAT1, MGAT2, and/or MGAT5 gene, wherein a polymorphism is associated with a genetic predisposition for the disease.

In another aspect, the invention provides a method for diagnosis of a disease disclosed herein (e.g. an autoimmune disease, in particular MS or rheumatoid arthritis) in a patient having, or at risk of developing the disease comprising determining a genotype including one or more polymorphism sites in a gene of a N-glycan pathway or hexosamine pathway, in particular a polymorphism in one or more of a GCS1, GANAB, MAN1A1, MGAT1, MGAT2, and MGAT5 gene, for the patient.

In another aspect the invention provides a method for the diagnosis of a single nucleotide polymorphism (SNP) in a gene of a N-glycan pathway or hexosamine pathway of the subject, in particular a GCS1, GANAB, MAN1A1, MGAT1, MGAT2, and MGAT5 gene, in a human comprising determining the sequence of the polynucleotide of the human at the position of the SNP, and determining the status of the human by reference to a polymorphism in the gene.

In another aspect, the invention provides a method for detecting whether a subject is suffering from or is predisposed to developing a disease disclosed herein comprising detecting in a nucleic acid sample from a subject one or more alleles shown in FIGS. 11, 22, and 23, and SEQ ID NOs.:5, 6, 7, 8, 9, and 35-47, wherein the presence of the one or more alleles indicates that the subject is predisposed to the development of the disease or has the disease. The detecting step can be selected from the group consisting of: a) allele specific oligonucleotide hybridization; b) size analysis; c) sequencing; d) hybridization; e) 5' nuclease digestion; f) single-stranded conformation polymorphism; g) allele specific hybridization; h) primer specific extension; and j) oligonucleotide ligation assay. Prior to or in conjunction with the detection step a nucleic acid sample is subject to an amplification step.

In an aspect the invention provides a method of analyzing a polynucleotide comprising obtaining a polynucleotide from an individual and determining the base occupying position of a SNP as shown in FIGS. 11, 22, and 23, and SEQ ID NOs.:5, 6, 7, 8, 9, and 35-47.

In an aspect the invention provides a method of analyzing a polynucleotide comprising obtaining a polynucleotide from an individual and determining the base occupying position of a SNP nucleotide as shown in FIGS. 11, 22, and 23, and SEQ ID NOs.:5, 6, 7, 8, 9, and 35-47.

In an aspect of the invention, a method is provided for the diagnosis of an autoimmune disease, in particular MS or rheumatoid arthritis comprising: (a) obtaining sample polynucleotide from an individual; (b) detecting the presence or absence of one or more variant nucleotide as shown in FIGS. 11,22, and 23, and SEQ ID NOs.:5, 6, 7, 8, 9, and 35-47 in a GCS1, GANAB, MAN1A1, MGAT1 and/or MGAT5 gene, respectively; and (c) determining the status of the individual by reference to the polymorphism in the GCS1, GANAB, MAN1A1, MGAT1 and/or MGAT5 gene.

In another aspect, the invention provides a method for diagnosis of an autoimmune disease in a patient having or at risk of developing an autoimmune disease, in particular MS or rheumatoid arthritis, comprising determining for the patient the genotype of one or more polymorphism site in a GCS1, GANAB, MAN1A1, MGAT1, MGAT2, and MGAT5 gene as shown in FIGS. 11, 22, and 23, and SEQ ID NOs.:5, 6, 7, 8, 9, and 35-47. The method may further comprise comparing the genotype with known genotypes which are indicative of an autoimmune disease.

The present invention therefore provides a method of diagnosing an autoimmune disease, in particular MS or rheumatoid arthritis, or determining the presence or absence of a GCS1, GANAB, MAN1A1, MGAT1, MGAT2, and MGAT5 haplotype in a patient by obtaining material from the patient comprising polynucleotides SNP-containing polynucleotides as shown in FIGS. 11, 22, and 23, and SEQ ID NOs.:5, 6, 7, 8, 9, and 35-47 and determining the GCS1, GANAB, MAN1A1, MGAT1 and MGAT5 gene haplotype.

In a further aspect, the invention provides a method for diagnosis of a patient having or at risk of developing an autoimmune disease, in particular MS or rheumatoid arthritis, comprising determining a genotype including a polymorphism site in the GCS1, GANAB, MAN1A1, MGAT1, MGAT2, and/or MGAT5 gene for the patient, wherein the polymorphism is as shown in FIGS. 11, 22, and 23, and SEQ ID NOs.:5, 6, 7, 8, 9, and 35-47 or a polymorphism site linked thereto.

In another aspect, the invention provides a method for diagnosis of rheumatoid arthritis in a patient having or at risk of developing rheumatoid arthritis, comprising determining for the patient the genotype of one or more polymorphism site in a, MGAT1 gene, in particular a MGAT1 SNP as shown in SEQ ID NO. 42, 43, and 44. The method may further comprise comparing the genotype with known genotypes which are indicative of rheumatoid arthritis.

Genotyping may be determined at a combination of multiple polymorphism sites within the promoter region or outside the promoter region of a gene(s) of the N-glycan pathway or hexosamine pathway co-localized in chromosomal regions associated with the disease, in particular a GCS1, GANAB, MAN1A1, MGAT1, MGAT2, and/or MGAT5 gene, or another gene of the N-glycan or hexosamine pathway.

In particular aspects, the presence of a polymorphism inherited from one of an individual's parents provides an indication of the individual's risk for a disease disclosed herein (e.g., an autoimmune disease, in particular MS or rheumatoid arthritis). In other aspects, the presence of the polymorphism inherited from both of the individual's parents provides an indication of the individual's risk for a disease disclosed herein (e.g., an autoimmune disease, in particular MS or rheumatoid arthritis).

In aspects of the invention methods for determining an individual's risk for a disease disclosed herein in particular an autoimmune disease, more particularly MS or rheumatoid arthritis, are provided comprising determining an individual's genotype at one or more polymorphic sites in a gene of the N-glycan pathway or hexosamine pathway, in particular a GCS1, GANAB, MAN1A1, MGAT1, MGAT2, and MGAT5 gene. A first genotype at the one or more polymorphic sites is statistically associated with an increased risk for an autoimmune disease as compared to a second genotype at the polymorphic site. Thus, for example, if the individual's genotype corresponds to the first genotype, the individual's risk for an autoimmune disease is greater than that of other individuals who have the second genotype.

In an aspect, the invention relates to the identification of individual's at risk of a disease disclosed herein (e.g., an autoimmune disease) by detecting allelic variation at one or more positions in a gene associated with an N-glycan pathway or hexosamine pathway, optionally in combination with any other polymorphism in the gene that is or becomes known.

In some aspects, the presence of a single allele of a particular polymorphism is sufficient to indicate whether the individual's risk of an autoimmune disease is increased or decreased. In other aspects, two copies of an allele of a particular polymorphism must be present to indicate an increased or decreased risk of a disease disclosed herein, in particular an autoimmune disease. Determining the individual's genotype typically involves obtaining a polynucleotide sample from the individual, and determining the individual's genotype by amplifying at least a portion of a gene of the N-glycan or hexosamine pathway from the sample, the portion comprising one or more polymorphic sites. Such amplification directly determines the genotype or facilitates detection of one or more polymorphisms by an additional step. In one aspect, the individual's genotype is determined by performing an allele-specific amplification or an allele-specific extension reaction. In another aspect, the individual's genotype is determined by sequencing at least a portion of the gene from the sample, the portion comprising at least one polymorphic site. In yet another aspect, the individual's genotype is determined by hybridization of a polynucleotide probe, optionally after amplification of at least a portion of the gene. In particular aspects, at least one polymorphic site consists of a single nucleotide position, and the sample is contacted with at least one sequence-specific oligonucleotide probe under stringent conditions. In an aspect, the probe hybridizes under stringent conditions to polynucleotides in the sample when a first nucleotide does not occupy the nucleotide position defining the polymorphic site but not when the first nucleotide occupies the nucleotide position. Hybridization of the probe to the polynucleotide sample is detected.

A diagnostic method of the invention may comprise (a) contacting a polynucleotide sample with one or more oligonucleotides that hybridize under stringent hybridization conditions to at least one polymorphism of a gene of an N-glycan pathway or hexosamine pathway and detecting the hybridization; (b) detection of at least one, two, three, four, five six, seven, eight, nine, ten, fifteen, twenty, or twenty-five polymorphisms by amplification of the polynucleotide sample by, for example, PCR; or (c) detection of at least two, three, four, five six, seven, eight, nine, ten, fifteen, twenty, or twenty-five polymorphism by direct sequencing of the polynucleotide sample. In certain aspects, an individual's risk for a disease disclosed herein (e.g. an autoimmune disease) is diagnosed from the individual's genotype more particularly the individual's N-glycan or hexosamine pathway genotype, in particular the individual's GCS1, GANAB, MAN1A1, MGAT1, MGAT2, and/or MGAT5 genotype. An individual who has at least one polymorphism statistically associated with a disease disclosed herein (e.g. an autoimmune disease) possesses a factor contributing to either an increased or a decreased risk as compared to an individual without the polymorphism. A statistical association of various polymorphisms (sequence variants) with an autoimmune disease is shown in the Examples. A genotype can be determined using any method capable of identifying nucleotide variation, e.g., nucleotide variation consisting of single nucleotide polymorphic sites. A number of suitable methods are described herein. For example, genotyping may be carried out using oligonucleotide probes specific to variant GCS1, GANAB, MAN1A1, MGAT1, MGAT2, and/or MGAT5 sequences. In an aspect, a region of the GCS1, GANAB, MAN1A1, MGAT1, MGAT2, and/or MGAT5 genes which encompasses a polymorphic site of interest is amplified prior to, or concurrent with, the hybridization of probes complementary to such sites. In the alternative, allele-specific amplification or extension reactions with allele-specific primers are used which support primer extension if the targeted allele is present. Typically, an allele-specific primer hybridizes to the gene such that the 3' terminal nucleotide aligns with a polymorphic position.

In one aspect, the invention provides a method for detecting an individual's increased or decreased risk for a disease disclosed herein (e.g. an autoimmune disease) by detecting the presence of one or more SNPs in a polynucleotide sample of the individual, wherein the presence of the SNP(s) indicates the individual's increased or decreased risk for the disease. The SNPs can be any SNPs in a gene of the N-glycan pathway or hexosamine pathway, including SNPs in exons, introns and/or upstream and/or downstream regions, in particular SNPs in the promoter region. Examples of such SNPs include, but are not limited to, those discussed in detail herein and in the Examples. In one embodiment, the SNPs present in a GCS1, GANAB, MAN1A1, MGAT1, MGAT2, and/or MGAT5 locus (or locus of another gene of the N-glycan and hexosamine pathway) are identified by genotyping the GCS1, GANAB, MAN1A1, MGAT1, MGAT2, and/or MGAT5 SNPs. In certain embodiments, the genotype of one SNP can be used to determine an individual's risk for an autoimmune disease. In other embodiments, the genotypes of a plurality of SNPs can be used. In other embodiments, certain combinations of SNPs at either the same or different loci can be used.

The methods of the invention may also comprise detecting other markers and polymorphisms associated with disease disclosed herein in particular an autoimmune disease, more particularly MS or rheumatoid arthritis. For example, other markers and polymorphisms associated with MS include one or more of the following: osteopontin polymorphisms, methionine synthase polymorphisms; interferon receptor polymorphisms, myelin oligodendrocyte glycoprotein polymorphisms, PTPRC gene polymorphisms, early B-cell factor gene (EBF-1) polymorphisms, APOE polymorphisms, CD24 gene polymorphisms, tumor necrosis factor β gene polymorphisms, interleukin (IL)-1B and IL-1 receptor antagonist (IL-1RN) gene polymorphisms; alpha-1 antitrypsin; INF [alpha], [beta], [gamma]; TAP; LMP; and HLA-DP region polymorphisms.

Evaluation of a candidate gene for association with various phenotypes pertaining to an autoimmune disease is described in the Examples. In addition, design and execution of various types of association studies have been described in the art; (see, e.g., Handbook of Statistical Genetics, John Wiley and Sons Ltd.; Borecki and Suarez, 2001, Adv Genet 42:45-66; Cardon and Bell, 200 1, Nat Rev Genet 2:91-99; and Risch, 2000, Nature 405:847). Association studies have been used to evaluate candidate genes for association with a phenotypic trait (e.g., Thornsberry et al., 2001, Nature Genetics 28:286-289) and to perform whole genome scans to identify genes that contribute to phenotypic variation.

Polymorphisms may be detected using analytical procedures well known to a person skilled in the art. Suitable methods for detection of allelic variation are described in standard textbooks (e.g. "Laboratory Protocols for Mutation Detection", U. Landegren (ed), Oxford University Press, 1996, and "PCR", $2^{nd}$ Edition by Newton & Graham, BIOS Scientific Publishers Limited, 1997, and reviewed by Nollau et al, Clin. Chem. 43, 114-1120, 1997). Generally, a method for detecting a polymorphism comprises a mutation discrimination technique, optionally an amplification reaction, and a signal generation system.

Suitable mutation discrimination techniques include without limitation mutation detection techniques such as DNA sequencing, sequencing by hybridization, scanning (e.g. single-strand conformation polymorphism analysis (SSCP), denaturing gradient gel electrophoresis (DGGE), temperature gradient gel electrophoresis (TGGE), cleavase, heteroduplex analysis, chemical mismatch cleavage (CMC), enzymatic mismatch cleavage), solid phase hybridization [e.g. dot blots, multiple allele specific diagnostic assay (MASDA)], reverse dot blots, oligonucleotide arrays (DNA Chips)], solution phase hybridization [eg. Taqman (U.S. Pat. Nos. 5,210,015 and 5,487,972 to Hoffman-LA Roche), and Molecular Beacons (Tyagi et al, 1996, Nature Biotechnology, 14: 303, WO 95/13399)], extension based techniques [e.g. amplification refractory mutation system linear extension (ALEX™) (EP Patent No. EP 332435), amplification refractory mutation system (ARMS™) (EP Patent NO. 332435; U.S. Pat. No. 5,595,890; Newton et al Polynucleotides Research 17:2503, 1989); competitive oligonucleotide priming system (COPS) (Gibbs et al, 1989, Polynucleotide Research 17:2347); incorporation based techniques [e.g. mini-sequencing, arrayed primer extension (APEX)], restriction enzyme based techniques (e.g. restriction fragment length polymorphism, restriction site generating PCR), ligation based techniques (oligonucleotide ligation assay (OLA)—Nickerson et al, 1990, PNAS 87:8923-8927); array-based tiling (EP 785280); Taqman allelic discrimination (Applied Biosystems), and other techniques known in the art.

Suitable signal generation or detection systems that may be used in combination with the mutation discrimination techniques include without limitation fluorescence (fluorescence resonance energy transfer, fluorescence quenching, fluorescence polarization (UK Patent No. 2228998), chemiluminescence, electrochemiluminescence, raman, radioactivity, colorimetric, hybridization protection assay, mass spectrometry, and surface enhanced raman resonance spectroscopy (WO 97/05280).

Various amplification methods known in the art can be used to detect nucleotide changes in a target polynucleotide. Suitable amplification methods include polymerase chain reaction (PCR), self sustained replication, branched DNA (b-DNA), ligase chain reaction (LCR), polynucleotide sequence based amplification (NASBA), and strand displacement amplification (SDA). Polymerase chain reaction (PCR), is well known in the art [See U.S. Pat. Nos. 4,683, 195; 4,683,202; 4,965,188; PCR Applications, 1999, (Innis et al., eds., Academic Press, San Diego), PCR Strategies, 1995, (Innis et al., eds., Academic Press, San Diego); PCR Protocols, 1990, (Innis et al., eds., Academic Press, San Diego); and PCR Technology, 1989, (Erlich, ed., Stockton Press, New York); Abramson et al., 1993, Current Opinion in Biotechnology, 4:41-47; commercial vendors include PE Biosystems (Foster City, Calif.)]. Reverse-transcription-polymerase chain reaction (RT-PCR) is also well known in the art and for example, is described in U.S. Pat. Nos. 5,310,652; 5,322,770; 5,561,058; 5,641,864; and 5,693,517. Other known amplification methods include the ligase chain reaction (Wu and Wallace, 1988, Genomics 4:560-569); the strand displacement assay (Walker et al., 1992, Proc, Natl. Acad. Sci. USA 89:392-396, Walker et al. 1992, Polynucleotides Res. 20:1691-1696, and U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., 1989, Proc. Natl. Acad. Sci. USA, 86:1173-1177); and self-sustained sequence replication (3 SR) (Guatelli et al., 1990, Proc. Natl. Acad. Sci, USA, 87:1874-1878 and WO 92/08800). Methods that amplify a probe to detectable levels can also be used, including QB-replicase amplification (Kramer et al., 1989, Nature, 339:401-402, and Lomeli et al., 1989, Clin. Chem., 35:1826-1831).

Certain methods of the invention may employ restriction fragment length analysis, sequencing, hybridization, an oligonucleotide ligation assay, polymerase proofreading methods, allele-specific PCR and reading sequence data. Particular methods of the invention are described herein.

Genotyping can be carried out by detecting and analyzing mRNA under conditions when both maternal and paternal chromosomes are transcribed. Amplification of RNA can be carried out by first reverse-transcribing the target RNA using, for example, a viral reverse transcriptase, and then amplifying the resulting cDNA, or using a combined high-temperature reverse-transcription-polymerase chain reaction (RT-PCR) [see for example, U.S. Pat. Nos. 5,310,652; 5,322,770; 5,561,058; 5,641,864; and 5,693,517 and Myers and Sigua, 1995, in PCR Strategies, supra, Chapter 5).

Alleles can also be identified using allele-specific amplification or primer extension methods which are based on the inhibitory effect of a terminal primer mismatch on the ability of a DNA polymerase to extend the primer (see, for example, U.S. Pat. Nos. 5,137,806; 5,595,890; 5,639,611; and U.S. Pat. No. 4,851,331). To detect an allele sequence using these methods, a primer complementary to the gene is selected such that the 3' terminal nucleotide hybridizes at the polymorphic position. In the presence of the allele to be identified, the primer matches the target sequence at the 3' terminus and the primer is extended. In the absence of the allele, the primer has a 3' mismatch relative to the target sequence and primer extension is either eliminated or significantly reduced. Using allele-specific amplification-based genotyping, identification of the alleles requires the detection of the presence or absence of amplified target sequences. Methods for the detection of amplified target sequences are well known in the art and include, for example, gel electrophoresis (see Sambrook et al., 1989, infra) and the probe hybridization assays described herein.

Allele-specific amplification-based methods of genotyping can facilitate the identification of haplotypes. Essentially, the allele-specific amplification is used to amplify a region encompassing multiple polymorphic sites from only one of the two alleles in a heterozygous sample. The SNP variants present within the amplified sequence are then identified by probe hybridization or sequencing.

A kinetic-PCR method in which the generation of amplified polynucleotide is detected by monitoring the increase in the total amount of double-stranded DNA in the reaction mixture can also be used to identify polymorphisms. The method is described, for example, in Higuchi et al., 1992, BioTechnology, 10:413-417; Higuchi et al., 1993, BioTechnology, 11: 10261030; Higuchi and Watson, in PCR Applications, supra, Chapter 16; U.S. Pat. Nos. 5,994,056 and 6,171,785; and European Patent Publication Nos. 487,218 and 512,334. The detection of double-stranded target DNA depends on the increased fluorescence that DNA-binding dyes, such as ethidium bromide or SYBR Green, exhibit when bound to double-stranded DNA. An increase of double-stranded DNA produced from the synthesis of target sequences provides an increase in the amount of dye bound to double-stranded DNA and a concomitant detectable increase in fluorescence. In the kinetic-PCR methods, amplification reactions are carried out using a pair of primers specific for one of the alleles, such that each amplification indicates the presence of a particular allele. For example, by performing two amplifications, one using primers specific for the wild-type allele and one using primers specific for the mutant allele, the genotype of the sample with respect to that SNP can be determined.

Alleles may also identified using probe-based methods, which rely on the difference in stability of hybridization duplexes formed between a probe and its corresponding target sequence comprising an allele. Under sufficient stringent hybridization conditions, stable duplexes are formed only between a probe and its target allele sequence and not other allele sequences. The presence of stable hybridization duplexes can be detected by methods known in the art.

Probes suitable for use in the probe-based methods of the invention, which contain a hybridizing region either substantially complementary or exactly complementary to a polymorphic site of a gene of the N-glycan pathway or hexosamine pathway, in particular a GCS1, GANAB, MAN1A1, MGAT1, MGAT2, and/or MGAT5 gene or the complement thereof, or a SNP-containing polynucleotide of the invention, can be selected using the guidance provided herein and well known in the art. Similarly, suitable hybridization conditions (e.g., stringent conditions), which depend on the exact size and sequence of the probe, can be selected empirically using the guidance provided herein and well known in the art (see, e.g., Polynucleotide Hybridization (B. D. Haines and S. F. Higgins. eds., 1984) and Sambrook et al., Molecular Cloning—A Laboratory Manual (3rd Ed.), Vol. 1-3, Cold Spring Harbor Laboratory, Cold Spring Harbor, N.Y., 2000).

In aspects of probe-based methods for determining genotypes, multiple polynucleotide sequences from the genes which comprise the polymorphic sites are amplified and hybridized to a set of probes under stringent conditions. The alleles present are determined from the pattern of binding of the probes to the amplified target sequences. In this aspect, amplification is carried out to provide sufficient polynucleotide for analysis by probe hybridization. Therefore, primers are designed to amplify the regions of the genes encompassing the polymorphic sites regardless of the allele present in the sample. Primers which hybridize to conserved regions of the genes are used for allele-independent amplification. Suitable allele-independent primers can be selected routinely. Assays suitable for detecting hybrids formed between probes and target polynucleotide sequences in a sample are well known in the art, for example, immobilized target (dot-blot) and immobilized probe (reverse dot-blot or line-blot) assay formats. (See, for example, Schollen et al, Clin. Chem. 43: 18-23, 2997; Gilles et al, Nat. Biotechnol. 1999, 17(40:365-70; and U.S. Pat. Nos. 5,310,893; 5,451,512; 5,468,613; and 5,604,099 for dot blot and reverse dot blot assay formats).

In an aspect of the invention, probe-based genotyping can be carried out using a 5'-nuclease assay. (See for example, Holland et al., 1988, Proc. Natl. Acad. Sci. USA, 88:7276-7280, and U.S. Pat. Nos. 5,108,892, 5,210,015, 5,487,972, and 5,804,375 describing 5'-nuclease assays). In this assay, labeled detection probes that hybridize within the amplified region are added during the amplification reaction mixture. The probes are modified so that they do not act as primers for DNA synthesis. The amplification is carried out using a DNA polymerase that possesses 5' to 3' exonuclease activity. Any probe which hybridizes to the target polynucleotide downstream from the primer being extended in the amplification is degraded by the 5' to 3' exonuclease activity of the DNA polymerase. Therefore, the synthesis of a new target strand also results in the degradation of a probe, and the accumulation of the probe degradation product provides a measure of the synthesis of target sequences. Any method suitable for detecting the products may be used in the assay. In an aspect of the invention, the probes are labeled with two fluorescent dyes, one of which is capable of quenching the fluorescence of the other dye. The dyes are attached to the probe (e.g., one is attached to the 5' terminus and the other is attached to an internal site), such that quenching occurs when the probe is not hybridized and the cleavage of the probe by the 5' to 3' exonuclease activity occurs in between the two dyes. Amplification results in cleavage of the probe between the dyes with the elimination of quenching and an increase in the fluorescence which is observable from the initially quenched dye. The accumulation of degradation product is determine by measuring the increase in reaction fluorescence. A 5-nuclease assay may employ allele-specific amplification primers such that the probe is used only to detect the presence of amplified product. Alternatively, the 5'-nuclease assay can employ a target-specific probe.

The methods described above typically employ labeled oligonucleotides to facilitate detection of the hybrid duplexes. Oligonucicotides can be labeled by incorporating a label detectable by spectroscopic, photochemical, biochemical, immunochemical, radiological, radiochemical or chemical means. Useful labels and methods for labeling oligonucleotides are described herein.

Kit

The invention also provides a kit for carrying out a method of the invention. Generally all of the features disclosed herein for the methods of the invention apply to the kits of the invention. A kit may typically comprise two or more elements required for performing a diagnostic assay. Elements include but are not limited to compounds, reagents, containers, and/or equipment.

A kit can comprise reagents for assessing one or more SNP-containing polynucleotides, variant polypeptides, N-glycans, and/or components of an N-glycan pathway or a hexosamine pathway. In an aspect, the invention provides diagnostic tools, and kits for detecting, diagnosing, and predicting a disease disclosed herein by monitoring SNP-containing polynucleotides, variant polypeptides, N-glycans, or components of an N-glycan pathway or a hexosamine pathway.

The methods described herein may be performed by utilizing pre-packaged diagnostic kits comprising one or more specific binding agent (e.g. antibody) or polynucleotide which may be conveniently used, e.g., in clinical settings to screen and diagnose patients and to screen and identify those individuals exhibiting a predisposition to developing a disease disclosed herein.

In an embodiment, a container is provided with a kit comprising a binding agent. By way of example, the kit may contain antibodies or antibody fragments or plant lectins (eg L-PHA, LEA) which bind specifically to epitopes of a component of a N-glycan or hexosamine pathway or a polypeptide variant, and antibodies against the antibodies or plant lectin labelled with a detectable substance. The kit may also contain microtiter plate wells, standards, assay diluent, wash buffer, adhesive plate covers, and/or instructions for carrying out a method of the invention using the kit.

In an aspect of the invention, the kit includes antibodies or fragments of antibodies which bind specifically to an epitope of one or more markers encoded by SNP-containing polynucleotides and means for detecting binding of the antibodies to their epitope, either as concentrates (including lyophilized compositions), which may be further diluted prior to use or at the concentration of use, where the vials may include one or more dosages.

In aspects of the invention, a kit may comprise a polynucleotide or oligonucleotide for detecting the presence of a polymorphism by hybridizing to the polymorphism under stringent conditions. In some embodiments, the oligonucleotide can be used as an extension primer in either an amplification reaction such as PCR or a sequencing reaction, wherein a polymorphism is detected either by amplification or sequencing. In particular embodiments, the kit also comprises amplification or sequencing primers which can, but need not, be sequence-specific. The kit can also comprise reagents for labeling one or more of the oligonucleotides, or comprise labeled oligonucleotides. A kit can optionally comprise reagents to detect the label.

In some embodiments, the kit can comprise one or more oligonucleotides that can be used to detect the presence of two or more predisposing or protective disease associated polymorphisms or combinations of predisposing and protective polymorphisms or both.

One aspect of the invention provides kits for detecting the presence of a first predisposing or protective disease associated polymorphism in a gene in a polynucleotide sample of an individual whose susceptibility or risk for a disease is being assessed. Thus, an aspect of the invention provides a kit including one or more oligonucleotides capable of detecting a polymorphism or SNP-containing polynucleotide, and instructions for detecting the polymorphism or SNP-containing polynucleotide, with the oligonucleotides and for correlating the detection to the individual's risk for an autoimmune disease, packaged in one or more containers.

A kit may be designed to detect the level of polynucleotides encoding one or more polymorphism (e.g., SNP-containing polynucleotides). Accordingly, the invention relates to a kit for determining the presence of a polymorphism or SNP-containing polynucleotide disclosed herein. In an aspect, the invention provides a kit for the detection of a polymorphism comprising at a minimum, at least one polynucleotide of at least 10 contiguous nucleotides of a gene of the N-glycan or hexosamine pathway co-localized in chromosomal regions associated with a disease disclosed herein, in particular a GCS1, GANAB, MAN1A1, MGAT1, MGAT2, and/or MGAT5 gene, or their complements, wherein at least one polynucleotide contains at least one polymorphic sited associated with the disease. In an embodiment of the invention, a kit comprises oligonucleotides complementary to at least one SNP shown in FIGS. 11, 22, and 23, and SEQ ID NOs.:5, 6, 7, 8, 9, and 35-47.

An aspect of the invention provides kits for detecting the presence of a first predisposing or protective polymorphism in a gene of the N-glycan pathway or hexosamine pathway, in particular a GCS1, GANAB, MAN1A1, MGAT1, MGAT2, and MGAT5 gene, e.g., in a polynucleotide sample of an individual whose risk for a disease disclosed herein (e.g, an autoimmune disease, in particular MS or rheumatoid arthritis) is being assessed. In an aspect, the invention provides a kit including one or more oligonucleotides capable of detecting a polymorphism in the one or more gene of the N-glycan pathway or hexosamine pathway and instructions for detecting the polymorphism with the oligonucleotides and for correlating the detection to the individual's risk for a disease disclosed herein (e.g, autoimmune disease, in particular MS or rheumatoid arthritis), packaged in one or more containers.

The invention relates to a kit useful for detecting the presence of a predisposing or a protective polymorphism in a gene of the N-glycan pathway or hexosamine pathway, in particular a GCS1, GANAB, MAN1A1, MGAT1, MGAT2, and/or MGAT5 gene, in a polynucleotide sample of an individual whose risk or susceptibility for an autoimmune disease is being assessed. The kit can comprise one or more oligonucleotides capable of detecting a predisposing or protective polymorphism in the locus as well as instructions for using the kit to detect risk or susceptibility to an autoimmune disease. In embodiments, the oligonucleotide or oligonucleotides each individually comprise a sequence that hybridizes under stringent conditions to at least one polymorphism. In some embodiments, the oligonucleotide or oligonucleotides each individually comprise a sequence that is fully complementary to a polynucleotide sequence comprising a polymorphism described herein.

In one aspect, the kit can be used to detect the presence of a polymorphism by hybridization of a polynucleotide probe to the polymorphism. Therefore, in an aspect of the invention, the oligonucleotides comprise at least one probe. In certain embodiments, the oligonucleotide hybridizes under stringent conditions to a region of a gene comprising an an autoimmune disease-associated polymorphism. In another aspect, the polymorphism is a single nucleotide polymorphism comprising a nucleotide at a particular nucleotide position. Under stringent conditions, the oligonucleotide hybridizes to a region of a gene comprising the single nucleotide polymorphism with a signal to noise ratio that is at least 2 times (e.g., at least 5 times or at least 10 times) the signal to noise ratio at which the oligonucleotide hybridizes to the region of the gene in the absence of the polymorphism at the nucleotide position. The oligonucleotide is typically fully complementary to the region of the gene comprising the polymorphism, and typically comprises at least about 10 to 30 contiguous nucleotides complementary to the gene.

To facilitate detection of a polymorphism the oligonucleotides in a kit optionally comprise a label (e.g., an isotopic, fluorescent, fluorogenic, luminescent or colorimetric label). In some aspects, the label itself directly produces a detectable signal (e.g., a fluorescent label). In other aspects, the kit also includes a reagent that detects the label (e.g., an enzyme that cleaves a colorimetric label and the like).

In an aspect of a kit of the invention, the oligonucleotides comprise primers. The primer(s) can be used to detect a polymorphism of the invention in an allele-specific amplification or extension reaction. The primer(s) can be used to amplify a region of a gene comprising the polymorphism for subsequent detection of the polymorphism by hybridization, sequencing, or the like. Thus, in one aspect, the oligonucleotides comprise amplification primers, wherein the amplification primers amplify a polynucleotide sequence comprising the polymorphism. The oligonucleotides can also comprise primers that flank the polymorphism.

A kit can optionally be used to detect more than one polymorphism (simultaneously or sequentially). Thus, in aspects of the invention, the kit also includes one or more second oligonucleotides capable of detecting a second polymorphism (and optionally third, fourth, fifth, etc. oligonucleotides capable of detecting third, fourth, fifth, etc. polymorphisms). A second polymorphism can be at the same polymorphic site as a first polymorphism, or at a different polymorphic site, and can be protective or predisposing.

The oligonucleotides in a kit can be optionally immobilized on a substrate. The substrate can be, for example, a planar substrate or a beaded substrate.

In an aspect, a kit comprises in a package a restriction enzyme capable of distinguishing alternate nucleotides at the polymorphism site or a labeled oligonucleotide being sufficiently complementary to the polymorphism site and capable of distinguishing the alternate nucleotides at the polymorphism site (i.e. probes). A kit may also comprise primers to amplify a region surrounding the polymorphism site, a polymerization agent and instructions for using the kit to determine genotype.

The invention also relates to a kit comprising a container unit and components for practicing a method of the invention. A kit can contain oligonucleotide probes specific for alleles as well as instructions for their use to determine risk or susceptibility for an autoimmune disease. In some cases, a kit may comprise detection probes fixed to an appropriate support membrane. The kit can also contain amplification primers for amplifying regions of a locus encompassing the polymorphic sites, as such primers are useful in aspects of the invention. Alternatively, useful kits can contain a set of primers comprising an allele-specific primer for the specific amplification of alleles. Other optional components of the kits include additional reagents used in the genotyping methods as described herein. For example, a kit additionally can contain an agent to catalyze the synthesis of primer extension products, substrate nucleoside triphosphates, reagents for labeling and/or detecting polynucleotides (for example, an avidin-enzyme conjugate and enzyme substrate and a chromogen if the label is biotin) and appropriate buffers for amplification or hybridization reactions.

Array

The invention relates to an array, a support with immobilized oligonucleotides, useful for practicing the present method. A useful array can contain oligonucleotide probes specific for alleles or certain combinations of alleles described herein or for SNP-containing polymorphisms. The oligonucleotides can be immobilized on a substrate. The oligonucleotides may be labeled. In some embodiments, the array can be a micro-array. In some embodiments, the array can comprise one or more oligonucleotides used to detect the presence of two or more alleles or certain combinations of alleles. Oligonucleotide(s) can be arranged in an array of other oligonucleotides which can be used to detect other polymorphisms.

In aspects of the invention, arrays are provided for detecting the presence of one or more predisposing and/or protective disease-associated polymorphisms in a gene (e.g, autoimmune disease associated polymorphisms), for example, in a polynucleotide sample of an individual whose risk for an autoimmune disease is being assessed. In a particular aspect, the array comprises a substrate and a plurality of oligonucleotides, each oligonucleotide capable of hybridizing to a region of the gene comprising at least one polymorphism. The hybridization detects the presence of the polymorphism, and provides an indication of the individual's risk for a disease (e.g., autoimmune disease). Typically, the array is used for detecting the presence of a plurality of polymorphisms, e.g., multiple alleles at a single polymorphic site and/or different polymorphic sites.

Generally all of the features noted for the method and kit aspects of the invention apply to an array of the invention. For example, the one or more polymorphisms preferably comprise one or more single nucleotide polymorphisms. For example, the polymorphism may be one or more SNP shown in FIGS. 11, 22, and 23, and SEQ ID NOs.:5, 6, 7, 8, 9, and 35-47.

The invention in particular contemplates an array that can be used to detect the presence of one or more SNPs comprising oligonucleotides which are capable of hybridizing under stringent conditions to a region of a gene comprising a single nucleotide polymorphism with a signal to noise ratio that is at least 2, 5 or 10 times that at which the oligonucleotide hybridizes to a region of the gene comprising another single nucleotide polymorphisms. Typically, one oligonucleotide is used to detect one SNP; that is, each oligonucleotide is capable of hybridizing to a distinct SNP.

A plurality of oligonucleotides may be immobilized on a substrate, e.g., a planar substrate, a membrane, a glass slide, or the like. Typically, each of the plurality of oligonucleotides is immobilized at a known, predetermined position on the substrate. Each oligonucleotide may be bound (e.g., electrostatically or covalently bound, directly or via a linker) to the substrate at a unique location. In order to facilitate detection of polymorphisms by specific hybridization with the oligonucleotides, each of the oligonucleotides is typically fully complementary to a region of a gene comprising one of the polymorphisms, and each of the plurality of oligonucleotides comprises at least about 10 to 30 contiguous nucleotides complementary to the gene. An oligonucleotide may optionally comprise a label that facilitates detection of hybridization between the oligonucleotide and the polymorphism.

An array can be part of a system. Thus, the invention provides a system comprising an array of the invention and system instructions that correlate the detection of the presence of one or more predisposing or protective disease-associated polymorphisms (e.g., autoimmune-associated polymorphisms) to the individual's risk for the disease.

Methods of making, using, and analyzing arrays such as micro-arrays are well known in the art (see, e.g., Wang et al., 1998, Science 280:1077-82; Lockhart and Winzeler, 2000, Nature 405:827-836; and Scherf et al., 2000, Nat Genet. 24:236). Arrays can be formed (e.g., printed), using commercially available instruments (e.g., a GMS 417 Arrayer, Affymetrix, Santa Clara, Calif.). Suitable solid supports are commercially available and include without limitation membranes (e.g., nylon, PVDF, and nitrocellulose membranes) and surface-modified and pre-coated slides with a variety of surface chemistries (e.g., from TeleChem International (www.arrayit.com), Corning, Inc. (Corning, N.Y.), or Greiner Bio-One, Inc. (www.greinerbiooneinc.com). Further, custom arrays of polynucleotides are commercially available (e.g., from Agilent Technologies (CA, USA) and from TeleChem International (CA, USA)(www.arrayit.com)).

Automated Methods

Various automated systems can be used to perform some or all of the methods of the invention. In addition, digital or analog systems, for example, comprising a digital or analog computer, can also control a variety of other functions such as a user viewable display to permit viewing of method results by a user and/or control of output features. For example, particular methods described herein may be implemented on a computer program or programs. The programs may correlate detection of the presence of one or more predisposing or protective polymorphisms to an individual's risk for a disease disclosed herein, in particular an autoimmune disease, more particularly MS. Therefore, the invention contemplates digital systems, including computers, computer readable media, and/or integrated systems comprising instructions (e.g., embodied in appropriate software) for performing the methods of the invention. In an aspect, the invention provides a digital system comprising instructions for correlating detection of the presence of one or more predisposing or protective polymorphisms to an individual's risk for a disease disclosed herein in particular an autoimmune disease, more particularly MS. A digital system may also include information corresponding to individual genotypes for a set of genetic markers, phenotypic information, and the like. The system may also assist in the detection of polymorphisms by, for example, controlling a microarray scanner.

Standard desktop applications can be adapted to the present invention by inputting data which is loaded into the memory of a digital system, and performing an operation on the data. Such applications include word processing software such as Microsoft Word, database software such as Microsoft Excel, and/or database programs such as Microsoft Access. For example, systems including these software applications containing appropriate genotypic information, associations between phenotype and genotype, and other relevant information may be used in conjunction with a user interface (e.g., a GUI in a standard operating system such as a Windows, Macintosh or LINUX system) to perform any analysis noted herein, or simply to retrieve data (e.g., in a spreadsheet) to be used in the methods disclosed herein. A system may include a digital computer with software for performing association analysis and/or risk prediction, and also data sets entered into the software system comprising genotypes for a set of genetic markers, phenotypic values and the like. The systems of the invention can use commercially available computers.

The methods of the invention may also be embodied within the circuitry of an application specific integrated circuit (ASIC) or programmable logic device (PLD). In such applications, a method of the invention is embodied in a computer readable descriptor language that can be used to create an ASIC or PLD. The methods of the invention can also be embodied within the circuitry or logic processors of other digital apparatus, such as PDAs, laptop computer systems, displays, image editing equipment, and the like.

Therapeutic Applications

Combinations of genetic defects and environmental factors that lead to relatively small reductions in Mgat5 expression represent candidate susceptibility factors for MS and other autoimmune diseases. Mgat5 glycan expression is dependent on the activity of multiple genes in two biochemical pathways: the N-glycan pathway and the hexosamine pathway. Genetic hypomorphism in the hexosamine and N-glycan pathways in mammals may increase susceptibility to autoimmune diseases by limiting Mgat5 glycan expression in T cells. Genes in these two pathways are disproportionately found in chromosomal regions previously associated with autoimmune diseases such as MS. White blood cells from patients display structural abnormalities in N-glycan profiles. DNA sequencing identified multiple SNPs in 5-glycosylation genes associated with autoimmune diseases such as MS. Observed genetic and structural N-glycan processing defects are associated with attenuated Mgat5 glycan up-regulation during T cell proliferation. Genetically determined defects in Mgat5 glycan expression are common in patients with autoimmune diseases (e.g., the defects were observed in greater than 85% of tested MS patients). In the animal models described herein, altered Mgat5 modified glycan expression leads to T cell hyper-proliferation, preferential Th1 differentiation and spontaneous autoimmune CNS demyelinating disease, indicating that the genotypic and phenotypic defects in Mgat5 modified glycan regulation identified in autoimmune disease patients (e.g, MS patients) directly promotes disease.

Mgat5-modified N-glycans are sensitive to changes in the intracellular concentrations of UDP-GlcNAc, the sugar donor synthesized de novo from glucose via the hexosamine pathway. Metabolic supplementation of the hexosamine pathway in T cells raises Mgat5 modified glycan levels; inhibits proliferation, Th1 differentiation and EAE; and can reverse Mgat5 modified glycan down regulation induced by blockade of proximal N-glycan processing. Vitamin D3 up-regulates MGAT5 mRNA expression in hepatoma cells, inhibits T cell activation, $T_H1$ differentiation, EAE and is an environmental factor whose deficiency is associated with MS. Addition of Vitamin D3 to Jurkat T cells or human PBMCs enhanced Mgat5 modified glycan expression, synergized with anti-CD3 in up-regulating mgat5 modified glycan levels, rescued swainsonine induced down-regulation of Mgat5 modified glycans and reversed attenuated Mgat5 N-glycan expression in MS patients.

Chemical blockade of Mgat5 glycan expression reversed Vitamin D3 induced inhibition of T cell proliferation, indicating that Vitamin D3 negatively regulates T cell function by enhancing Mgat5 modified glycan expression. Thus, Vitamin D3 levels and metabolic flux through the hexosamine pathway provide two independent mechanisms for environmental and therapeutic modulation of Mgat5 modified glycan expression and disease promotion by the identified SNPs. The data herein define genetic and environmental regulation of Mgat5 glycan expression as a major susceptibility factor for autoimmune diseases such as MS.
Treatments, Compositions, and Kits Comprising Agonists, Regulators, Metabolites Etc.

The invention provides a method of treating a disease disclosed herein, in particular an autoimmune disease, more particularly MS, in a subject comprising modulating one or more of N-glycans (e.g., expression or levels), N-glycan processing, an N-glycan pathway, and a hexosamine pathway. In an aspect, N-glycans, N-glycan processing, an N-glycan pathway, and/or a hexosamine pathway are modulated by modulating one or more of glucosidase I (GI), mannosidase I (MI), mannosidase II (MII/MIIx), MGAT1, MGAT2, and MGAT5. In a particular embodiment, N-glycans, N-glycan processing, an N-glycan pathway, and/or a hexosamine pathway are modulated by administering a substance that raises N-glycan levels or up-regulates MGAT5 expression. A substance may be an agonist to polypeptides encoded by genes of the N-glycan pathway or hexosamine pathway associated with a disease disclosed herein, a compound that change the concentration of upstream regulators or downstream effector molecules of a polypeptide encoded by a gene of the N-glycan pathway or hexosamine pathway.

Agonists to polypeptides encoded by genes of the N-glycan pathway or hexosamine pathway associated with a disease disclosed herein can be antibodies, peptides, proteins, polynucleotides, small organic molecules, or polymers. Agonists may be prepared as a composition with a pharmaceutically acceptable carrier, vehicle or diluent. Antibodies can be prepared by conventional methods and peptides, proteins, polynucleotides, small organic molecules, and polymers may be identified by combinatorial methods. Agonists may be prepared as a composition with a pharmaceutically acceptable carrier, vehicle or diluent.

An aspect of the invention is directed towards a method to treat a disease disclosed herein, in particular an autoimmune disease, more particularly MS. The method may comprise selecting a subject diagnosed with an autoimmune disease and administering to the subject an agonist, in particular an agonist of the expression or activity of GCS1, GANAB, MAN1A1, Mgat1, Mgat2, and/or Mgat5. The agonist can be administered at a concentration suitable to reduce the effects of the disease. The concentration of the agonist may be less than about 100 mM, about 10 mM, about 1 mM, 100 µM, about 10 µM, about 1 µM, about 0.1 µM, about 0.01 µM, about 0.001 µM or about 0.0001 µM.

Another aspect embodiment of the invention is directed to the use of compounds that change the concentration of upstream regulators or downstream effector molecules of a polypeptide encoded by a gene of the N-glycan pathway or hexosamine pathway, in treating or preventing a disease disclosed herein, in particular an autoimmune disease, more particularly MS. The method can comprise selecting a subject diagnosed with the disease, and administering to the mammal one or more agonist, in particular a Mgat5 agonist. The concentration of agonist can be less than about 100 µM, about 10 µM, about 1 µM, about 0.1 µM, about 0.01 µM, about 0.001 µM or about 0.0001 µM.

In an embodiment of the invention, a method of treatment comprises increasing N-glycan levels, in particular Mgat5 modified glycan levels, by administering an agonist of Mgat5 and/or metabolites to raise UDP-GlcNAc levels in the cell.

The invention also provides methods and compositions for treating or preventing a disease discussed herein in a subject comprising increasing in the subject expression or amount of one or more of (a) N-glycans, in particular, Mgat5 modified glycans and/or polylactosamine modified glycans, and (b) a component of the N-glycan pathway or hexosamine pathway. Aspects of the methods of the invention comprise administering to a subject one or more of the following: N-glycans (e.g., Mgat5 modified glycans or polylactosamine modified glycans); an agonist of a component of the N-glycan or hexosamine pathways (e.g., an agonist of an enzyme of the N-glycan pathway, especially Mgat5); a substance that increases expression or synthesis of a component of the N-glycan or hexosamine pathways (e.g., an enzyme of the N-glycan pathway, especially Mgat5); an acceptor for an enzyme of the N-glycan pathway (e.g., an acceptor for Mgat5); a donor for an enzyme of the N-glycan pathway (e.g., a donor for Mgat5), or a hexosamine pathway metabolites.

In an aspect, the invention provides methods and compositions for treating or preventing a disease discussed herein, in particular an autoimmune disease, more particularly an autoimmune demyelinating disease, most particularly multiple sclerosis, in a subject comprising increasing in the subject expression or amount of Mgat5, Mgat5 modified glycans and/or polylactosamine modified glycans or a polypeptide or a gene or polypeptide comprising a polymorphism identified using a method of the invention. The expression or amount of Mgat5 modified glycans or polylactosamine modified glycans can be increased by administering Mgat5 modified glycans or polylactosamine modified glycans to the subject or an agonist of Mgat5, or increasing expression or synthesis of Mgat5, an acceptor for Mgat5, or a donor for Mgat5.

In an aspect of a preventive and therapeutic method of the invention, expression of Mgat5 modified glycans are increased by administering an agonist of Mgat5. In a particular aspect, the agonist up-regulates MGAT5 polynucleotides, in particular MGAT5 mRNA. Examples of agonists of MGAT5 expression include insoluble lipid vitamins agonists such as Vitamin D3, retinoic acid, analogs and derivatives thereof, and the like. In embodiments of the methods and compositions of the invention a Vitamin D3 compound including vitamin D3, 1-hydroxy Vitamin D3, and 1,25 dihydroxy-Vitamin D3 are utilized.

In another aspect of a preventive and therapeutic method of the invention, the amount of a sugar donor for Mgat5 is increased. A sugar donor concentration can be increased by administering one or more of a sugar donor, a metabolite of pathways for synthesis of the sugar donor or precursors thereof, regulators or agonists of a sugar donor or pathway for synthesis of a sugar donor, or hexosamine pathway metabolites. A sugar donor may be a nucleotide sugar, dolichol-phosphate-sugar or dolichol-pyrophosphate-oligosaccharide, for example, cytidine or uridine diphospho-N-acetylglucosamine (CDP-GlcNAc or UDP-GlcNAc), or derivatives or analogs thereof. Metabolites for use in the methods of the invention include without limitation one or more of nucleotides (e.g. UMP, UDP, UTP, CMP, CDP, or CTP), nucleosides (e.g. cytidine or uridine), nucleobases (e.g., uracil, cytosine) sugars (e.g. glucose), acetoacetate, glutamine, glucosamine, N-acetyl-glucosamine (GlcNAc), and analogs and derivatives thereof.

In particular aspects of the invention a sugar donor comprises one or more metabolite of a pathway for synthesis of a sugar donor, wherein the metabolite is selected from the group consisting of nucleotides (e.g., UMP, UDP, UTP, CMP, CDP, or CTP); nucleosides (e.g. cytidine or uridine), nucleobases (e.g., uracil, cytosine), sugars (e.g. glucose), acetoacetate, glutamine, glucosamine or GlcNAc or analogs and derivatives thereof.

In some embodiments the metabolites comprise a nucleotide, nucleoside, nucleobase, a sugar, and/or a combination of a nucleotide, nucleoside, nucleobase, and a sugar, more particularly uridine or cytidine and a sugar, most particularly UDP, uracil, uridine, GlcNAc, and/or analogs or derivatives thereof.

In certain embodiments an analog or derivative of a metabolite is used. For example, an acetylated GlcNAc, peracetylated GlcNAc, or GlcNAc tetraacetate (e.g., N-acetyl-beta-D-glucosamine tetraacetate or alpha-D-N-acetylglucosamine tetraacetate) may be used in any of the methods of the invention.

In an embodiment of the invention, a method is provided for treating or preventing a disease discussed herein, in particular an autoimmune disease, more particularly rheumatoid arthritis or an autoimmune demyelinating disease, most particularly multiple sclerosis, in a subject comprising administering a therapeutically effective amount of one or more hexosamine pathway metabolites.

In an embodiment of the invention, a method is provided for treating or preventing a disease discussed herein, in particular an autoimmune disease, more particularly rheumatoid arthritis or an autoimmune demyelinating disease, most particularly multiple sclerosis, in a subject comprising administering a therapeutically effective amount of glucosamine, GlcNAc, and/or vitamin D3 compounds, or analogs or derivatives thereof.

In a particular embodiment of the invention, a method is provided for treating or preventing a disease discussed herein, in particular an autoimmune disease, more particularly rheumatoid arthritis or an autoimmune demyelinating disease, most particularly multiple sclerosis, comprising administering a therapeutically effective amount of one or more of GlcNAc or an analog or derivative thereof, a Vitamin D3 compound, a nucleotide (e.g, UMP, UDP, UTP, CMP, CDP, or CTP), nucleoside (e.g. cytidine or uridine), a nucleobase (e.g., uracil, cytosine), sugar (e.g., glucose), acetoacetate, glutamine, and glucosamine.

In another particular embodiment of the invention, a method is provided for treating or preventing a disease discussed herein, in particular an autoimmune disease, more particularly rheumatoid arthritis or an autoimmune demyelinating disease, most particularly multiple sclerosis, comprising administering a therapeutically effective amount of one or more of GlcNAc or an analog or derivative thereof, a Vitamin D3 compound, nucleoside (e.g. cytidine or uridine), a nucleobase (e.g., uracil, cytosine), sugar (e.g., glucose), acetoacetate, glutamine, and glucosamine.

In a further particular embodiment of the invention, a method is provided for treating or preventing a disease discussed herein, in particular an autoimmune disease, more particularly rheumatoid arthritis or an autoimmune demyelinating disease, most particularly multiple sclerosis, comprising administering a therapeutically effective amount of one or more of acetylated GlcNAc, uracil, uridine, and a Vitamin D3 compound.

In an aspect of the invention, a method is provided for treating or preventing a disease discussed herein, in particular an autoimmune disease, more particularly rheumatoid arthritis or an autoimmune demyelinating disease, most particularly multiple sclerosis, comprising administering synergistically therapeutically effective amounts of one or more of GlcNAc, or an analog or derivative thereof, a Vitamin D3 compound, a nucleotide (e.g, UMP, UDP, UTP, CMP, COP, or CTP), nucleoside (e.g. cytidine or uridine), nucleobase (e.g., uracil, cytosine), sugar (e.g., glucose), acetoacetate, glutamine, and glucosamine.

In an embodiment of the invention, a method is provided for treating or preventing a disease discussed herein, in particular an autoimmune disease, more particularly rheumatoid arthritis or an autoimmune demyelinating disease, most particularly multiple sclerosis, comprising administering synergistically therapeutically effective amounts of one or more of GlcNAc, or an analog or derivative thereof, a Vitamin D3 compound, a nucleoside (e.g. cytidine or uridine) and glucosamine, in particular GlcNAc, uridine, and Vitamin D3.

The invention also contemplates a method of increasing Mgat5 modified glycans in a cell comprising administering to the cell an amount of one or more of GlcNAc or an analog or derivative thereof, a Vitamin D3 compound, nucleotide (e.g, UMP, UDP, UTP, CMP, CDP, or CTP), nucleoside (e.g. cytidine or uridine), nucleobase (e.g., uracil, cytosine), sugar (e.g., glucose), acetoacetate, glutamine, and/or glucosamine, to provide an increase in the MGAT5 modified glycans which is greater compared to administration of GlcNAc, Vitamin D3 compound, a nucleotide (e.g, UMP, UDP, UTP, CMP, CDP, or CTP), a nucleoside (e.g. cytidine or uridine), or a nucleobase (e.g., uracil, cytosine) sugar (e.g., glucose), acetoacetate, glutamine, and/or glucosamine, alone.

The invention further provides a combination therapy comprising administering GlcNAc and/or glucosamine or analogs or derivatives thereof, and one or more of a Vitamin D3 compound a nucleotide (e.g, UMP, UDP, UTP, CMP, CDP, or CTP), nucleoside (e.g. cytidine or uridine), nucleobase (e.g., uracil, cytosine), sugar (e.g., glucose), acetoacetate, or glutamine, for the treatment and/or prevention of an autoimmune disease in particular rheumatoid arthritis or a autoimmune demyelinating disease, in particular multiple sclerosis.

Another aspect of this invention is a method of treating a disease discussed herein, in particular an autoimmune disease, more particularly rheumatoid arthritis or an autoimmune demyelinating disease, most particularly multiple sclerosis, comprising the steps of administering to a patient, either together or separately, GlcNAc and/or glucosamine analogs or derivatives thereof, and one or more of a nucleotide (e.g, UMP, UDP, UTP, CMP, CDP, or CTP), nucleoside (e.g. cytidine or uridine), nucleobase (e.g., uracil, cytosine), sugar (e.g., glucose), acetoacetate, or glutamine.

An additional aspect of the invention is directed to methods for the prevention of a disease disclosed herein, in particular an autoimmune disease, more particularly MS or rheumatoid arthritis. The methods may comprise selecting a subject, and administering to the mammal an agonist, in particular a Mgat5 agonist. The agonist is preferably administered at a concentration suitable to reduce the occurrence or effects of the disease relative to a subject which did not receive the administration. The concentration of the agonist is preferably less than about 100 mM, about 10 mM, about 1 mM, 100 µM, about 10 µM, about 1 µM, about 0.1 µM, about 0.01 µM, about 0.001 µM or about 0.0001 µM.

In the methods of the invention the administering step can be performed by any acceptable means, including oral, inhalation, topical, intravenous, intraperitoneal, and intramuscular administration.

In an embodiment, this invention provides methods of treating or preventing a disease discussed herein, in particular an autoimmune disease, more particularly rheumatoid arthritis or an autoimmune demyelinating disease, most particularly multiple sclerosis, in a mammal comprising the step of administering to the mammal any of the compositions and combinations described herein.

The invention includes combination treatments providing synergistic activity or delivering synergistically effective amounts of one or more hexosamine pathway metabolite; GlcNAc or glucosamine or analogs or derivatives thereof and other hexosamine pathway metabolites; an agonist of a component of the N-glycan pathway or hexosamine pathway; and/or, one or more of Vitamin D3, GlcNAc or an analog or derivative thereof, of a nucleotide (e.g, UMP, UDP, UTP, CMP, CDP, or CTP), nucleoside (e.g. cytidine or uridine), nucleobase (e.g., uracil, cytosine), sugar (e.g., glucose), acetoacetate, glutamine, or glucosamine. Compositions suitable for use in the present invention include compositions wherein the active ingredients are contained in a synergistically effective amount. Such a composition comprises sufficient amounts of each component to achieve a desired result that is greater than the result achieved with each component on its own.

An aspect of this invention is the use of a sugar donor, metabolite, regulator or agonist discussed herein, in particular UDP-GlcNAc, or a combination of GlcNAc and/or glucosamine or analogs or derivatives thereof, and one or more hexosamine pathway metabolite, or GlcNAc and/or glucosamine or analogs or derivatives thereof and one or more of Vitamin D3, a nucleotide (e.g, UMP, UDP, UTP, CMP, CDP, or CTP), nucleoside (e.g. cytidine or uridine), nucleobase (e.g., uracil, cytosine), sugar (e.g., glucose), acetoacetate, or glutamine, in the preparation of a medicament, to treat or prevent a disease discussed herein, in particular an autoimmune disease, more particularly rheumatoid arthritis or an autoimmune demyelinating disease, most particularly multiple sclerosis.

The present invention provides a combination therapy pharmaceutical composition comprising GlcNAc or an analog or derivative thereof, and one or more hexosamine pathway metabolite, or GlcNAc and/or glucosamine or analogs or derivatives thereof, and one or more of a Vitamin D3 compound, a nucleotide (e.g, UMP, UDP, UTP, CMP, CDP, or CTP), nucleoside (e.g. cytidine or uridine), nucleobase (e.g., uracil, cytosine), sugar (e.g., glucose), acetoacetate, or glutamine. Accordingly, the invention relates to a multi-component composition comprising GlcNAc or an analog or derivative thereof, and one or more hexosamine pathway metabolite, or GlcNAc and/or glucosamine or analogs or derivatives thereof, and one or more of a Vitamin D3 compound, a nucleotide (e.g, UMP, UDP, UTP, CMP, CDP, or CTP), nucleoside (e.g. cytidine or uridine), nucleobase (e.g., uracil, cytosine), sugar (e.g., glucose), acetoacetate, or glutamine, and a pharmaceutically acceptable carrier, diluent, or excipient. In an embodiment, the multi-component composition comprises additive amounts, in particular synergistic amounts, of GlcNAc or an analog or derivative thereof, and one or more hexosamine pathway metabolite, or GlcNAc and/or glucosamine or analogs or derivatives thereof, and one or more of a Vitamin D3 compound, a nucleotide (e.g, UMP, UDP, UTP, CMP, CDP, or CTP), nucleoside (e.g. cytidine or uridine), nucleobase (e.g., uracil, cytosine), sugar (e.g., glucose), acetoacetate, or glutamine.

In accordance with another aspect, a composition is provided comprising a combination of GlcNAc or an analog or derivative thereof, and one or more hexosamine pathway metabolite, or GlcNAc and/or glucosamine or analogs or derivatives thereof, and one or more of a Vitamin D3 compound, a nucleotide (e.g, UMP, UDP, UTP, CMP, CDP, or CTP), nucleoside (e.g. cytidine or uridine), nucleobase (e.g., uracil, cytosine), sugar (e.g., glucose), acetoacetate, or glutamine effective to exert a synergistic effect in preventing and/or treating rheumatoid arthritis or a CNS demyelinating autoimmune disease, in particular multiple sclerosis. In an embodiment, the composition comprises a GlcNAc or an analog or derivative thereof, and one or more hexosamine pathway metabolite, or GlcNAc and/or glucosamine or analogs or derivatives thereof, and one or more of a Vitamin D3 compound, a nucleotide (e.g, UMP, UDP, UTP, CMP, CDP, or CTP), nucleoside (e.g. cytidine or uridine), nucleobase (e.g., uracil, cytosine), sugar (e.g., glucose), acetoacetate, or glutamine, in doses that are at least 1 to 10 fold, 2 to 10 fold, or 5 to 10 fold lower than the doses of each component required to prevent and/or treat the disease.

The compositions of the invention preferably contain a pharmaceutically acceptable carrier diluent, or excipient suitable for rendering the compounds administrable orally, intranasally, parenterally, intravenously, intradermally, intramuscularly or subcutaneously, rectally, via inhalation or via buccal administration, or transdermally. The active ingredients may be admixed or compounded with any conventional pharmaceutically acceptable carrier or excipient. It will be understood by those skilled in the art that any mode of administration, vehicle or carrier conventionally employed and which is inert with respect to the active agents may be utilized for preparing and administering the pharmaceutical compositions of the present invention. Illustrative of such methods, vehicles and carriers are those described, for example, in *Remington: The Science and Practice of Pharmacy*, 21$^{st}$ Edition. University of the Sciences in Philadelphia (Editor), Mack Publishing Company. Those skilled in the art, having been exposed to the principles of the invention, will experience no difficulty in determining suitable and appropriate vehicles, excipients and carriers or in compounding the active ingredients therewith to form the pharmaceutical compositions of the invention.

The present invention provides a process for making a pharmaceutical composition comprising combining a GlcNAc or an analog or derivative thereof, and one or more hexosamine pathway metabolite, or GlcNAc and/or glucosamine or analogs or derivatives thereof, and one or more of a Vitamin D3 compound, a nucleotide (e.g, UMP, UDP, UTP, CMP, CDP, or CTP), nucleoside (e.g. cytidine or uridine), nucleobase (e.g., uracil, cytosine), sugar (e.g., glucose), acetoacetate, or glutamine, and a pharmaceutically acceptable carrier or excipient.

The present invention provides a dietary supplement composition comprising one or more of a Vitamin D3 compound, retinoic acid, hexosamine pathway metabolite, nucleotides (e.g. UMP, UDP, UTP, CMP, CDP, or CTP), nucleosides (e.g. cytidine or uridine), nucleobases (e.g., uracil, cytosine) sugars (e.g. glucose), acetoacetate, glutamine, glucosamine, N-acetyl-glucosamine (GlcNAc), or nutraceutically acceptable derivatives thereof. The invention also provides a method of manufacturing a nutritional or dietary supplement composition of the invention effective in the prevention, stabilization, reversal and/or treatment of a disease disclosed herein comprising combining one or more of a Vitamin D3 compound, retinoic acid, hexosamine pathway metabolite, nucleotides (e.g. UMP, UDP, UTP, CMP, CDP, or CTP), nucleosides (e.g. cytidine or uridine), nucleobases (e.g., uracil, cytosine) sugars (e.g. glucose), acetoacetate, glutamine, glucosamine, N-acetyl-glucosamine (GlcNAc), or nutraceutically acceptable derivatives thereof with a nutraceutically acceptable carrier.

In an aspect, the invention provides a dietary supplement for mammalian consumption, particularly human consumption for the purpose of treating or preventing a disease disclosed herein, in particular an autoimmune disease, more particularly rheumatoid arthritis or MS, comprising one or more of Vitamin D, retinoic acid, hexosamine pathway metabolites, nucleotides (e.g. UMP, UDP, UTP, CMP, CDP, or CTP), nucleosides (e.g. cytidine or uridine), nucleobases (e.g., uracil, cytosine) sugars (e.g. glucose), acetoacetate, glutamine, glucosamine, N-acetyl-glucosamine (GlcNAc), or nutraceutically acceptable derivatives thereof.

In another aspect, the invention provides a dietary supplement for mammalian consumption, particularly human consumption for the purpose of improving N-glycan regulation or function, modulating the immune response (e.g. by modulating T cell function or cytokine production), reducing inflammation, and/or improving CNS function in a disease disclosed herein, in particular an autoimmune disease, more particularly MS, comprising one or more of a Vitamin D3 compound, retinoic acid, hexosamine pathway metabolites, nucleotides (e.g. UMP, UDP, UTP, CMP, CDP, or CTP), nucleosides (e.g. cytidine or uridine), nucleobases (e.g., uracil, cytosine) sugars (e.g. glucose), acetoacetate, glutamine, glucosamine, N-acetyl-glucosamine (GlcNAc), or nutraceutically acceptable derivatives thereof.

In another aspect, the invention provides a supplement comprising one or more of a Vitamin D3 compound, retinoic acid, hexosamine pathway metabolites, nucleotides (e.g. UMP, UDP, UTP, CMP, CDP, or CTP), nucleosides (e.g. cytidine or uridine), nucleobases (e.g., uracil, cytosine) sugars (e.g. glucose), acetoacetate, glutamine, glucosamine, N-acetyl-glucosamine (GlcNAc), or nutraceutically acceptable derivatives, thereof for improving N-glycan regulation or function, modulating the immune response (e.g. by modulating T cell function or cytokine production), reducing inflammation, and/or improving CNS function of individuals who suffer from a disease disclosed herein and who have taken the supplement.

A dietary supplement of the invention is preferably pleasant tasting, effectively absorbed into the body and provides substantial therapeutic effects.

This invention also includes a regimen for supplementing a healthy individual's diet to prevent a disease disclosed herein, in particular an autoimmune disease, more particularly MS or rheumatoid arthritis, by administering one or more of a Vitamin D3 compound, retinoic acid, hexosamine pathway metabolites, nucleotides (e.g. UMP, UDP, UTP, CMP, CDP, or CTP), nucleosides (e.g. cytidine or uridine), nucleobases (e.g., uracil, cytosine) sugars (e.g. glucose), acetoacetate, glutamine, glucosamine, N-acetyl-glucosamine (GlcNAc), and an acceptable carrier, to the individual. The invention further includes a regimen for supplementing a healthy individual's diet to prevent a disease disclosed herein by administering daily to the human one or more of vitamin D, retinoic acid, nucleotides (e.g. UMP, UDP, UTP, CMP, CDP, or CTP), nucleosides (e.g. cytidine or uridine), nucleobases (e.g., uracil, cytosine) sugars (e.g. glucose), acetoacetate, glutamine, glucosamine, N-acetyl-glucosamine (GlcNAc), or a nutraceutically acceptable derivative thereof.

In an aspect, the invention provides a regimen for supplementing a diet of an individual suffering form a disease disclosed herein, in particular an autoimmune disease, more particularly MS or rheumatoid arthritis, comprising administering to the human a supplement comprising one or more of a Vitamin D3 compound, retinoic acid, hexosamine pathway metabolite, nucleotides (e.g. UMP, UDP, UTP, CMP, CDP, or CTP), nucleosides (e.g. cytidine or uridine), nucleobases (e.g., uracil, cytosine) sugars (e.g. glucose), acetoacetate, glutamine, glucosamine, N-acetyl-glucosamine (GlcNAc), or nutraceutically acceptable derivatives thereof.

An individual may be treated with a supplement at least about every day, or less frequently, such as every other day or once a week. A supplement of the invention may be taken daily but consumption at lower frequency, such as several times per week or even isolated doses, may be beneficial.

A supplement of the present invention may be ingested with or after a meal. Thus, a supplement may be taken at the time of an individual's morning meal, and/or at the time of an individual's noontime meal. A portion may be administered shortly before, during, or shortly after the meal. For daily consumption, a portion of the supplement may be consumed shortly before, during, or shortly after the individual's morning meal, and a second portion of the supplement may be consumed shortly before, during, or shortly after the individual's noontime meal. The morning portion and the noontime portion can each provide approximately the same quantity of one or more of a Vitamin D3 compound, retinoic acid, hexosamine pathway metabolites, nucleotides (e.g. UMP, UDP, UTP, CMP, CDP, or CTP), nucleosides (e.g. cytidine or uridine), nucleobases (e.g., uracil, cytosine) sugars (e.g. glucose), acetoacetate, glutamine, glucosamine, N-acetyl-glucosamine (GlcNAc) or nutraceutically acceptable derivatives thereof. A supplement and regimens described herein may be most effective when combined with a balanced diet according to generally accepted nutritional guidelines, and a program of modest to moderate exercise several times a week.

The compositions, supplements, and methods described herein are indicated as therapeutic or nutraceutical agents or methods either alone or in conjunction with other therapeutic agents or other forms of treatment. They may be combined or formulated with one or more therapies or agents used to treat a condition described herein. Compositions of the invention may be administered concurrently, separately, or sequentially with other therapeutic agents or therapies. For example, a composition or method of the invention may be used to treat MS in conjunction with β-interferon (Avonex® (interferon-beta 1a), Rebiff® (by Serono); Biogen, Betaseron® (interferon-beta 1b) Berlex, Schering), glatiramer acetate copolymer-1 (Copaxone®; Teva), antineoplastics (such as mitoxantrone; Novatrone® Lederle Labs), human monoclonal antibodies (such as natalizumab; Antegren® Elan Corp. and Biogen Inc.), immonusuppressants (such as mycophenolate mofetil; CellCept® Hoffman-La-Roche Inc.), paclitaxel (Taxol®; Bristol-Meyers Oncology), cyclosporine (such as cyclosporin A), corticosteroids (glucocorticoids, such as prednisone and methyl prednisone), azathioprine, cyclophosphamide, methotrexate, cladribine, 4-aminopyridine and tizanidine.

A pharmaceutical pack or kit is provided comprising one or more containers filled with one or more of the ingredients of a composition of the invention to provide a therapeutic effect. Associated with such container(s) can be various written materials such as labels instructions for use, or a notice in the form prescribed by a governmental agency regulating the manufacture, use or sale of pharmaceuticals, dietary supplements, or biological products, which notice reflects approval by the agency of manufacture, use, or sale for human administration.

Polymorphism Based Treatments

The invention provides a method of treatment or prophylaxis of a disease disclosed herein, in particular an autoimmune disease, more particularly MS or rheumatoid arthritis, based on the presence of a polymorphism in a gene or polypeptide of the N-glycan pathway or hexosamine pathway (e.g., SNP-containing polynucleotides and variant polypeptides).

In an aspect, the invention provides a method for treating a disease disclosed herein, in particular an autoimmune disease, more particularly MS or rheumatoid arthritis, comprising obtaining a sample of biological material containing at least one polynucleotide from the subject; analyzing the polynucleotide to detect the presence of at least one polymorphism in a gene of the N-glycan pathway or hexosamine pathway associated with the disease; and treating the subject in such a way as to counteract the effect of any such polymorphism detected. In a particular aspect, the invention provides a method for treating a disease disclosed herein, in particular an autoimmune disease, more particularly MS or rheumatoid arthritis, comprising obtaining a sample of biological material containing at least one polynucleotide from the subject; analyzing the polynucleotide to detect the presence of at least one SNP-containing polynucleotide; and treating the subject in such a way as to counteract the effect of any such polymorphism detected.

In another aspect, the invention provides a method for treating a disease disclosed herein, in particular an autoimmune disease, more particularly MS or rheumatoid arthritis, comprising obtaining a sample of biological material containing at least one polypeptide from the subject; analyzing the polypeptide to detect the presence of at least one polymorphism in a polypeptide of the N-glycan pathway or hexosamine pathway associated with the disease; and treating the subject in such a way as to counteract the effect of any such polymorphism detected. In an embodiment, the invention provides a method for treating a disease disclosed herein, in particular an autoimmune disease, more particularly MS, comprising obtaining a sample of biological material containing at least one polypeptide from the subject; analyzing the polypeptide to detect the presence of at least one polypeptide variant; and treating the subject in such a way as to counteract the effect of any such polymorphism detected.

In a particular aspect of the invention, a method is provided for the prophylactic treatment of a subject with a genetic predisposition to a disease disclosed herein, in particular an autoimmune disease, more particularly MS or rheumatoid arthritis, comprising obtaining a sample of biological material containing at least one polynucleotide from the subject; analyzing the polynucleotide to detect the presence of at least one polymorphism in a gene of the N-glycan pathway or hexosamine pathway associated with the disease; and treating the subject.

In another particular aspect, the invention provides a method for treating a disease disclosed herein, in particular an autoimmune disease, more particularly MS or rheumatoid arthritis, comprising obtaining a sample of biological material containing at least one polynucleotide from the subject; analyzing the polynucleotide to detect the presence of at least one polymorphism in a gene of the N-glycan pathway or hexosamine pathway associated with the disease; and treating the subject in such a way as to counteract the effect of any such polymorphism detected.

A subject suffering from a disease disclosed herein, ascribed to one or more polymorphism may be treated so as to correct the genetic defect. Such a subject is identified by any method that can detect the polymorphism(s) in a sample from the subject. A genetic defect may be permanently corrected by administering a nucleic acid fragment incorporating a repair sequence that supplies the wild-type nucleotide at the position of the polymorphism. A site-specific repair sequence may comprise an RNA/DNA oligonucleotide which operates to promote endogenous repair of a subject's genomic DNA. A site-specific repair sequence can be administered in an appropriate vehicle, such as a complex with polyethylenimine, encapsulated in anionic liposomes, a viral vector such as an adenovirus, or other pharmaceutical composition that promotes intracellular uptake of the administered nucleic acid.

In cases in which a polymorphism leads to a variant polypeptide that is ascribed to be the cause of, or a contributing factor to, a disease disclosed herein, a method of treating such a condition includes administering to a subject a wild type cognate of the variant polypeptide to provide complementation or remediation of the pathological condition.

Pharmacogenomics

The invention provides methods for assessing the pharmacogenomic susceptibility of a subject harboring a particular polymorphism or haplotype to a particular pharmaceutical compound, or to a class of such compounds. Pharmacogenomics relates to clinically significant hereditary variations, such as SNPs, in the response to therapeutics due to altered drug disposition and abnormal action in affected subjects. The clinical outcomes of these variations result in severe toxicity or failure of therapeutics in certain subjects as a result of individual variation in metabolism.

Accordingly, a SNP genotype of an individual can determine the way a drug acts on the body or the way the body metabolizes the compound. As an alternative to genotyping, specific variant polypeptides can be identified. Pharmacogenomic characterization of an individual permits the selection of effective therapeutics and effective dosages for prophylactic or therapeutic treatment based on the individual's SNP genotype, thereby enhancing and optimizing the therapeutic effectiveness of the therapy. In addition, recombinant cells and transgenic animals containing these SNPs/haplotypes allow effective clinical design of treatments and dosage regimens.

A polymorphism that occurs in the promoter region in the intron or is a synonymous polymorphism in the coding region is not expected to alter the amino acid sequence of the encoded polypeptide but may affect transcription and/or mRNA splicing, mRNA stability or translation of the sequences. Assays (e.g. reporter-based assays) may be devised to detect whether one or more polymorphism affects transcription and/or mRNA splicing, mRNA stability or translation. Individuals who carry allelic variants in the promoter region, in the intron or is a synonymous polymorphism in the coding region of a gene associated with an autoimmune disease may exhibit differences in polypeptide levels under different physiological conditions and may display altered abilities to react to disease disclosed herein, in particular an autoimmune disease. Further, differences in polypeptide levels resulting from allelic variation may have an effect on the response of an individual to drug therapy. For example, a GCS1, GANAB, MAN1A1, MGAT1, MGAT2, and/or MGAT5 polymorphisms may have an effect on the efficacy of drugs designed to modulate the activity of a GCS1, GANAB, MAN1A1, MGAT1, MGAT2, and/or MGAT5. The polymorphisms may also affect the response to agents acting on other pathways regulated by a GCS1, GANAB, MAN1A1, MGAT1, MGAT2, and/or MGAT5. Accordingly, diagnostic methods of the invention may be useful to assess the efficacy of therapeutic compounds in the treatment of an autoimmune disease, predict the clinical response to a therapeutic compound, and/or to determine therapeutic dose.

The invention also provides a method for determining the efficacy of a treatment for a particular patient with disease disclosed herein (e.g., an autoimmune disease, in particular MS or rheumatoid arthritis), based on genotype comprising (a) determining the genotype for one or more polymorphism sites in a gene of the N-glycan pathway or hexosamine pathway, in particular a GCS1, GANAB, MAN1A1, MGAT1, MGAT2, and MGAT5, for a group of patients receiving a treatment; (b) sorting patients into subgroups based on their genotype; (c) identifying correlations between the subgroups and the efficacy of the treatment in the patients, (d) determining the genotype for the same polymorphism sites in the gene(s) of the particular patient and determining the efficacy of the treatment for the particular patient based on a comparison of the genotype with the correlations identified in (c).

The invention further provides a method for classifying a subject who is or is not at risk for developing a disease disclosed herein (e.g. an autoimmune disease, in particular MS or rheumatoid arthritis) as a candidate for a particular course of therapy or a particular diagnostic evaluation based on a polymorphism procedure disclosed herein. The invention still further provides a method for selecting a clinical course of therapy or a diagnostic evaluation to treat a subject who is or is not at risk for developing a disease disclosed herein (e.g. an autoimmune disease, in particular MS) based on a polymorphism procedure disclosed herein.

Modulators of SNP-Containing Polynucleotides

The invention also contemplates a method for identifying a compound that can be used to treat a disease disclosed herein comprising assaying the ability of the compound to modulate the activity and/or expression of a SNP-containing polynucleotide and thus identifying a compound that can be used to treat a disease characterized by undesired activity or expression of the SNP-containing polynucleotide. The assays can be cell-based including cells naturally expressing the SNP-containing polynucleotides or recombinant cells genetically engineered to express the SNP-containing polynucleotides.

The assay for SNP-containing polynucleotides can involve direct assay of nucleic acid levels, such as mRNA levels, or on collateral compounds. Further, the expression of genes that are up- or down regulated in response to the variant SNP-containing polynucleotides can also be assayed. In this embodiment the regulatory regions of these genes can be operably linked to a reporter gene such as luciferase.

Accordingly modulators of SNP-containing polynucleotides can be identified in a method comprising contacting a cell with a test compound and determining the expression of SNP-containing mRNA wherein the level of expression of SNP-containing mRNA in the presence of the candidate compound is compared to the level of expression of SNP-containing mRNA in the absence of the test compound. The test compound can then be identified as a modulator of SNP-containing polynucleotide expression based on this comparison and be used, for example to treat a disease characterized by expression of the SNP-containing polynucleotides, such as autoimmune diseases. When expression of mRNA is statistically significantly greater in the presence of the test compound than in its absence, the test compound is identified as an agonist of nucleic acid expression. When nucleic acid expression is statistically significantly less in the presence of the test compound than in its absence, the candidate compound is identified as an antagonist of nucleic acid expression.

The invention further provides methods of treatment, with a SNP-containing polynucleotide as a target, using a compound identified through drug screening as a gene modulator to modulate SNP-containing polynucleotide expression. Modulation includes up-regulation (i.e. activation or agonization) or down-regulation (suppression or antagonization) of nucleic acid expression. Alternatively, a modulator of SNP-containing polynucleotide nucleic acid expression can be a small molecule or drug identified using the screening assays described herein as long as the drug or small molecule modulates the expression of a SNP-containing polynucleotide.

The polymorphisms of the present invention are useful for improving the process of drug development. Subjects can be selected for clinical trials based on their genotype. Individuals with genotypes that indicate that they are most likely to respond to a treatment can be included in the trials, and those individuals whose genotypes indicate that they would not respond to the treatment, or suffer adverse reactions, can be eliminated from the clinical trials. In addition, the polymorphisms of the present invention may assist in explaining why certain, prior developed treatments performed poorly in clinical trials and may help identify a population subset that would benefit from such treatment.

The following non-limiting examples are illustrative of the present invention.

Example 1

Summary

Genetic and metabolic control of fractional differences in β1,6 GlcNAc branched N-glycans provide a continuum of TCR sensitivity and susceptibility to spontaneous and induced demyelinating disease. The encephalomyelitis (EAE) susceptible strains PL/J, SJL and NOD mice have reduced Mgat5 N-glycan expression in T-cells compared to EAE resistant 129/Sv, Balb/cj and B10.S strains. Wild type PL/J mice displaying the lowest levels develop late onset spontaneous inflammatory demyelinating disease, which is enhanced by Mgat5$^{+/-}$ and Mgat5$^{-/-}$ backgrounds in a gene-dose dependent manner. Clinical disease was slowly progressive, displaying paralysis, tremor and focal dystonic posturing in association with axonal damage in demyelinated lesions and normal white matter; phenotypes characteristic of the progressive phase of MS (1,2). Gene targeted reduction in Mgat5 N-glycan expression linearly enhanced TCR sensitivity while increasing Mgat5 N-glycan levels by utilizing biosynthetic precursors to raise UDP-GlcNAc supply to the Golgi suppresses T-cell proliferation, INFγ production and EAE induced in PL/J mice by adoptive T-cell transfer.

The following methods were used in the study described in this Example.

Spontaneous Demyelinating Disease, Dystonia and Adoptive Transfer EAE.

PL/J mice at two facilities were assessed for clinical disease using a standard EAE scale (Table 1) (4). The first cohort was at backcross 4 from 129/Sv (Table 1) and was housed at the Samuel Lunenfeld Research Institute (SLRI) vivarium, a colony infected with mouse hepatitis virus, EDIM, Minute virus, Mouse parvovirus, GDVII, pinworm and fur mites. These mice were initially assessed by blindly examining all Mgat5$^{-/-}$ (n=43), Mgat5$^{+/-}$ (n=22) and Mgat5$^{+/+}$ (n=15) PL/J mice in the colony over 6 months of age. Only mice over 1 year of age were found to have weakness and this smaller cohort (n=21, 13 and 10, respectively) was scored for clinical severity every 1-2 weeks over the next ~4 months. Weakness was slowly progressive without recovery in all affected mice, an observation confirmed by daily assessment of a smaller cohort (n=12) of clinically affected mice over a 4 week period. At sacrifice, mice were perfused with paraformaldehyde via cardiac perfusion and harvested brain and spinal cord were embedded in paraffin, sectioned and stained with H&E or Luxol Fast Blue. Additional organ screening in 4 clinically affected mice confirmed the only autoimmune disease present in the mice was demyelinating disease. The second cohort (Table 3) at backcross 6 were re-derived from the SLRI mice by embryo transfer and housed at the University of California, Irvine (UCI) vivarium which is pathogen free except for mouse parvovirus.

Adoptive Transfer EAE.

Adoptive transfer EAE was induced by s.c. immunization of wild type PL/J mice housed in the UCI vivarium with 100 µg of bovine MBP (Sigma) emulsified in Complete Freund's Adjuvant containing 4 mg/ml heat-inactivated *Mycobacterium tuberculosis* (H37 RA; Difco, Detroit, Mich.) distributed over three spots on the hind flank. Splenocytes were harvested after 11 days and stimulated in vitro with 50 µg/ml MBP in the presence or absence of 40 mM N-Acetyl-D-glucosamine (Sigma) added daily. After 96 hours incubation, CD3$^+$ T cells were purified by negative selection (R&D Systems) and 3.5×10$^6$ T-cells were injected i.p. into naïve PL/J Mgat5$^{+/-}$ recipient mice. Trypan blue exclusion determined <3% dead cells under both culture conditions. The mice were scored daily for clinical signs over the next 30 days with the observer blinded to treatment conditions.

L-PHA Staining, Jurkat T Cells and Mouse T-Cell Proliferation.

Mice used for L-PHA staining and quantitative RT-PCR were sex and age matched. The PL/J and C57/B6 mice used were congenic at backcross 6 from 129/Sv and showed no difference in L-PHA staining compared to PL/J and C57/B6 obtained from Jackson laboratories. 129/Sv mice were from an original Mgat5 gene targeted population (28). All other mice (SJL, NOD, Balb/c and B10.S) were obtained from Jackson Laboratories. CD3$^+$ T cells were purified from spleens by negative selection (CD3$^+$ T-cell purification columns R&D Systems), labeled with 5 µM 5,6-carboxyfluorescein diacetate succinimidyl ester (CFSE; Molecular Probes) in PBS for 8 minutes at room temperature and cultured in RPMI-1640, 10% FBS, 50 µM 2-Mercaptoethanol with plate bound anti-CD3 (2C11, ebioscience) in the presence or absence of Swainsonine (Sigma) and/or N-Acetyl-D-glucosamine (Sigma). Jurkat T cells were cultured in either RPMI 1640, 10% FBS, penicillin (200 unit/ml) and streptomycin (200 µg/ml) media at 10 mM/20 mM glucose or non-glucose containing DMEM base media supplemented as with RPMI as well as 1.5 mM glucose, both of which did not contain glutamine. The indicated monosaccharides and/or metabolites were added daily except glucose which was added only at time zero and were titrated until a plateau was reached in L-PHA staining or toxicity was observed. The plateau or highest non-toxic dose is shown in FIG. 4D. Mouse and Jurkat cells were stained with L-PHA and LEA by first blocking with PBA (2% bovine serum albumin/0.01% azide/PBS) for 10 min at 4° C. and then incubated with 4 µg/ml of L-PHA-FITC (Vector Laboratories Inc.) or 20 µg/ml of LEA-FITC (Sigma) in PBA for 40 min at 4° C. and analyzed by a BD FACSCalihur (BD Pharmingen, San Diego, Calif.). The level of lectin binding was normalized by untreated control and calculated as a percentage (Sample intensity/control intensity-1) %.

TCR Signaling.

10$^6$ purified splenic CD3+ T cells from Mgat5$^{+/+}$, Mgat5$^{+/-}$ and Mgat5 mice and 5×10$^6$ polystyrene beads (6 micron, Polysciences) coated with 0.5 µg/ml anti-CD3ε antibody (2C11, eBioscience) overnight at 4° C. were mixed, pelleted at 5,000 rpm for 15 s, incubated at 37° C. for the indicated times, and then solubilized with ice-cold 50 mM Tris pH7.2, 300 mM NaCl, 1.0% Triton X-100, protease inhibitor cocktail (Boehringer Mannheim) and 2 mM Orthovanadate for 20 min. Cell lysates were separated on Nupage10% BIS-TRIS gels (Invitrogen) under reducing conditions, transferred to polyvinylidene difluoride membranes and immunoblotted with rabbit anti-phospho-lck Tyr$^{505}$ Ab (Cell Signaling Technology (CST)), rabbit anti-phospho-Src family Tyr$^{416}$ Ab (CST), which cross reacts with phospho-lck Tyr$^{394}$, rabbit anti-phospho-Zap70 Ab (CST), rabbit anti-phospho-LAT Ab (Upstate), and anti-actin Ab (Santa Cruz).

Cytokine ELISA.

Supernatant from spleenocyte cultures used for adoptive transfer EAE at day 4 of stimulation with MBP in the presence or absence of GlcNAc (40 mM) were tested for INFγ levels. Microtiter plates were coated with 50 µl of anti-IFN-γ (1 µg/ml, clone AN-18; eBiosciences) overnight at 4° C. Supernatants were applied at 50 µl/well in duplicate and incubated for 2 hours at room temperature. Captured cytokines were detected using biotinylated anti-IFN-γ (1 μg/ml, clone R4-6A2; eBiosciences) and detected using Avidin Horse Radish Peroxidase (eBiosciences) at 1:500× dilution and o-Phenylenediamine dihydrochloride OPD tablets (Sigma) according to the manufacturer's protocols. Recombinant IFN-γ (eBiosciences) was used as a standard. Colorimetric change was measured at 450 nm on a microplate autoreader (Labsystems).

Quantitative Real Time PCR.

RNA from purified CD3+ T lymphocytes of 129/sv, PL/J and C57/B6 mice was purified using the RNeasy® Mini Kit (Qiagen) and used to synthesize cDNA with the RETROscript® Kit (Ambion). For expression of MGAT5 and β-actin, a 79001HT platform (3840 well plate, Applied Biosystems) was used with SYBR® Green PCR master mix and the following primers: MGAT5-5'-GGAAATGGCCTT-GAAAACACA-3' [SEQ ID NO. 1] and 5'-CAAGCACAC-CTGGGATCCA-3' [SEQ ID NO. 2]; for β-actin 5'-CCA-GCAGATGTGGATCAGCA-3' [SEQ ID NO. 3] and 5'-TTGCGGTGCACGATGG-3' [SEQ ID NO. 4]. Automatically detected threshold cycle (Ct) values for Mgat5 were normalized relative to β-actin. Fold differences in expression were calculated based on a cDNA standard dilution curve.

MS/MS Mass Spectroscopy.

Jurkat cell pellets ($20\times10^6$) were resuspended in a cold 300 μl methanol:water (1:1) solution containing maltose as internal standard, vortexed for 10 seconds, and then pipetted into tubes containing 600 μl of chloroform:methanol (C:M) (3:2). Samples were vortexed for 1 minute, and then centrifuged at 14,000 rpm for 5 minutes at 4° C. Supernatants were collected, and an equal volume of C:M (1:1) was added, followed by a second extraction. The pooled aqueous fraction containing the hydrophilic metabolites was dried with a speedvac and stored at –80° C. Prior to injection, the samples were dissolved in 100 μl methanol:water (1:1). The samples were injected at a flow rate of 150 μl/hr into the API3000 Mass Spectrometer (SCIEX). The metabolites were identified by their transitions in MS/MS, and quantified using the Analyte Software (SCIEX), which measured the area under the curve for the fragment ions corresponding to each parent ion. Quantities for the given substrates are graphed as pmole/min/$10^6$ cells.

Electromyography and Nerve Conduction Studies.

Mice were anesthetized with Avertin and given 0.4 ml to 0.9 ml Temgesic IM for pain relief. Temperature was maintained around 35-37° C. using infra-red heat lamps. Monopolar needle electrodes (Ambu Inc., Glen Burnie, Md.) were used for stimulation as well for recording motor nerve potentials as well as late responses. The active recording electrode was placed in the medial gastrocnemius muscle with the indifferent recording electrode placed in the ipsilateral footpad. Active stimulating electrode was placed percutaneously at the popliteal region (for distal stimulation) and in the sciatic notch (proximally). Occasionally, the sciatic nerve had to be surgically exposed, using a standardized gluteal splitting approach, to optimize proximal stimulation. Reference stimulating electrode was placed in the ipsilateral thoraco-lumbar paraspinal muscle. A pre-gelled strip electrode was wrapped around the tail to act as a ground. Responses obtained from supramaximal electrical stimulation (pulse width of 0.05 msec) were analyzed; the distance between the stimulation sites were measured accurately using a caliper. Addition stimulations were done to record late responses (F waves and H reflexes). H reflexes were identified when successive late responses had identical morphology and onset latency; F waves were identified when successive late responses had variable onset latency and morphology. For needle EMG recording, the recording monopolar needle electrode was inserted into one or more of the following hindlimb muscles: quadriceps, hamstrings, lumbar paraspinals, gatrocnemius and tibialis anterior. Presence of spontaneous muscle activity (i.e. fasiculations, fibrillations or myokymia) was assessed in at least three regions of the muscle. All recordings were made on a Sierra LT portable machine (Cadwell Laboratories, Kennewick, Wash.) and analyzed using the proprietary software supplied by the manufacturer.

Description of Study and Results

To further explore the role of Mgat5 N-glycans in autoimmune demyelinating disease, the Mgat5 null allele from the EAE resistant 129/Sv background was backcrossed onto the EAE sensitive PL/J strain. After the fourth backcross, signs of tail and hindlimb weakness were observed in mice over 1 year of age. All mice in the colony over 1 year were scored for severity using a standard EAE clinical scale (4) over the next ~4 months (Table 1). All 3 genotypes displayed limb weakness, but the incidence, severity and mortality were inversely correlated with Mgat5 (Table 1). The clinical course was chronic and slowly progressive without relapses or recovery, a clinical picture typical of PPMS and SPMS (1,2). Clinically affected mice also displayed involuntary movements in a gene dose dependent manner, including tremor and/or focal dystonic posturing of the tail, hindlimbs and/or spine (FIG. 1A) as well as paroxysmal episodes of dystonia. These movement disorders are common in patients with MS (15) but rarely reported in EAE (16). Dystonia is a neurological disorder characterized by sustained postures and twisting movements resulting from abnormal co-contraction of agonist and antagonist muscles. Episodes of dystonia in the mice could be precipitated by anxiety (i.e. drop from a modest height) and relieved by touch, phenomenon typical of dystonia in humans (15).

Pathological examination revealed sub-meningeal perivascular lymphocyte cuffing, multi-focal demyelination of the brainstem, spinal cord and spinal roots (FIG. 1B-E, FIG. 5 A-F). The CNS pathology was similar to chronic MS plaques and was characterized by mononuclear cells admixed with myelin debris centered around blood vessels, gliosis, neuronophagia, axonal swelling (spheroids) and axonal degeneration (FIG. 1C,D, FIG. 5 A,B), the latter correlating with the progressive clinical disease observed (17). In addition, axonal pathology was frequently observed in otherwise normal appearing CNS white matter (FIG. 5C). Axonal damage has long been recognized in MS plaques (17), and more recently in normal-appearing white matter, and is associated with the irreversible neurological deterioration in SPMS (18). The PNS pathology was characterized by multi-focal spinal root demyelination with naked and swollen axons (FIG. 1D, 5D-F). Neuronal bodies with prominent central chromatolysis were observed in the spinal cord (FIG. 5E), consistent with anterograde reaction to peripheral damage. Electromyography and nerve conduction studies revealed myokymia, positive sharp waves and delayed spinal root nerve conduction velocity as evidenced by abnormal F and H responses (FIG. 5 G,H), findings typical of physiologic spinal root demeylination and the human PNS autoimmune demyelinating disease Chronic Inflammatory Demyelinating Polyneuropathy (CIDP). Anti-CD3 activated splenocytes donated from Mgat5 mice with moderate to severe demyelinating pathology efficiently transferred disease to naïve wild type recipients (Table 2), confirming spontaneous disease was autoimmune.

CNS and/or PNS pathology was present in all mice with clinical weakness and frequently co-existed in the same individual. PNS demyelination was seen with similar frequency in all 3 genotypes (FIG. 1F). In contrast, CNS demyelination was ~2 and 3 fold more frequent in Mgat5$^{+/+}$ and Mgat5$^{-/-}$ mice than wild type mice, respectively (FIG. 1F). This indicates that Mgat5 N-glycans specifically inhibit spontaneous CNS demyelinating disease in a gene dose dependant manner and suggest that the more severe clinical disease in Mgat5$^{-/-}$ and Mgat5$^{+/-}$ mice was secondary to increased frequency of CNS disease.

Spontaneous clinical and pathological disease was observed after 1 year of age in non-congenic wildtype PL/J mice acquired from Jackson Laboratories, as well as the mice at backcross 6 to 9 (Table 2), indicating that the presence of disease in wild type PL/J mice was not significantly influenced by the stage of backcrossing from 129/Sv. Environmental pathogens have been suggested to promote spontaneous demyelinating disease in MBP-TCR transgenic mice (11). In contrast, similar frequency of disease was observed when mice were housed in vivariums containing only a single pathogen (Table 3) or a multitude of pathogens (Table 1); suggesting genetic rather then environmental factors dominate in disease pathogenesis.

Figure 2:
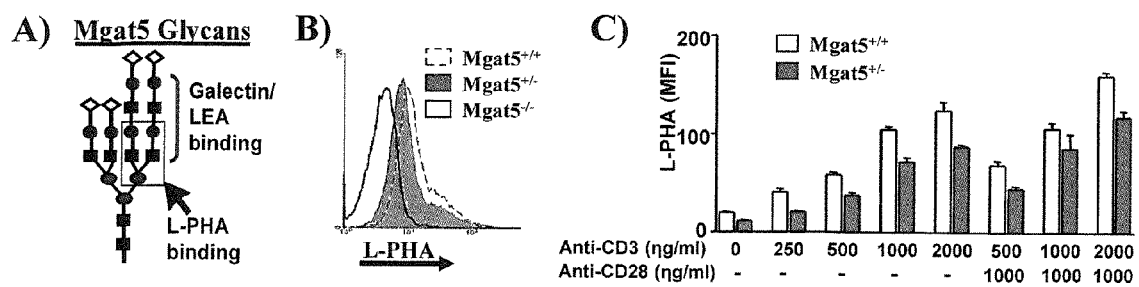
FIG. 2. Mgat5$^{-/-}$ T-cells have intermediate Mgat5 glycan expression and TCR sensitivity A) Mgat5 modified glycans and binding of L-PHA, LEA and galectin B,C) FACS analysis with L-PHA-FITC of resting splenocytes (A) and 3 day anti-CD3 stimulated (B) CD3+ T cells from PL/J mice with the indicated genotypes. Data shown gated on CD4$^+$ population. Error bars in C) are standard error of triplicate staining. D) Purified CD3$^+$ PL/J T-cells were labeled with CFSE, stimulated for 72 hrs as indicated and analyzed by FACS. Plots shown are gated on CD4$^+$ cells. E) Purified CD3$^+$ T-cells were incubated at 37° with anti-CD3 antibody coated beads for various times, lysed and western blotted for the indicated phosphorylated proteins. Reduced phosphorylation of lck at 3 minutes relative to rest is likely secondary to clustering of the lck phosphatase CD45 at the immune synapse during this time.
Figure 2:
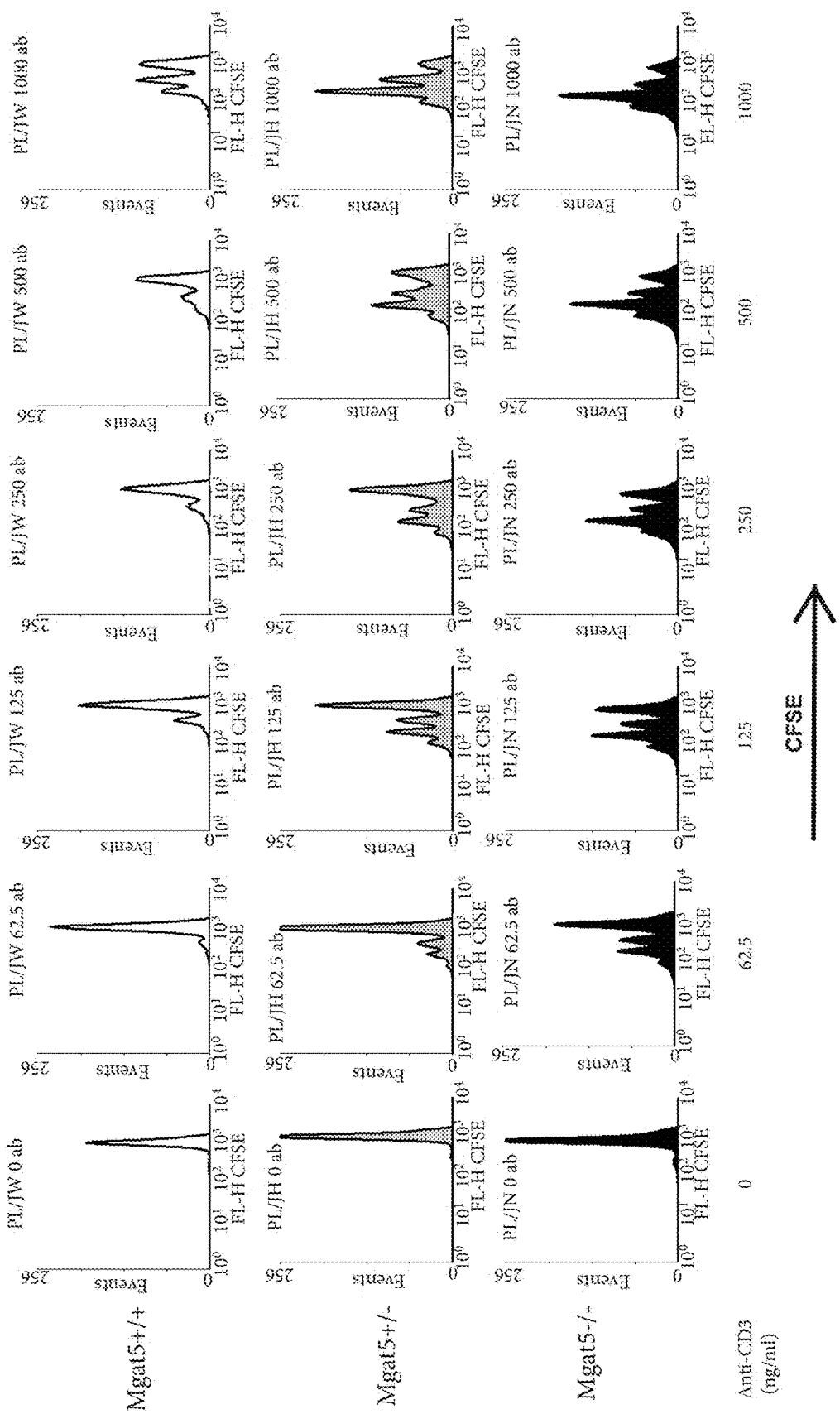
Figure 2:
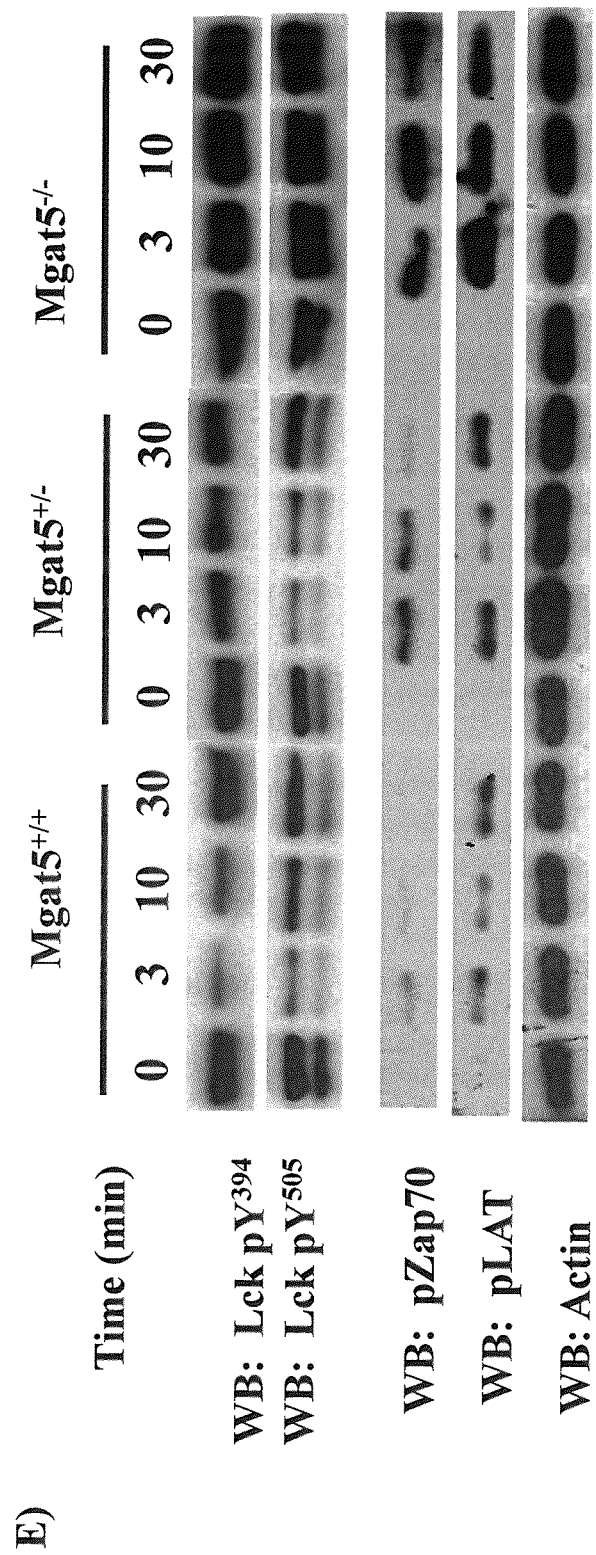

Mgat5$^{+/-}$ mice display an intermediate incidence of autoimmune disease, indicating Mgat5 gene dosage is limiting for modification of N-glycans on T-cells and suppression of autoimmune activation. Indeed, flow cytometry with the Mgat5 glycan specific plant lectin L-PHA (FIGS. 2A,3A) demonstrated that β1,6 branched N-glycan levels in Mgat5$^{+/-}$ CD4$^+$ T-cells are ~30-50% lower than Mgat5$^{+/-}$ cells in PL/J, 129/Sv and C57/B6 mice (4,5) (FIGS. 2A-C, 3A and data not shown). The transcriptionally controlled increase in Mgat5 N-glycans following TCR stimulation (4,5) is also attenuated in Mgat5$^{+/-}$ T-cells (FIG. 2C). Moreover, the Mgat5$^{+/-}$ T-cell phenotype is intermediate for TCR-mediated proliferation (FIG. 2D, FIG. 6), activation of lck as shown by enhanced phosphorylation at activating tyrosine 394 ($Y^{394}$) relative to inhibitory tyrosine 505 ($Y^{505}$)[19] and phosphorylation of Zap-70 and LAT (Figure E). Therefore, a ~30-50% reduction in Mgat5 N-glycan expression in resting and proliferating Mgat5$^{+/-}$ T-cells is sufficient to enhance TCR sensitivity and susceptibility to spontaneous demyelinating disease in PL/J mice.

Both PL/J and 129/Sv Mgat5$^{-/-}$ mice develop spontaneous autoimmune disease with pathology in different organs, notably the nervous system (Table 1) and kidneys (4), respectively. However, Mgat5-deficiency enhances demyelinating disease in both strains (Table 1 and 4), indicating that Mgat5 regulates autoimmune thresholds irrespective of antigen, while strain-dependent genetic factors such as MHC determine target antigens for spontaneous disease. Although the self-antigen targeted in PL/J mice is unknown, EAE in H-2$^\mu$ PL/J mice is efficiently induced with MBP, a myelin antigen expressed in central and peripheral myelin. Moreover, MBP-TCR transgenic H-2$^\mu$ mice develop spontaneous demyelination in both the CNS and PNS (12). These data suggest that MBP is likely the pathogenic self-antigen. Interestingly, CNS and PNS demyelination have been reported to co-exist in human autoimmune demyelinating disease, with several studies suggesting co-occurrence in up to ~40% of MS and CIDP patients (20-22).

Figure 3:
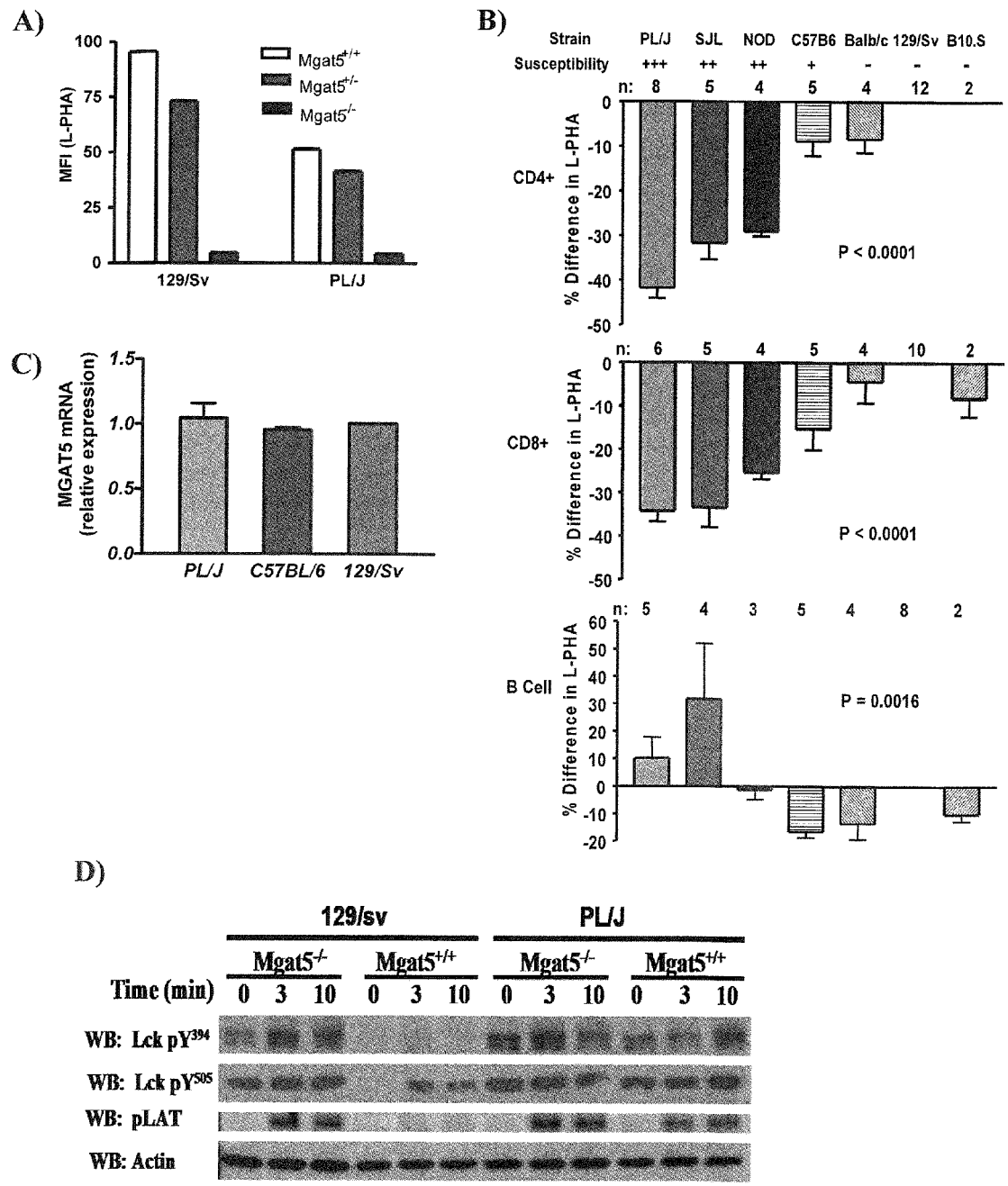
FIG. 3. Differential expression of Mgat5 glycans in multiple inbred strains of mice. A-C) Mgat5$^{+/+}$ (A-C), Mgat5$^{+/-}$ (A) and Mgat5$^{-/-}$ (A) resting splenocytes (A,B) or CD3+ T-cells (C) from the indicated inbred mouse strains were stained with L-PHA-FITC and anti-CD4 (A,B), anti-CD8 (B) or anti-13220 (13) antibodies and analyzed by FACS (A,B) or used to isolate mRNA for cDNA synthesis and analysis by quantitative real time-PCR (C) (5). Shown in B and C is relative expression normalized to wild type 129/Sv cells. Data in C are averaged from two mice for each genotype repeated once. Error bars refer to standard error (A-C). D) Purified CD3$^+$ T-cells from Mgat5$^{+/-}$ and Mgat5$^{-/-}$ 129/Sv and PL/J mice were stimulated with anti-CD3 antibody coated beads for the specified times and western blotted for the indicated proteins.
Figure 4:
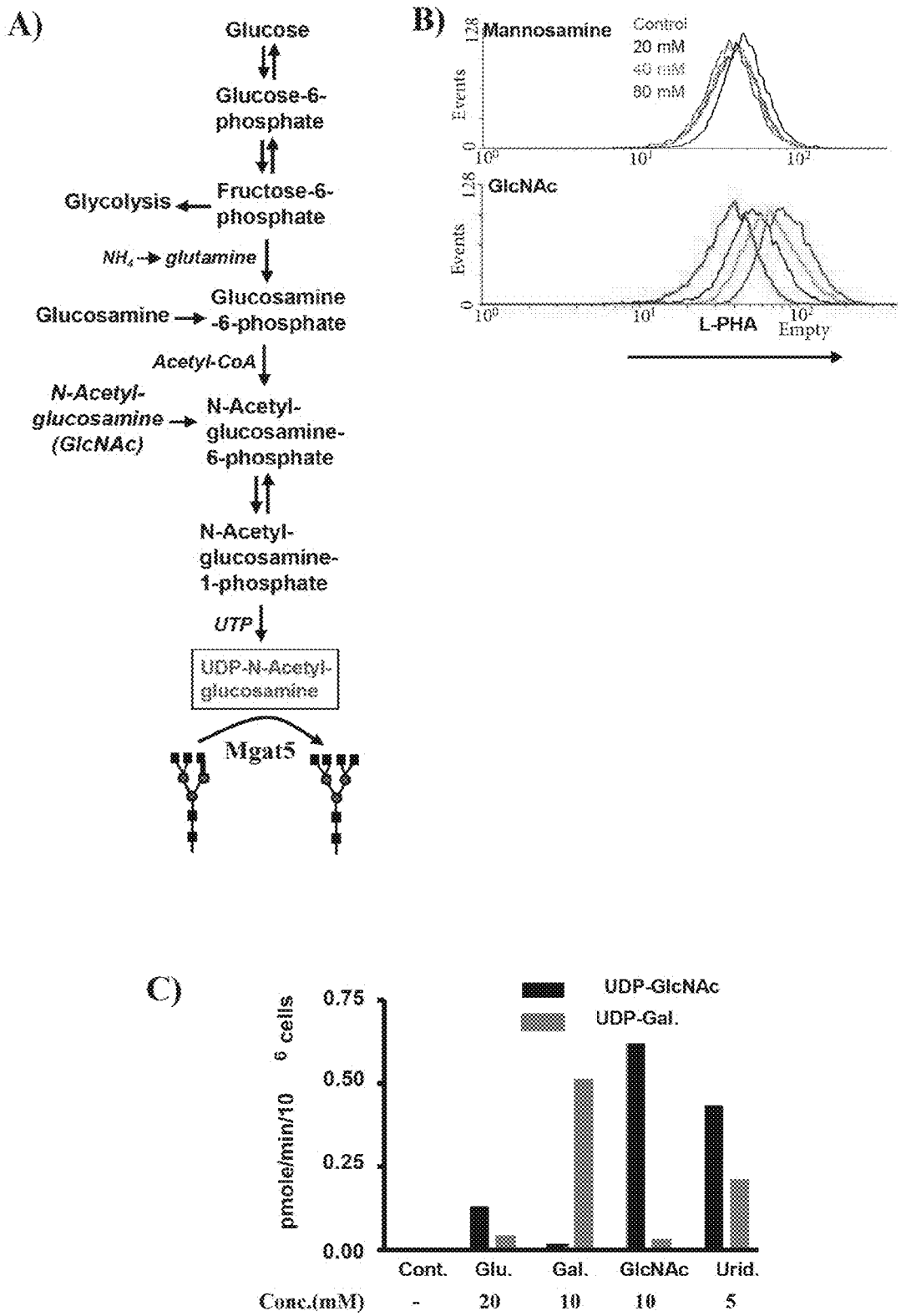
FIG. 4. Metabolic regulation of Mgat5 glycan expression, T cell function and EAE by the hexosamine pathway. A) Hexosamine pathway and biosynthesis of UDP-GlcNAc, the sugar nucleotide donor for Mgat5. B-D) The indicated monosaccharides and metabolites were cultured with Jurkat T-cells for 3 days (D), stained with L-PHA-FITC or LEA-FITC, a lectin specific for poly-N-acetyllactosamine, and analyzed by FACS (B,D) or lysed and analyzed by MS/MS mass spectroscopy for sugar-nucleotide expression (C). Lines with symbols ■, ▲, ▼ refer to altered glucose concentration in the culture media as indicated; all others were grown in 10 mM glucose. Error bars in D are standard error of triplicate staining. E, F) PL/J wild type CD3$^+$ T cells left unlabelled (E) or labeled with CFSE (F) were stimulated with anti-CD3 antibody, swainsonine and/or GlcNAc as indicated for 3 days and analyzed by FACS for L-PHA (E) and CFSE staining (F). Arrow defines undivided cell population. Shown are gated on CD4+ cells. G-I) Splenocytes isolated from PL/J wild type mice 11 days following immunization with MBP+CFA were re-stimulated in vitro with MBP for 4 days in the presence (light gray) or absence (dark gray) of GlcNAc (40 mM), stained with L-PHA-FITC and LEA-FITC (G), tested for IFNγ secretion in harvested supernatant (H) and injected into naïve Mgat5$^{+/-}$ PL/J mice (n=7 for each condition) and scored for signs of EAE daily for 30 days (1). Shown in H is standard error of duplicate values. I) P values for disease incidence and mean clinical score was determined by Fishers exact test and the Mann-Whitney nonparametric test, respectively.
Figure 4:
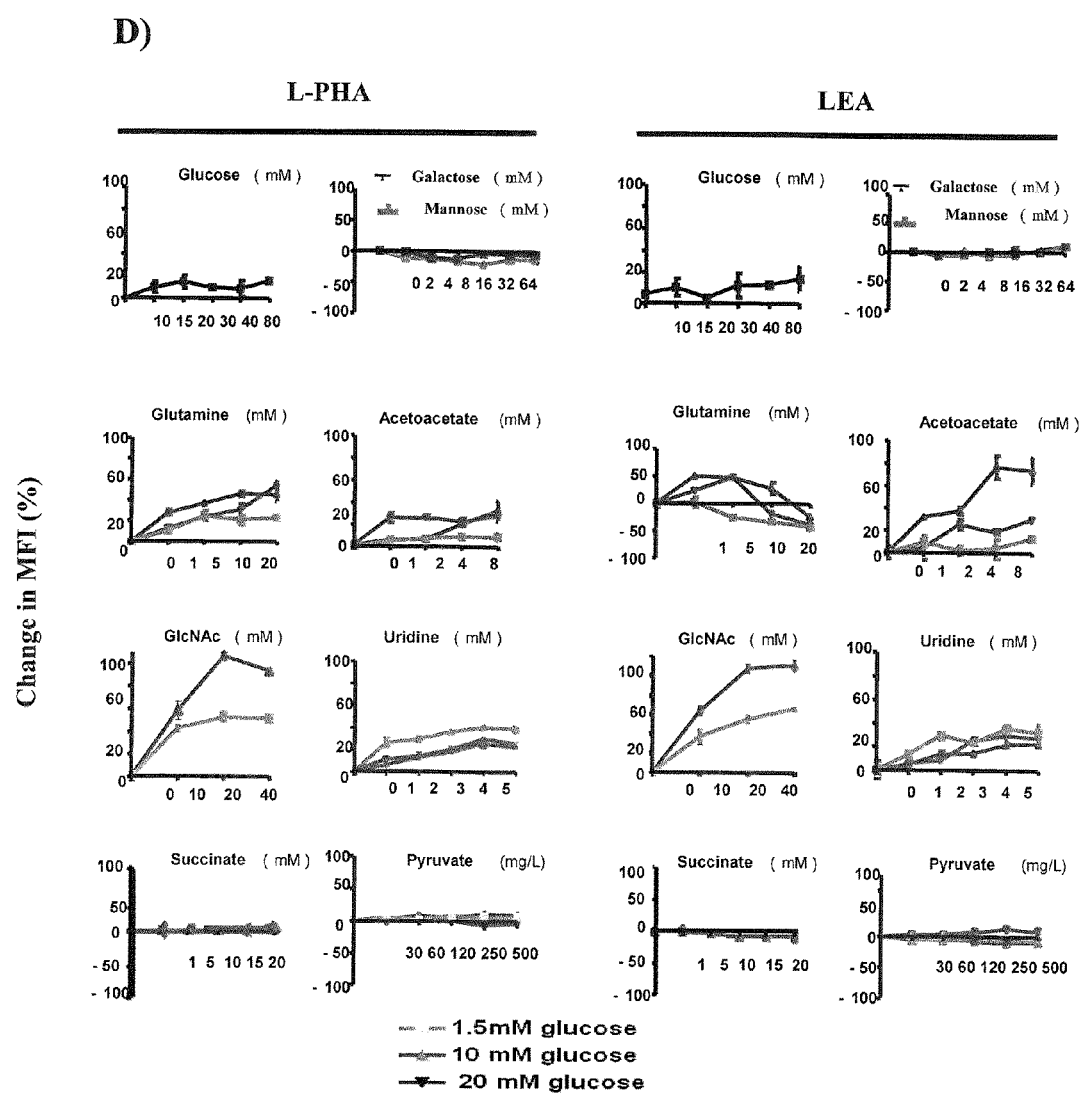
Figure 4:
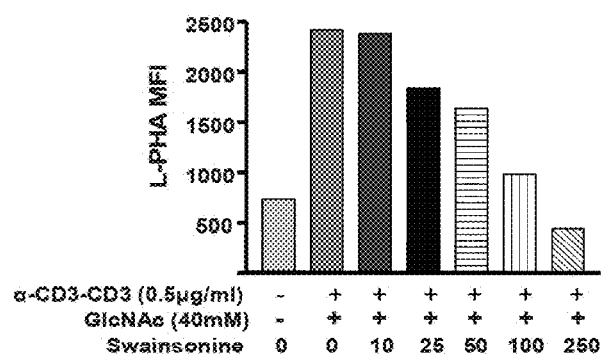
Figure 4:
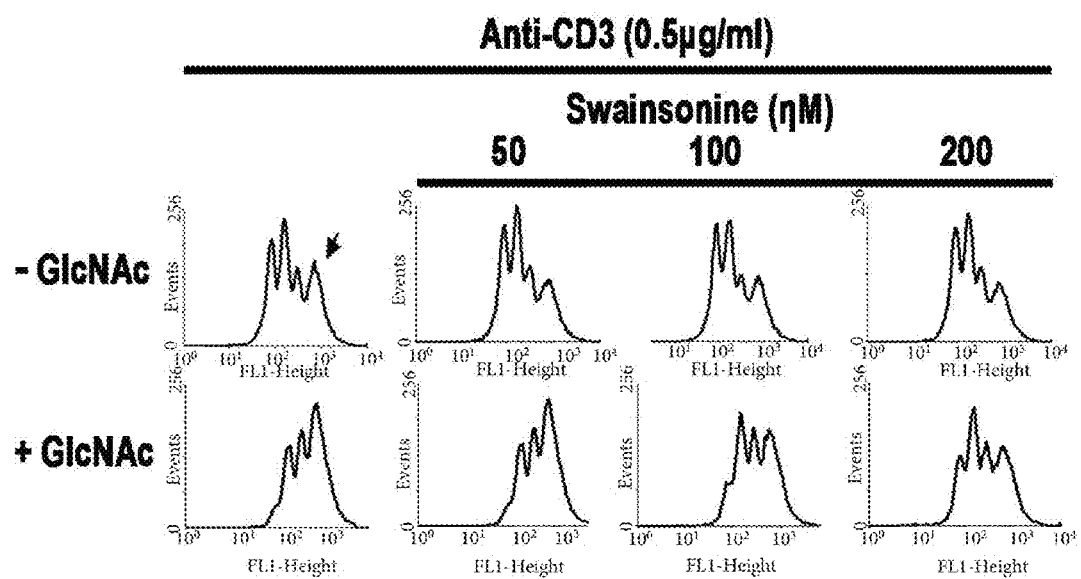
Figure 4:
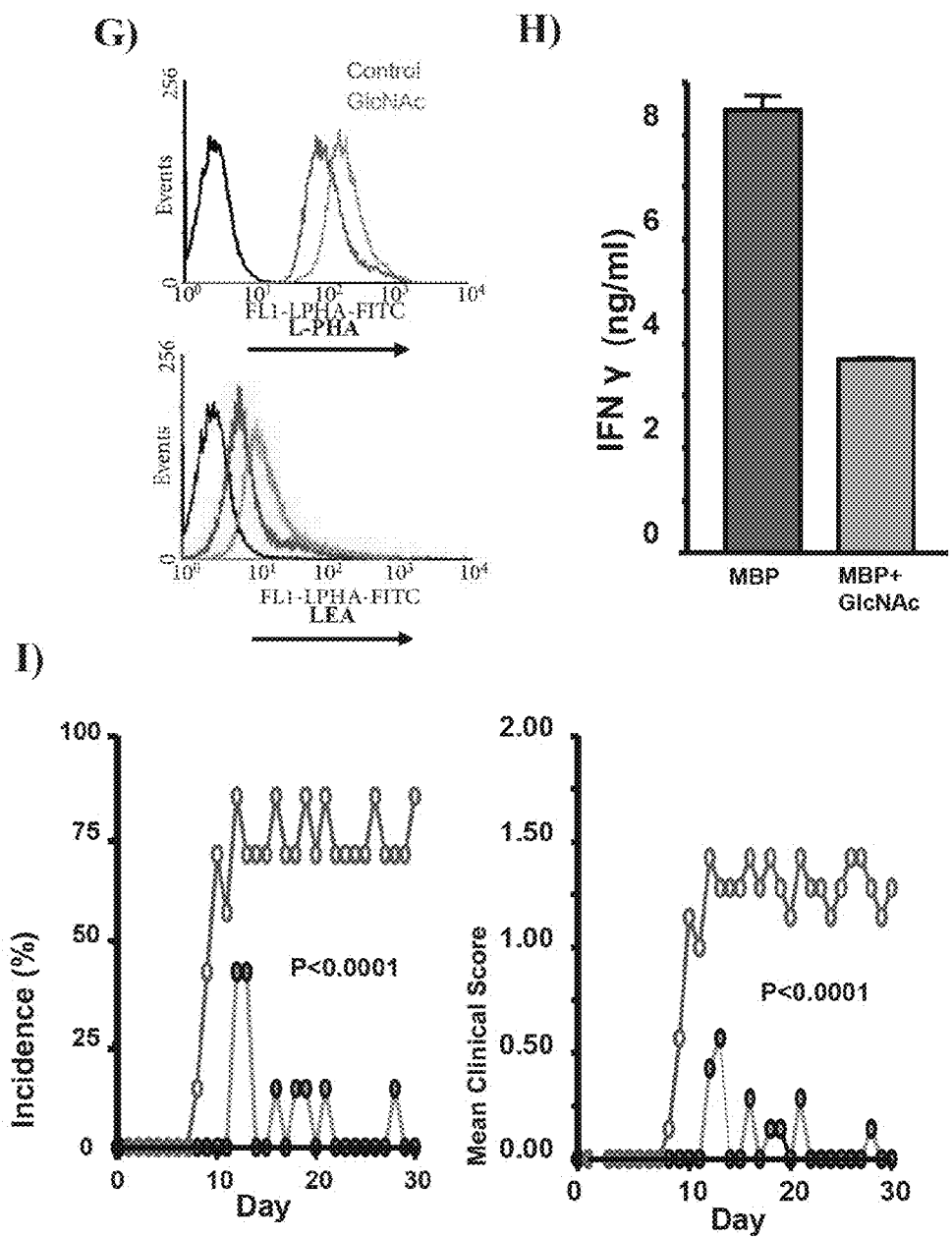
Figure 5:
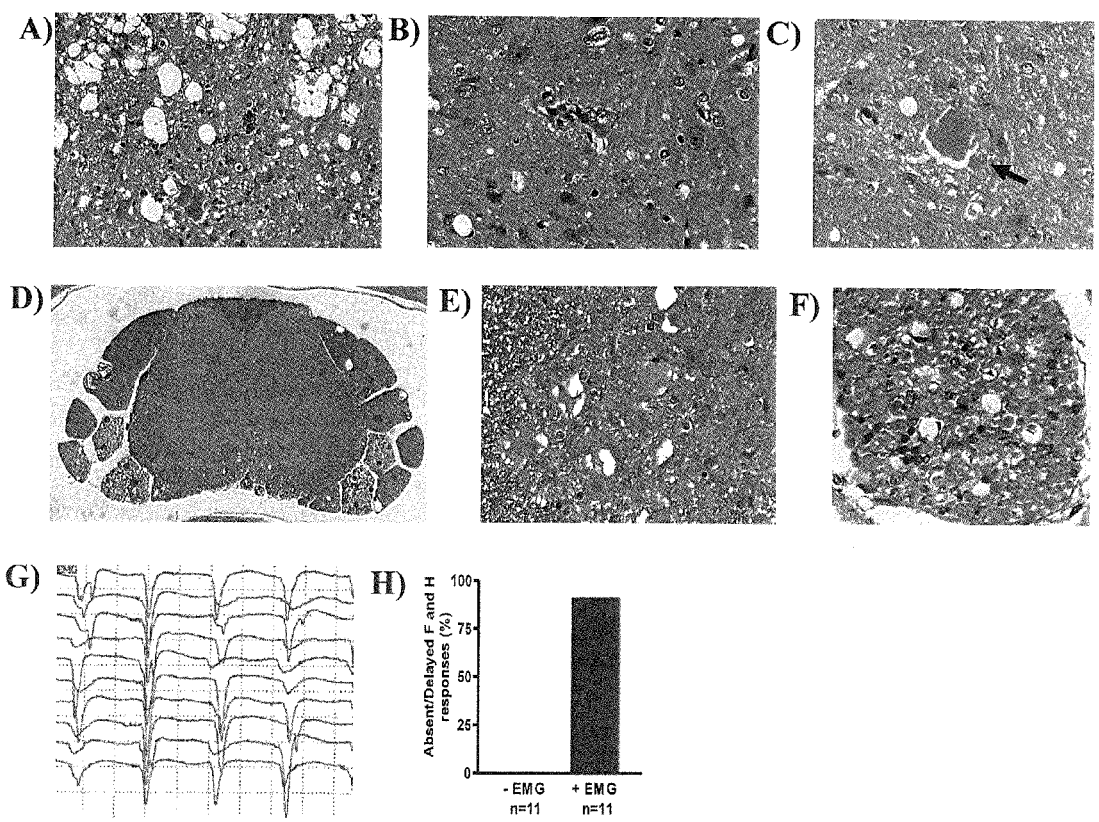
FIG. 5. Demyelinating and axonal pathology and Electromyography and Nerve Conduction Studies in PL/J mice. A-F) Paraffin embedded sections were stained with Haematoxylin & Eosin (A-C,F) or Luxol Fast Blue (D-E). A-B) Shows spinal cord demyelination, gliosis and neuronophagia. C) Shows axonal swelling in spinal cord surrounded by otherwise normal appearing white matter. D) Shows multifocal myelin degeneration of spinal roots. E) Shows neuronal bodies with central chromatolysis in the spinal cord. F) Shows spinal root with swollen axons. G-H) PL/J mice underwent needle electromyography (EMG) and nerve conduction studies for assessment of F waves and H responses, a clinical physiological test for spinal root demyelination. G) Example of positive sharp waves observed. H) Frequency of delayed or absent F and H responses in mice with normal and abnormal needle EMG.
Figure 6:
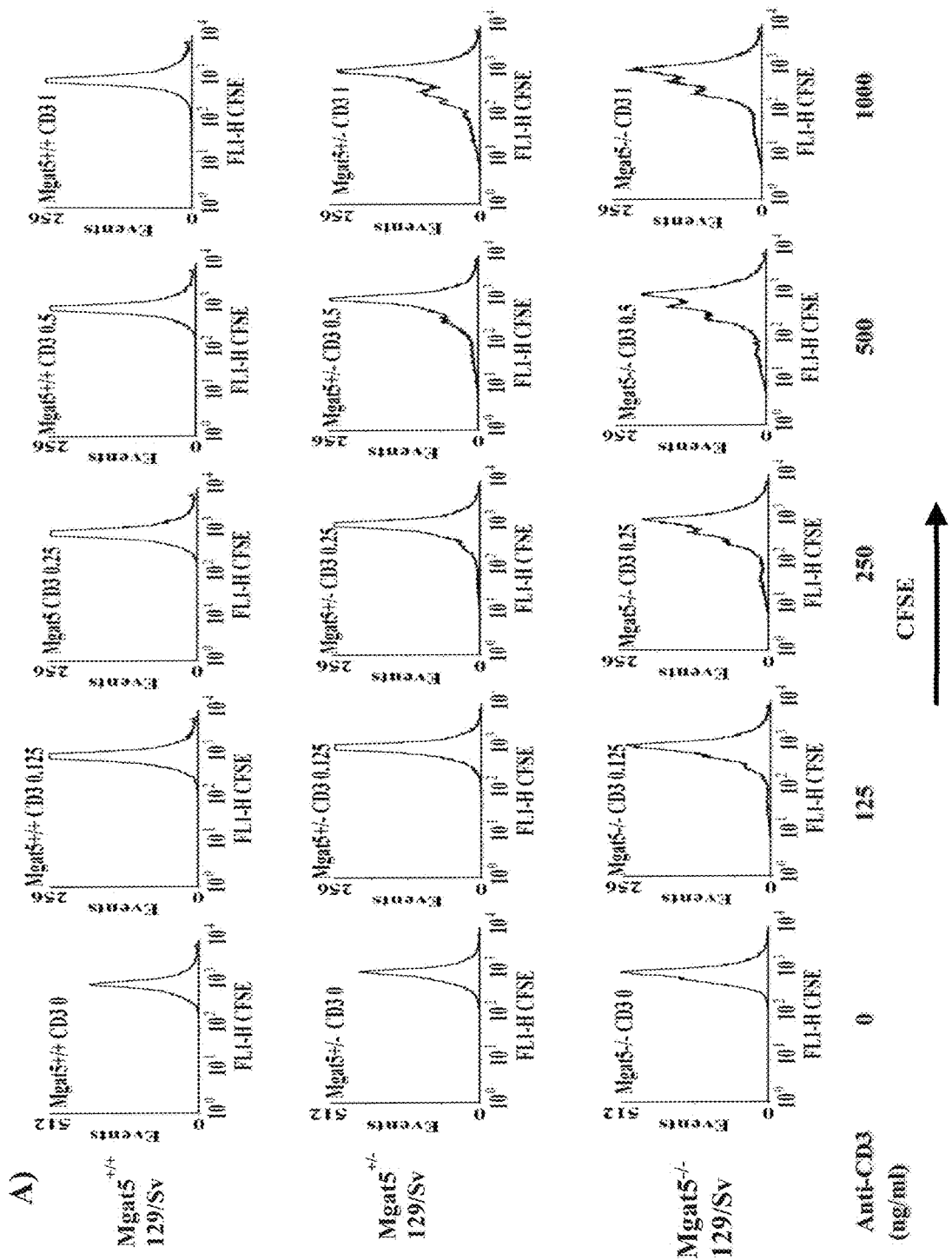
FIG. 6. Intermediate T cell activation thresholds in Mgat5$^{+/-}$ 129/Sv T cells and additive effect of Uridine plus GlcNAc. A) Purified CD3$^+$ 129/Sv T-cells were labeled with CFSE, stimulated for 72 hrs as indicated and analyzed by FACS. Plots shown are gated on CD$^+$ cells. B,C) Jurkat T cells were incubated as indicated for 3 days and stained with L-PHA-FITC and analyzed by flow cytometry. Error bars are standard error of triplicate staining. D) Wildtype C57/B6 CD3$^+$ T cells labeled with CFSE were stimulated with anti-CD3 antibody, swainsonine and/or GlcNAc as indicated for 3 days and analyzed by FACS.
Figure 6:
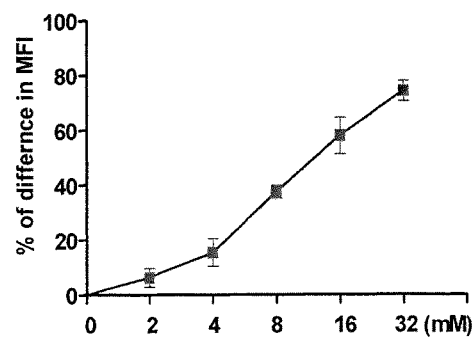
Figure 6:
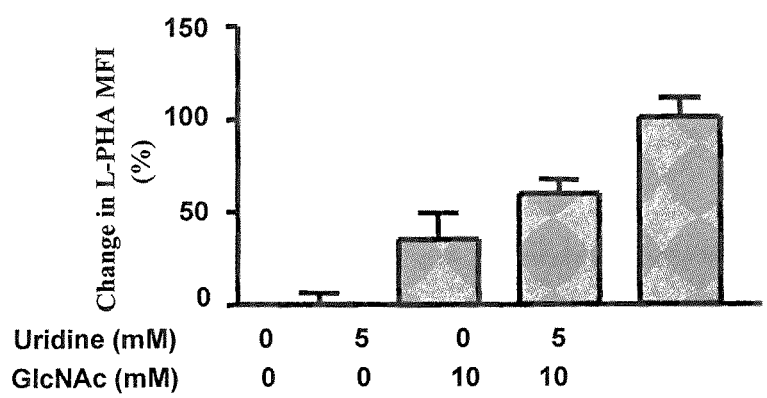
Figure 6:
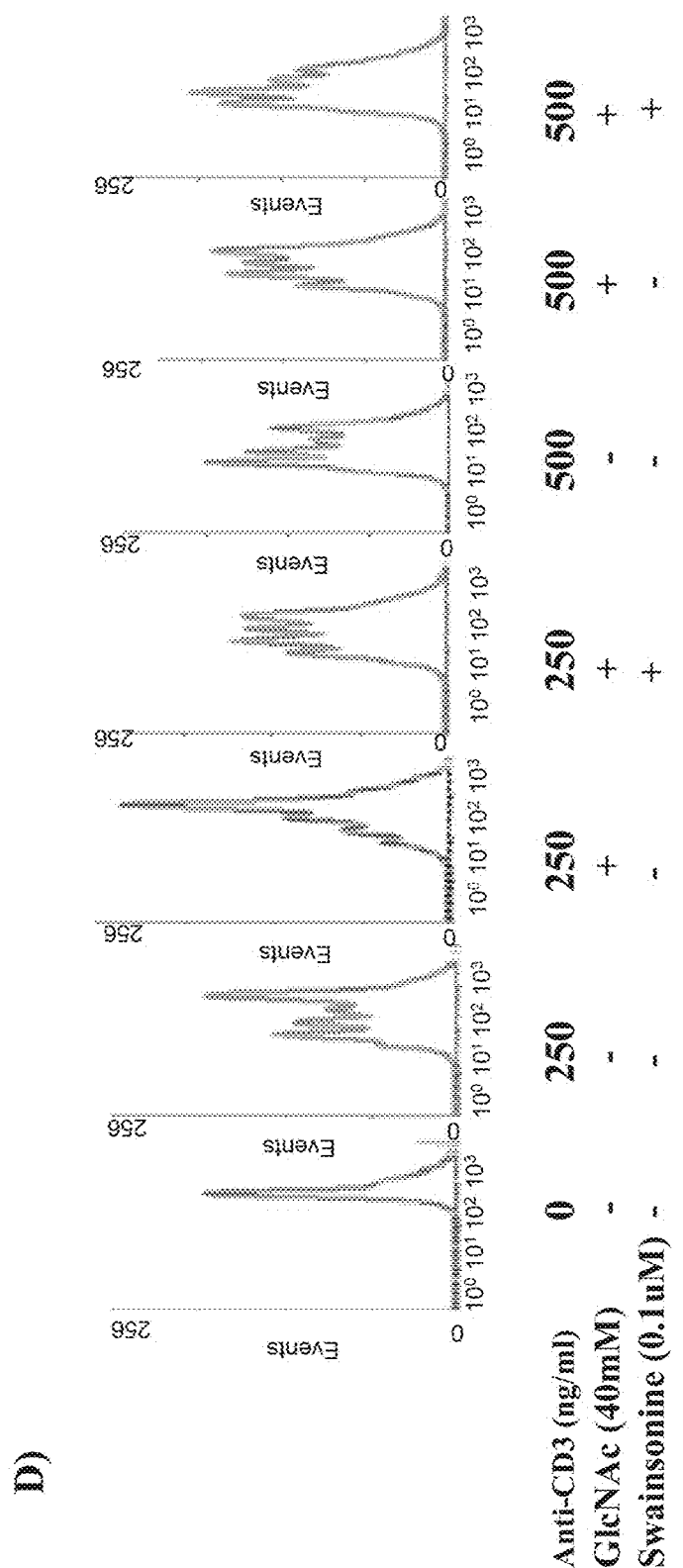

Unlike the PL/J strain, Mgat5 wildtype and heterozygous 129/Sv mice do not develop spontaneous autoimmune disease, a result consistent with the low autoimmune susceptibility of the 129/Sv strain. This differential sensitivity to autoimmunity may in part be due to strain dependent reduction in Golgi pathway activity and expression of Mgat5-modified N-glycans in T-cells. Indeed, CD4$^+$T$^-$ cells from Mgat5$^{+/+}$ PL/J mice express ~40% less Mgat5 N-glycans then 129/Sv Mgat5$^{+/+}$ cells, and remarkably, ~25% less then 129/Sv Mgat5$^{+/-}$ cells (FIG. 3A, B). Furthermore, CD4$^+$ and CD8$^+$ T-cells, but not B cells, from EAE high susceptibility strains SJL and non-obese diabetic (NOD), which also develops spontaneous autoimmune diabetes, expressed ~30% less Mgat5 N-glycans then the three EAF, resistant strains 129/Sv, Balb/c and B10.S (FIG. 3B). The C57/BL6 strain is less sensitive then SJL mice to active EAE, as evidenced by differential requirement for CD28 co-stimulation (23), and displays intermediate reduction in Mgat5-modified N-glycans in T-cells. Amongst these strains, PL/J is the only one known to develop spontaneous demeylinating disease, and T-cells from these mice expressed the lowest amount of Mgat5 N-glycans without a reduction in B cells. MGAT5 mRNA expression in resting CD3$^+$ T-cells from PL/J, C57/B6 and 129/Sv mice are similar, indicating altered MGAT5 transcription is not responsible for reduced Mgat5 N-glycan levels in PL/J mice (FIG. 3C). Taken together this data demonstrates an inverse relationship between susceptibility to autoimmune demyelinating disease and Mgat5 N-glycan expression in T-cells with rank order PL/J>SJL, NOD>C57BL6>129/Sv, Balb/cj, B10.S and indicates that susceptible strains harbor genetic polymorphisms that reduce Mgat5 N-glycan expression in T-cells. Since T but not B cell activation thresholds are regulated by Mgat5 N-glycans (4), these data strongly suggest that differences in Golgi N-glycan processing leading to Mgat5 N-glycans controls strain dependant autoimmune susceptibility. Indeed, TCR agonist induced phosphorylation of lck at $Y^{394}$ and LAT in wild type PL/J T cells was significantly enhanced relative to wild type 129/Sv T cells, while Mgat5-deficient T cells from PL/J and 129/Sv were equally hypersensitive (FIG. 3D), confirming reduced Mgat5 glycan expression in wild type PL/J T cells functions to enhance TCR sensitivity.

β1,6GlcNAc-branched products are sub-saturating on glycoproteins (FIGS. 2 B,C, FIGS. 3A,B) (24), due in part to the high Km (~10 mM) for UDP-GlcNAc displayed by the Mgat5 enzyme (25). As such, the levels of Mgat5-modified N-glycans are sensitive to changes in the intracellular concentration of UDP-GlcNAc (26), the sugar donor synthesized de novo from glucose via the hexosamine pathway (FIG. 4A). The addition of GlcNAc to cultured cells can be used to supplement cellular UDP-GlcNAc, as the amino-sugar is salvaged by 6-phosphorylation and converted to UDP-GlcNAc (FIG. 4A) (26). Glutamine, Acetyl-CoA and UTP are additional metabolites required for UDP-GlcNAc biosynthesis, donating an amine, acetate and UDP to glucose, respectively (FIG. 4A). Supplementing human Jurkat T-cell cultures with high glucose, GlcNAc, acetoacetate, glutamine, ammonia or uridine but not control mannosamine, galactose, mannose, succinate or pyruvate dose dependently increased Mgat5 N-glycans (L-PHA staining) and poly-N-acetyllactosamine (LEA staining) expression (FIGS. 4B,D, 6B). Mass spectroscopy confirmed that GlcNAc and uridine dramatically raised intracellular UDP-GlcNAc levels (FIG. 4C). Supplementing with both GlcNAc and uridine were additive for enhancement of Mgat5 N-glycans (FIG. 6 C). Supplements to wild type PL/J and C57/B6 T cell cultures raised Mgat5 N-glycan expression and inhibited anti-CD3 induced proliferation, an effect that could be reversed by blocking Mgat5 N-glycan expression with the α-mannosidase II inhibitor swainsonine (FIGS. 4 E,F, 6D). Furthermore, re-stimulation of splenocytes harvested from MBP immunized wild type PL/J mice with antigen in the presence of GlcNAc doubled Mgat5 N-glycan and poly-N-acetyllactosamine expression, inhibited INFγ production, and dramatically reduced the incidence and severity of EAE following adoptive transfer of T-cells into naïve wildtype PL/J mice (FIGS. 4G-I). Taken together, these data confirm that reduced Mgat5 N-glycan expression in PL/J wild type T cells functions to lower T cell activation thresholds and enhance demyelinating disease susceptibility. Moreover, the data indicate that Mgat5 N-glycan levels and autoimmune susceptibility are dependent on key metabolic intermediates shared by glycolysis, oxidative respiration, as well as lipid, nitrogen and nucleotide metabolism and provide a mechanism for synergism of environmental and genetic factors in the promotion of autoimmunity.

Mgat5 glycans inhibit agonist induced T cell activation and $T_H1$ differentiation by incorporating TCR in a galectin-glycoprotein lattice that restricts TCR clustering at the immune synapse (4,5). Here it is shown that regulation of T cell function by the Mgat5 controlled lattice is highly adaptable at both the genetic and metabolic levels, providing a molecular mechanism for tunable T cell activation thresholds (27) that is independent of TCR ligand affinity and antigen concentration. The continuous spectrum of increasing autoimmune susceptibility controlled by fractional reductions in Mgat5 glycan expression in T cells implies that hypomorphisms and/or environmental factors that modestly alter Golgi N-glycan and hexoamine pathway processing represent prime candidate susceptibility factors for MS and other human autoimmune diseases. The spontaneous demyelinating disease induced by Mgat5 deficiency in PL/J mice phenocopies several important clinical features of MS; notably, spontaneous occurrence in mid-life, movement disorders such as tremor and dystonia and a slow progressive decline in neurological function in association with neuronal loss and axonal damage (1, 2, 15). As such, Mgat5 deficient PL/J mice represent a unique tool to further investigate both the inflammatory and neurodegenerative phases of MS. Mgat5 N-glycans are expressed on glycoproteins in other tissues, including neurons, where they may regulate adhesion, receptor signaling, endocytosis, metabolism and apoptosis (24, 28, 29). Mgat5 N-glycans have been shown to promote cytokine signaling, motility and phagocytosis (29), a phenotype which may also contribute to suppression of spontaneous demyelinating disease (30). More broadly, the data indicates a general strategy for glycotherapy, whereby protein glycosylation can be tailored by differentially enhancing sugar-nucleotide biosynthesis with targeted monosaccharides and metabolic precursors.

Example 2

Summary

The T cell mediated autoimmune demyelinating disease Multiple Sclerosis (MS) is a complex trait disorder, where environmental factors influence the penetrance of mutations and complicate identification of susceptibility genes[1]. Genetic and metabolic regulation of Mgat5 modified N-glycan expression in mice sets thresholds for T cell activation, $T_H1$ differentiation and spontaneous demyelinating disease by controlling clustering of T cell receptor (TCR) at the immune synapse (4,5) (Example 1). Here it is demonstrated that MS is associated with multiple genetic deficiencies in the N-glycan pathway that reduce Mgat5 glycan expression in T cells. Approximately 14/23 genes in the N-glycan and hexosamine pathways required for Mgat5 glycan expression non-randomly map to 18 MS and other autoimmune loci. MALDI-TOF mass spectroscopy of peripheral blood mononuclear cells (PBMC) from MS patients demonstrated high frequency blockade of N-glycan processing at three sequential steps. Multiple single nucleotide polymorphisms (SNP) were identified in five N-glycan genes controlling the defective steps that were associated with disease. MS patient T cells have attenuated up-regulation of Mgat5 glycans following TCR stimulation; a phenotype that enhances activation, is reproduced by minimal inhibition of proximal N-glycan processing and can be reversed metabolically with Hexosamine pathway metabolites and Vitamin D3. Taken together these data identify genetic and environmental control of N-glycosylation as a major defective pathway in MS and imply that a significant proportion of the genetic heterogeneity in autoimmunity can be collapsed into genes regulating Mgat5 glycan expression. The following methods were used in the study described in this Example.

Methods

MS patients and Control Subjects.

Patients diagnosed with Multiple Sclerosis (MS) based on the McDonald Criteria (56) were randomly recruited from the MS clinic at the University of California, Irvine. PA1, 2,3,4,6,7,J represented 7 of the first 8 consecutive patients enrolled in the study. All were untreated except for PA7, who was on low dose Methotrexate once a week and monthly corticosteroid infusion. Four were female (PA1,3,4,J) and three were male (PA2,6,7). Four had relapsing remitting MS (PA1,2,3,4), one had secondary progressive MS (PA7) and two had primary progressive MS (PA6,J). Three patients had a positive family history for MS (PA3,7,J). Controls were healthy volunteers from the University of California, Irvine campus and lacked personnel or family history of MS and other autoimmune diseases except C2 who had a sister with autoimmune thyroid disease.

MALDI-TOF Mass Spectroscopy.

This was done as a service at the Glycotechnology core facility, a resource of the Glycobiology Research and Training Center (GRTC) at the University of California, San Diego. Resting PBMC's (6 million) were lysed with 1% SDS in 100 mM Tris pH 7.4, dialyzed to remove SDS, digested with trypsin to generate glycopeptides and then treated with PNGaseF to release the N-glycans. To focus on early processing, N-glycans were desialyated by mild acid digestion prior to permethylation and MALDI-TOF mass spectroscopy. Removal of sialic acid reduces the size and heterogeneity of the glycans, which significantly increases sensitivity by collapsing multiple glycans only differing in their sialic acid content into single species with common GlcNAc branching and galactosylation patterns. Monoisotopic peaks in the spectra were identified using GlycanMass and GlycoMod online software, with specific targeting of the N-glycan intermediates occurring during Golgi processing.

Isolation and Activation of PBMC's.

Mononuclear cells were isolated from the blood of subjects using Histopaque-1077™ gradients (Sigma, Saint Louis, Mo.) and cultured in RPMI 1640 medium supplemented with 4 mM glutamine, 1 mM sodium pyruvate, 1% non-essential amino acids, 1% RPMI vitamins, 100 units/ml penicillin, 100 μg/ml streptomycin, and 50 μM 3-mercaptoethanol. T lymphocytes were left unstimulated or were activated for 48 hours with 20 ng/ml anti-CD3 antibody (Biomeda, Foster City, Calif.) or a combination of 20 myelin peptides at 1 mg/ml with 10 mg/ml myelin basic protein (MBP). The myelin peptides were immunodominant peptides from human proteolipid protein (PLP 30-49, PLP 40-60, PLP 95-118, PLP 118-150, PLP-180-189, PLP 185-206), human myelin oligodendrocyte glycoprotein (MOG 38-60, MOG 63-87, MOG 76-100, MOG 89-113, MOG 112-132 and MOG 162-188) and cryptic peptides from MBP (MBP 41-69, MBP 61-79, MBP 121-139 and MBP 131-149) and PLP (PLP 73-104, PLP 145-186, PLP 218-248 and PLP 241-272) that are not normally derived from antigen processing but may be made by extracellular proteolytic activity (57). Whole MBP was isolated from frozen guinea pig spinal cords (Harlan Bioproducts, Indianapolis, Ind.). Cells were double-stained with PE-Cy5-conjugated anti-CD4 antibody (BD Pharmingen, San Diego, Calif.) and FITC-conjugated LPHA (5). The stained cells were analyzed on a FACScan (BD Biosciences, San Jose, Calif.) using the CellQuest software. Unstimulated cells were gated on the resting lymphoid population and the activated cells were gated on blasts based on forward and side scatter. Background fluorescence was subtracted for each population. To directly compare L-PHA staining in resting T cells from all subjects, PBMCs frozen in liquid nitrogen (90% FCS, 10% DMSO) were thawed and stained the same day.

Quantitative Real Time PCR and Taqman Allelic Discrimination.

Total RNA form Jurkat cell and MS patients PBMC were isolated by the RNeasy kit (Qiagen). For the time course experiments, mRNA from Jurkat cells were extracted after 0, 3, 6, 12, 24, 48, 72 hours incubation with anti-CD3 and anti-CD28 antibody (eBioscience, San Diego, Calif., USA). RNAs were reverse transcribed into cDNAs by M-MLV Reverse Transcriptase (Ambion, Inc., Austin, Tex., USA) as per the manufacture's instructions. Real-time PCR were performed on the resulting cDNAs by the use of TaqMan Gene Expression Assay (Applied Biosystem). Real-time PCR Primers used were purchased form Applied System Assays on Demand. Real-time reactions and SNP analysis were run and analyzed by use of an ABIPRISM 7500 sequence detection system and SDS2.1 software (Applied Biosystems). And the following cycle parameters: 50° C. for 2 minutes, 1 cycle; 95° C. for 10 minutes, 1 cycle; 95° C. for 15 seconds, 60° C. for 1 minute, 40 cycles were used for real-time PCR and SNP analysis. Data were then analyzed with the comparative cycle threshold (CT) method. The relative mRNA expression was determined from threshold cycle values normalized for Actin expression and then normalized to the value derived from cells at corresponding time without treatment.

DNA Sequencing and SNPs.

Primers designed to amplify exons of GCS1, GCS1, GANAB, MAN1A1, MGAT1 and MGAT5 including ~20-50 nucleotides of intronic sequence at both the 5' and 3' ends were used to amplify genomic DNA isolated from PBMCs (Qiagen). Sequencing was done on gel purified PCR products (Qiagen) as a service by Seqwright. Chromatograms and derived sequences were inspected for homozygous and heterozygous single nucleotide base pair changes. All novel SNPs were sequenced in both directions at least once, with most being confirmed with a Taqman allelic discrimination assay using custom designed probes (ABI). Introns, except for ~20-100 nt at the 5' and 3' end of each exon, upstream promoter regions and open boxes were not sequenced.

Novel SNPs

```
GCS1 SNP I:
                                        [SEQ ID NO.: 5]
TGGGTATGTCGGGGCGCTGG[G/A]TGCTGGCGTGGTACCGTGCG

GANAB
```

```
MAN1A1 SNP X:
                                        [SEQ ID NO.: 6]
GAAATAGTACAACTTAATG[G/A]ATTAGCTTTTGGGTTTAACT

MGAT1 SNP VI:
                                        [SEQ ID NO.: 7]
GGTGGAGTTGGTGGGTCATC[G/A]GGGCTCACTGCCTCCTGCCC

MGAT5 SNP I:
                                        [SEQ ID NO.: 8]
CCACTTTCTTGCTCACCTCA[C/G]CAGTTGCATGTTCTAGTCCT

MGAT5 SNP II:
                                        [SEQ ID NO.: 9]
GGAATCTTCTAGAAATGCCA[A/G]CTATAACCTGAAATAGTGTT
```

Known SNPs

GCS1 SNPs: II-rs1063588, III-rs2268416. GCS1, GANAB: I-rs2957121, II-10897289, V-rs11231166. MAN1A1 SNPs: I-rs6915947, II-rs195092, III-rs9481891, IV-rs2072890, V-rs2142887, VI-rs3756943, VII-rs18513744, VIII-rs3798602, IX-rs1042800, XI-rs1046226. MGAT1 SNPs: I-rs3733751, II-rs7726357, III-rs2070924, IV-rs2070925, V-rs634501. MGAT5 SNPs: III-rs3214771, IV-rs3748900, V-rs2289465.

Since the first confirmation ~20 years ago that MS is promoted by genetic susceptibility (6), numerous population based whole genome screens and candidate gene studies have failed to identify strongly linked genes other then the MHC class II allele HLA-DRB1*15 at 6p21 (8, 31-43). In Example 1 it is demonstrated that fractional reductions of 30% or more in Asparagine (N)-linked glycans produced by the Golgi enzyme Mgat5 promote spontaneous CNS autoimmune demyelinating disease in PL/J mice. MGAT5 encodes Golgi β1,6 N-acetylglucosaminyltransferase V, an enzyme late in the linear pathway of N-glycan branching which generates the preferred intermediate for extension with poly N-acetylacsosamine (44), the high affinity ligand for galectins that controls TCR sensitivity by incorporating TCR in a galectin-glycoprotein lattice (FIG. 7A) (4). The fraction of N-glycans modified by Mgat5 is sensitive to donor UDP-GlcNAc levels and metabolites supplying the hexosamine pathway (Example 1, FIG. 1A). T cell hypersensitivity and EAE demyelinating disease can be suppressed by increasing flux through the hexosamine and Golgi pathways via increased Mgat5 glycan expression (Example 1). A role for the hexosamine pathway in human autoimmunity is also suggested by the association of a regulatory SNP near the putative glucosamine acetyltransferase gene NAT9 (FIG. 7A, Table 4)(45). Moreover, TCR signaling increases mRNA expression of multiple upstream N-glycan processing genes along with MGAT5, suggesting proximal N-glycan enzymes are also rate limiting for Mgat5-modified N-glycans (FIG. 7B,C). Indeed, flow cytometry with L-PHA, a plant lectin that specifically binds to β1,6 GlcNAc branched N-glycans (FIG. 7A) (4,5), revealed dose dependent reduction of Mgat5 glycan expression in Jurkat T cells following up-stream inhibition of glucosidase I/II (GCS1/GCS1, GANAB) with castanospermine (CST), mannosidase I (MAN1A1, 1A2 and 1C1) with deoxymannojirimycin (DMN) and mannosidase II/fix (MAN2A1, 2A2) with swainsonine (SW, FIG. 7A,C).

Based on these considerations, hyphomorphic alleles of enzymes in the hexosamine and Golgi N-glycan processing pathways leading to Mgat5-modified N-glycans combine to provide a large group of potential autoimmune susceptibility genes (FIG. 7A, Table 4). To investigate this hypothesis, linkage data for MS (8, 31, 41) and its mouse model EAE (9) were reviewed. By inclusion of genomic regions with suggestive linkage or better in three or more studies 18 potential loci covering ~34% of the human genome were identified (Table 4, Table 5). The identified regions also frequently overlapped with other autoimmune loci (Table 4) (41, 44-50). Remarkably, 14/17 (82%) N-glycan and 11/17 (65%) hexosamine pathway genes co-localized to one of the 18 loci (Table 4 and genes labeled blue in FIG. 7A). In contrast, 85/241 (35.3%) randomly selected glycosylation and carbohydrate metabolic genes not known to regulate Mgat5 glycan expression co-localized to the loci, a number predicted by chance given the ~34% genome coverage of the 18 regions (Table 4, Table 6). After controlling for this large percentage of the genome by subtracting genes expected to map randomly, 13.5 of 22.5 Mgat5 regulatory vs 3/159 Mgat5 non-regulatory genes co-localized to the MS associated loci ($p<0.0001$, Table 4B). This result suggests that MS and other autoimmune diseases are associated with mutations in multiple genes from the two key pathways that control Mgat5 glycan levels.

Figure 8:
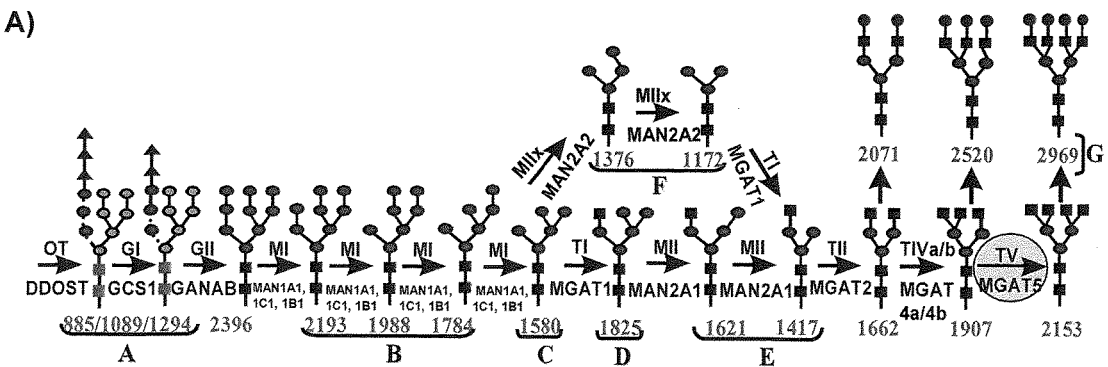
FIG. 8. N-Glycan processing in controls and MS patients. A) N-glycan processing pathway demonstrating Golgi intermediates and associated monoisotopic mass (permethylated, Na$^+$) on MALDI-TOF mass spectroscopy. Glycan species were grouped based on enzymatic function. Structures in group A were found as 4, 5 and 6 hexose fragments as shown. Mass species 2396, 1662, 1907 and 2153 were not reliably detected in control samples and not included in the analysis. B) MALDI-TOF mass spectroscopy profile of control 1 (C1) and MS patient 1 (PA1) with the peaks labeled with the glycans they represent. C) The relative intensity of structures A-G for controls and MS patients were obtained by adding the intensity of structures from each group and dividing by the combined intensity of the mature bi-antennary (2071) and tri-antennary (2520) glycans. Coefficient of determination $R^2$ values were derived by averaging the relative intensity of each glycan structure group from the 5 controls and comparing this to each MS patient. The presence of the abnormal glycan profiles in 6/7 patients and 0/5 normal controls is associated with MS (p=0.0152, Fishers exact test).
Figure 8:
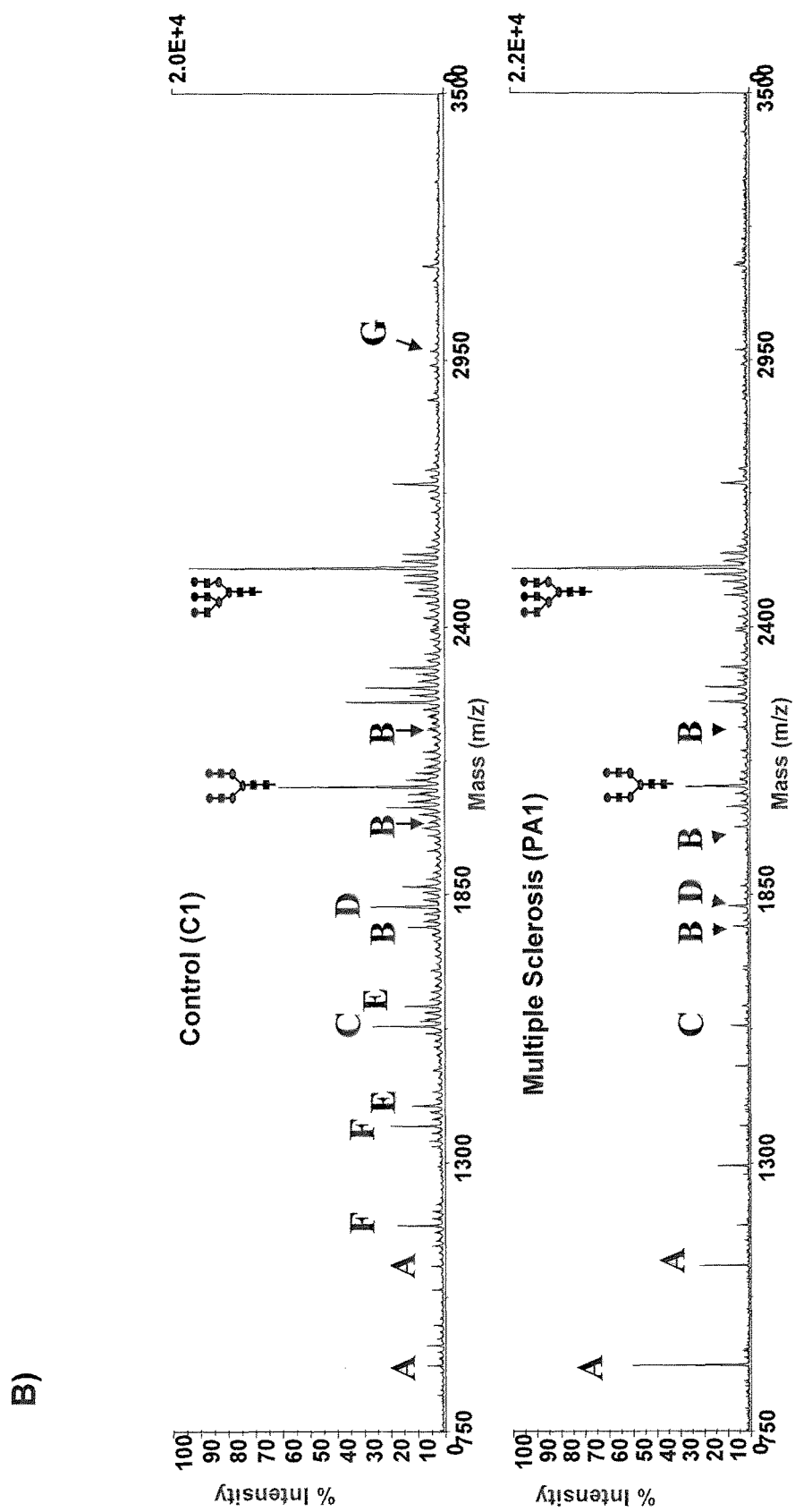
Figure 8:
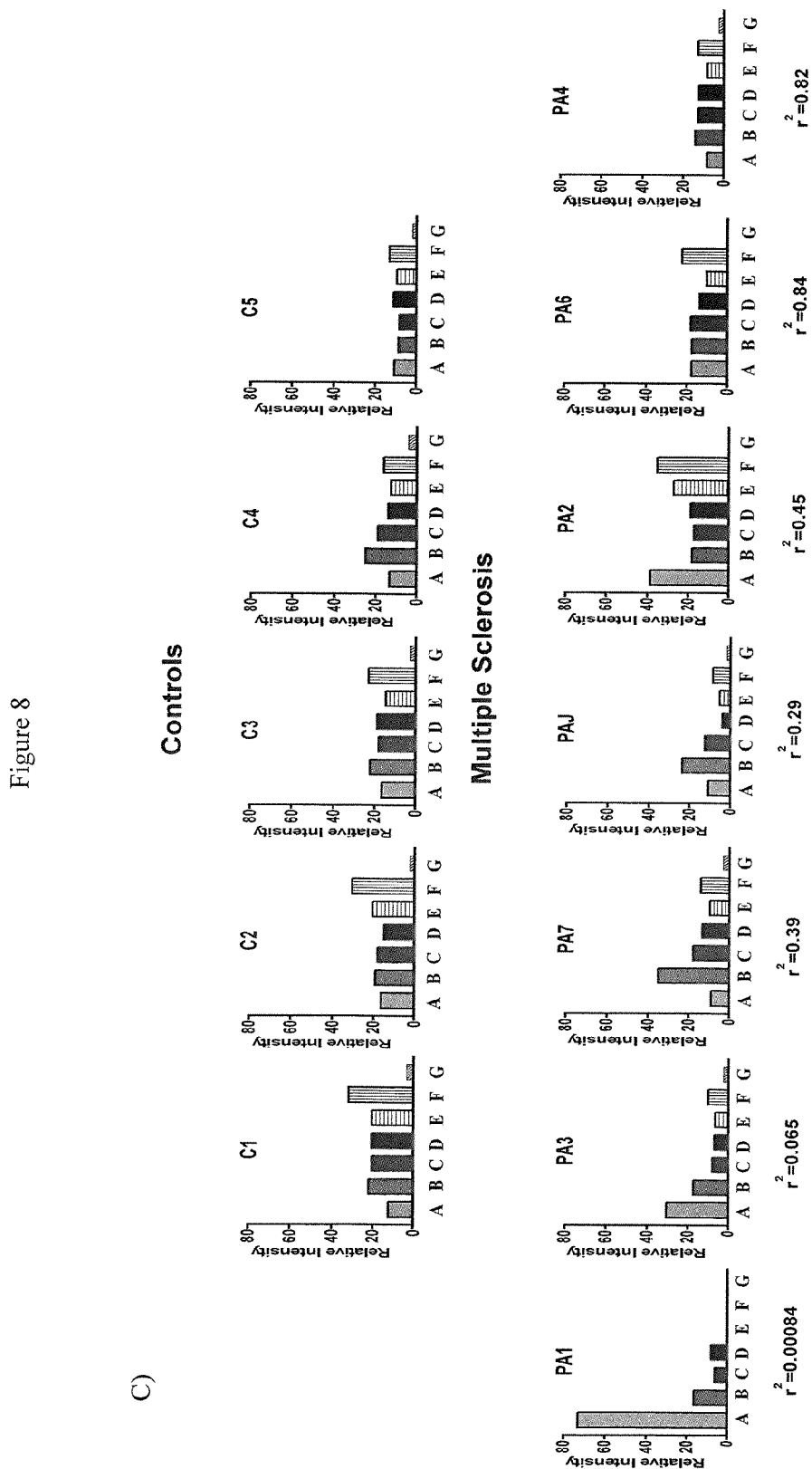
Figure 10:
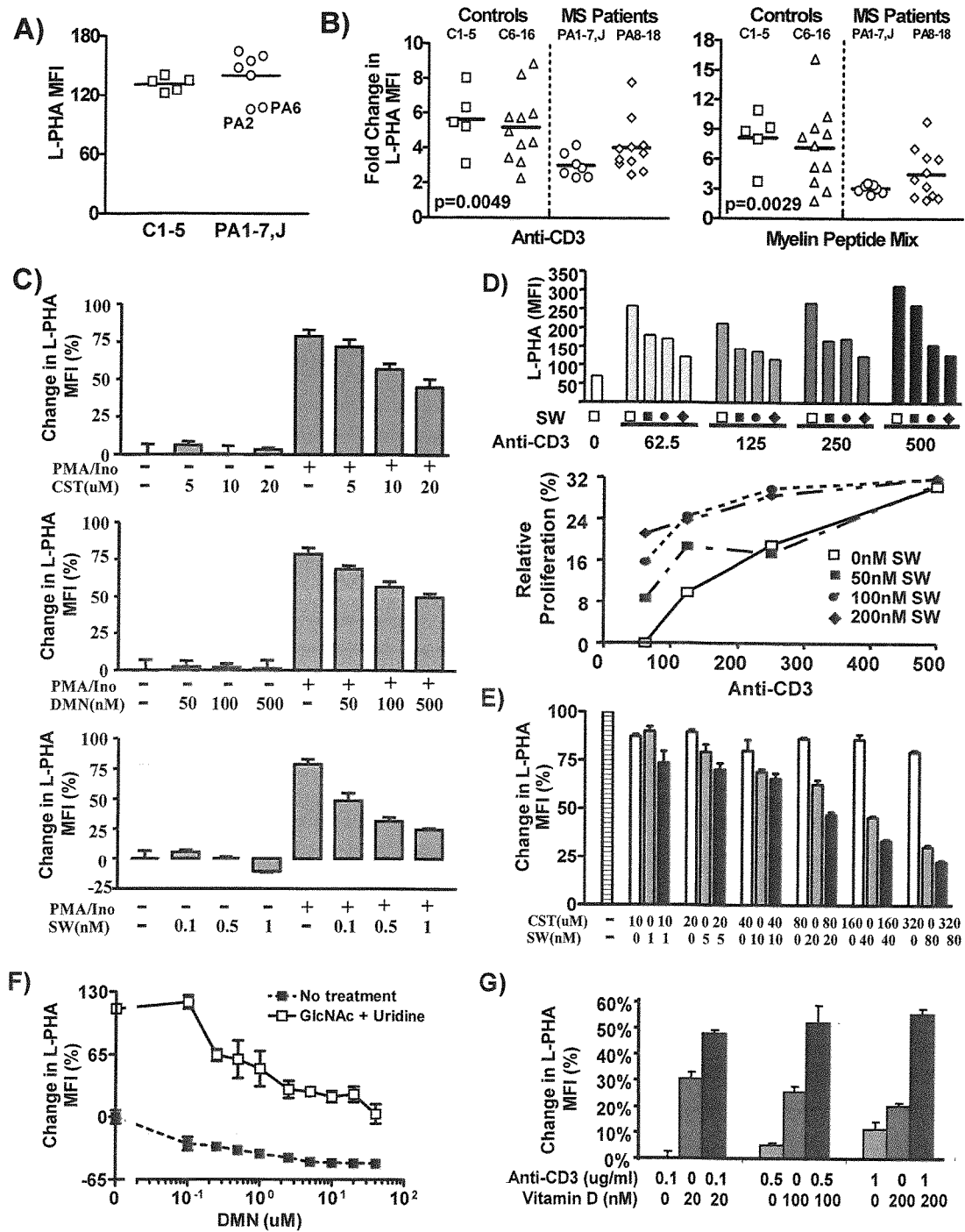
FIG. 10. Reduced Mgat5 glycan expression in MS patient T cells and with blockade of glycosidase activity. A) Resting PBMC from the 7 MS patients and 5 controls were directly compared for Mgat5 glycan expression by L-PHA-FITC staining and flow cytometry analysis; shown is gated on CD4$^+$ population. B) Freshly isolated PBMC were left unstimulated or stimulated with anti-CD3 antibody or a mixture of myelin antigens for 48 hrs and analyzed for L-PHA staining levels. Fold change in L-PHA MFI was calculated by comparing the MFI of blasting cells vs unstimulated cells as defined by side vs forward scatter in stimulated and non-stimulated cultures. Shown is gated on CD4$^+$ population. C) Jurkat T cells were untreated or stimulated with PMA and ionomycin in the presence or absence of minimal concentrations of the indicated glycosidase inhibitors for three days and stained with L-PHA-FITC. D) Mouse T cells purified by negative selection (R&D) were left unstained or stained with CFSE and stimulated with anti-CD3 antibody in the presence or absence of the indicated doses of SW for 5 days. Shown is the L-PHA MFI for non-CFSE labeled cells (top panel) and the percentage increase in the number of proliferating CD4$^+$ T cells relative to cells stimulated at 62.5 ng/ml anti-CD3 (bottom panel). Proliferating vs non-proliferating cells were determined by defining the latter with a gate on CFSE labeled cells not stimulated with antibody. E-G) Jurkat T cells were treated with the indicated concentrations of SW/CST (E), DMN in the absence or presence of GlcNAc (20 mM) and Uridine (10 mM) (E) or Anti-CD3+/−1α25-dihydroxyvitamin D3 for 3 days and analyzed by FACS for L-PHA staining.

If MS patients harbor polymorphisms that lead to deficiencies in N-glycan processing, this should be detected by testing for accumulation and/or deficiencies of Golgi N-glycan intermediates by MALDI-TOF mass spectroscopy (51). Analysis of the relative expression of N-glycan Golgi transients obtained from PBMC's of 5 control subjects (C1 to C5) revealed similar patterns (FIG. 8). The same analysis in 7 of 8 consecutively obtained MS patients revealed significant N-glycan processing deficiencies in 6 of 7 patients at three distinct enzymatic steps: Glucosidase I/II (structures A), Mannosidase I/Mgat1 (structures B) and Mgat5 (structure G). PA1 had a dramatic reduction in glycan diversity as seen by the absence of the majority of mass peaks in the spectra relative to controls (FIG. 8B), implicating a processing block early in the pathway. Indeed, a marked accumulation of glycans from the most proximal steps in protein bound N-glycan processing were observed (structures A in FIG. 8) coupled with the absence of later species (structures E-G FIG. 8), suggesting mutation in GCS1 and/or GCS1, GANAB. PA3 showed a similar but less dramatic pattern, implying deficiency in the same enzymes. In contrast, PA7 and PAJ displayed accumulation of high mannose glycans (structure B in FIG. 8A), suggesting enzymatic defects in Mannosidase I (MAN1A1, 1B1, 1C1) or Mgat1. PA2 and PA6 displayed a pattern similar to controls in the proximal pathway (structures A-F), but lacked non-core-fucosylated $\beta1,6$ GlcNAc branched tetra-antennary glycans (structure G), suggesting deficiency of MGAT5. FACS analysis with L-PHA confirmed reduced expression of Mgat5 glycans in these two patients (FIG. 10A). Remarkably, Mgat5 glycan deficient PL/J mice, a strain that develops spontaneous autoimmune demyelinating disease (Example 1), displayed accumulation of glycan structures at the GI/GII step (Structure A, FIG. 11A) similar to PA1 and PA3. In contrast, C57BL/6 and 129/Sv mice displayed patterns comparable to the normal human controls. Together, these data establish that defects in N-glycan processing are frequently associated with spontaneous demyelinating disease in humans and mice ($p=0.0014$, Fishers exact test).

Figure 9:
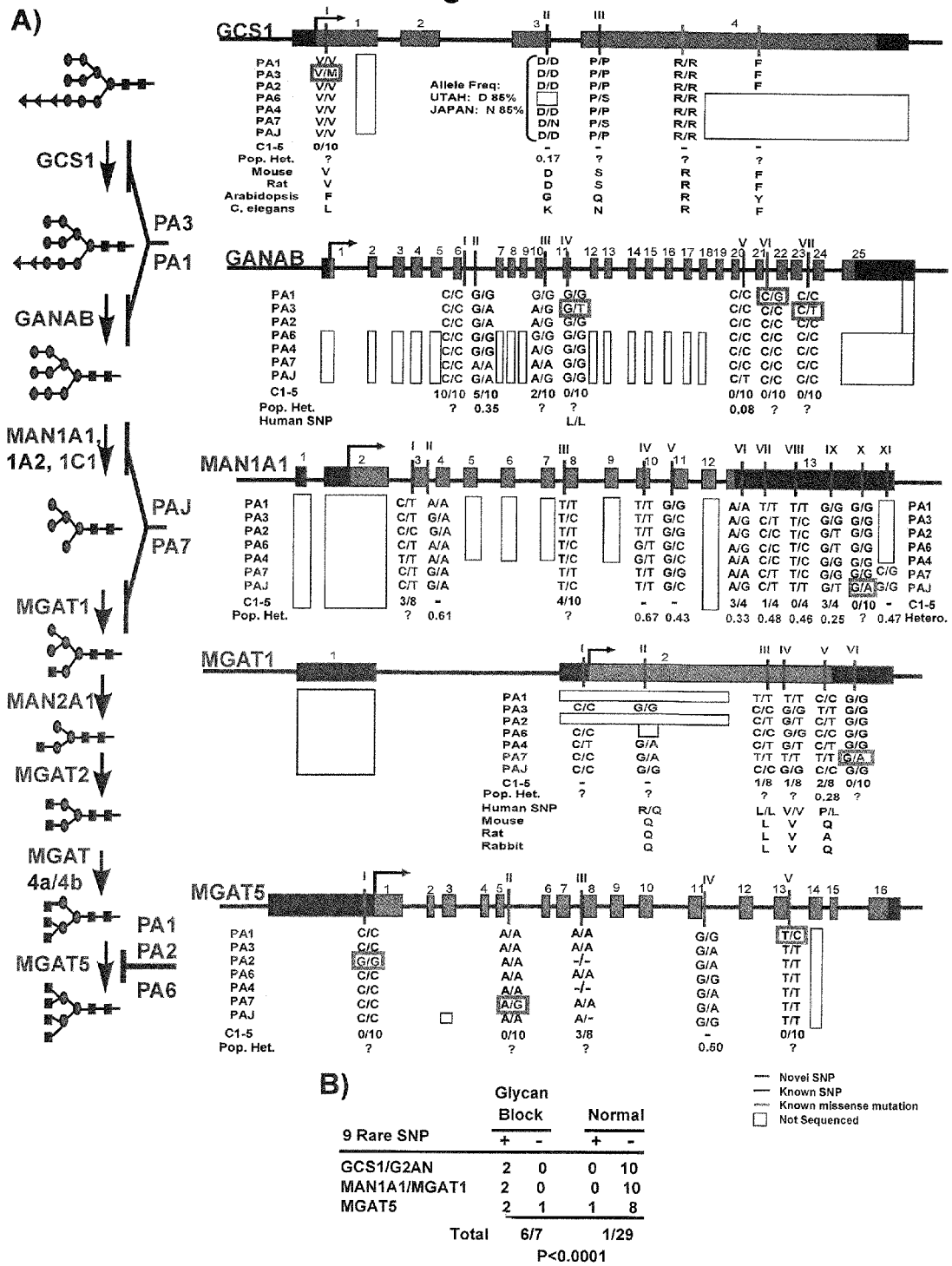
FIG. 9. Association of novel single nucleotide polymorphisms in genes controlling obstructed N-glycan processing in MS patients. A) MS patients with altered N-glycan processing are shown along with the genes controlling the defective steps. Sequencing of genomic DNA derived PCR products for each exon identified multiple heterozygous and homozygous unknown (red) and previously identified SNPs (blue, NCBI SNP database) as indicated. Exon and introns are not to scale. Controls C1-5 are shown as number of chromosomes with each SNP as determined by DNA sequencing and/or allelic discrimination. Pop. Het. refers to predicted heterozygosity of each SNP as defined in the NCBI SNP database. MAN1A2 and MAN1C1 were not targeted for sequencing as the former does not map to the 18 MS loci and the latter is not significantly expressed in T cells (FIG. 7B) (See Tremblay, L.O. & Herscovics, A. Characterization of a cDNA encoding a novel human Golgi alpha 1, 2-mannosidase (IC) involved in N-glycan biosynthesis. J. Biol. Chem. 275, 31655-31660 (2000)). Sequences for the previously unknown SNPs are in FIG. 11. The known SNPs are GCS1: II-rs1063588, III-rs2268416; GCS1, GANAB: I-rs2957121, 11-rs11231168, III-rs10897289, V-rs11231166; MAN1A1: I-rs6915947, II-rs195092, III-rs9481891, IV-rs2072890, V-rs2142887, VI-rs3756943, VII-rs18513744, VIII-rs3798602, IX-rs1042800, XI-rs1046226. MGAT1: I-rs3733751, II-rs7726357, III-rs2070924, IV-rs2070925, V-rs634501. MGAT5: III-rs3214771, IV-rs3748900, V-rs2289465, B) Table showing presence or absence of rare SNPs in genes controlling the obstructed steps for the 7 MS patients and 5 controls. Rare SNPs are defined as present in one or more individuals at the obstructed step and were either previously unknown or possess an allele frequency of ≤4%.

Exons from the relevant human N-glycan genes for DNA sequencing were next targeted (FIG. 9).

Figure 12:
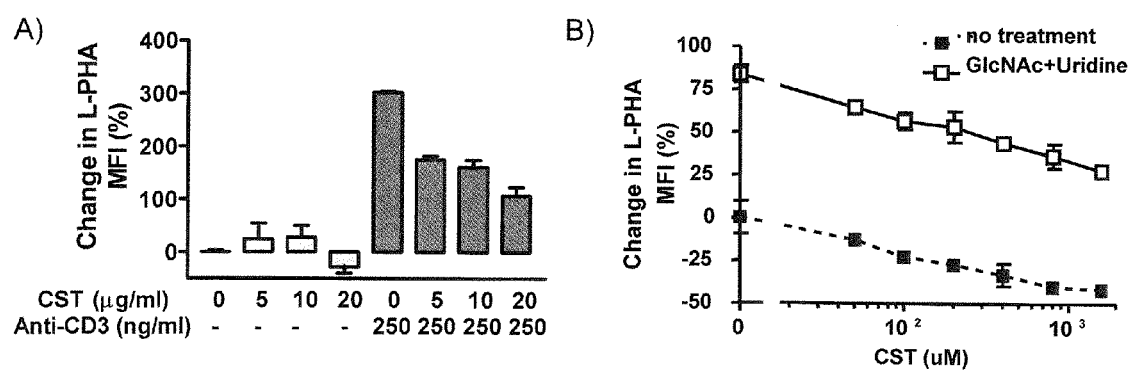
FIG. 12. Inhibition of Mgat5 glycan expression by Glucosidase I/II with CST. A) Mouse T cells purified by negative selection (R&D Systems) were left unstimulated or stimulated with Anti-CD3 for 4 days in the presence or absence of CST and analyzed by FACS for L-PHA staining. Shown is gated on $CD4^+$ population. B) Jurkat T cells cultured with increasing concentrations of CST were left untreated or co-cultured with GlcNAc (20 mM)+Uridine for 3 days and analyzed by FACS for L-PHA staining.

Numerous known SNPs were identified (SNPs in blue FIG. 9A), with only 1/24 (PA1 MGAT5 SNP V) correlating with the glycan profiles in FIG. 8. In contrast, 7/11 previously unknown SNPs in GCS1, GCS1, GANAB, MAN1A1, MGAT1 and MGAT5 (SNPs in red FIG. 9A, 12) were predictive of glycan processing defects in the relevant patients (1/24 vs 7/11, $p=0.0003$). The absence or presence of the 8 rare correlating SNPs (cSNP, black boxed SNPs in FIG. 9A, FIG. 11) in patients and controls (FIG. 9B, $p<0.0001$) as well as a comparison of the cSNPs with the other 27 identified SNPs (8/8 vs 0/27, $p<0.0001$, Fishers exact test) were both highly predictive of the MALDI-TOF glycan profiles. Within the 27 non-correlating SNPs, 12 were more frequent in the MS samples (ncSNPs, dashed green box FIG. 9A, 11). As the MALDI-TOF N-glycan profiles were obtained from resting PBMCs, the ncSNPs may synergize with cSNPs during T cell activation to attenuate the physiological increase in N-glycan processing (FIG. 7C, 10B,C). Indeed, the ncSNPs alone (33/154 vs 8/106, $p=0.0029$) or combined with the 8 cSNP (41/266 vs 8/186, $p=0.0002$) were disproportionately represented in MS patient chromosomes. Moreover, the presence of the 8 cSNPs in 5/7 MS patients or the unique cSNP/ncSNP haplotypes in the 7 MS patients and 0 of 5 controls were both independently associated with MS ($p=0.0278$ and $p=0.0013$, respectively, Fishers exact test). Taken together, these data indicate cSNPs and associated ncSNP haplotypes function to promote MS via disruption of N-glycan biosynthesis.

To determine the significance of the genetic and biochemical block in N-glycan processing on the regulation of Mgat5 glycan expression, ($\beta1,6$ GlcNAc branched N-glycans were measured by L-PHA flow cytometry. At rest, CD4$^+$ T cells from PA2 and PA6 had reduced Mgat5 glycan expression, a reduction consistent with their MALDI-TOF N-glycan profile. Mouse T cells increase Mgat5 glycan levels ~6-8 fold 48-72 hrs following TCR stimulation (Example 1), a fold increase that was similar to controls C1-5 stimulated with anti-CD3 antibody or a mixture of myelin antigens (FIG. 10B). In contrast, the 7 MS patient T cells had a marked attenuation of this physiological up-regulation under both stimulatory conditions (FIG. 10B). A second cohort of MS patients (PA8-19) and controls (C6-15) showed similar results, indicating dysregulation of Mgat5 glycan expression is common in MS (FIG. 10B). The defect in Mgat5 glycan up-regulation was phenocopied in Jurkat and mouse T cells by treatment with minimal concentrations of the N-glycan processing inhibitors CST, DMN or SW (FIG. 10C, 11B). The low doses used significantly attenuated the up-regulation of $\beta1,6$ GlcNAc branched N-glycans following stimulation with PMA/ionomycin or anti-CD3 without affecting resting levels, a result identical to that observed in the four MS patients—PA1, PA3, PA7 and PAJ—with cSNPs at these enzymatic steps. Moreover, T cell proliferation is enhanced by reducing the up-regulation of Mgat5 glycans by only 30-50%, with a magnitude equivalent to increasing TCR agonist dose ~3-4 fold (FIG. 10D). Taken together, these data indicate that polymorphisms which minimally alter N-glycan enzyme activity or expression are sufficient to limit the up-regulation of Mgat5 glycans and induce T cell hyperactivity. In mice this phenotype leads to preferential $T_H1$ differentiation and spontaneous autoimmune CNS demyelinating disease (5) (Example 1), implying that the genotypic and phenotypic defects in Mgat5 glycan regulation identified here directly promoted disease in each individual.

The data confirm MS is genetically heterogeneous when assessed mathematically by gene linkage analysis, but is homogeneous when gene function is considered. The large diversity of polymorphisms in multiple N-glycan genes identified in only 7 MS patients coupled with the ~14 Mgat5 regulatory genes that non-randomly map to MS and other autoimmune loci strongly suggest the identified SNPs represent only a small fraction of the associated polymorphisms in the two pathways. Indeed, only 2 of the cSNPs were present in other MS patients, despite 8/10 displaying attenuated up-regulation of Mgat5 glycans.

Inhibition of enzymatic activity at two separate steps in the N-glycan pathway via co-incubation of CST and SW or DMN and SW are additive in reducing Mgat5 glycan expression in Jurkat T cells (FIG. 11C), suggesting mutations in two or more genes may compound to promote disease. This model is consistent with our observation that 6 of 7 MS patients—PA1, PA2, PA3, PA4, PA7 and PM—had cSNPs/ncSNPs in at least two genes in the N-glycan pathway that were absent in the C1-5 control samples (FIG. 7C). Moreover, 2 control subjects (C6, C9) with a single copy cSNP (MGAT5 SNP I and GCS1 SNP I, respectively, had normal Mgat5 glycan up-regulation following TCR activation, which is in contrast to PA2, who was homozygous for MGAT5 SNP I and possessed 3 additional ncSNPs, and PA3 who had 2 cSNPs in GCS1, GANAB in addition to the GCS1 SNP I (FIG. 9A,C). Furthermore, the single control subject (C10) with two cSNPs (homozygous MAN1A1 SNP XII FIG. 9A) had attenuated Mgat5 glycan up-regulation. Together these data indicate two or more copies of cSNPs/ncSNPs are required to produce the Mgat5 glycan phenotype.

Monozygotic twins have a ~30% concordance rate for MS, indicating strong environmental influences on genetic susceptibility (6). Supplementing the hexoasmine pathway with various metabolic intermediates common to glucose, nitrogen, lipid and nucleotide metabolism raises Mgat5 glycan levels in T cells, inhibits proliferation, INFγ production, EAE (Example 1) and can reverse Mgat5 glycan down regulation induced by blockade of proximal N-glycan processing (FIG. 10E, 11E). 1α,25-Dihydroxyvitamin D3 (Vitamin D3) up-regulates Mgat5 mRNA expression in hepatoma cells (52), inhibits T cell activation (53), INFγ production (54), EAE (54) and is an environmental factor controlling susceptibility to MS (55). Addition of Vitamin D3 to Jurkat T cells enhanced Mgat5 glycan expression, synergized with anti-CD3 in up-regulating Mgat5 glycan levels and reversed SW induced downregulation of Mgat5 glycans (FIG. 10F, 11F). Moreover, inhibition of T cell proliferation induced by Vitamin D3 is reversed with SW. Taken together, these data indicate that Vitamin D3 negatively regulates T cell function by enhancing Mgat5 glycan expression. Thus, Vitamin D3 exposure and metabolic flux through the hexosamine pathway provide two independent mechanisms for environmental modulation of disease promotion by the identified SNPs and raise the possibility that genetic defects leading to altered Mgat5 glycan expression may be relatively frequent in the normal population but masked environmentally. Indeed, a number of normal controls also displayed this phenotype (FIG. 10B).

Taken together the data indicate a model where the absence or presence of disease is dependent on the additive effects of genetic and environmental factors controlling flux through the hexosamine and N-glycan pathways. Moreover, treatment of MS patients with various hexosamine pathway metabolites and/or Vitamin D alone or in combination should provide a simple targeted therapy to correct the underlying biochemical deficiency promoting disease. More broadly, the data provides a comprehensive approach to investigate the genetics of other complex trait diseases, whereby genetic heterogeneity can be simplified by using structural and functional analysis of entire candidate biochemical pathways in combination with linkage data to highly focus DNA sequencing efforts.

Example 3

The following methods were used in the study described in this Example.
Methods
Spontaneous Demyelinating Disease and Dystonia.

PL/J mice at two facilities were assessed for clinical disease using a standard EAE scale (Tables 1, 3) (4). The first cohort was at backcross 4 from 129/Sv (Table 1) and was housed at the Samuel Lunenfeld Research Institute (SLRI) vivarium, a colony infected with mouse hepatitis virus, EDIM, Minute virus, Mouse parvovirus, GDVII, pinworm and fur mites. These mice were initially assessed by blindly examining all Mgat5$^{-/-}$ (n=43), Mgat5$^{+/-}$ (n=22) and Mgat5$^{+/+}$ (n=15) PL/J mice in the colony over 6 months of age. Only mice over 1 year of age were found to have weakness and this smaller cohort (n=21, 13 and 10, respectively) was scored for clinical severity every 1-2 weeks over the next ~4 months. Weakness was slowly progressive without recovery in all affected mice, an observation confirmed by daily assessment of a smaller cohort (n=12) of clinically affected mice over a 4 week period. At sacrifice, mice were perfused with paraformaldehyde via cardiac perfusion and harvested brain and spinal cord were embedded in paraffin, sectioned and stained with H&E or Luxol Fast Blue. Additional organ screening in 4 clinically affected mice confirmed the only autoimmune disease present in the mice was demyelinating disease. The second cohort (Table 3) at backcross 6 were re-derived from the SLRI mice by embryo transfer and housed at the University of California, Irvine (UCI) vivarium which is pathogen free except for mouse parvovirus. Disease was observed in both pathogen-free and mouse parvovirus-containing rooms.
Adoptive Transfer EAE.

Adoptive transfer EAE was induced by s.c. immunization of wild type PL/J mice housed in the UCI vivarium with 100 μg of bovine MBP (Sigma) emulsified in Complete Freund's Adjuvant containing 4 mg/ml heat-inactivated *Mycobacterium tuberculosis* (H37 RA; Difco, Detroit, Mich.) distributed over three spots on the hind flank. Splenocytes were harvested after 11 days and stimulated in vitro with 50 μg/ml MBP in the presence or absence of 40 mM GlcNAc (Sigma) added daily. After 96 hours incubation, CD3$^+$ T-cells were purified by negative selection (R&D Systems) and 3.6×10$^6$ T-cells were injected i.p. into naïve PL/J Mgat5$^{+/-}$ recipient mice. Trypan blue exclusion determined <5% dead cells under both culture conditions. Mice were scored daily for clinical signs of EAE over the next 30 days with the observer blinded to treatment conditions.
FACS Analysis, L-PHA Staining and In Vitro Proliferation Assays.

Mice used for L-PHA staining and quantitative RT-PCR were sex and age matched. The PL/J and C57/BL6 mice were congenic at backcross 6 from 129/Sv and showed no difference in L-PHA staining compared to PL/J and C57/BL6 obtained from Jackson Laboratories. 129/Sv mice were from the original Mgat5 gene targeted population (28). All other mice (SJL, NOD, Balb/c and B10.S) were obtained from Jackson Laboratories. Mouse cells were stained with anti-CD4 (RM4-5), anti-CD8 (53-6.7), anti-CD45R (RA3-6B2) from eBioscience, and L-PHA (4 μg/ml) and LEA (20 μg/ml) from Sigma. CD3$^+$ T-cells (R&D Systems) were labeled with 5 μM 5,6-carboxyfluorescein diacetate succinimidyl ester (CFSE; Molecular Probes) in PBS for 8 minutes at room temperature and stimulated with plate bound anti-CD3 (2C11, eBioscience) and/or anti-CD28 (37.51 eBioscience) in the presence or absence of swainsonine (Sigma)

GlcNAc, castanospermine (CST) and/or deoxymannojirimycin (DMN, Sigma). Jurkat T-cells were cultured in either glutamine free RPMI 1640, 10% FBS, 10 mM/20 mM glucose or glucose/glutamine free DMEM base media supplemented with 10% FBS, 1.5 mM glucose. The indicated monosaccharides and/or metabolites were added daily except glucose which was added only at time zero. Doses were titrated until a plateau was reached in L-PHA staining or toxicity was observed. The plateau or highest non-toxic dose is shown.

TCR Signaling.

$10^6$ purified splenic CD3$^+$ T-cells from Mgat5$^{+/+}$, Mgat5$^{+/-}$ and Mgat5$^{-/-}$ mice and $5\times10^6$ polystyrene beads (6 micron, Polysciences) coated with 0.5 µg/ml anti-CD3ε antibody (2C11, eBioscience) overnight at 4° C. were mixed, pelleted at 5,000 rpm for 15 s, incubated at 37° C. for the indicated times, and then solubilized with ice-cold 50 mM Tris pH 7.2, 300 mM NaCl, 1.0% Triton X-100, protease inhibitor cocktail (Boehringer Mannheim) and 2 mM Orthovanadate for 20 mM. Cell lysates were separated on Nupage10% BIS-TRIS gels (Invitrogen) under reducing conditions, transferred to polyvinylidene difluoride membranes and immunoblotted with rabbit anti-phospho-lck Tyr$^{505}$ Ab (Cell Signaling Technology (CST)), rabbit anti-phospho-Src family Tyr$^{416}$ Ab (CST) which cross reacts with phospho-lck Tyr$^{394}$, rabbit anti-phospho-Zap70Ab (CST), rabbit anti-phospho-LAT Ab (Upstate), and anti-actin Ab (Santa Cruz).

Cytokine ELISA.

Supernatant from splenocyte cultures used for adoptive transfer EAE at day 4 of stimulation with MBP in the presence or absence of GlcNAc (40 mM) were tested for IFN-γ and IL-6 levels. Microtiter plates were coated with 50 µl of anti-IFN-γ (1 µg/ml, clone AN-18; eBiosciences) or anti-IL-6 (1.5 µg/ml, clone MP5-20F3; eBiosciences) overnight at 4° C. Supernatants were applied at 50 µl/well in duplicate and incubated for 2 hours at room temperature. Captured cytokines were detected using biotinylated anti-IFN-γ (1 µg/ml, clone R4-6A2; eBiosciences) or anti-IL-6 (1 µg/ml, clone MP5-32C11; eBiosciences) and detected using Avidin Horse Radish Peroxidase (eBiosciences) at 1:500× dilution and o-Phenylenediamine dihydrochloride OPD tablets (Sigma) according to the manufacturer's protocols. Recombinant IFN-γ or IL-6 (eBiosciences) was used as a standard. Colorimetric change was measured at 450 nm on a microplate autoreader (Labsystems).

Quantitative Real Time PCR.

RNA from purified CD3$^+$ T lymphocytes of 129/sv, PL/J and C57/BL6 mice, Jurkat I cells and transfected Lec1 cells was purified using the RNeasy® Mini Kit (Qiagen) and used to synthesize cDNA with the RETROscript® Kit (Ambion). For expression of MGAT1, 2, and 5 and β-actin, a 7900HT platform (3840 well plate, Applied Biosystems) was used with SYBR® Green PCR master mix and the following primers: MGAT5-5'-GGAAATGGCCTTGAAAACACA-3' [SEQ ID NO.1] and 5'-CAAGCACACCTGGGATCCA-3' [SEQ ID NO. 2]; for β-actin 5'-CCAGCAGATGTG-GATCAGCA-3' [SEQ ID NO. 3] and 5'-TTGCGGTGCAC-GATGG-3' [SEQ ID NO. 4]; MGAT1-5'-CGTTGTTGGGA-GATGGAAAG-3' [SEQ ID NO. 10] and 5'-TCAGGCAACAAACAAGGACA-3' [SEQ ID NO. 11] and MGAT2-5'-AGTAGCAATGGGCGACAAAG-3' [SEQ ID NO. 12] and 5'-GCTTTGCGAAGCGAGTCTAT-3' [SEQ ID NO.13]. For N-glycan pathway gene expression in human Jurkat T cells, Taqman primers obtained from Applied System Assays on Demand were used in the TaqMan Gene Expression Assay (Applied Biosystem). For pCMV-MGAT1 transfected LEC1 cells, the following exon 2 specific primers were used with SYBR® Green PCR master mix: 5'-CCCCGGACTTCTTCGAGTA-3' [SEQ ID NO. 14] and 5'-CGAACGTTGCCAAACTCTCT-3' [SEQ ID NO.15]. Automatically detected threshold cycle (Ct) values were normalized relative to β-actin and fold differences in expression were calculated based on a cDNA standard dilution curve.

Enzymatic assays.

Enzyme activity was measured using synthetic specific acceptors. The acceptors for Mgat5 (GnTV), Mgat2 (GnTII) and Mgat1 (GnTI) were βGlcNAc(1,2)βMan(1,6)βGlc-O(CH$_2$)$_7$CH$_3$, βGlcNAc(1,2)αMan(1,3)[αMan(1,6)] βMan-O(CH$_2$)$_7$CH$_3$ and αMan(1,3)βMan-O(CH$_2$)$_7$CH$_3$, respectively (Toronto Research Chemicals). 10 µl cell lysate (0.9% NaCl, 1% Triton X-100 on ice, centrifuged 5000 g for 15 min at 4° C.) was added to 1 mM acceptor, 1 mM [6$^3$H]-UDP-GlcNAc (Amersham) in 50 mM MES pH 6.5, 0.1 mM GlcNAc and 25 mM AMP for a total reaction volume of 20 µl. Mgat2 and Mgat1 reactions also contained 5 mM MnCl$_2$ and were incubated for 1 h; Mgat5 for 3 h at 37° C. Reaction was stopped with 1 ml of ice-cold water. Enzyme products were separated from radioactive substrates by binding to 50 mg C$_{18}$ cartridges (Alltech) preconditioned with methanol rinsing and water washing. Reactions were loaded and the columns washed 5 times with 1 ml water. Radio-labeled products were eluted directly into scintillation vials with two separately applied 0.5 ml aliquots of methanol and the radioactivity was determined by liquid scintillation counting.

MS/MS Mass Spectroscopy.

JurkaT-cell pellets ($20\times10^6$) were resuspended in cold 300 µl methanol:water (1:1) solution containing maltose as an internal standard, vortexed for 10 seconds, and then pipetted into tubes containing 600 µl of chloroform:methanol (C:M) (3:2). Samples were vortexed for 1 minute, and then centrifuged at 14,000 rpm for 5 minutes at 4° C. Supernatants were collected, and an equal volume of C:M (1:1) was added, followed by a second extraction. The pooled aqueous fraction containing the hydrophilic metabolites was dried with a speedvac and stored at −80° C. Prior to injection, the samples were dissolved in 100 µl methanol:water (1:1). The samples were injected at a flow rate of 150 µl/hr into the API3000 Mass Spectrometer (SCIEX). The metabolites were identified by their transitions in MS/MS, and quantified using the Analyte Software (SCIEX), which measured the area under the curve for the fragment ions corresponding to each parent ion. Quantities for the given substrates are graphed as pmole/min/$10^6$ cells.

MALDI-TOF Mass Spectroscopy.

This was done as a service at the Glycotechnology core facility, a resource of the Glycobiology Research and Training Center (GRTC) at the University of California, San Diego. CD3+ murine T cells ($6\times10^6$), resting PBMCs from human controls and MS subjects ($6\times10^6$) and CHO cells ($10\times10^6$) were lysed with 1% SDS in 100 mM Tris pH 7.4, dialyzed to remove SDS, digested with trypsin to generate glycopeptides and treated with PNGaseF to release the N-glycans. To focus on early processing, N-glycans were desialylated by mild acid digestion prior to permethylation and MALDI-TOF mass spectroscopy. Monoisotopic peaks in the spectra were identified using GlycanMass and GlycoMod online software, with specific targeting of the N-glycan intermediates occurring during Golgi processing.

Carbohydrate Related Genes and MS Associated Chromosomal Regions.

β1,6GlcNAc-branched N-glycan regulatory and non-regulatory carbohydrate related genes were identified from the literature as well as by inspection of the Kegg metabolic pathways. Additional family members were obtained by searches for similar gene names in the NCBI genome website, resulting in identification of gene families with the same or similar putative function. This identified 275 carbohydrate related genes (Table 6). This represents ~1% of the predicted number of human genes in the human genome and is consistent with previous estimates of the total number of carbohydrate related genes in humans (71). This indicates that a high percentage of human carbohydrate related genes were incorporated in Table 4 and Table 6.

Identification of MS associated loci has been difficult with few studies finding significant LOD scores other than the MHC association at 6p21. Multiple groups have identified suggestive chromosomal regions but these are often different among populations and investigators. Therefore a simple and broad approach was adopted by assuming that if three or more studies identified a similar chromosomal cytogenetic region that this may represent a potential MS associated region (Table 5). This approach identified 18 regions which represented approximately 34% of the genome, the latter estimated by the proportion of nucleotides within each of the 18 cytogenetic regions relative to the total as defined on the NCBI genome website.

Electromyography and Nerve Conduction Studies.

Mice were anesthesized with Avenin. Temperature was maintained at 35-37° C. using infrared heat lamps. Monopolar needle electrodes (Ambu Inc., Glen Burnie, Md.) were used for stimulation and recording motor nerve potentials. The active and indifferent recording electrodes were placed in medial gastrocnemius and ipsilateral footpad, respectively. The active and reference stimulating electrodes were placed percutaneously in the popliteal or sciatic notch and ipsilateral thoraco-lumbar paraspinal muscle, respectively. A pre-gelled strip electrode at the tail acted as a ground. Responses from supramaximal electrical stimulation (pulse width 0.05 msec) were analyzed with addition stimulations done to record late responses (F waves and H reflexes). H reflexes were identified when successive late responses had identical morphology and onset latency; F waves were identified when successive late responses had variable onset latency and morphology. For needle EMG recording, the recording monopolar needle electrode was inserted into one or more hindlimb muscles: quadriceps, hamstrings, lumbar paraspinals, gastrocnemius and tibialis anterior. The presence of spontaneous muscle activity (i.e. fasiculations, fibrillations or myokymia) was assessed in at least three regions of the muscle. All recordings were made on a Sierra LT portable machine (Cadwell Laboratories, Kennewick, Wash.) and analyzed using the proprietary software supplied by the manufacturer.

MS Patients and Control Subjects.

Patients diagnosed with clinically definite Multiple Sclerosis (MS) based on the McDonald Criteria (71) were randomly recruited from the MS clinic at the University of California, Irvine. PA1,2,3,4,6,7,J represented 7 of the first 8 consecutive patients enrolled in the study. Both relapsing remitting and primary progressive MS patients were included. Controls were healthy volunteers from the University of California, Irvine campus and lacked personal history of MS and other autoimmune diseases.

Isolation and Activation of PBMCs.

Mononuclear cells were isolated from the blood of subjects using Histopaque-1077™ gradients (Sigma) and cultured in RPMI 1640 medium supplemented with 4 mM glutamine, 1 mM sodium pyruvate, 1% non-essential amino acids, 1% RPMI vitamins, 100 units/ml penicillin, 100 μg/ml streptomycin, and 50 μM β-mercaptoethanol. T lymphocytes were left unstimulated or were activated for 48 hours with 20 ng/ml anti-CD3 (Biomeda) or a combination of 20 immunodominant myelin peptides at 1 mg/ml each with 10 mg/ml myelin basic protein (MBP): [human proteolipid protein (PLP 30-49, PLP 40-60, PLP 95-118, PLP 118-150, PLP-180-189, PLP 185-206), human myelin oligodendrocyte glycoprotein (MOG 38-60, MOG 63-87, MOG 76-100, MOG 89-113, MOG 112-132 and MOG 162-188), and cryptic peptides from MBP (MBP 41-69, MBP61-79, MBP 121-139 and MBP 131-149), and PLP (PLP 73-104, PLP 145-186, PLP218-248 and PLP 241-272) that are not normally derived by antigen processing but may be produced by extracellular proteolytic activity]. Whole MBP was isolated from frozen guinea pig spinal cords (Harlan Bioproducts). Cells were stained with anti-CD4 (BD Pharmingen) and L-PHA. Unstimulated cells were gated on the resting lymphoid population and the activated cells were gated on blasts based on forward and side scatter. To directly compare L-PHA staining in resting T cells, PBMCs frozen in liquid nitrogen (90% FCS, 10% DMSO) were thawed and stained the same day.

Cloning of Human MGAT1 and Transient Transfections.

pCMV-Script PCR Cloning Kit (Stratagene) was used for human MGAT1 cloning. Primers 5'-CCCCCATTTCCTCTACCTGT-3' [SEQ ID NO.16] and 5'-CCCTCCCACTCATCTGCTTTC-3' [SEQ ID NO. 17] for human MGAT1 were used to PCR amplify exon 2 from the two exon MGAT1 gene (see FIG. 22) using genomic DNA of subjects with or without SNP IV/V. Exon2 contains a small 5' untranslated (UTR) region, the entire coding region and all of the 3' UTR. PCR products were sequenced and the presence or absence of SNP IV/V was confirmed after cloning into the pCMV vector by an allelic discrimination assay. 1×105 Lec1 cells (MGAT1-deficient Chinese Hamster Ovary cell line) were seeded onto a 6 mm culture dish one day before transfection. 3 μg of plasmid DNA was diluted into 200 serum-free DMEM and 15 μl of LIPOFECTAMINE™ Reagent kit (Invitrogen) was added. After incubation for 30 min. at room temperature, the cells were washed once with 2 ml serum-free DMEM. For each transfection, 2 ml serum-free DMEM was added to each tube containing the LIPOFECTAMINE™-DNA complexes and were overlain onto cells. Cells were incubated for 5 hours at 37° C. in a $CO_2$ humidified incubator. The DNA-containing media was replaced with 2 ml of DMEM supplemented with 10% FCS and cells were incubated for an additional 72 hours. Cells were stained with L-PHA and transfection positive cells were determined by FACS as L-PHA-positive cells compared to L-PHA negative vector-only transfected cells.

DNA Sequencing and SNP Analysis.

Primers designed to amplify exons of GCS1, GCS1, GANAB, MAN1A1, MGAT1 and MGAT5 including ~20-100 nucleotides (nt) of intronic sequence at both the 5' and 3' ends were used to amplify genomic DNA isolated from PBMCs using hi-fidelity Taq. Sequencing was done on gel purified PCR products (Qiagen) as a service by Seqwright. Chromatograms and derived sequences were visually inspected for homozygous and heterozygous single nucleotide base pair changes. Introns, except for ~20-100 nt at the 5' and 3' end of each exon, upstream promoter regions and open boxes in FIG. 22 were not sequenced. All previously unknown SNPs were sequenced in both directions at in two separate PCR reactions at least once, and confirmed with a Tatman allelic discrimination assay using custom designed probes (Assay by Design, Applied Biosystems). This SNP analysis assay is independent of Taq error and was run and analyzed by use of an ABI PRISM 7500 sequence detection system and SDS2.1 software (Applied Biosystems). Taqman SNP probes could not be made for MAN1A1 IV and GCS1, GANAB SNP V and required sequencing to genotype.

Generalized Mass Action Model of Golgi N-Glycan Processing.

The Golgi N-glycan processing pathway was modeled using a series of ordinary differential equations, and generates structures up to a maximum size of tetra-antennary with N-acetyllactosamine and (Galβ1-4GlcNAcβ1-3)2 extensions. The biochemical reaction network for N-glycan processing was represented by a series of ordinary differential equations (ODE) constructed using the generalized mass action (GMA) formulation (72). The change in concentration of each component [Ci] over time was determined by the sum of the rates of [Ci] production minus the rates of [Ci] consumption according to the following differential equation, where Ci represents one of the 143 compounds.

$$\frac{d[Ci]}{dt} = \sum V \text{ production} - \sum V \text{ consumption} \quad \text{Equation [1]}$$

The model includes the enzyme activities; GlcNAc-TI, II, III, IV, V, ManII, β3GlcNAc-T(i), and β4GalT, and generates structures up to a maximum size of a tetraantennary N-glycan with N-acetyllactosamine plus two additional N-acetyllactosamine repeat extensions. The kinetic properties of these enzymes, their estimated Golgi concentrations are taken from literature sources. The key assumptions implicit to the model are:

1) The medial and trans Golgi compartments are each considered as spatially homogeneous compartments.
2) There is no loss of glycoproteins during their transport through the Golgi, and mass is conserved in the system.
3) Increase in components due to cell growth is negligible, as cell doubling time is ~20 times greater than transport rates through the Golgi.
4) The following processes are considered to be linear:
   a) Transit through the medial- and trans-Golgi
   b) Glc3Man9 to Glc3Man5 N-glycan trimming in the ER and cis-Golgi
   c) Glycoproteins entering (protein synthesis) and exiting (protein degradation) the system
5) Transport rates of glycoproteins to the cell surface are the same for all glycoforms.
6) The reverse to forward (k−1/k2) ratio is assumed to be 4 for a system operating below saturation (14) (see reaction scheme below).

Assumptions 1 to 4a were made based on structural and biochemical data in the literature, and necessary approximations to generate an ODE model as previously described by Umana and Bailey (74). The Umana and Bailey model employed the Briggs-Haldane (Michaelis-Menten) approximation, a condition that is only satisfied during the initial phases of a reaction unless the amount of enzyme is very small. This situation may not be valid for all enzymes in the Golgi at steady state. Enzyme product inhibition is significant in steps where the rate of product output is faster than its removal. Examination of cellular N-glycan profiles in Mgat5+/+ and Mgat5−/− cells by mass spectroscopy reveals that the accumulation of the product is not limited to the step prior to Mgat5, and this is likely to hold for earlier steps in the pathway as well. Rather, product accumulation is spread through the whole pathway, suggesting extensive product inhibition. Taking the above ideas into account, enzyme reactions were broken down and modeled in their elementary forms, as outlined below. One exception was made; the Briggs-Haldane approximation was used for UDP-GlcNAc/UMP transport where the amount of transporter protein is much lower than the amount of cytosolic UDP-GlcNAc and Golgi UMP (75). The transporter operates at its Vmax for most Golgi UDP-GlcNAc concentrations due to its low Km (0.00713 mM), as such, establishing a direct proportionality between the steady state amounts of UDP-GlcNAc inside the Golgi and in the cytosol. The Vmax of transport is on the order of ~0.2 mM/s, which corresponds to the mM concentration of UDP-GlcNAc in the Golgi. The GlcNAc-T enzymes (E) follow an ordered sequential bi-bi reaction mechanism beginning with binding of the donor UDP-GlcNAc and then acceptor (A) (76). The dissociation of UDP from the enzyme was assumed be fast, and N-glycan product (P) was allowed to re-bind to the enzyme.

[2]

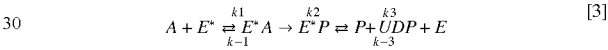

[3]

E*A is the activated enzyme-acceptor complex, and E*P is the activated enzyme product complex.

Simulations of Golgi N-glycan processing were run for an arbitrary time needed to establish steady-state conditions and generate the N-glycan profiles. The model allows for graded positive feedback as linear functions of increasing TCR activation by: (1) progressive stimulation of glucose flux through the hexosamine pathway, and (2) increased expression of N-glycan branching enzymes Mgat1, 2, 4 and 5, and GlcNAc-T(i), for the production of polylactosamine.

Summary

The autoimmune demyelinating disease Multiple Sclerosis (MS) results from poorly understood genetic and environmental interactions. β1,6 GlcNAc-branching of N-glycans by MGAT5 titrates thresholds for T-cell activation and autoimmunity. Here it is demonstrated MS patients and inbred mouse models have inherent genetic defects in N-glycan processing that reduce β1,6 GlcNAc-branching and promote autoimmunity conditional to metabolite flux through the hexosamine pathway. Defective N-glycan processing in PL/J mice induces spontaneous demyelinating disease. Metabolically supplementing the hexosamine pathway rescues this phenotype and inhibits disease by increasing supply of UDP-GlcNAc to MGAT5. N-glycan and hexosamine pathway genes are over represented at putative MS loci. Glycomic analysis led to the identification of rare MS associated single nucleotide polymorphisms (SNPs) within the N-glycan pathway. MS associated SNP IV/V doubles upstream MGAT1 activity and reduces β1-6 GlcNAc branching by limiting Golgi supply of UDP-GlcNAc. Thus, metabolic regulation of N-glycan processing by the hexosamine pathway provides a molecular intervention to reduce genetic risk to disease.

Introduction

Multiple Sclerosis (MS) is a complex trait (1) disease, where environmental factors influence the penetrance of mutations and complicate identification of susceptibility genes. Whole genome screens have identified a number of candidate loci associated with MS and the animal model Experimental Autoimmune Encephalomyelitis (EAE), but non-MHC genes with a strong association are yet to be identified (8, 9, 31-41). The majority of cell surface receptors in the innate and adaptive immune responses are modified by glycosylation. The N-glycosylation processing enzymes N-acetylglucosaminyltransferases I, II, IV and V (MGAT1, 2, 4, 5) transfer GlcNAc from the sugar nucleotide donor UDP-GlcNAc to N-glycan intermediates transiting the medial Golgi, producing hybrid, bi-, tri- and tetra-antennary N-glycans, respectively (59) (FIG. 7A). Galectins, a family of N-acetyllactosamine-binding lectins, bind N-glycans with increasing affinity proportional to GlcNAc branching and poly-N-acetyllactosamine expression, the latter preferentially expressed on β1,6GlcNAc branched tetra-antennary N-glycans produced by MGAT5 (FIG. 7A). Galectin-3 cross-links cell surface glycoprotein receptors (4, 29) and on T-cells, binds the T-cell receptor (TCR) and inhibits recruitment into the immune synapse (4). Reduced β1,6GlcNAc-branching and poly-N-acetyllactosamine expression in Mgat5$^{-/-}$ T-cells induces TCR hypersensitivity and enhances $T_H1$ differentiation (4, 5). Mice deficient in MGAT5 display spontaneous kidney autoimmunity and hyper-sensitivity to EAE (4).

Regulatory mechanisms controlling expression of β1,6GlcNAc-branched N-glycans are poorly understood. The medial Golgi branching enzymes MGAT1, 2, 4 and 5 display decreasing affinities for UDP-GlcNAc, and enzyme concentrations also decline across the pathway (59) (FIG. 7A). This is consistent with observations that N-glycan structures on mature glycoproteins are sub-saturating for MGAT4 and MGAT5 products, while MGAT1 and MGAT2 products are closer to saturation (59). Considering the hexosamine pathway supply of UDP-GlcNAc to the Golgi (FIG. 7A), hybrid and bi-antennary N-glycans are produced at higher efficiency, while tri- and tetra-antennary N-glycans increase only at higher sugar-nucleotide concentrations when the earlier enzymes become saturated. The hexosamine pathway for de novo biosynthesis of UDP-GlcNAc utilizes glucose, acetyl-CoA, glutamine and UTP (FIG. 7A), positioning UDP-GlcNAc production downstream of key allosteric regulators of metabolism. Finally, the majority of glucose uptake by activated T-cells is converted to lactate and released, and it has been suggested that in addition to energy demands, glucose may be required for growth related signaling (60). Based on these considerations, it was hypothesized that metabolite flux into the hexosamine pathway and genetic variation in Golgi N-glycan processing efficiency may determine differences in TCR sensitivity and autoimmune susceptibility among humans and inbred mouse strains.

Figure 13:
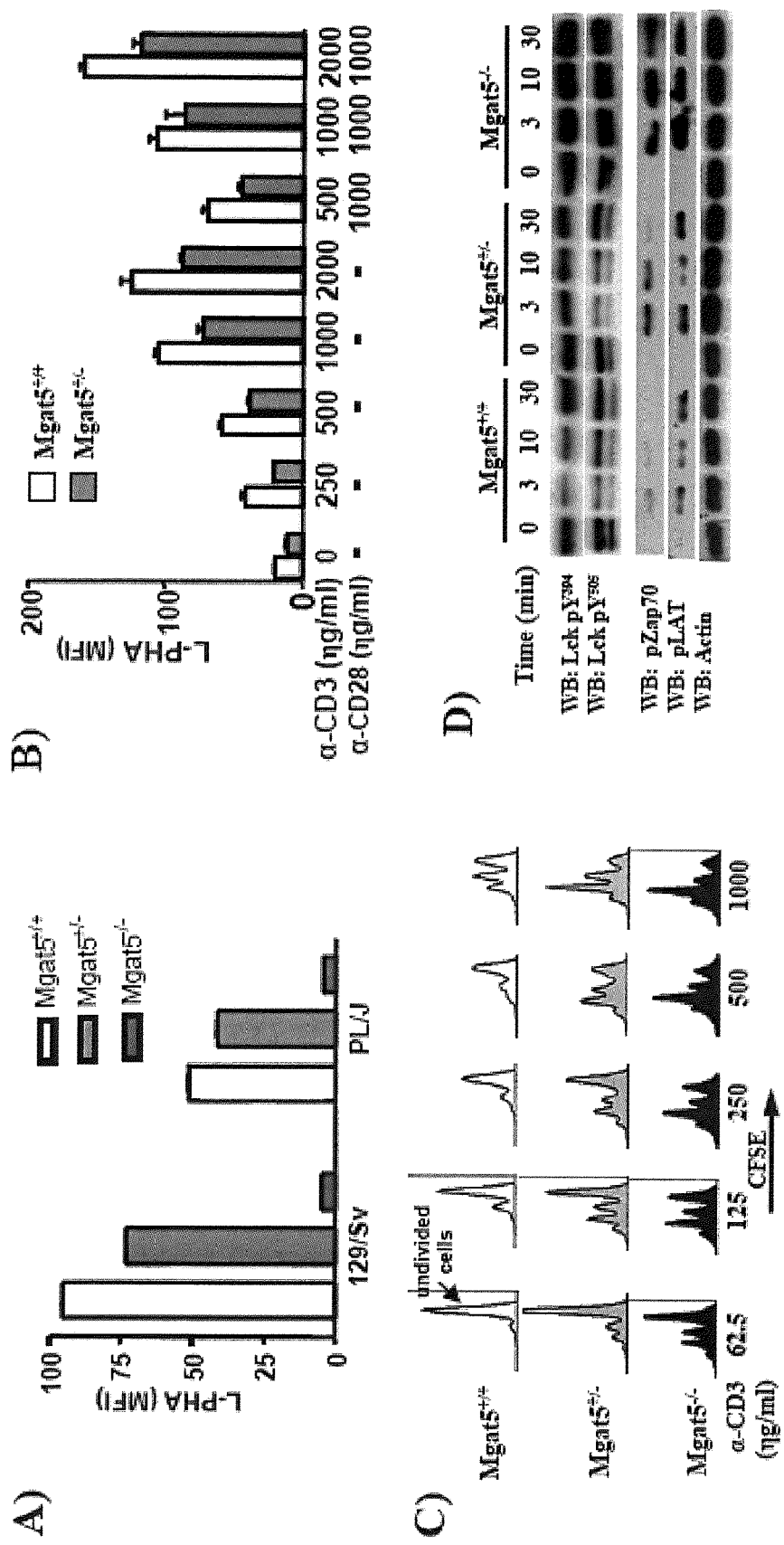
FIG. 13. β1,6GlcNAc-branched N-glycans titrate TCR sensitivity and are differentially expressed in inbred strains of mice. (A, B) FACS analysis of resting (A) and 3 day stimulated CD4+ T-cells from PL/J (A,B) and 129/Sv (A) mice using L-PHA, a plant lectin that specifically binds β1,6GlcNAc-branched N-glycans (FIG. 7A). Error bars are standard error of triplicate staining. MFI=Mean Fluorescence Intensity. (C) Purified CD3+ PL/J T-cells were labeled with CFSE, stimulated for 72 hrs and analyzed by FACS. Plots shown are gated on CD4+ cells. (D,F) Purified PL/J CD3+ T-cells were incubated at 37° C. with anti-CD3 antibody-coated beads for various times, lysed and western blotted (WB). (E) Splenocytes from the indicated inbred mouse strains were stained with L-PHA and anti-CD4, anti-CD8 or anti-B220 antibodies and analyzed by FACS. Shown is relative expression normalized to wild type 129/Sv cells. n=number of mice. Error bars are standard error and p values are by the Kruskal-Wallis Anova test. (G, H) CD3+ T-cells (G,H) or splenocytes (G) were lysed and used to assess enzyme activity (G) or to isolate mRNA for cDNA synthesis and analysis by quantitative real time-PCR (2) (H). Shown in H is relative expression normalized to 129/Sv cells and represents 3 mice done in triplicate. Error bars are standard error.
Figure 13:
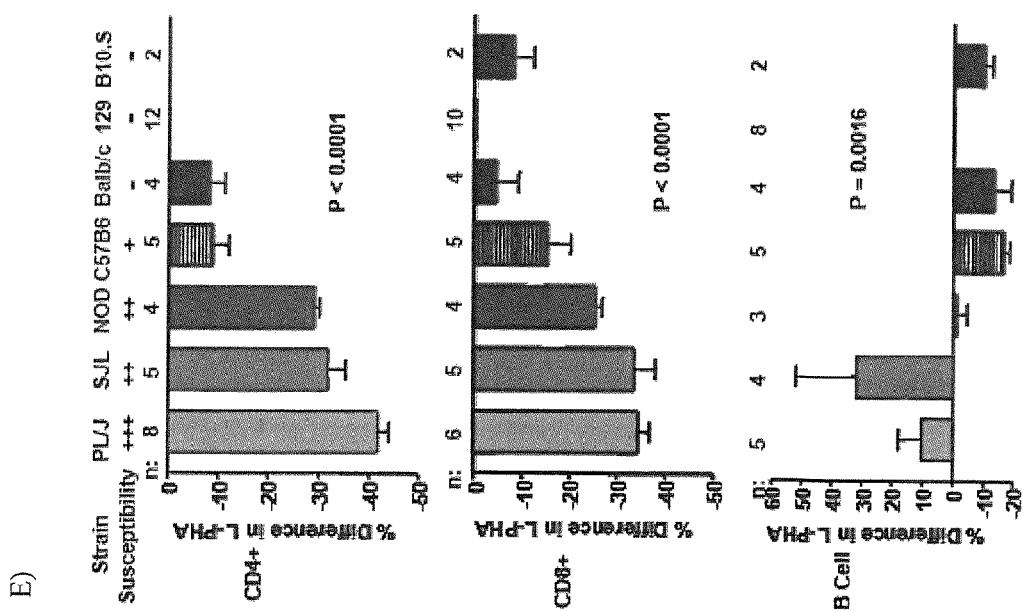
Figure 13:
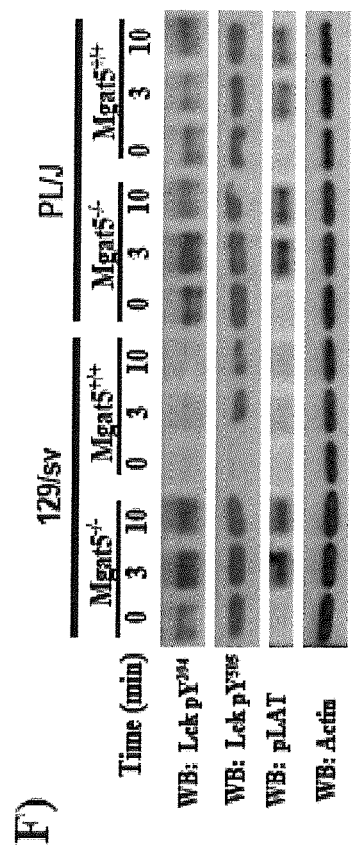
Figure 13:
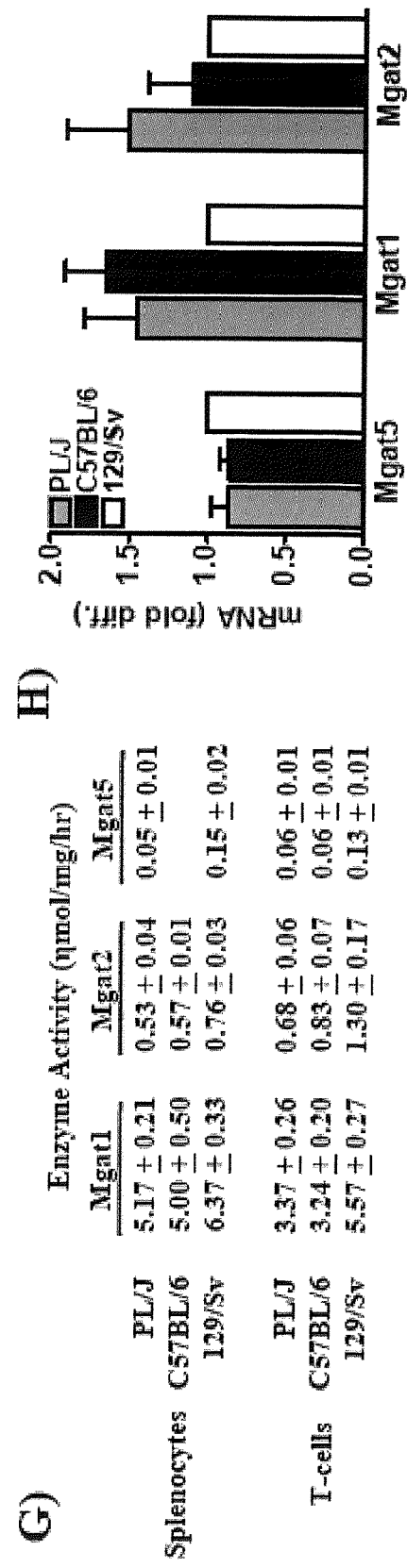
Figure 17:
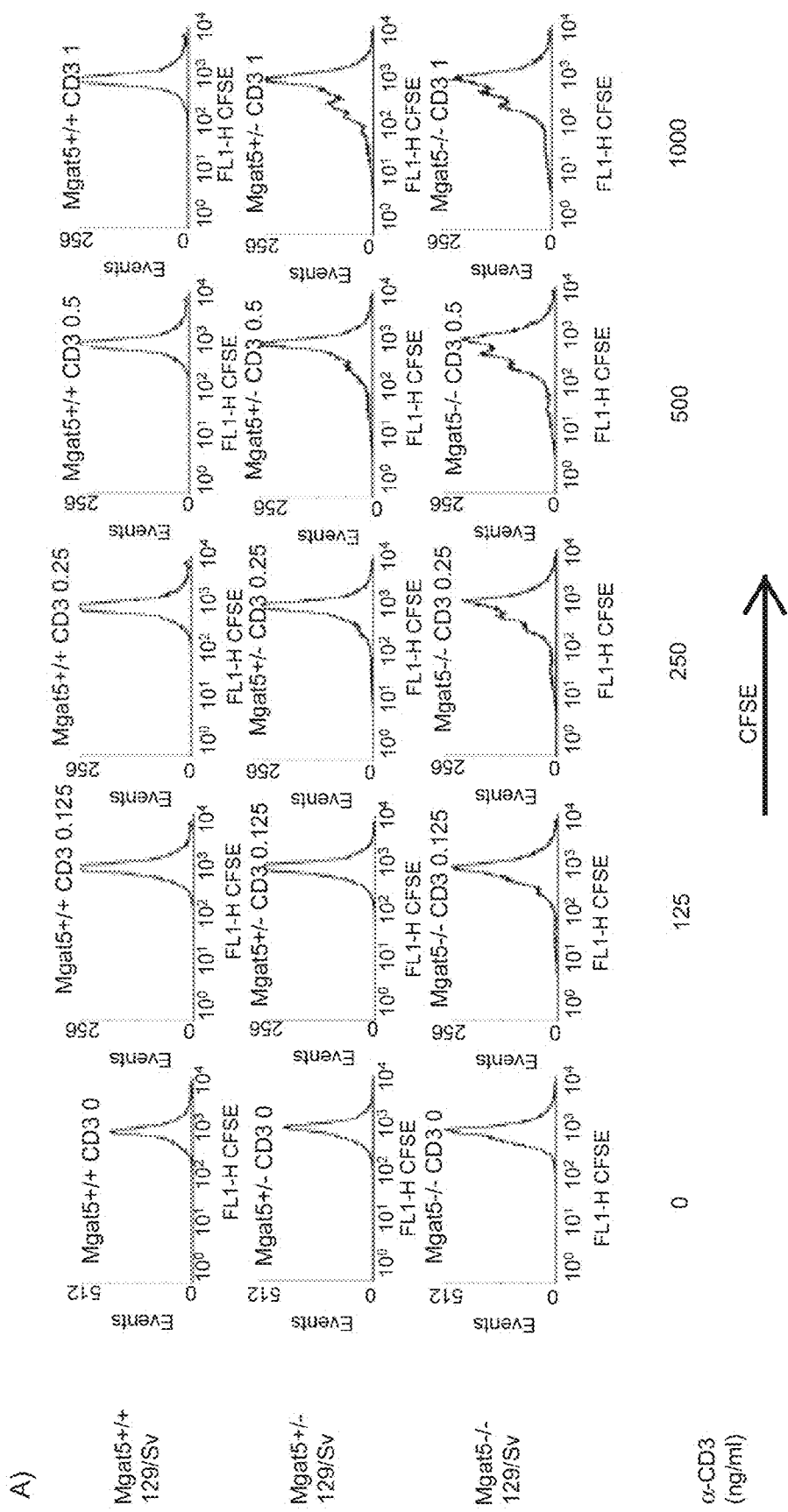
FIG. 17. Intermediate T-cell activation thresholds in Mgat5+/−129/Sv T cells and computational model of N-glycan processing. (A) Purified CD3+ 129/Sv T cells were labeled with CFSE, stimulated for 72 hrs as indicated and analyzed by FACS. Plots shown are gated on CD4+ cells. (B) β1,6GlcNAc-branched N-glycan as a fraction of total cellular N-glycans computed using experimentally determined enzyme activities of Mgat1,2 and 5 for the three indicated mouse strains. Last three bars are simulations beginning with 129/Sv parameters and substitution of PL/J Mgat1, Mgat2 and Mgat5 enzyme activities individually.
Figure 17:
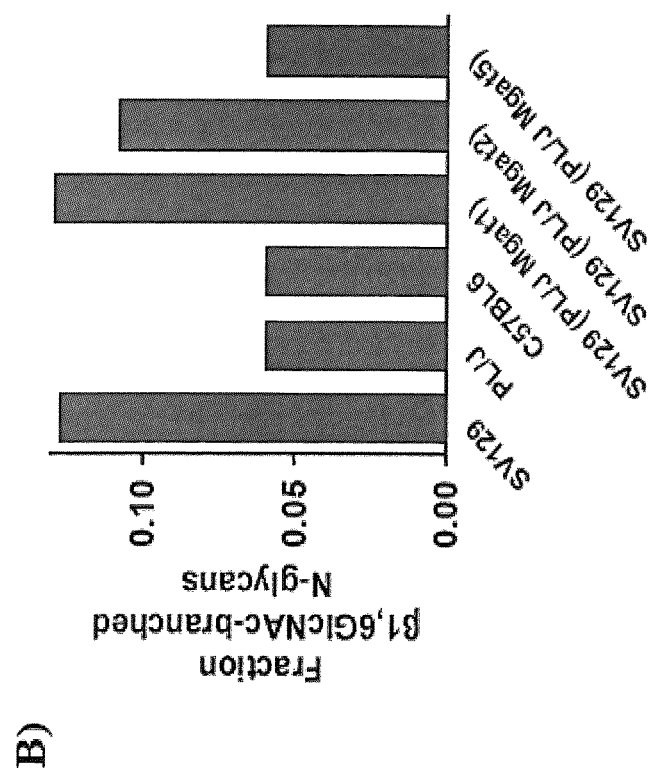

Results:

Incremental Differences in β1,6GlcNAc-Branched N-Glycans Titrate TCR Sensitivity Mgat5+/- T-cells from 129/Sv, PL/J and C57BL/6 mice have ~20-25% reduction in L-PHA reactive β1,6GlcNAc branched N-glycans relative to wildtype cells (FIG. 7A, 13A,B) and are intermediate compared to Mgat5+/+ and Mgat5-/- cells for TCR-mediated proliferation (FIG. 13C, FIG. 17) and TCR signaling as shown by enhanced phosphorylation of lck at activating tyrosine 394 ($Y^{394}$) relative to inhibitory tyrosine 505 ($Y^{505}$) and phosphorylation of Zap-70 and LAT (FIG. 13D). Therefore, the association of differential expression of β1,6GlcNAc-branched N-glycans with sensitivity to EAE autoimmunity among inbred mouse strains was explored. Indeed, CD4$^+$ and CD8$^+$ T-cells, but not B cells, from the EAE high susceptibility strains PL/J, SJL and NOD, which also develops spontaneous autoimmune diabetes, expressed ~30-40% less β1,6GlcNAc-branched N-glycans than the three EAE resistant strains 129/Sv, Balb/c and B10.S (FIG. 13E). Moreover, CD4$^+$ T-cells from wildtype PL/J mice express ~25% less β1,6GlcNAc-branched N-glycans than Mgat5+/-129/Sv cells (FIG. 13A), indicating genetic defects inherent to the PL/J strain are significantly greater than loss of an MGAT5 allele. The C57BL/6 strain is less sensitive than SJL to induced EAE, as evidenced by differential requirement for CD28 co-stimulation (23). C57BL/6 CD8+ T-cells display intermediate levels of β1,6GlcNAc-branched N-glycans relative to PL/J and 129/Sv cells (FIG. 13E). Therefore, susceptibility to EAE correlated inversely with β1,6GlcNAc-branched N-glycan expression in T-cells with rank order PL/J>SJL, NOD>C57BL6>Balb/c, 129/Sv, B10.S. Indeed, PL/J T-cells were more sensitive to TCR agonist than 129/Sv T-cells as indicated by phosphorylation levels of lck at $Y^{394}$ and LAT (FIG. 13F). In contrast, Mgat5-deficient T-cells from PL/J and 129/Sv backgrounds were equally hypersensitive to TCR agonist, indicating that strain dependent suppression of β1,6GlcNAc-branched N-glycans in PL/J T-cells is causal in TCR hypersensitivity (FIG. 13F).

N-Glycan Processing Efficiency Regulates β1,6GlcNAc-Branched N-Glycans

Figure 15:
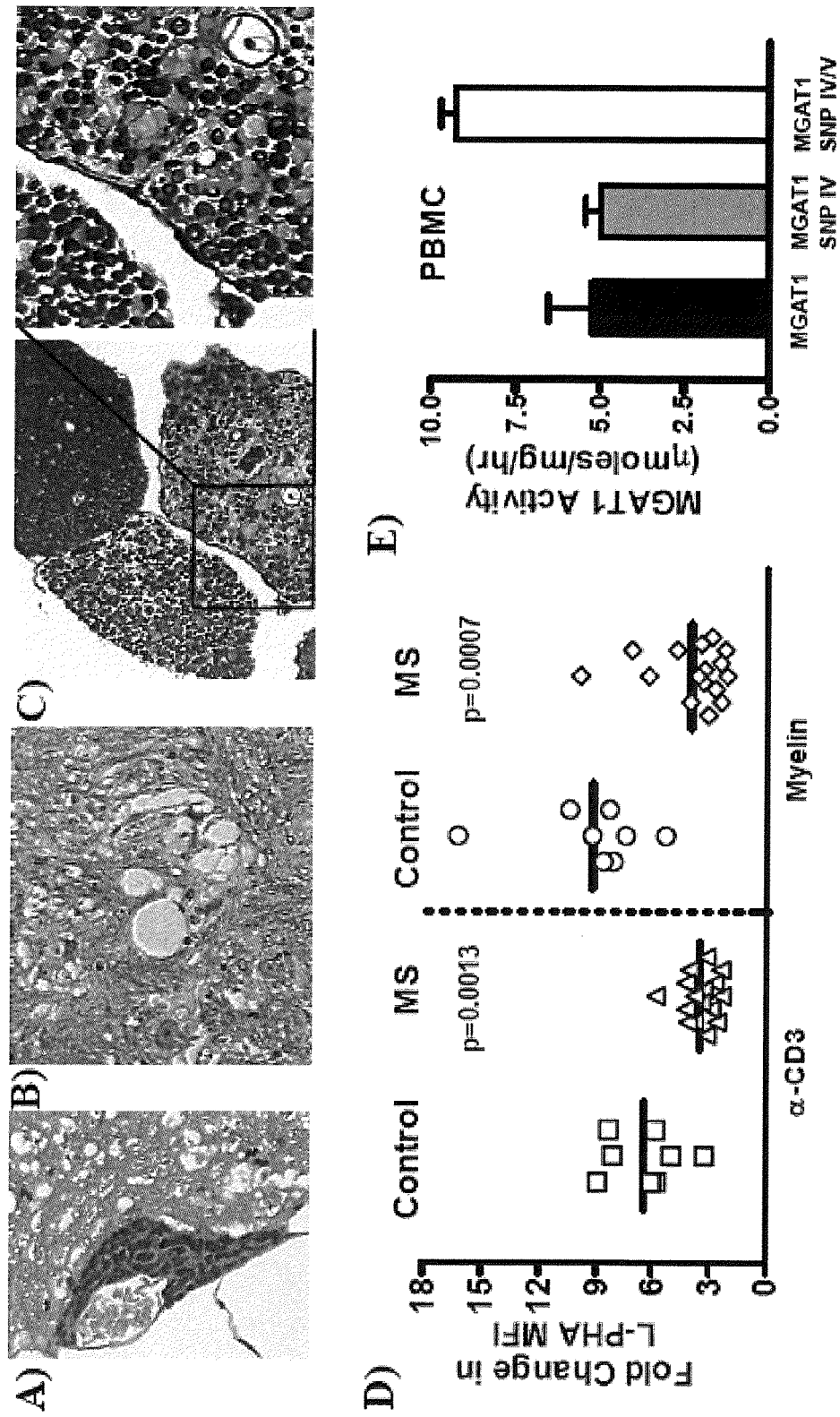
FIG. 15. Demyelinating pathology in PL/J mice, β1,6GlcNAc-branched N-glycan expression in MS patient T-cells and functional analysis of MGAT1 SNP IV/V. (A-C) Paraffin embedded sections from spinal cord (A), brainstem (B) and spinal roots (C) from clinically affected PL/J mice were stained with Luxol Fast Blue (B,C) or Haematoxylin & Eosin (A). Green arrows point to large naked axons. (D) Freshly isolated PBMCs from Caucasian MS patients and Caucasian controls were left unstimulated or stimulated with anti-CD3 antibody or a mixture of myelin antigens for 48 hrs and then analyzed for L-PHA staining levels. Fold change was calculated by comparing the MFI of blasting cells vs. non-stimulated cells as defined by side vs. forward scatter. Shown is gated on CD4+. P values are by the Mann-Whitney t test. (E) MGAT1 enzyme activity in PBMCs containing MGAT1 SNP IV/V (n=3), MGAT1 SNP IV (n=1) or the common allele (n=1). (F-H) Lec1 cells transiently transfected with human pCMV-MGAT1 with or without SNP IV/V were lysed to assess enzyme activity (F), isolate mRNA for cDNA synthesis and quantitative real time PCR (G) or L-PHA FACS analysis in the absence (H,J) or presence of GlcNAc (J). L-PHA MFI was determined on L-PHA+ population. F and G were normalized for transfection efficiency as determined by L-PHA+ vs. L-PHA-cells. Result in H was the same in 8 separate transient transfections. All error bars are standard error of duplicate (F) or triplicate and greater (E, G, H, J) values. (I) Ordinary Differential Equation (ODE) model of medial Golgi enzyme reactions showing predicted alterations in β1, 6GlcNAc branched N-glycans with two-fold changes in MGAT1 activity.
Figure 15:
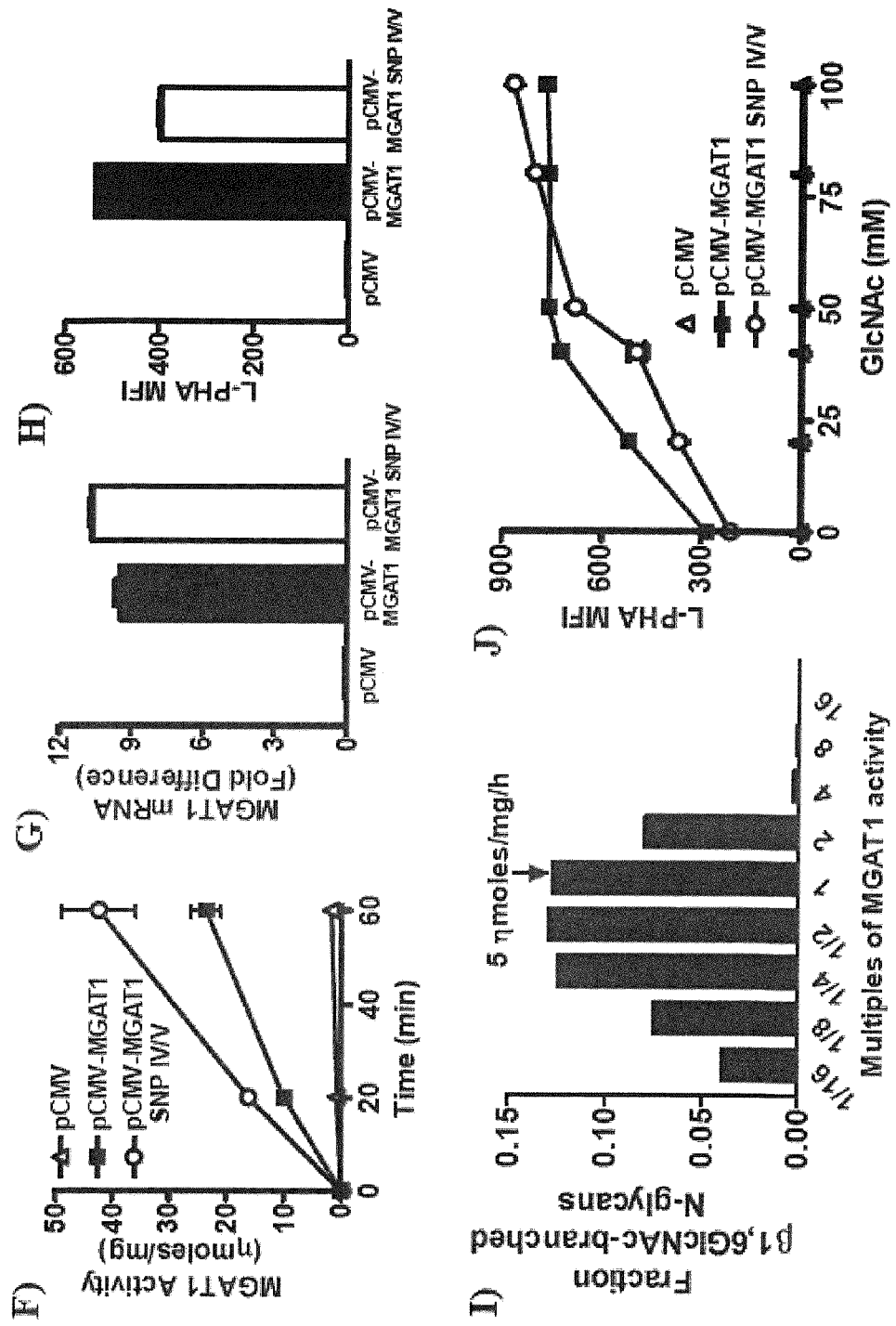
Figure 18:
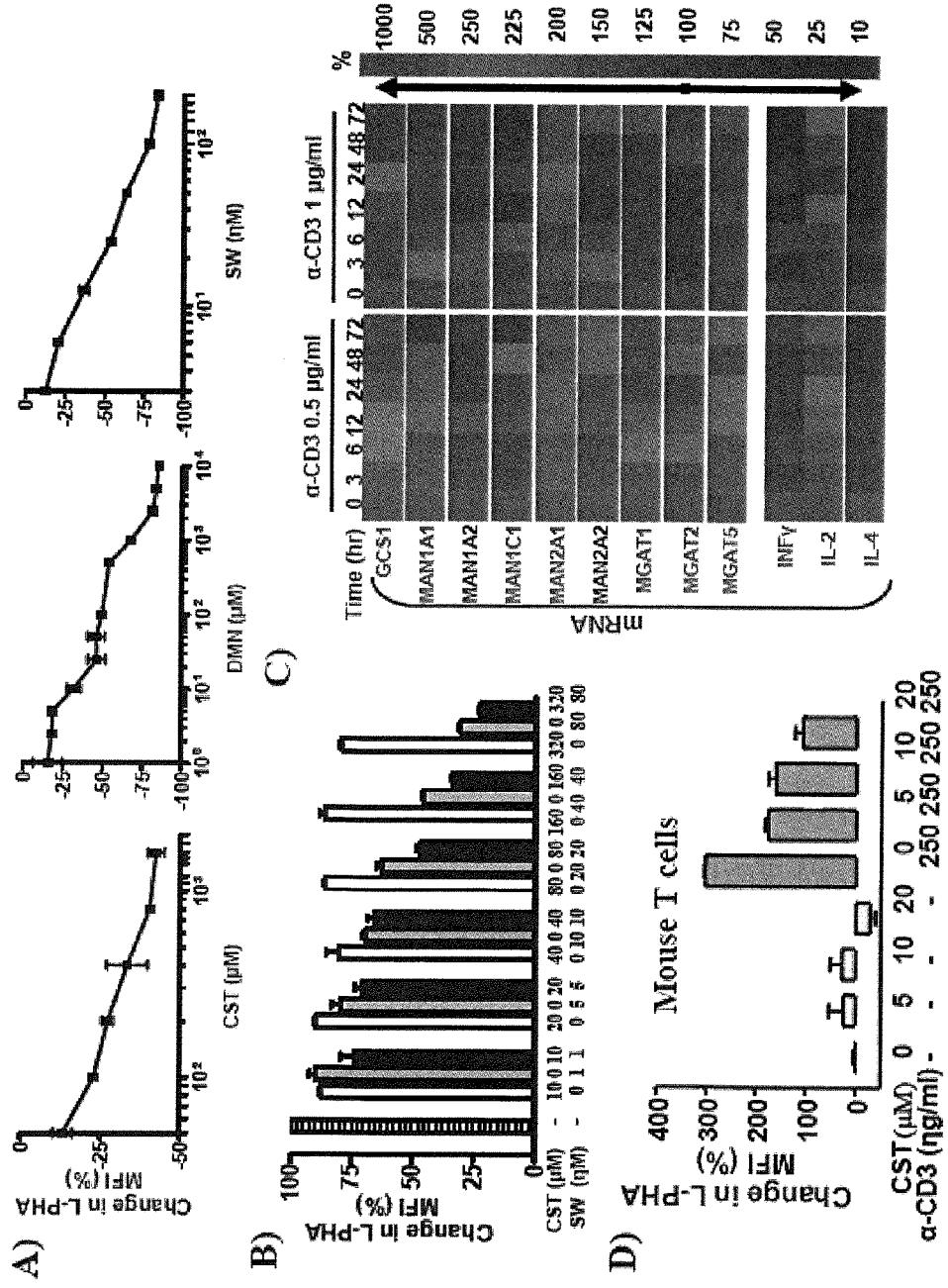
FIG. 18. Proximal N-glycan processing regulates β1,6GlcNAc-branched N-glycan expression. (A-B) Jurkat T cells were incubated with the alkaloids castanospermine (CST), deoxymannojirimycin (DMN) and/or swainsonine (SW) for 3 days to inhibit proximal N-glycan processing (see FIG. 7A) and analyzed by L-PHA flow cytometry. Shown is the relative change in staining compared to untreated. Error bars are S.E.M for triplicate staining. (C) mRNA isolated from Jurkat T cells at rest and stimulated with anti-CD3 antibody for the indicated doses and times was reverse transcribed into cDNA and analyzed by Taqman quantitative RT-PCR. Change in mRNA expression of the indicated genes following TCR stimulation is normalized to the resting state. (D,E) Mouse CD3+ T cells (D) or Jurkat T cells (E) were cultured with anti-CD3 in the presence of minimal doses of CST, DMN and SW as indicated for 3 days and analyzed by FACS for L-PHA staining. Shown is gated on CD4+ population. (F) Mouse CD3+ T cells were left unstained or stained with CFSE and stimulated with anti-CD3 antibody in the presence or absence of the indicated doses of SW for 5 days. Shown is the LPHA MFI for non-CFSE labeled cells (left panel) and the percentage increase in the number of proliferating CD4+ T cells relative to cells stimulated with 62.5 ng/ml anti-CD3 (right panel).
Figure 18:
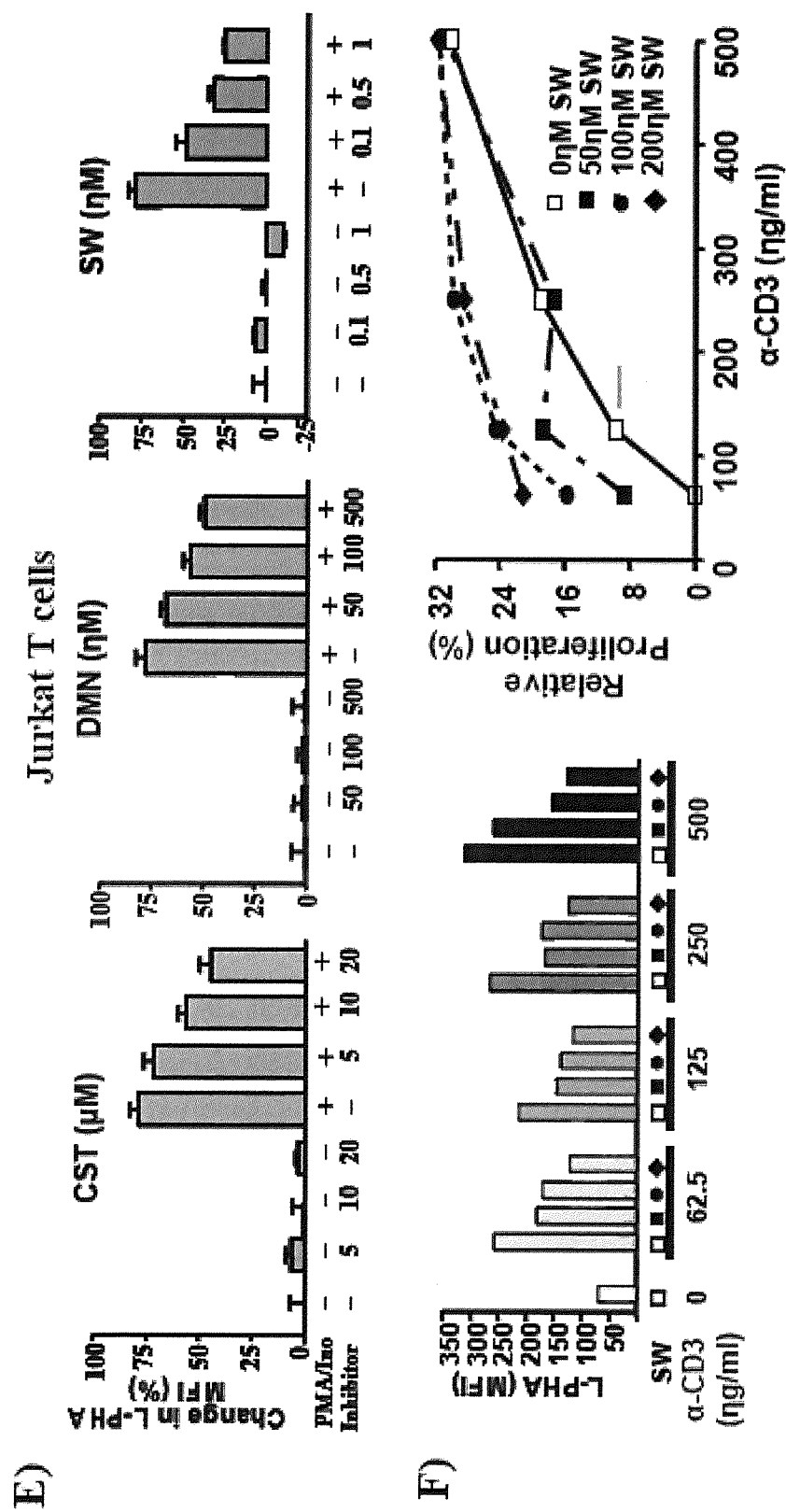
Figure 19:
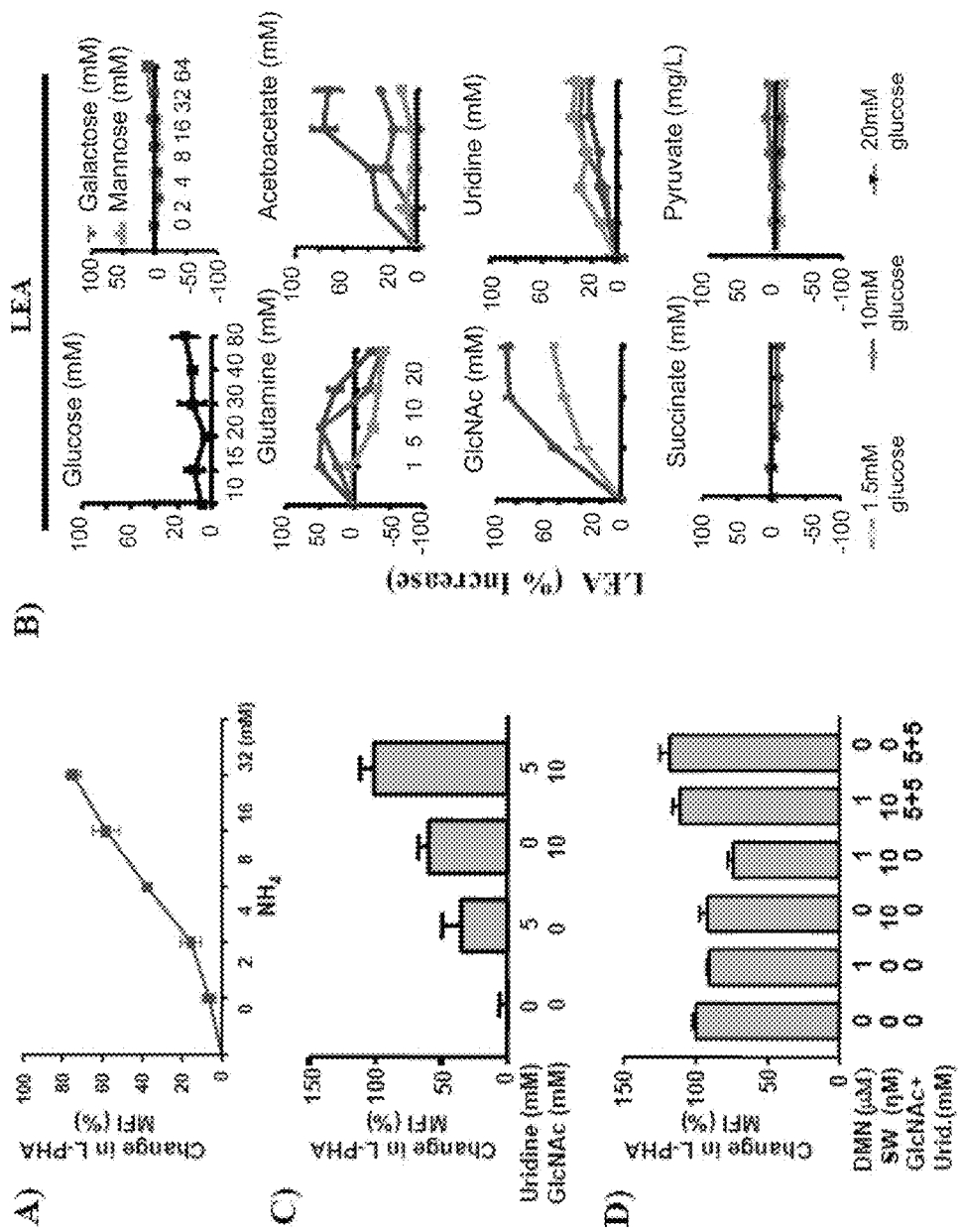
FIG. 19. Metabolic regulation of β1,6GlcNAc-branched N-glycans and TCR sensitivity by the Hexosamine pathway (A-D) The indicated monosaccharides, metabolites and glycosidase inhibitors were cultured with Jurkat T cells for 3 days, stained with L-PHA or LEA, a lectin specific for poly-N-acetyllactosamine, and analyzed by FACS. Green, blue and red lines refer to altered glucose concentration in the culture media as indicated; all others were grown in 10 mM glucose. Error bars are standard error of triplicate staining. (E) Jurkat T cells were treated with the indicated concentrations of DMN or CST in the presence or absence of GlcNAc (20 mM) and Uridine (10 mM) for 3 days and analyzed by FACS for L-PHA staining. (F) Wild-type C57/BL6 CD3+ T cells labeled with CFSE were stimulated with anti-CD3 antibody in the presence or absence of swainsonine and/or GlcNAc as indicated for 3 days and analyzed by FACS.
Figure 19:
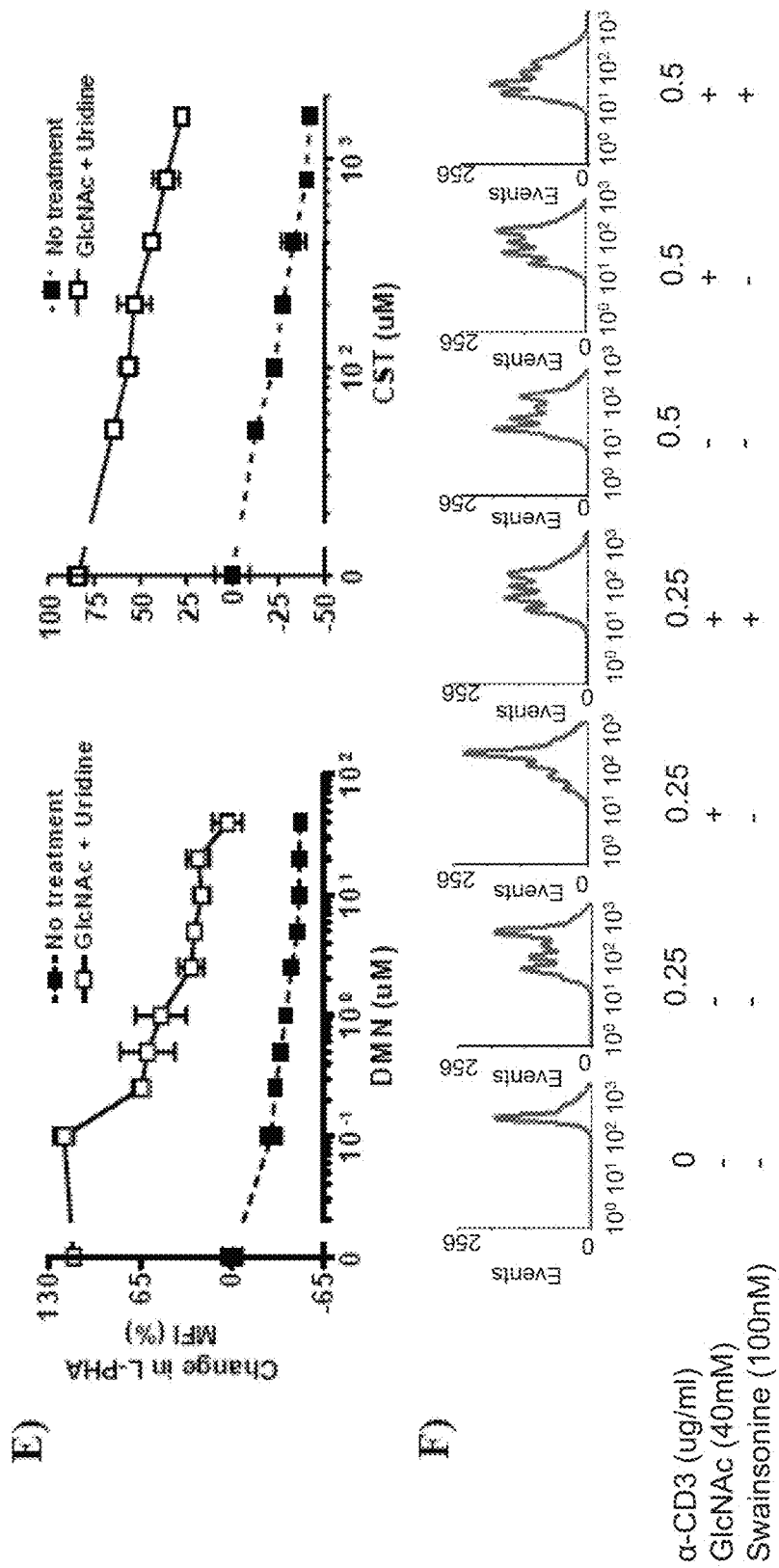
Figure 21:
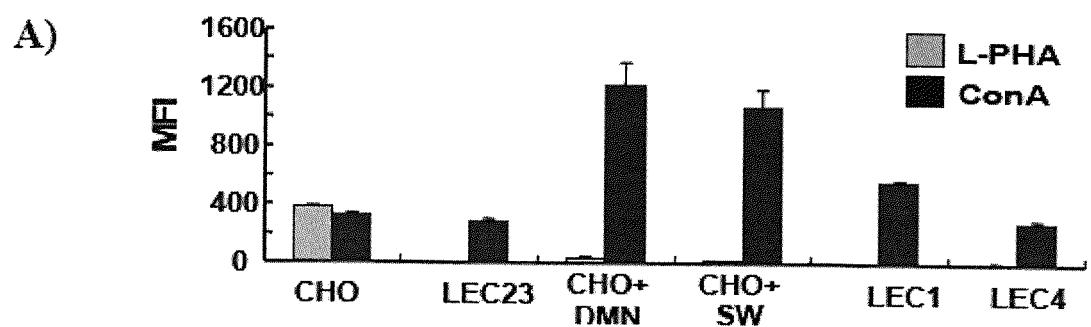
FIG. 21. N-glycan profiling of CHO cells with defects in N-glycan processing. (A-F) CHO cells untreated or treated with DMN (mannosidase I inhibition) or SW (mannosidase II inhibition) along with LecR mutant CHO cells Lec23 (Glucosidase I deficient), Lec1 (MGAT1 deficient) and/or LEC4 (MGAT5 deficient) were stained with ConA (binds high mannose N-glycans), or L-PHA and analyzed by FACS (A) or total cellular lysates were used to obtain N-glycans by PNGaseF digestion for MALDI-TOF mass spectroscopy (B-F). MALDI-TOF spectra B-F are representative of triplicate samples. Letters in red refer to N-glycan structures in FIG. 16A. Lec23 cells demonstrated a large and specific increase in hexose oligomers of 4, 5 and 6 residues in all three samples, consistent with Golgi endo-mannosidase activity. (G) CHO and Lec1 cells were mixed in the indicated proportions and lysed. PNGaseF derived N-glycans were analyzed by MALDI-TOF and the relative intensity of C and G ions as a proportion of the total N-glycan intensities are plotted versus mixture ratios. (H) PBMC from MS patients PA2 and PA6 and Caucasian controls were thawed and compared directly by L-PHA flow cytometry.
Figure 21:
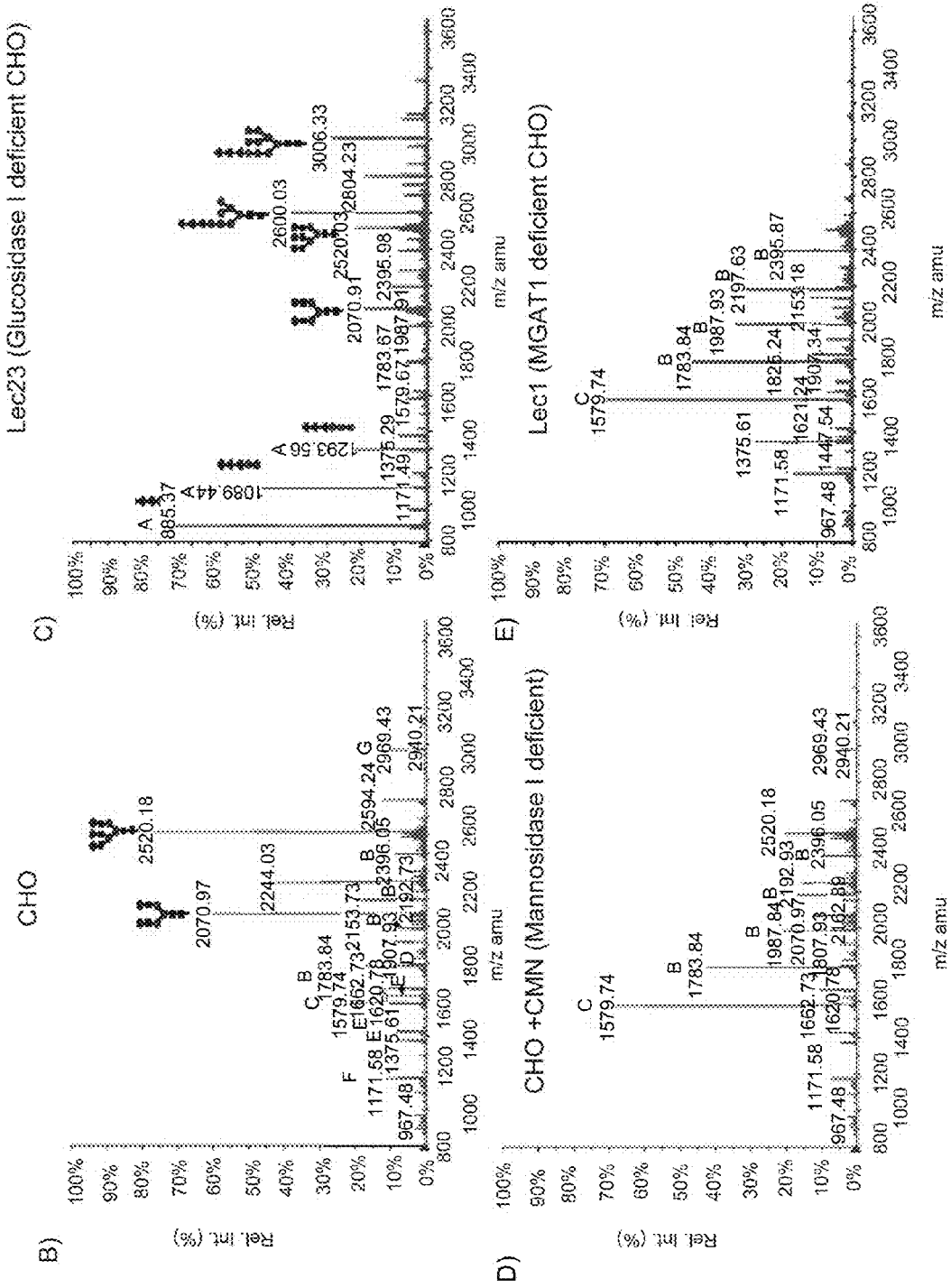
Figure 21:
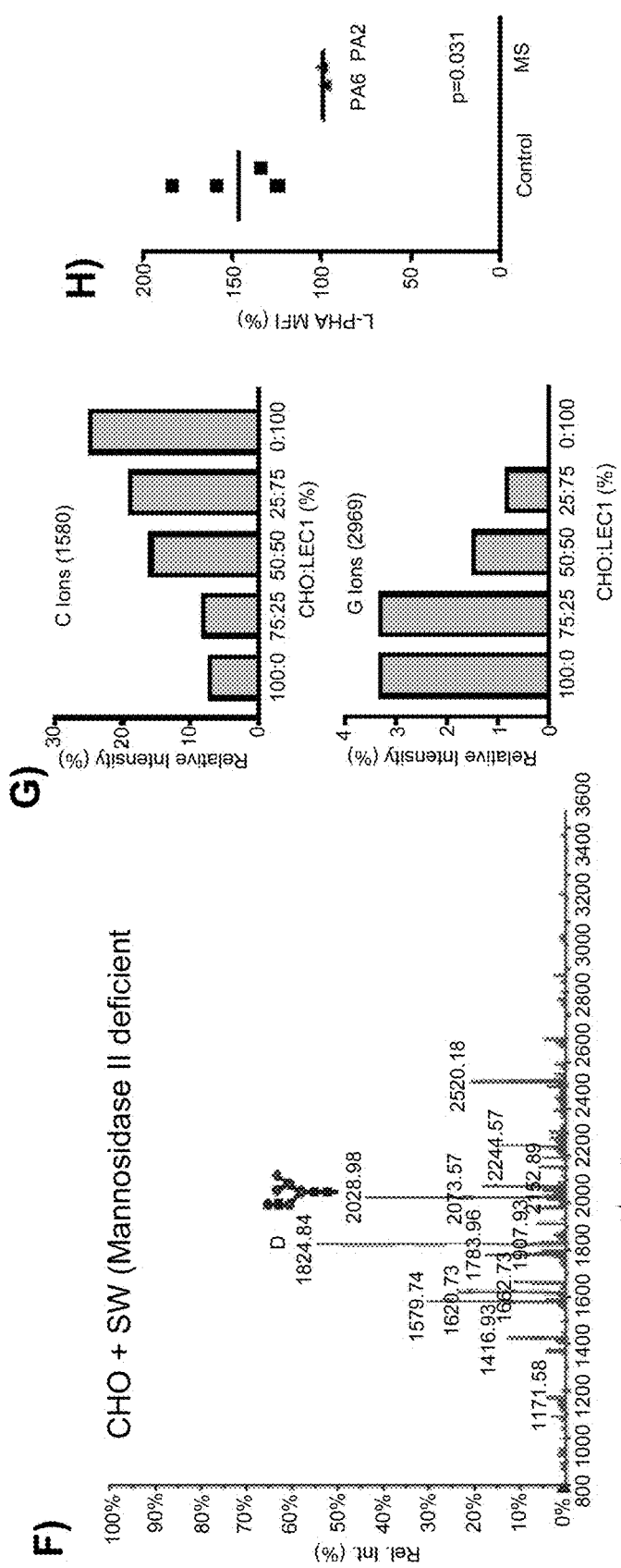

Mgat5 enzyme activity but not mRNA expression is reduced ~50% in PL/J and C57BL/6 splenocytes and T-cells relative to 129/Sv mice (FIG. 13G,II). As PL/J T-cells have a greater reduction in β1,6GlcNAc-branched N-glycans than C57BL/6 T-cells, the former must possess additional N-glycan processing defects. Indeed, MALDI-TOF mass spectroscopy demonstrates that PL/J T-cells accumulate pathway intermediates upstream of MGAT2 (i.e., E,F ions) and MGAT1 (i.e., B,C ions, FIG. 16A,B, supplementary text and FIG. 21). MGAT2 and MGAT1 enzymatic activity but not mRNA transcript levels are reduced in PL/J>C57BL/6>129/Sv and PL/J, C57BL/6>129/Sv, respectively (FIG. 13G). An ordinary differential equation (ODE) model of medial-Golgi enzyme reactions (materials and methods) suggests that within the kinetic parameters of the pathway, reductions in MGAT5 and MGAT2 but not MGAT1 contribute to reduced β1,6GlcNAc-branching in PL/J>C57BL/6>129/Sv T-cells (FIG. 17B, 15I, materials and methods). This data indicate that partial deficiencies at the posttranscriptional level in MGAT2 and MGAT5 greater than MGAT1 combine to reduce GlcNAc branching in PL/J>C57BL/6>129/Sv T-cells. However, defects in other N-glycan processing enzymes may also contribute to the phenotype.

β1,6GlcNAc-branched N-glycan expression is also reduced by inhibition of glucosidase VII (GI/GII) with castanospermine (CST), mannosidase I (MI) with deoxy-mannojirimycin (DMN) and mannosidase II/IIx (MII/IIx) with swainsonine (SW) (FIG. 7A, FIG. 18A). Partial inhibition of enzymatic activity at two separate steps via coincubation with CST and SW or DMN and SW are additive in reducing β1,6GlcNAc branched N-glycan expression (FIG. 18B, 19D). TCR signaling increases mRNA expression of multiple upstream N-glycan processing genes along with MGAT5, suggesting up-regulation of all processing enzymes proximal to MGAT5 are required to physiologically increase β1,6GlcNAc-branched N-glycan expression (4,5) (FIG. 13B, 18C). Indeed, increased expression of β1,6GlcNAc-branched N-glycans in activated T7 cells is attenuated with concentrations of CST, DMN and SW that do not affect resting levels (FIG. 18D,E), indicating small decreases in N-glycan processing efficiency disproportionately reduce expression in activated T-cells. Moreover, limiting upregulation of β1,6GlcNAc-branched N-glycans by ~50% or less is sufficient to enhance T cell proliferation (FIG. 18F). Thus, N-glycan processing efficiency is a key modulator of β1,6GlcNAc-branched N-glycan expression in T-cells and small changes in Golgi N-glycan processing lead to large functional effects on TCR sensitivity and proliferation.

Metabolic Regulation of N-Glycan Processing, TCR Sensitivity and EAE

β1,6GlcNAc-branched products are sub-saturating on glycoproteins (FIG. 13A,B,E) (24), due in part to the high Km (~11 mM) for UDP-GlcNAc displayed by the MGAT5 enzyme. Therefore, expression of β1,6GlcNAc-branched N-glycans is sensitive to changes in the intracellular concentration of UDP-GlcNAc (26). Glucose, glutamine, acetyl-CoA and UTP are metabolites required by the hexosamine pathway for de novo UDP-GlcNAc biosynthesis (FIG. 7A). The addition of N-acetyl-D-glucosamine (GlcNAc) to cultured cells also supplements UDP-GlcNAc pools, following its 6-phosphorylation and conversion to UDP-GlcNAc (FIG. 7A) (26). Surface levels of β1,6GlcNAc-branched N-glycans (L-PHA staining) and poly-N-acetyllactosamine (LEA staining) on human Jurkat T-cells were increased by supplementation with high glucose, GlcNAc, acetoacetate, glutamine, ammonia or uridine but not with control metabolites mannosamine, galactose, mannose, succinate or pyruvate (FIG. 14A,C, 19A,B). Mass spectroscopy confirmed that GlcNAc and uridine each raised intracellular UDP-GlcNAc levels (FIG. 14B), and their co-supplementation displayed additive enhancement of β1,6GlcNAc-branched N-glycan expression and rescued proximal N-glycan processing insufficiency (FIG. 19C,D,E). These data demonstrate that glucose, lipid and nitrogen metabolites are limiting for UDP-GlcNAc biosynthesis and β1,6GlcNAc-branched N-glycans in T-cells. Moreover, they provide a molecular mechanism for metabolic modulation of GlcNAc branching in N-glycans.

Supplements to the hexosamine pathway in wild type PL/J and C57BL/6 T cell cultures raised Mgat5 N-glycan expression and inhibited anti-CD3 induced proliferation, an effect that could be reversed by blocking β1,6GlcNAc-branched N-glycan expression with SW (FIG. 14D-F, 19F). Furthermore, re-stimulation of splenocytes harvested from MBP immunized wild type PL/J mice with antigen in the presence of GlcNAc increased β1,6GlcNAc-branched N-glycans and poly-Nacetyllactosamine expression, inhibited IFN-γ production, promoted IL-6 secretion and dramatically reduced the incidence and severity of EAE following adoptive transfer of T-cells into naïve PL/J mice (FIG. 14F-H). This confirms that defective N-glycan processing in PL/J wild type T-cells enhances EAE susceptibility. Moreover, the data demonstrate that the hexosamine pathway regulates TCR sensitivity and autoimmune susceptibility via key metabolic intermediates shared by glycolysis as well as lipid (free fatty acids to acetyl-CoA), amino acid (ie ammonia/glutamine) and nucleotide metabolism.

N-Glycan Processing Defects Inherent to PL/J Mice Induce Spontaneous Autoimmune Demyelinating Disease Although myelin-specific TCR transgenic mice develop spontaneous CNS autoimmune demyelinating disease (11-14), spontaneous disease secondary to physiologically-relevant gene dysfunction has not been reported. In addition to having significant defects in N-glycan processing, PL/J mice possess the H-2μ MHC class II haplotype which limits negative selection of MBP 1-11 reactive T-cells in the thymus (61,62). Loss of central tolerance to MBP1-11 combined with reduced β1,6GlcNAc-branched N-glycan expression in T-cells should induce spontaneous CNS demyelinating disease in PL/J mice. Indeed, clinical observation of Mgat5+/+, Mgat5+/− and Mgat5−/− PL/J mice at backcross 4 and 6 from 129/Sv as well as non-congenic wild-type PL/J mice from Jackson Laboratories demonstrated that all 3 genotypes displayed signs of tail and/or hindlimb weakness after 1 year of age (Table 1, 3, supplemental text). As predicted by differences in TCR sensitivity, the incidence, severity and mortality were inversely correlated with β1,6GlcNAc-branched N-glycan expression (Table 1, 3). The clinical course was chronic and slowly progressive without relapses or recovery and associated with involuntary movements such as tremor and focal dystonic posturing (Table 1, FIG. 20A, supplemental text), a clinical picture typical of progressive MS (1). Pathological examination revealed sub-meningeal perivascular lymphocyte cuffing and multi-focal demyelination of the brainstem, spinal cord and spinal roots (FIG. 15A-C, 20B-H). The CNS pathology was similar to chronic MS plaques and characterized by mononuclear cells admixed with myelin debris centered around blood vessels, gliosis, neuronophagia, axonal swelling (spheroids) and axonal degeneration (FIG. 15B, 17B-E, G), the latter correlating with the progressive clinical disease observed (supplemental text). Anti-CD3 antibody activated splenocytes from Mgat5−/− mice with moderate to severe demyelinating pathology efficiently transferred disease to naïve wild type recipients (Table 2), confirming spontaneous disease was autoimmune. Raising β1,6GlcNAc-branched N-glycans expression in wild type PL/J T-cells inhibits adoptive transfer EAE (FIG. 14F-H), indicating defective N-glycan processing in this strain is causal in promoting disease. These results are the first demonstration of genetic deficiency leading to spontaneous CNS autoimmune demyelination and confirm the robustness of small changes in the hexosamine and N-glycan pathways in titrating autoimmune susceptibility.

Multiple Sclerosis is Associated with Genetic Defects in N-Glycan Processing

MS patients were examined for defects in N-glycan processing by assessing the up-regulation of β1,6GlcNAc-branched N-glycans following TCR stimulation, which serves as a sensitive test for proximal N-glycan processing insufficiency (FIG. 13B, 18D,E). Murine T-cells increase β1,6GlcNAc-branched N-glycan levels ~6-8 fold 48-72 hrs following TCR stimulation (FIG. 13B). A similar fold increase was observed in T-cells from human controls (n=8) stimulated with anti-CD3 antibody or a mixture of myelin antigens (FIG. 15D). In contrast, T-cells from MS patients (n=16) had a marked atenuation of this physiological up-regulation under both stimulatory conditions (FIG. 15D), indicating defects in N-glycan processing occur at high frequency. Indeed, ALDI-TOF mass spectroscopy of peripheral blood monocytes (PBMCs) derived N-glycans showed 6 of 7 MS patients had significant changes in the expression of N-glycan Golgi transients relative to controls, indicating reduced pathway output (i.e., structures A, B and G, FIG. 16A,C). Comparison with MALDI-TOF N-glycan profiles of CHO cells defective in glucosidase I (GI), mannosidase I (MI), MGAT1 or mannosidase II (MII/MIIx) confirmed N-glycan processing deficiency in MS patients and indicated defects predominate at three enzymatic steps: Glucosidase I/II in PA1 and PA3 (i.e., increased structure A), MI/MGAT1 in PA7 and PAJ (i.e., increased structure B) and MGAT5 in PA2 and PA6 (i.e., absence of structure G) (FIGS. 16A,C and 21 and supplemental text). These data demonstrate that MS patients frequently display defects in N-glycan processing, a phenotype that induces spontaneous demyelinating disease in PL/J mice.

Based on these data, MS patients may harbor polymorphic alleles of enzymes in the hexosamine and/or N-glycan pathways regulating β1,6GlcNAc-branching. A review of linkage data for MS (8, 31-41) obtained from 10 distinct populations as well as EAE (9) identified 18 potential MS-associated chromosomal regions with suggestive linkage or better in three or more studies (Tables 4, 5, and 6, materials and methods). The identified regions cover an estimated-34% of the human genome (materials and methods) and also frequently overlap with other autoimmune loci (Table 4) (41, 46-50). Remarkably, 14 of 17 (82%) N-glycan and 11 of 17 (65%) hexosamine pathway genes co-localized to one of the 18 regions (Table 4 and genes labeled blue in FIG. 7A). In contrast, 85 of 241 (35.3%) glycosylation and carbohydrate metabolic genes not known to regulate β1,6GlcNAc-branched N-glycan expression co-localized to the regions, a number predicted by chance given the ~34% genome coverage of the 18 regions (Table 4B, Table 6, materials and methods). After controlling for this large percentage of the genome, 13.5 of 22.5 Mgat5 regulatory vs. 3 of 159 Mgat5 non-regulatory genes co-localized to the MS loci (Odds ratio (OR)=80.9, p<0.0001, Fishers Exact Test (FET), Table 2B). Thus, hexosamine and N-glycan pathway genes are significantly over represented in putative MS-associated genomic regions, supporting the hypothesis that diverse MS populations may harbor multiple disease-associated polymorphisms in the two pathways.

To further investigate this possibility, exons of the human N-glycan genes that appeared to be defective by MALDI TOF were sequenced, namely GCS1, GCS1, GANAB, MAN1A1, MGAT1 and MGAT5 (FIG. 22, 23). This identified 24 known (blue) and 14 previously unknown (red) single nucleotide polymorphisms (SNPs) within 5 genes from 7 MS patients (FIG. 22, 23). Of these, 6 correlated with the stage of defective N-glycan processing observed in individual MS patients and were absent or rare in controls (ie allele frequencies of 0%, 0%, 1.4%, 0%, 2.8% and 1.5%), suggesting they may functionally contribute to the observed phenotype (SNPs boxed in green, FIG. 22). However, altered N-glycan processing in PL/J mice results from partial deficiency of at least 2 enzymes (FIG. 13G), suggesting two or more SNPs may contribute to the phenotype and promote disease. Indeed, GANAB SNP IV (OR=2.22, p=0.015), MGAT SNP V and the MGAT1 SNP IV/V allele (OR=17, p=0.005) are associated with disease (Table 7, FIGS. 22, 23). A large number of the SNPs were rare (grey background FIG. 22), including 8 SNPs that were absent in controls. These rare SNPs were identified by sequencing in both directions in two separate PCR reactions and were confirmed multiple times in an allelic discrimination assay that is independent of Taq error (FIG. 22). Of the SNPs with allele frequency <5% in control subjects (SNPs with grey background FIG. 22), 15 of 15 were more frequent in the MS cohort, having an average allele frequency of 4.2+/-0.75% in MS vs 1.0+/-0.35% in controls (p=0.0014, Mann Whitney t test). The combined chromosomal burden of these rare SNPs was associated with MS (OR=3.90, p<0.0001, Table 7). Strikingly, the presence of two or more rare SNP alleles in an individual was highly predictive of disease (OR=44.9, p<0.0001, Table 7). For comparison, the strongest autoimmune disease associated polymorphism in the 300 Kb region containing CD28, CTLA-4 and ICOS has a Relative Risk (RR) of 1.18 (34). Together, these data demonstrate MS is associated with genetic polymorphisms in the N-glycan pathway and suggest that combinations of two or more rare SNPs strongly promote disease.

Next the function of MGAT1 SNP IV/V (FIG. 22, 23), the strongest disease-associated allele (OR-17, p=0.005) consisting of an upstream non-synonymous coding polymorphism (ie SNP IV: G→A, Arg→Gln) and two synonymous coding polymorphisms (ie SNP V: C→T (Leu→Leu) and G→T (Val→Val) 10 nucleotides apart) were assessed. Paradoxically, PBMCs containing MGAT1 SNP IV/V have ~2 fold increase in MGAT1 enzyme activity (FIG. 15E). In contrast, PBMC with only SNP IV had baseline MGAT1 activity, suggesting the Arg→Gln change does not contribute to enhanced enzyme activity. Transient transfection of human MGAT1 with SNP IV/V or the common allele into MGAT1 deficient CHO cells (i.e., Lec1 cells) confirmed that the SNP IV/V allele increases MGAT1 enzyme activity ~2 fold (FIG. 15F). This was associated with minimal increase in mRNA levels (FIG. 15G), suggesting the SNP IV/V allele increases enzyme activity at the translational level or later.

Despite enhanced enzyme activity, transfection of MGAT1 with SNP IV/V was ~25% less efficient than the common allele at rescuing β1,6GlcNAc-branched N-glycan expression in Lec1 cells (FIG. 15H). A 25% decrease in β1,6GlcNAc-branched N-glycan expression is highly significant as it is equivalent to being heterozygous for the MGAT5 null allele (FIG. 13A,B) and is sufficient to enhance TCR sensitivity (FIG. 13C,D,F) and susceptibility to spontaneous and induced autoimmune demyelinating disease (Table 1, 3, FIG. 13D).

Figure 14:
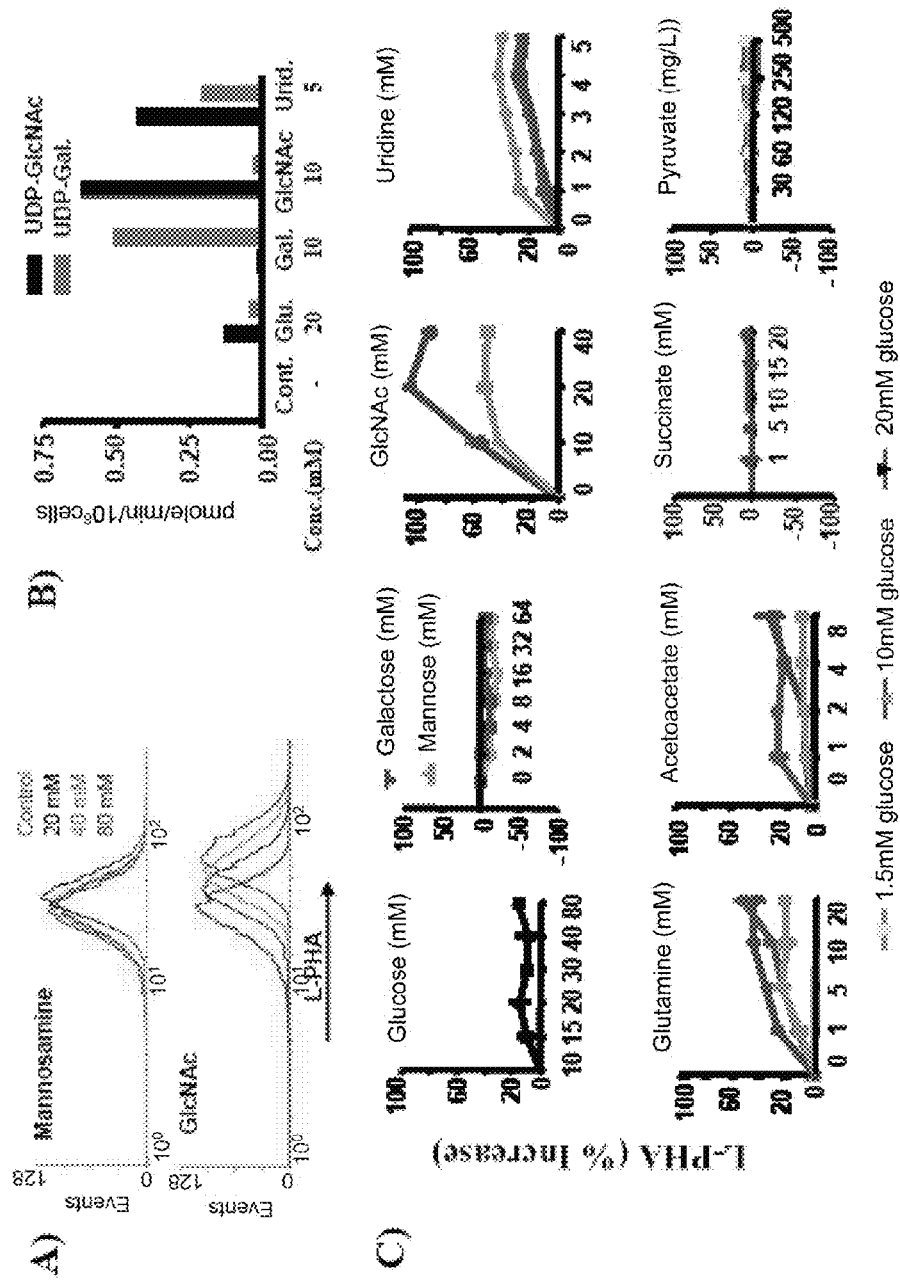
FIG. 14. Metabolic regulation of β1,6GlcNAc-branched N-glycan expression, T-cell function and EAE by the hexosamine pathway. (A-C) The indicated monosaccharides and metabolites were cultured with Jurkat T-cells for 3 days, stained with L-PHA-FITC and analyzed by FACS (A,C) or lysed and analyzed by MS/MS mass spectroscopy for sugar-nucleotide expression (B). Lines with symbols ■, ▲, ▼ refer to altered glucose concentration in the culture media as indicated; all others were grown in 10 mM glucose. Error bars in C are standard error of triplicate staining. (D,E) Wildtype PL/J CD3+ T-cells unlabelled (D) or labeled with CFSE (E) were stimulated with anti-CD3 antibody in the presence of swainsonine and/or GlcNAc as indicated for 3 days and analyzed for L-PHA (I)) or CFSE (E) staining. Shown are gated on CD4+ cells. (F-H) Splenocytes isolated from wild type PL/J mice 11 days after immunization with MBP+CFA were re-stimulated in vitro with MBP for 4 days in the presence (green) or absence (red) of GlcNAc (40 mM), stained with L-PHA-FITC and LEA-FITC (F), tested for IFN-γ and IL-6 production in harvested supernatant (G) and 3.6 million CD3+ cells were injected into naïve Mgat5+/−PL/J mice (n=7 for each condition) and scored for signs of EAE daily for 30 days (H). Shown in G is standard error of duplicate values. P values for disease incidence and mean clinical score were determined by Fisher's exact test and Mann-Whitney test, respectively.
Figure 14:
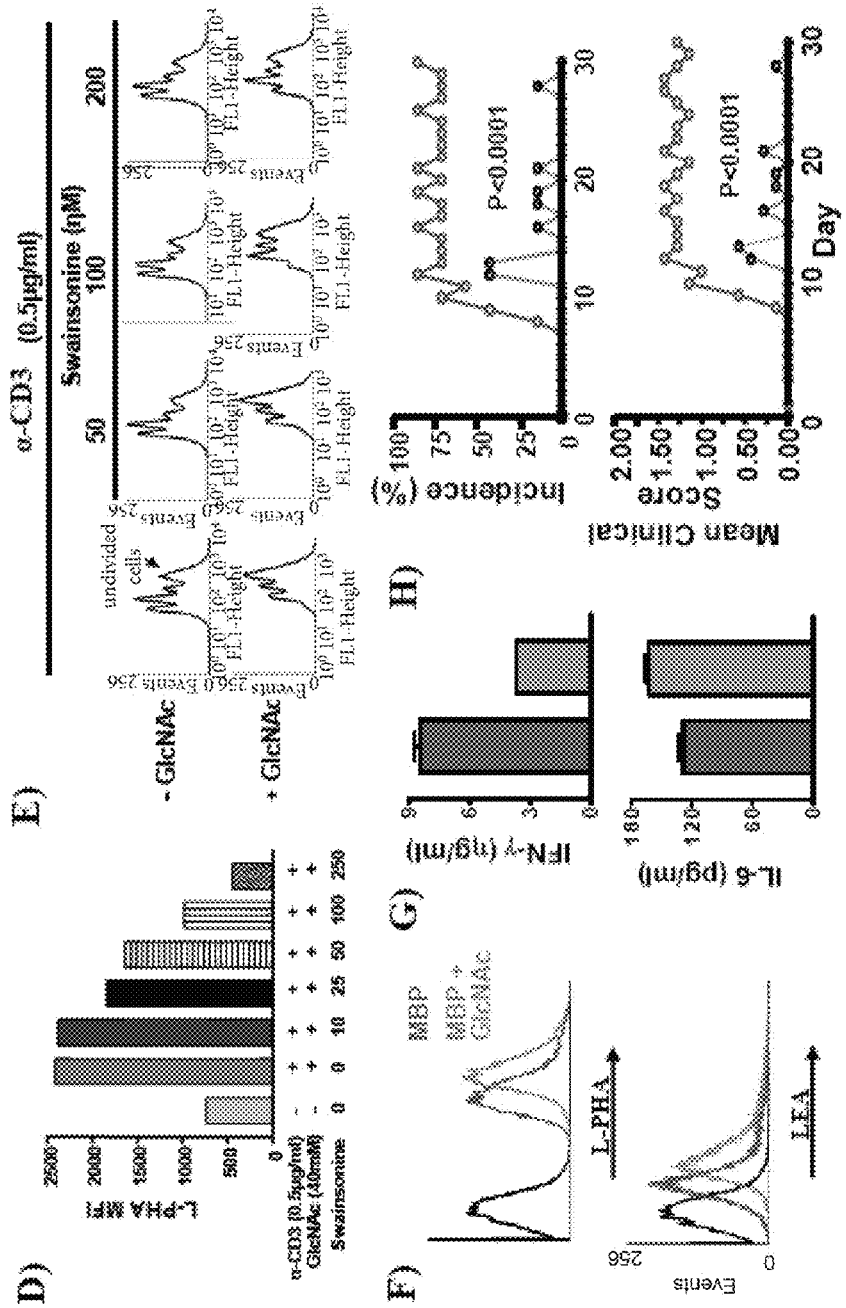

UDP-GlcNAc is limiting for β1,6GlcNAc-branched N-glycan expression (FIG. 14). The MGAT1, 2, 4 and 5 GlcNAc branching enzymes display declining affinity for UDP-GlcNAc in rank order with Km equal to 0.04, 0.9, ~5 and 11 mM, respectively, suggesting increased MGAT1 activity may reduce β1,6GlcNAc-branched N-glycans by limiting access of the MGAT5 enzyme to UDP-GlcNAc in the Golgi. Indeed, computational modeling of medial-Golgi enzyme reactions indicated that a 2-fold increase in baseline MGAT1 activity should reduce β1,6GlcNAc-branched N-glycan expression ~35% (FIG. 15I, materials and methods, 60). Critically, hexosamine pathway supplementation of Lec1 cells transfected with MGAT1 SNP IV/V rescued surface levels of β1,6GlcNAc-branched N-glycans to that of the common allele (FIG. 15J). These data indicate increased MGAT1 activity produced by SNP IV/V reduces β1,6 GlcNAc-branching by limiting Golgi supply of UDP-GlcNAc. Taken together these data provide proof of principle that as in mice, genetic and metabolic interactions between the N-glycan and hexosamine pathways regulate autoimmune demyelinating disease in humans. Moreover, the data demonstrates how metabolism via the hexosamine pathway can directly influence the ability of a single human allele to promote a complex trait disease like MS.

Conclusion

The data demonstrates that genetic variability in N-glycan processing efficiency among humans and inbred mouse strains is an inherited trait that regulates susceptibility to autoimmune demyelinating disease in a manner sensitive to metabolic flux through the hexosamine pathway. Genetic susceptibility to autoimmunity is modulated by the environment via unclear mechanisms. In this regard, metabolic regulation of N-glycan processing provides an environmental mechanism to alter inherent genetic risk to autoimmunity. Moreover, metabolically supplementing the hexosamine pathway to increase β1,6GlcNAc-branching represents a glyco-therapeutic (65) intervention to rescue defective N-glycan processing in MS patients.

MS is a two stage disease characterized by T cell induced autoimmune destruction of the myelin sheath followed by a secondary progressive neurodegenerative phase distinguished by axonal damage and neuronal loss (31); phenotypes also present in PL/J mice. Loss of GlcNAc branched N-glycans induces neuronal apoptosis in vivo (66), suggesting defective GlcNAc branching in MS patients and PL/J mice may also directly contribute to the neurodegenerative phase of the disease. Moreover, Mgat5 deficiency inhibits macrophage motility and phagocytosis (29), which may promote autoimmune demyelinating disease by reducing clearance of apoptotic neurons (66). β1,6GlcNAc-branched N-glycans also regulate cell adhesion, motility and endocytosis (24, 28,29), phenotypes that may also contribute to disease pathogenesis.

The diversity of rare polymorphisms in multiple N-glycan genes identified in a small number of MS patients suggests that the SNPs identified here comprise a small fraction of potential disease-associated polymorphisms. It appears that the rarity of individual SNPs is compensated for by a large number of polymorphisms distributed over the N-glycan pathway. Furthermore, the genetic and biochemical results provide a model whereby combinations of two or more rare SNPs in various N-glycan pathway genes are additive in reducing N-glycan processing and promoting disease. Loss of β1,6GlcNAc-branched N-glycans induces kidney autoimmune disease in 129/Sv mice, suggesting this model is likely relevant to a broad range of T cell mediated autoimmune diseases. Finally, the results demonstrate an approach to identify genes and alleles of complex trait diseases, whereby problems of genetic heterogeneity are overcome by knowledge of a biochemical network, validation in an animal model of the disease, use of existing human linkage data, and robust methods predictive of molecular and cellular pathology.

MALDI TOF N-Glycan Analysis

For comparison of N-glycan profiles of mice and human MS patients, CHO cells and CHO cells deficient at 5 different steps in the N-glycan pathway (Glucosidase I, Mannosidase I, MGAT1, Mannosidase II and MGAT5, FIG. 7A) were used to define relative L-PHA and Concanavillin A (ConA) lectin staining levels by FACS along with MALDI TOF N-glycan processing profiles. All deficiencies induced dramatic reductions in β1,6GlcNAc-branched N-glycan expression by L-PHA staining while only Mannosidase I, MGAT1 and Mannosidase II deficiency increased high-mannose structures as seen by ConA staining (FIG. 21A). Lack of increased ConA staining in Glucosidase I deficient CHO cells (Lec23)[67] suggests Golgi endo-mannosidase activity (68, 69), an alternative processing pathway that by-passes Glucosidase I/II and allows Mannosidase I and Mannosidase II action. Indeed, a human infant with severe human glucosidase I deficiency accumulates $Glc_3Man$ (885

A ion in FIG. 16A, 21C) in the urine, a 4 hexose oligomer which derives from the Glucosidase I substrate $Glc_3Man_9GlcNAc_2$ via endo-mannosidase activity (70). MALDI TOF analysis of Lec23 cells identified a dramatic increase in a 4 hexose oligomer (885 A ion) as well as oligomers of 5 (1089) and 6 (1294) residues (structure A in FIG. 16A, 21C), consistent with endo-mannosidase activity at all three mannose linkages in the α1-3 mannose arm of $Glc_3Man_9GlcNAc_2$ (arrowheads FIG. 16A). Such activity would produce $Man_8GlcNAc_2$, $Man_7GlcNAc_2$ and $Man_6GlcNAc_2$ structures and allow processing by Mannosidase I/II. Indeed, N-glycans of these 3 compositions accumulate in Glucosidase I/II inhibited cells when Mannosidase I activity is blocked with DMN (69). The larger structures $Glc_3Man_9GlcNAc_2$ (mass 3008) and $Glc_3Man_7GlcNAc_2$ (mass 2600) were also observed (67), however they were at lower relative intensities compared to the A ion group (FIG. 21C). As the amount of these ions depend on the extent of endo-mannosidase activity in the cell, which is considered low in CHO cells (67), these data indicate analysis of A ion expression (885, 1089, 1294) provide a significantly more sensitive MALDI TOF screening test for Glucosidase I/II deficiency when endo-mannosidase activity is present. MALDI TOF profiles of N-glycans from Mannosidase I (i.e., DMN treated cells) and MGAT1 (i.e., Lee 1 cells) deficient CHO cells were similar, displaying dramatic increases in high mannose structures (i.e., structures B and C, FIG. 21D,E). In contrast, Mannosidase II (SW treated) CHO cells displayed accumulation of hybrid structures (structure D, FIG. 21F). β1,6GlcNAc-branched tetra-antennary N-glycans (i.e., mass 2969, structure G FIG. 16A) were present in CHO cells, diminished in DMN treated cells and absent in Lec23, Lec1 and SW treated cells. Mixing CHO and Lec1 cells in various proportions confirmed that relative differences in expression of N-glycan structures can be determined using MALDI TOF (FIG. 21G).

Figure 16:
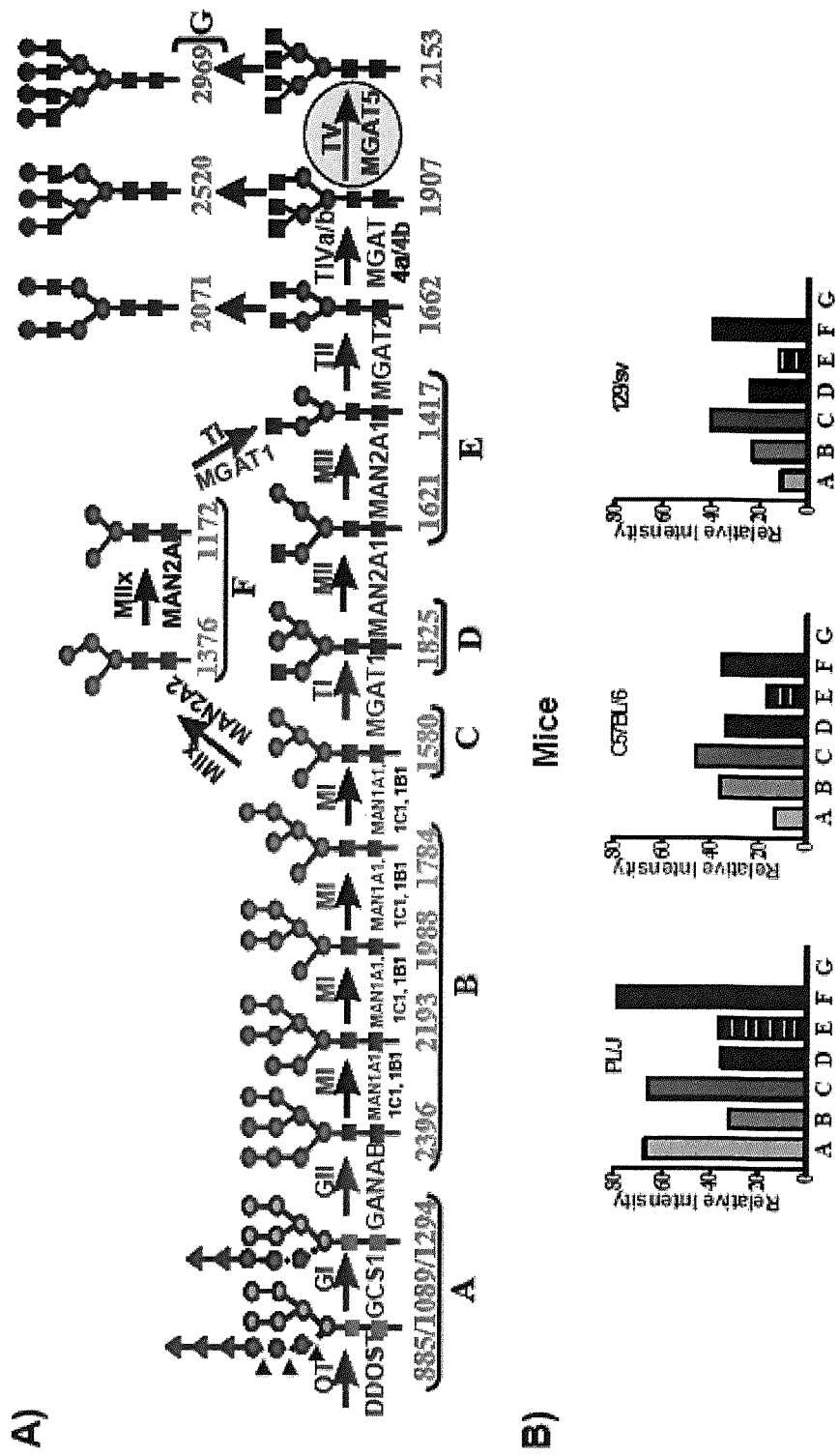
FIG. 16. MALDI-TOF mass spectroscopy of N-Glycans from mice and human controls and MS patients. (A) N-glycan processing pathway demonstrating Golgi intermediates and associated monoisotopic mass (permethylated, Na+) on MALDI-TOF mass spectroscopy. Glycan species were grouped based on enzymatic function and MALDI-TOF profiles of CHO cells defective at various steps in the N-glycan pathway (FIG. 21). Structures in group A were found as 4, 5 and 6 hexose fragments as observed in Glucosidase I (GI) deficient CHO (Lec23) cells (see FIG. 21) and are likely produced by endo-mannosidase activity at the arrowheads. Mass species 1662, 1907 and 2153 were not reliably detected. (B, C) N-glycans obtained from mouse CD3+ T-cells and MS and control PBMCs were analyzed by MALDI-TOF mass spectroscopy. Relative intensity of structures A-G were obtained by adding the intensity of structures from each group and dividing by the combined intensity of mature bi-antennary (2071) and tri-antennary (2520) glycans.
Figure 16:
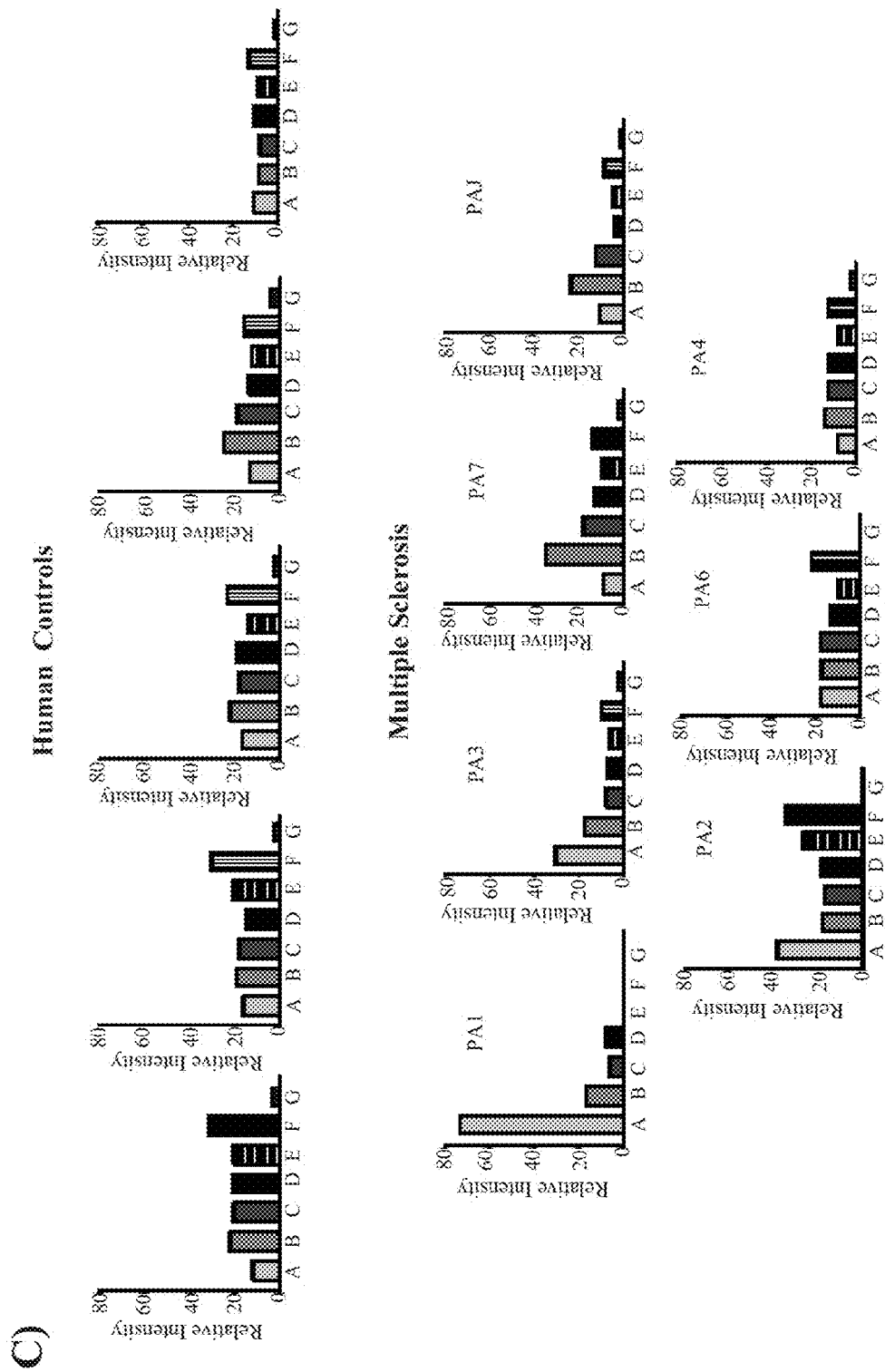

MALDI TOF analysis of the relative expression of N-glycans obtained from mouse T cells demonstrated accumulation of the E and F N-glycan structures in PL/J relative to C57BL/6 and 129/Sv mice (FIG. 16A,B). These structures are both directly upstream of MGAT2 (FIG. 16A) and MGAT2 enzymatic activity is decreased in PL/J>C57BL/6>129/Sv (FIG. 13G). PL/J>C57BL/6 T cells also had higher relative expression of the high mannose C and B ions that are increased in Mannosidase I and MGAT1 deficient CHO cells (FIG. 16), a result consistent with MAGT1 enzyme activity being reduced in both strains relative to 129/Sv (FIG. 13G). PL/J and C57BL/6 mice also have reduced MGAT5 activity relative to 129/Sv (FIG. 13G), however, tetra-antennary β1,6 branched N-glycans (i.e., 2969, ion G) were below the level of detection in all three mouse strains. These structures were detected in human samples, suggesting species dependent differences in expression. Indeed, it is well established that mouse T cell proliferation is induced with ConA>L-PHA while the opposite is true for human T cells. Indeed, direct comparison of L-PHA staining in 129/Sv (mouse) and human T cells revealed a ~3.5 fold higher expression in the latter. Taken together, these data confirm that PL/J T cells have significant N-glycan processing defects secondary to multiple enzymatic deficiencies.

MALDI TOF analysis of N-glycans derived from PBMC of 5 human control subjects revealed similar patterns and no significant accumulation of structures A-G (FIG. 16A,C). The same analysis in 7 of 8 consecutively obtained MS patients revealed N-glycan processing deficiencies in 6 of 7 patients. PA1 was similar to Lec23 cells, displaying a dramatic increase in A ions and absence of later species (i.e., ions E-G), suggesting Glucosidase I (GCS1) or Glucosidase II (GCS1, GANAB) deficiency. PA3 showed a similar but less dramatic pattern, implying deficiency in the same enzymes (FIG. 16C). PA7 and PAJ displayed accumulation of high mannose glycans (structure B in FIG. 16A,C) similar to DMN treated CHO cells and Lec1 cells, suggesting enzymatic defects in Mannosidase I (MAN1A1, 1B1, 1C1) or MGAT1. PA2 and PA6 displayed a pattern similar to controls in the proximal pathway (structures A-F), but lacked detectable non-core-fucosylated β1,6 GlcNAc branched tetra-antennary glycans (structure G FIG. 16A,C), suggesting deficiency of MGAT5. Indeed, FACS analysis with L-PHA confirmed reduced expression of β1,6GlcNAc-branched N-glycans in resting T cells from these two patients (FIG. 21H). These data indicate MS patients frequently display defects in N-glycan processing.

Spontaneous Demyelinating Disease in PL/J Mice

Spontaneous clinical and pathological disease were observed after 1 year of age in non-congenic wild type PL/J mice acquired from Jackson Laboratories, as well as the mice at backcross 4 to 9 (Tables 1 and 3), indicating that the presence of disease at backcross four and six was not significantly influenced by the stage of backcrossing from 129/Sv. Environmental pathogens have been implicated in the promotion of spontaneous demyelinating disease in MBP-TCR transgenic mice (II). In contrast, similar frequency of disease was observed when mice were housed in vivariums containing no pathogens, a single pathogen (Table 3) or a multitude of pathogens (Table 1), suggesting genetic rather than infectious factors dominate in disease pathogenesis.

Clinically affected mice also displayed involuntary movements in a gene dose-dependent manner, including tremor and/or focal dystonic posturing of the tail, hindlimbs and/or spine (Table 1, FIG. 20A) as well as paroxysmal episodes of dystonia. These movement disorders are common in patients with MS (15) but rarely reported in EAE. Dystonia is a neurological disorder characterized by sustained postures and twisting movements resulting from abnormal co-contraction of agonist and antagonist muscles. Episodes of dystonia in the mice could be precipitated by anxiety (i.e., drop from a modest height) and relieved by touch, phenomena typical of dystonia in humans (15).

Figure 20:
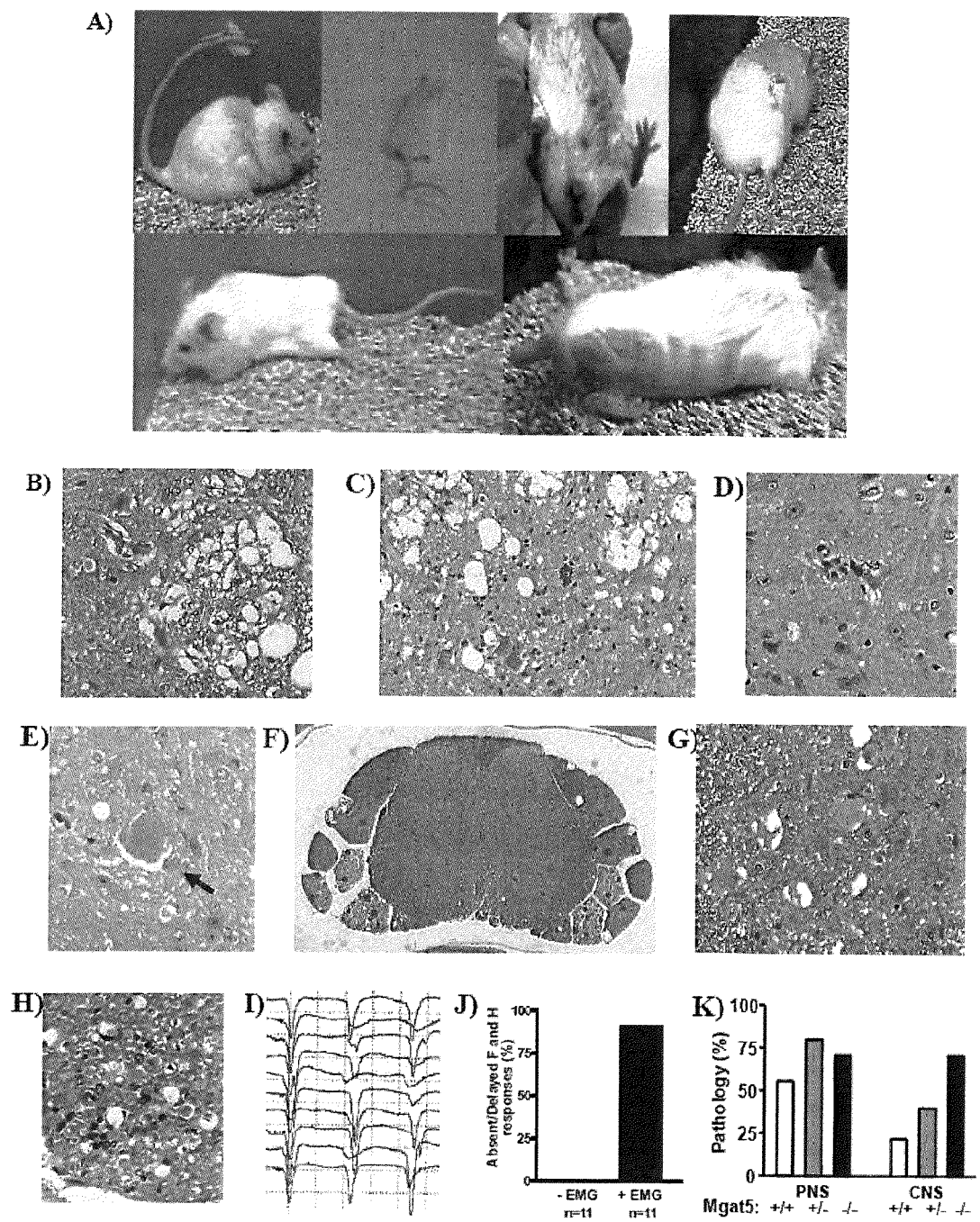
FIG. 20. Dystonic posturing and pathological/physiological demyelination in PL/J mice. (A) Clinically affected mice were observed to have dystonic posturing of the tail, hind limbs and/or axial skeleton. (B-H) Paraffin-embedded sections were stained with Haematoxylin & Eosin (C-E,H) or Luxol Fast Blue (B,F-G). B-D shows spinal cord demyelination, gliosis and neuronophagia. E shows axonal swelling in spinal cord surrounded by otherwise normal appearing white matter. F shows multi-focal myelin degeneration of spinal roots. G shows neuronal bodies with central chromatolysis in the spinal cord. H shows spinal root with swollen axons. (I-J) PL/J mice underwent needle electromyography (EMG) and nerve conduction studies (NCS) for assessment of F waves and H responses, a clinical physiological test for spinal root demyelination. I shows example of the positive sharp waves observed. J shows the frequency of delayed or absent F and H responses as assessed by NCS in mice with normal and abnormal needle EMG. (K) Frequency of spinal root (PNS) and CNS pathology in Mgat5+/+ (n=9), Mgat5+/− (n=10) and Mgat5−/− (n=17) PL/J mice (p=0.048, chi square for CNS).

Axonal pathology was frequently observed in otherwise normal appearing CNS white matter (FIG. 17E). Axonal damage has long been recognized in MS plaques, more recently in normal-appearing white matter, and is associated with the irreversible neurological deterioration in SPMS[2]. The PNS pathology was characterized by multi-focal spinal mot demyelination with naked and swollen axons (FIG. 15C, 20F,H). Neuronal bodies with prominent central chromatolysis were observed in the spinal cord (FIG. 20G), consistent with anterograde reaction to peripheral damage. Electromyography and nerve conduction studies revealed myokymia, positive sharp waves and delayed spinal root nerve conduction velocity as evidenced by abnormal F and H responses (FIG. 20I,J), findings typical of physiologic spinal root demyelination and the human PNS autoimmune demyelinating disease, Chronic Inflammatory Demyelinating Polyneuropathy (CIDP).

CNS and/or PNS pathology was present in all mice with clinical weakness and frequently co-existed in the same individual. PNS demyelination was seen with similar frequency in all 3 Mgat5 genotypes (FIG. 20K). In contrast, CNS demyelination was ~2 and 3 fold more frequent in Mgat5$^{+/-}$ and Mgat5$^{-/-}$ mice than wild type mice, respectively (FIG. 20K). This indicates that β1,6GlcNAc-branched N-glycans d N-glycans suppress spontaneous CNS demyelinating disease in a gene dose dependent manner and suggests the more severe clinical disease in Mgat5$^{-/-}$ and Mgat5$^{+/-}$ mice was secondary to increased frequency of CNS demyelination.

The spontaneous demyelinating disease induced by Mgat5 deficiency in PL/J mice phenocopies several important clinical features of MS: spontaneous occurrence in mid-life, movement disorders such as tremor and dystonia and a slow progressive decline in neurological function in association with neuronal loss and axonal damage (2,15). As such, Mgat5-deficient PL/J mice represent a unique model to study both the inflammatory and neurodegenerative phases of MS.

Example 4

To determine whether MGAT1 SNP V is associated with other autoimmune diseases in addition to MS patients were analyzed with Rheumatoid Arthritis (RA) and Thyroid Autoimmunity (ie Graves disease and Hashimoto's) as well as MS and control cohorts were expanded (Table 7). Case control analysis demonstrated that both MS and RA are associated with disease with similar odds ratio's, while Thyroid Autoimmunity has little or no association. The transmission disequilibrium test (TDT), a family based test of association that eliminates bias from population selection, confirmed MS and RA but not Thyroid Autoimmunity are associated with MGAT1 SNP V.

Example 5

Figure 24:
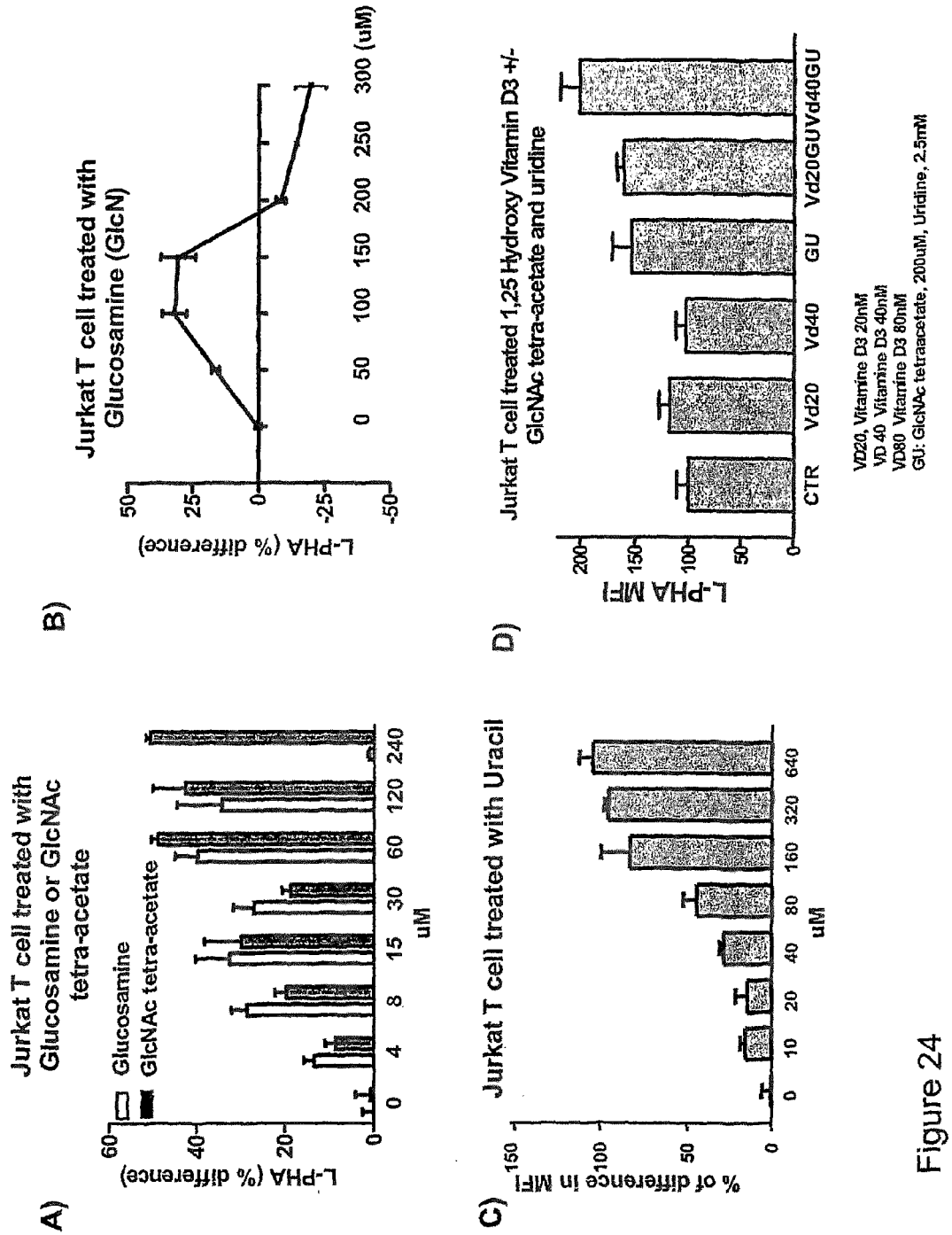
FIG. 24 Enhanced expression of β1,6GlcNAc-branched N-glycan by Vitamin D3 and supplements to the hexosamine pathway. (A-D) The indicated monosaccharides and/or metabolites were cultured with Jurkat T-cells for 3 days, stained with L-PHA-FITC and analyzed by FACS.

Low concentrations of Glucosamine increase Mgat5-modified N-glycan expression in Jurkat T while high concentrations do the opposite (FIG. 24 A,B). As glucosamine but not GlcNAc also competes with glucose for the glucose transporter, may promote insulin resistance and can be converted to Fructose-6-phosphate to enter glycolysis (FIG. 24A), GlcNAc is a preferred therapeutic. However, due to its lack of hydrophobicity, GlcNAc enters the cell poorly. This can be significantly improved by acetylating GlcNAc (ie GlcNAc-tetra-acetate) to increase hydrophobicity and cell entry. Cytoplasmic de-acetylases will remove the acetyl groups to produce GlcNAc following cell entry. Indeed, GlcNAc-tetra-acetate is able to increase Mgat5-modified N-glycan expression at effective concentrations ~1000 fold less than GlcNAc (FIG. 24 A). Similarly, removal of the hydrophilic ribose from uridine to form the base uracil significantly increases hydrophobicity and reduces the effective concentration required to raise Mgat5-modified N-glycan expression ~100 fold compared to uridine (FIG. 24 C).

Vitamin D3 increases Mgat5-modified glycan expression by increasing mRNA expression of Mgat5 and possibly other N-glycan and hexosamine pathway genes while hexosamine pathway supplementation increases Mgat5 modified N-glycan expression by increasing UDP-GlcNAc, the sugar nucleotide donor for Mgat1 1, 2, 4 and 5. As these are two independent mechanisms to raise Mgat5-modified N-glycan expression, combining these should be synergistic. Indeed, Vitamin D3 coupled with hexosamine pathway supplementation (ie GlcNAc-tetra-acetate and uridine) synergistically increased Mgat5-modified N-glycan expression. Thus, this combination may be particularly useful to therapeutically raise Mgat5-modified N-glycan expression in autoimmune disease patients (eg MS and RA). Combination therapy utilizing multiple hexosamine pathway metabolites and/or Vitamin D3 will also ensure that supply of metabolites is not limiting as well as minimize the concentration of individual therapeutics and thereby limit potential toxicity and negative feedback. shows that acetylated GlcNAc and uracil increase Mgat5 glycan expression at ~100-1000 fold lower concentrations than GlcNAc and uridine. The new data also shows that Glucosamine works at low concentrations but then declines at later concentrations, which does not occur with the other supplements. Thus GlcNAc is a better agent than glucosamine. The data also show that Vitamin D3 plus GlcNAc+uridine are synergistic in increasing Mgat5 modified N-glycans.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. All publications, patents and patent applications mentioned herein are incorporated herein by reference for the purpose of describing and disclosing the molecules, methodologies etc. which are reported therein which might be used in connection with the invention. Nothing herein is to be construed as an admission that the invention is not entitled to antedate such disclosure by virtue of prior invention.

It must be noted that as used herein and in the appended claims, the singular forms "a", "an", and "the" include plural reference unless the context clearly dictates otherwise. Thus, for example, reference to "an agonist" includes a plurality of such agonists, and equivalents thereof known to those skilled in the art, and so forth.

TABLE 1

Table 1: Clinical Observations of Spontaneous Disease In PL/J mice

| Genotype | n | Age(m) | Weakness | | Dystonia | | Death(%)[¥] |
|---|---|---|---|---|---|---|---|
| | | | Incidence(%)[*] | Score[#] | Incidence(%)[§] | Score[†] | |
| Mgat5[+/+] | 10 | 14 +/− 0.4 | 20 | 0.4 +/− 0.27 | 0 | 0 | — |
| | | 17.5 +/− 0.6 | 40 | 0.8 +/− 0.33 | 10 | 0.1 | 0 |
| Mgat5[+/−] | 13 | 15.6 +/− 0.7 | 38.5 | 0.8 +/− 0.28 | 23.1 | 0.69 +/− 0.37 | — |
| | | 18.2 +/− 0.8 | 69.2 | 1.6 +/− 0.38 | 38.5 | 0.92 +/− 0.37 | 7.7 |
| Mgat5[−/−] | 21 | 15.4 +/− 0.5 | 61.9 | 1.3 +/− 0.25 | 42.9 | 0.86 +/− 0.26 | — |
| | | 18.2 +/− 0.4 | 81.0 | 2.9 +/− 0.44 | 52.4 | 1.10 +/− 0.28 | 38.1 |

Severity of weakness was scored on a scale of 0-5 with: 0, no weakness; 1, limp tail; 2, hindlimb weakness; 3, hindlimb paralysis; 4, forelimb weakness/paralysis and hindlimb paralysis; and 5, moribundity or death. Severity of dystonia was scored on a scale of 0-3 with: 0, no dystonia, 1, tail dystonia; 2, hindlimb dystonia; 3, axial skeleton and/or paroxysmal dystonia. Time and age are given in months. Percentages for spontaneous death and incidence were cumulative. Severity is mean +/− standard error. n was the denominator for all calculations.

[*]$p = 0.0234$ (0 m), $p = 0.0263$ (4 m) chi square test for trend comparing all 3 genotypes

[#]$p = 0.0007$; Two Way Anova comparing all 3 genotypes at both time points

[§]$p = 0.04$ chi square (time 0); $p = 0.0263$ (4 m) chi square test for trend comparing all 3 genotypes

[†]$p = 0.0076$; Two Way Anova comparing all 3 genotypes at both time points

[¥]$p = 0.0194$ chi square comparing all 3 genotypes

TABLE 2

Adoptive Transfer of Demyelinating Disease into wildtype PL/J mice

| Donor | | | Recipient | | |
|---|---|---|---|---|---|
| Genotype | Severity | Incidence* | Onset(w) | Score# | Pathology |
| Mgat5−/− | + | 0/6 | 0 | 0 | 0/6 |
| Mgat5+/− | ++/+++ | 1/6 | 3 | 0.33 +/− 0.33 | 1/4 |
| Mgat5−/− | ++/+++ | 3/3 | 3 +/− 1.3 | 3.0 +/− 1.0 | 3/3 |

Spontaneously diseased donor mice were scored for severity of demyelinating pathology (+ to +++) and harvested splenocytes were stimulated 48 hrs in vitro with anti-CD3 + anti-CD28 antibody and then injected ip into naive wildtype PL/J mice. The recipient mice were scored for weakness and presence of demyelinating pathology. Score is mean +/− standard error. w = weeks
*p = 0.0114, chi square comparing all 3 genotypes
p = 0.0056; One Way Anova (Kruskal-Wallis)

TABLE 3

Clinical Observations of Spontaneous Disease in PL/J mice at UCI

| Genotype | n | Age(m) | Incidence(%) | Score | Death(%) |
|---|---|---|---|---|---|
| Mgat5+/− | 27 | 13.7 ± 0.2 | 3.70 | 0.19 ± 0.19 | — |
| | 25 | 15.6 ± 0.2 | 16.0 | 0.72 ± 0.34 | 7.4 |
| | 22 | 17.5 ± 0.2 | 59.1 | 2.05 ± 0.40 | 18.5 |
| Mgat5−/− | 17 | 13.0 ± 0.4 | 11.8 | 0.59 ± 0.40 | — |
| | 14 | 15.0 ± 0.4 | 35.7 | 1.36 ± 0.53 | 17.7 |
| | 8 | 16.3 ± 0.5 | 87.5 | 3.13 ± 0.55 | 53.0 |

PL/J mice at backcross six from 129/Sv housed in the University of California, Irvine (UCI) vivarium were examined twice weekly for clinical signs of spontaneous demyelinating disease and scored in a blinded fashion as described in Table 1. Data are tabulated at 3 separate time points over 4 months. Percentages for Death and Incidence are cumulative. Data are presented as mean ± s.e.m.

TABLE 4

β1,6GlcNAc-branched N-glycan regulatory genes and 18 putative MS loci

A)

| Autoimmune Loci | | β1,6GlcNAc-branched N-glycan regulatory genes | | |
|---|---|---|---|---|
| MS | Other# | Gene | Location | Enzyme |
| 1p21-p36 | IBD, SLE, EAE | DDOST | 1p36.1 | Oligodolichol Transferase |
| | | MAN1C1 | 1p35-p36 | Golgi Mannosidase IC |
| | | SLC35A3 | 1p21 | UDP-GlcNAc Tansporter, Golgi |
| 1q11-q45 | IDDM, PS, SLE | UAP1 | 1q23 | UDP-GlcNAc Pyrophosphorylase 1 |
| | | B4GALT3 | 1q21-q23 | GlcNAc β1,4 galactosyltransferase III |
| 2q14-q32 | | MGAT5 | 2q21-q22 | N-Acetylglucosaminyl Transferase V |
| 2q36-q37 | SLE | — | — | — |
| 2p11-24 | IDDM, AITD, EAE | GCS1 | 2p12-p13 | Glucosidase I |
| | | GFPT1 | 2p13 | Fructose-6-PO4-transaminase 1 |
| | | NAGK | 2p13 | N-acetylglucosamine kinase |
| | | HK2 | 2p13 | Hexokinase 2 |
| 4q28-35 | PS, EAE | — | — | — |
| 5p12-p15 | SLE, EAE | — | — | — |
| 5q14-q35 | IDDM, PS, IBD AITD, EAE | MAN2A1 | 5q21-q23 | Mannosidase II |
| | | MGAT1 | 5q35 | N-Acetylglucosaminyl Transferase I |
| | | MGAT4b | 5q35 | N-Acetylglucosaminyl Transferase IVb |
| | | GNPDA | 5q21 | Glucosamine-6-PO4-deaminase 1 |
| | | GFPT2 | 5q34-q35 | Fructose-6-PO4-transaminase 1 |
| | | HK3 | 5q35.2 | Hexokinase 3 |
| 6q22-q27 | IDDM, PS | MAN1A1 | 6q22 | Mannosidase Ia |
| 10p12-p15 | | — | — | — |
| 11p13-p15 | IDDM | — | — | — |
| 11q12-q15 | IDDM, AITD, EAE | GANAB | 11q12 | Glucosidase II |
| | | B3GNT6 | 11q13.2 | β1,3-GlcNAc Transferase VI (IGnT) |
| 12q21-q24 | IBD, AITD | B3GNT4 | 12q24 | β1,3-GlcNAc Transferase IV |
| 14q21-q32 | IDDM, PS, AITD | MGAT2 | 14q21 | N-Acetylglucosaminyl Transferase II |
| | | GNPNAT1 | 14q22.1 | Glucosamine-6-PO4-N-acetyltransferase |
| 16p12-p13 | IDDM, EAE | — | — | — |
| 17q11-q25 | IDDM, IA, PS, EAE | NAT9 | 17q25 | Glucosamine-6-PO4-N-acetyltransferase |
| 19q12-q13 | IA, SLE | GPI | 19q13 | Glucose Phosphate Isomerase |
| 22q12-q13 | EAE | MGAT3 | 22q13.1 | N-Acetylglucosaminyl Transferase III |

B)

| Carbohydrate Genes | Map to 18 MS Loci | | |
|---|---|---|---|
| | Observed* | Expected | Observed-Expected# |
| β1,6GlcNAc Non-regulatory | 85/241 (35.3%) | 82/241 (34%) | 3/159 (1.9%) |
| β1,6GlcNAc Regulatory | 25/34 (73.5%) | 11.5/34 (34%) | 13.5/22.5 (60%) |

*,#p < 0.0001, Fishers Exact test, # Relative Risk 32.3, Odds Ratio 80.9

MS loci are defined by their suggestive or better association/linkage (ie LOD >1) to MS/EAE in at least 3 of 12 studies shown in Table S3, excluding the known MHC association at 6p21. These cytogentic regions account for ~34% of the human genome (materials and methods), a number controlled for in B. Other autoimmune loci are shown if they co-localize to the MS loci. β1,6GlcNAc-branched N-glycan regulatory and non-regulatory genes are shown in FIG. 1 and Table S4, respectively. Non-regulatory genes control metabolism of other carbohydrates. IDDM: autoimmune diabetes. IBD: inflammatory bowel disease, SLE: systemic lupus erythematosis. PS: psoriasis. AITD: autoimmune thyroid disease. IA: inflammatory arthritis. EAE: experimental autoimmune encephalomyelitis.

TABLE 5

MS and EAE linked/associated loci

| Loci | Canada (Dyment et al) | USA/France (Pericak-Vance et al) | Britain (Sawcer et al) | Italian (Broadley et al) | Finland (Kuokkanen et al) | Sweden (Giedraitis et al) | Norway (Akkesson et al) |
|---|---|---|---|---|---|---|---|
| 1p21-p36 | 1p31-36 | 1p34 | 1p34 | — | — | — | — |
| 1q11-q45 | 1q24-q25 | — | 1q43 | 1q25-1q44 | — | — | 1q11-q24 |
| 2q14-q32 | 2q21-22 | — | — | — | — | 2q14-q31 | 2q24-q32 |
| 2q36-q37 | 2q37-qtel | — | — | 2q36 | — | — | — |
| 2p11-p24 | — | — | 2p21 | — | — | — | — |
| 4q28-35 | 4q32 | — | — | — | — | — | — |
| 5p12-p15 | 5p15-ptel | — | — | — | 5p12 | — | — |
| 5q14-q35 | — | — | — | 5q33 | — | 5q22-q23 | — |
| 6q22-q27 | 6q27 | — | — | 6q22-25 | — | 6q25-q27 | — |
| 10p12-p15 | 10p15 | — | — | 10p11-cen | — | — | 10p15 |
| 11p13-p15 | 11p13-p15 | — | — | — | — | — | 11p15 |
| 11a12-q15 | — | — | — | — | — | — | — |
| 12q21-q24 | 12q21-q23 | — | — | — | — | — | 12q21 |
| 14q21-q32 | — | — | — | — | — | 14q24-q32 | — |
| 16p12-p13 | — | — | — | — | — | 16p12-p13 | 16p13 |
| 17q11-q25 | 17q21-q23 | — | 17q23-q24 | — | 17q22-q24 | 17q12-q24 | 17q25 |
| 19q12-q13 | — | 19q13 | 19q13.3 | — | — | — | — |
| 22q12-q13 | — | — | — | — | — | — | 22q12-q13 |

| Loci | Sardinian (Coraddu et al) | Australian (Ban et al) | GAMES (2003) | Becker et al | EAE (Butterfield et al) |
|---|---|---|---|---|---|
| 1p21-p36 | — | — | — | 1p21-p36 | 1p12-p31 |
| 1q11-q45 | — | — | — | — | — |
| 2q14-q32 | — | — | — | — | — |
| 2q36-q37 | 2q36 | — | — | — | — |
| 2p11-p24 | — | — | 2p14 | 2p11-p24 | 2p12-p23 |
| 4q28-q35 | — | — | — | 4q28-q35 | 4q28-q33 |
| 5p12-p15 | — | — | — | 5p16 | 5p13-p15 |
| 5q14-q35 | — | — | — | 5q14 | 5q31-p35 |
| 6q22-q27 | — | — | — | — | — |
| 10p12-p15 | 10p12 | — | 10p15 | — | — |
| 11p13-p15 | — | — | 11ptr | — | — |
| 11a12-q15 | — | 11q12 | — | 11q14 | 1q13-q15 |
| 12q21-q24 | — | — | — | 12q21-q24 | — |
| 14q21-q32 | — | 14q21 | — | 14q32 | — |
| 16p12-p13 | — | 16p13 | 16p13 | 16p13 | 16p13 |
| 17q11-q25 | — | — | 17q21 | 17q21-q23 | 17q11-23 |
| 19q12-q13 | — | 19q13 | — | 19q12-q13 | — |
| 22q12-q13 | — | — | 22q13 | 22q13 | 22q12 |

TABLE 6

Carbohydrate genes not required for β1,6GlcNAc-branched N-glycan synthesis

| Gene | Location | Enzyme | Glycan type |
|---|---|---|---|
| A) Genes that Map to 18 MS Loci in Table 5 | | | |
| B3GNT1 | 2p15 | β1,3 N-Acetylglucosaminyltransferase I | GAG, Glycolipid |
| B3GNT7 | 2q37.1 | β1,3 N-Acetylglucosaminyltransferase VII | ? |
| B4GALT2 | 1p33-p34 | β1,4 Galactosyltransferase II | N-Glycans, Glycolipid |
| B4GALT7 | 5q35 | β1,4 Galactosyltransferase VII | Proteoglycans |
| B3GALT1 | 2q24.3 | β1,3 Galactosyltransferase I | Glycolipid |
| B3GALT2 | 1q31 | β1,3 Galactosyltransferase II | N-,O-Glycan |
| B3GALT6 | 1q36 | β1,3 Galactosyltransferase VI | N-,O-Glycan |
| B3GALT7 | 19q13 | β1,3 Galactosyltransferase VII | N-,O-Glycan |
| GALNT2 | 1q41-q42 | N-Acetylgalactosaminyltransferase II | O-Glycans |
| GALNT3 | 2q24-q31 | N-Acetylgalactosaminyltransferase III | O-Glycans |
| GALNT4 | 12q21.3-q22 | N-Acetylgalactosaminyltransferase IV | O-Glycans |
| GALNT5 | 2q24.2 | N-Acetylgalactosaminyltransferase V | O-Glycans |
| GALNT7 | 4q31.1 | N-Acetylgalactosaminyltransferase VII | O-Glycans |
| GALNT9 | 12q24.3 | N-Acetylgalactosaminyltransferase IX | O-Glycans |
| GALNT10 | 5q33.2 | N-Acetylgalactosaminyltransferase X | O-Glycans |
| GALNT13 | 2q24.1 | N-Acetylgalactosaminyltransferase XIII | O-Glycans |
| GALNT14 | 2p23.2 | N-Acetylgalactosaminyltransferase XIV | O-Glycans |
| GALGT2 | 17q21.33 | N-Acetylgalactosaminyltransferase | Blood Group Antigen |
| SIAT6 | 1p34.1 | α2,3 Siayltransferase (ST3Gal III) | N-,O-Glycans, Glycolipid |
| SIAT7A & B | 17q25.3 | α2,6 Siayltransferase (ST6GalNAc I) | O-Glycan |
| SIAT7C & E | 1p31.1 | α2,6 Siayltransferase (ST6GalNAc III) | O-glycan, Glycolipid |
| SIAT8D | 5q21 | α2,8 Siayltransferase IV (ST8Sia IV) | N-glycan |

TABLE 6-continued

Carbohydrate genes not required for β1,6GlcNAc-branched N-glycan synthesis

| Gene | Location | Enzyme | Glycan type |
|---|---|---|---|
| SIAT9 | 2p11.2 | α2,3 SiayltransferaseV (ST3Gal V) | Glycolipid |
| FUT1, 2 & 3 | 19q13.3 | α1,2 Fucosyltransferase | ? |
| FUT5 & 6 | 19q13.3 | α1,3 Fucosyltransferase | ? |
| FUT8 | 14q24.3 | α1,6 Fucosyltransferase | N-Glycan |
| DPM3 | 1q22 | Dol-P-mannosyltransferase 3 | GPI-linked |
| LOC402458 | 11p15.4 | Similar to β1-4 mannosyltransferase | ? |
| LOC399914 | 11q13.1 | Similar to β1-4 mannosyltransferase | ? |
| LOC401658 | 11p15.5 | Similar to β1-4 mannosyltransferase | ? |
| HS3ST2 | 16p12 | Heparin Sulfate 3-O-sulfotransferase II | GAG |
| HS3ST6 | 16p13.3 | Heparin Sulfate 3-O-sulfotransferase VI | GAG |
| HS2ST1 | 1p22-p31 | Heparan Sulfate 2-O-sulfotransferase | GAG |
| HS6ST1 | 2q21 | Hepran Sulfate6-O-sulfotransferase | GAG |
| CHST8 | 19q13.1 | N-Acetylgalactoasaminyltransferase-4-O-Sulfotransferase VIII | GAG |
| CHST11 | 12q24 | Chondroitin-4-O-Sulfotransferase | GAG |
| UST | 6q24 | Uronyl-2-sulfotransferase | GAG |
| NDST1 | 5q33 | N-deacetylase/N-sulfotransferase I | GAG |
| EXTL1 | 1p36.1 | α1,4 GlcNAc transferase | GAG |
| EXTL2 | 1p21 | α1,4 GlcNAc transferase | GAG |
| B3GAT3 | 11q12.3 | β1,3 glucuronyltransferase III | GAG |
| XYLT2 | 17q21-q22 | Xylosetransferase II | GAG |
| NAGLU | 17q21 | α-N-acetylglucosaminidase | GAG |
| CTBS | 1p22 | Chitobiase | ? |
| NEU2 | 2q37 | Sialidase | cytosolic sialidase |
| NEU3 | 11q13 | Sialidase | N-glycan degradation |
| NEU4 | 2q37.3 | Sialidase | N-glycan degredation |
| GBA | 1q21 | Glucosidase B | Glycolipid |
| GAA | 17q25 | Glucosidase (Pompes Disease) | Glycan degradation |
| FLJ21865 | 17q25.3 | N-aetylglucosaminidase | N-glycan degradation |
| FUCA1 | 1p34 | Fucosidase | N-glycan degradation |
| UGP1 | 1q21-q22 | UDP-glucose pyrophosphorylase 1 | Sugar-nucleotide |
| UGP2 | 2p13-p14 | UDP-glucose pyrophosphorylase 2 | Sugar-nucleotide |
| GMPPA | 2q36.1 | GDP-mannose pyrophorylase | Sugar-nucleotide |
| PGM1 | 1p31 | Phosphoglucomutase 1 | Glycolysis |
| ACYP1 | 14q24 | Acylphosphatase 1 | Gluconeogenesis |
| ACYP2 | 2p16.2 | Acylphosphatase 2 | Gluconeogenesis |
| ENO1 | 1p36 | Enolase 1 | Glycolysis |
| PKLR | 1q21 | Pyruvate Kinase | Gluconeogenesis |
| PFKP | 10p15 | Phosphofructokinase-platelet | Glycolysis |
| LDHA | 11p15 | Lactate dehydrogenase A | Glycolysis |
| AKR1A1 | 1p32-p33 | Aldehyde reductase A1 | Glycolysis |
| ASML3B | 1p35 | Sphingomyelin phosphodiesterase, acid-like 3B | Monosaccharide Metabolism |
| DIA1 | 22q13 | NADH-cytochrome b5 reductase (diaphorase) | Monosaccharide Metabolism |
| GALK1 | 17q24 | Galactokinase 1 | Monosaccharide Metabolism |
| LCT | 2q21 | Lactase | Monosaccharide Metabolism |
| KHK | 2p23 | Ketohexokinase (fructokinase) | Monosaccharide Metabolism |
| PMM1 | 22q13 | Phosphomannomutase 1 | Monosaccharide Metabolism |
| FPGT | 1p31 | Fucose-1-phosphate guanylyltransferase | Monosaccharide Metabolism |
| H6PD | 1p36 | Hexose-6-phosphate dehydrogenese | Pentose Phosphate |
| PGD | 1p36 | Phosphogluconate dehydrogenase | Pentose Phosphate |
| RPIA | 2p11 | Ribose 5-phosphate Isomerase A | Pentose Phosphate |
| RBKS | 2p23 | Ribokinase | Pentose Phosphate |
| TALDO1 | 11p15 | Transaldolase 1 | Pentose Phosphate |
| GYS1 | 19q13 | Glycogen synthase 1 (muscle) | Starch/Sucrose Metabolism |
| AGL | 1p21 | Amylo-1,6-glucosidase, 4-alpha-glucanotransferase | Starch/Sucrose Metabolism |
| TESK2 | 1p32 | Testis-specific kinase 2 | Starch/Sucrose Metabolism |
| AMY1A | 1p21 | Salivary alpha-amylase | Starch/Sucrose Metabolism |
| RUVBL2 | 19q13 | RuvB-like 2 | Starch/Sucrose Metabolism |
| GAL3ST1 | 22q12 | Galactose-3-O-sulfotransferase 1 | Glycolipid |
| POMT2 | 14q24 | Protein-O-mannosyltransferase 2 | O-linked mannose |
| POMGNT1 | 1p34.1 | GlcNAc transferase | O-linked mannose |
| SLC35A4 | 5q31.3 | UDP-Galactose Transporter | Sugar Nucleotide Transport |
| SLC35D1 | 1p31-p32 | UDP-GalNAc Transporter | Sugar Nucleotide Transport |
| SLC35B1 | 17q21.33 | UDP-Galactose Transporter | Sugar Nucleotide Transport |

B) Genes that do not map to 18 MS Loci in Table 5

| Gene | Location | Enzyme | Glycan type |
|---|---|---|---|
| B3GNT3 | 19p13.1 | β1,3 N-acetylglucosominyltransferase III | O-glycan, GPI |
| B3GNT5 | 3q28 | β1,3 N-acetylglucosominyltransferase V | Glycolipid |
| B4GALT1 | 9q13 | β1,4 Galactosyltransferase I | ? |
| B4GALT4 | 3q13.3 | β1,4 Galactosyltransferase IV | Glycolipid, N-Glycan |
| B4GALT5 | 20q13.1-13.2 | β1,4 Galactosyltransferase V | N-Glycan |
| B4GALT6 | 18q11 | β1,4 Galactosyltransferase IV | Glycolipd |
| B3GALT3 | 3q25 | β1,3 Galactosyltransferase III | N-,O-Glycan |
| B3GALT4 | 6p21 | β1,3 Galactosyltransferase IV | N-,O-Glycan |
| B3GALT5 | 21q22.3 | β1,3 Galactosyltransferase V | N-,O-Glycan |
| GALNT1 | 18q12.1 | N-Acetylgalactosaminyltransferase I | O-Glycan |
| GALNT6 | 12q13 | N-Acetylgalactosaminyltransferase VI | O-Glycan |

TABLE 6-continued

Carbohydrate genes not required for β1,6GlcNAc-branched N-glycan synthesis

| Gene | Location | Enzyme | Glycan type |
|---|---|---|---|
| GALNT8 | 12p13.3 | N-Acetylgalactosaminyltransferase VIII | O-Glycan |
| GALNT11 | 7q34-q36 | N-Acetylgalactosaminyltransferase XI | O-Glycan |
| GALNT12 | 9q31.1 | N-Acetylgalactosaminyltransferase XII | O-Glycan |
| GALNT15 | 7q36.2 | N-Acetylgalactosaminyltransferase XV | O-Glycan |
| GALGT | 12q13 | N-Acetylgalactosaminyltransferase | Glycolipid |
| ChGn | 8p21.3 | N-Acetylgalactosaminyltransferase | Glycosaminoglycan |
| SIAT1 | 3q27-q28 | α2,6 Siayltransferase I (ST6Gal I) | N-Glycan |
| SIAT4A | 8q24.22 | α2,3 Siayltransferase I (ST3Gal IA) | O-Glycan |
| SIAT4B | 16q22 | α2,3 Siayltransferase II (ST3Gal II) | Glycolipid, O-Glycan |
| SIAT4C | 11q23-q24 | α2,3 Siayltransferase IV (ST3Gal IV) | O-Glycan |
| SIAT7D & F | 9q34 | α2,6 Siayltransferase | O-Glycan, glycolipid |
| SIAT8A | 12p11.2-p12.1 | α2,8 Siayltransferase I (ST8Sia I) | Glycolipid |
| SIAT8B | 15q26 | α2,8 Siayltransferase II (ST8Sia II) | N-Glycan |
| SIAT8C | 18q21.31 | α2,8 Siayltransferase III (ST8Sia III) | N-Glycan |
| SIAT8E | 15q21.1 | α2,8 Siayltransferase V (ST8Sia V) | Glycolipid |
| SIAT10 | 3q12.2 | α2,3 Siayltransferase (ST3 VI) | N-,O-Glycan, Glycolipid |
| FUT4 | 11q21 | α1,3 Fucosyltransferase IV (FucT IV) | ? |
| FUT7 | 9q34.3 | α1,3 Fucosyltransferase VII (FucT VII) | ? |
| FUT9 | 6q16 | α1,3 Fucosyltransferase IX (FucT IX) | ? |
| FUT10 | 8p12 | α1,3 Fucosyltransferase | ? |
| FUT11 | 10q22.3 | α1,3 Fucosyltransferase | ? |
| OGT | Xq13 | O-linked N-acetylglucosaminyltransferase | O-GlcNAc |
| ABO | 9q34.1-q34.2 | ABO Blood Group Transferase A and B | ABO Blood group |
| GCNT1 | 9q13 | Core2 N-acetylglucosaminyltransferase I | O-glycan |
| GCNT2 | 6p24 | Core2 N-acetylglucosaminyltransferase II | O-Glycan |
| GCNT3 | 15q21.3 | Core2 N-acetylglucosaminyltransferase III | O-Glycan |
| EDEM1 | 3p26.1 | ER degradation enhancer, mannosidase-alpha-like 1 | N-Glycan |
| MANBA | 4q22-25 | mannosidase, beta A, lysosomal | N-Glycan |
| KIAA0935 | 4p16.2 | mannosidase, alpha calss 2B member 2 | N-Glycan |
| MANEA | 6q16.2 | mannosidase, endo alpha (eM) | N-Glycan |
| MAN1B1 | 9q34 | mannosidase, alpha, class 1B, member I (ER M1) | N-Glycan |
| MAN2C1 | 15q11-q13 | mannosidase, alpha, class 2C, member 1 | N-Glycan |
| MAN2B1 | 19p13 | mannosidase, alpha, class 2B, member 1 | N-Glycan |
| MANBAL | 20q11-q12 | mannosidase, beta A, lysosomal like | N-Glycan |
| SMP3 | 3q29 | GPI-linked mannosyltransferase | GPI |
| DPM1 | 20q13 | Dol-P-mannosyltransferase 1 | GPI |
| DPM2 | 9q34.13 | Dol-P-mannosyltransferase 2 | GPI |
| LOC200810 & LOC285407 | 3q21.2 | Similar to β1-4 mannosyltransferase | ? |
| LOC339879 | 3p14.1 | Similar to β1-4 mannosyltransferase | ? |
| LOC285544 & LOC391613 | 4p16.1 | Similar to β1-4 mannosyltransferase | ? |
| LOC401305 | 7p22.2 | Similar to β1-4 mannosyltransferase | ? |
| LOC200810 | 3q21 | Similar to β1-4 mannosyltransferase | ? |
| LOC392191 & LOC392199 | 8p23.1 | Similar to β1-4 mannosyltransferase | ? |
| LOC401712 | 12p13 | Similar to β1-4 mannosyltransferase | ? |
| UGCG | 9q31 | Cerimide Glucosyltransferase | Glycolipid |
| HS3ST1 | 4p16 | Heparin Sulfate 3-O-sulfotransferase I | GAG |
| HS3ST3A1 & B1 | 17p12-p11 | Heparin Sulfate 3-O-sulfotransferase IIIA | GAG |
| HS3ST4 | 16p11.2 | Heparin Sulfate 3-O-sulfotransferase IV | GAG |
| HS3ST5 | 6p22.31 | Heparin Sulfate 3-O-sulfotransferase V | GAG |
| HS6ST2 | Xq26.2 | Heparin Sulfate 6-O-sulfotransferase II | GAG |
| HS6ST3 | 13q32.1 | Heparin Sulfate 6-O-sulfotransferase III | GAG |
| CHST1 | 11p11.2-p11.1 | Keratan Sulfate Gal-6-Sulfotransferase | GAG |
| CHST2 | 3q24 | N-Acetylglucosaminyltransferase-6-O-Sulfotransferase II | ? |
| CHST3 | 10q22.2 | Chondroitin-6-O-sulfotransferase III | GAG |
| CHST4, 5 & 6 | 16q22 | N-Acetylglucosaminyltransferase-6-O-Sulfotransferase IV | GAG |
| CHST7 | Xp11.23 | N-Acetylglucosaminyltransferase-6-O-Sulfotransferase VII | ? |
| CHST9 | 18q11.2 | N-Acetylgalactoasaminyltransferase-4-O-Sulfotransferase IX | ? |
| CHST10 | 2q12.1 | Carbohydrate Sulfotransferase X | ? |
| CHST12 | 7q22 | Chondroitin-4-O-Sulfotransferase XII | GAG |
| NDST2 | 10q22 | N-deacatylase/N-sulfotransferase II | GAG |
| NDST3 | 4q27 | N-deacatylase/N-sulfotransferase III | GAG |
| NDST4 | 4q25-26 | N-deacatylase/N-sulfotransferase IV | GAG |
| UGCG | 9q31 | UDP-Glucose Ceramide glucosyltransferase | GAG |
| B3GAT1 | 11q25 | β1,3 Glucuronyltransferase I | GAG |
| B3GAT2 | 6q13 | β1,3 Glucuronyltransferase II | GAG |
| XYLT1 | 16p12 | Xylosetransferase I | GAG |
| EXT1 | 8q36 | Glucuronyl/N-acetylglucosaminyltransferase I | GAG |
| EXT2 | 11p11-p12 | Glucuronyl/N-acetylglucosaminyltransferase II | GAG |
| EXTL3 | 8p21 | α1,4 GlcNAc tranferase | GAG |
| GLCE | 15q22.31 | Glucuronyl C5 Epimerase | GAG |
| IDS | Xq28 | Iduronate-2-sulfatase | GAG |
| IDUA | 4p16.3 | Iduronadase | GAG |
| HEXA | 15q23-q24 | Hexosamindase | GAG |

TABLE 6-continued

Carbohydrate genes not required for β1,6GlcNAc-branched N-glycan synthesis

| Gene | Location | Enzyme | Glycan type |
|---|---|---|---|
| GUSB | 7q21.11 | Glucuronidase | GAG |
| GNS | 12q14 | N-acetylglucosamine-6-sulfatase | GAG |
| GALNS | 16q24.3 | N-acetylgalactosamine-6-sulfatase | GAG |
| GLB1 | 3p21.33 | β Galactosidase | GAG, Glycolipid |
| GLA | Xq22 | α Galactosidase | Glycolipid |
| GBA2 | 9p13 | β Glucosidase II | |
| GBA3 | 4p15.31 | β Glucosidase | |
| GANC | 15q15.2 | α Glucosidase, neutral C | |
| FUCA2 | 6q24 | Fucosidase (plasma) | |
| NEU1 | 6p21.3 | Sialidase (lysosomal) | |
| AGA | 4q32-33 | Aspartylglucosaminidase | N-glycan degradation |
| GNE | 9p13.1 | ManNAc Kinase/UDP-GlcNAc 2 epimerase | Sugar-nucleotide |
| RENBP | Xq28 | Renin binding protein | Sugar-nucleotide |
| GMPPB | 2q36.1 | GDP-mannose pyrophosphorylase | Sugar-nucleotide |
| FBP1 | 9q22.3 | Fructose 1,6-bisphosphatase | Glycolysis |
| FBP2 | 9q22.3 | Fructose 1,6-bisphosphatase | Glycolysis |
| PFKL | 21q22 | Phosphofructokinase-liver | Glycolysis |
| PFKM | 12q13 | Phosphofructokinase-muscle | Glycolysis |
| PFKX | 12ptel | Phosphofructokinase-X | Glycolysis |
| ALDOA | 16q22-q24 | Aldolase A | Glycolysis |
| ALDOB | 9q21-q22 | Aldolase B | Glycolysis |
| ALDOC | 17cent-q12 | Aldolase C | Glycolysis |
| GAPD | 12p13 | Glyceraldehyde-3-phosphate dehydrogenase | Glycolysis |
| PGK1 | Xq13 | Phosphoglycerate Kinase 1 | Glycolysis |
| PGK2 | 6p12 | Phosphoglycerate Kinase 2 | Glycolysis |
| PGAM1 | 10q25 | Phosphoglyceromutase 1 | Glycolysis |
| PGAM2 | 7p12-p13 | Phosphoglyceromutase 2 | Glycolysis |
| ENO2 | 12p13 | Enolase 2 | Glycolysis |
| ENO3 | 17pter-p11 | Enolase 3 | Glycolysis |
| PDHA1 | Xp22 | Pyruvate dehydrogenase (lipoamide) alpha 1 | Glycolysis |
| DLAT | 11q23 | Dihydrolipoamide S-acetyltransferase | Glycolysis |
| DLD | 7q31-q32 | Dihydrolipoamide dehydrogenase | Glycolysis |
| ACAS2 | 20q11 | Acetyl-Coenzyme A synthetase 2 | Glycolysis |
| ALDH1A1 | 9q21 | Aldehyde dehydrogenase 1 family, member A1 | Glycolysis |
| ALDH3A1 | 17p11 | Aldehyde dehydrogenase 3 family, member A1 | Glycolysis |
| ADH1A | 4q21-q23 | Alcohol dehydrogenase 1A (class I), alpha polypeptide | Glycolysis |
| C) Genes that do not map to 18 MS Loci in Table 5 | | | |
| MTMR1 | Xq28 | Myotubularin related protein 1 | Monosaccharide Metabolism |
| NANS | 9p23-p24 | Sialic acid synthase | Monosaccharide Metabolism |
| CMAS | 12p12 | Cytidine monophospho-N-acetylneuraminic acid synthetase | Monosaccharide Metabolism |
| GLB1 | 3p21 | Beta-galactosidase 1 | Monosaccharide Metabolism |
| GLA | Xq22 | Alpha-galactosidase | Monosaccharide Metabolism |
| AKR1B1 | 7q35 | Aldo-keto reductase family 1, member B1 | Monosaccharide Metabolism |
| UGT2B11 | 4q13 | UDP glycosyltransferase 2 family, polypeptide B11 | Monosaccharide Metabolism |
| GMDS | 6p25 | GDP-mannose 4,6-dehydratase | Monosaccharide Metabolism |
| UGDH | 4p15 | UDP-glucose dehydrogenase | Monosaccharide Metabolism |
| SORD | 15q15 | Sorbitol dehydrogenase | Monosaccharide Metabolism |
| MPI | 15q22 | Mannose phosphate isomerase | Monosaccharide Metabolism |
| TSTA3 | 8q24 | Tissue specific transplantation antigen P35B | Monosaccharide Metabolism |
| FUK | 16q22 | Fucokinase | Monosaccharide Metabolism |
| TPI1 | 12p13 | Triosephosphate isomerase 1 | Monosaccharide Metabolism |
| PFKFB1 | Xp11 | 6-Phosphofructo-2-kinase/fructose-2,6-biphosphatase 1 | Monosaccharide Metabolism |
| G6PD | Xq28 | Glucose-6-phosphate dehydrogenase | Pentose Phosphate |
| PGLS | 19p13 | 6-Phosphogluconolactonase | Pentose Phosphate |
| TKT | 3p14 | Transketolase | Pentose Phosphate |
| PRPS1 | Xq21-q27 | Phosphoribosyl pyrophosphate synthetase 1 | Pentose Phosphate |
| GALT | 9p13 | Galactose-1-phosphate uridylyltransferase | Sugar nucleotide |
| TGDS | 13q32 | TDP-glucose 4,6-dehydratase | Sugar nucleotide |
| LTB4DH | 9q32 | Leukotriene B4 12-hydroxydehydrogenase | Sugar nucleotide |
| SI | 3q25-q26 | Sucrase-isomaltase | Starch/Sucrose Metabolism |
| ENPP1 | 6q22-q23 | Ectonucleotide pyrophosphatase/phosphodiesterase 1 | Starch/Sucrose Metabolism |
| PYGB | 20p11 | Glycogen phosphorylase (brain) | Starch/Sucrose Metabolism |
| GBE1 | 3p12 | Glucan (1,4-alpha-), branching enzyme 1 | Starch/Sucrose Metabolism |
| UGT2B11 | 4q13 | UDP glycosyltransferase 2 family, polypeptide B11 | Starch/Sucrose Metabolism |
| TREH | 11q23 | Trehalase | Starch/Sucrose Metabolism |
| MGAM | 7q34 | Maltase-glucoamylase | Starch/Sucrose Metabolism |
| SLC35A2 | Xp11 | UDP-galactose transporter | Sugar nucleotide transport |
| SLC35A1 | 6q15 | CMP-Sialic Acid transporter | Sugar nucleotide transport |
| SLC35A5 | 3q13.2 | Solute carrier family 35, member A5 | Sugar nucleotide transport |
| SLC35B3 | 6p24.3 | Solute carrier family 35, member B3 | Sugar nucleotide transport |
| SLC35B4 | 7q33 | Solute carrier family 35, member B4 | Sugar nucleotide transport |
| SLC35C1 | 11p11.2 | GDP-fucose transporter 1 | Sugar nucleotide transport |
| SLC3BE3 | 12q15 | Solute carrier family 35, member E3 | Sugar nucleotide transport |

TABLE 7

Table Association of MGAT1 SNPV with Multiple Sclerosis and Rheumatoid Arthritis

| | Case Control | | | | Transmission Disequilbrium Test (TDT) | | | |
|---|---|---|---|---|---|---|---|---|
| | Subjects | | | | Transmissions | | | |
| | SNP+:SNP− | p-value | OR | 95% CI | Observed | Expected | TDT Chi$^2$ | p-value |
| Multiple Sclerosis | 21:103 | 0.0004 | 4.52 | 1.85-11.0 | 12 | 8 | 4.0 | 0.046 |
| Rheumatoid Arthritis | 8:39 | 0.0068 | 4.54 | 1.51-10.3 | | | | |
| Thyroid Autoimmunity | 10:103 | 0.101 | — | — | 8 | 9.5 | 0.474 | 0.491 |
| Control | 7:155 | | | | | | | |

For case control the Odds Ratio, P values and 95% Confidence Intervals were calculated with Contingency Tables and Fisher's Exact Test (1 tailed, FET). For TDT, over 300 parent sets with at least one affected child were screened for MGAT1 SNP V. Affected children of MGAT1 SNP V heterozygous parents were then genotyped and used to calculate the TDT Chi2 statistitic and p-value. Due too the rarity of parents positive for MGAT1 SNP V and the similar strength of association (ie OR) of Multiple Sclerosis and Rheumatoid Arthritis by case control, affected children with these two diseases were grouped together for purposes of transmission in the TDT. All subjects are Caucasian. Control subjects for case control did not have personal history of autoimmune disease.

REFERENCES

1. Noseworthy, J. H. Progress in determining the causes and treatment of multiple sclerosis. *Nature* 399, A40-A47 (1999),
2. Steinman, L. Multiple sclerosis: a two-stage disease. *Nat. Immunol.* 2, 762-764 (2001).
3. Steinman, L. Multiple sclerosis: a coordinated immunological attack against myelin in the central nervous system. *Cell* 85, 299-302 (1996).
4. Demetriou, M., Granovsky, M., Quaggin, S. & Dennis, J. W. Negative regulation of T-cell activation and autoimmunity by Mgat5 N-glycosylation. *Nature* 409, 733-739 (2001).
5. Morgan, R. et al. N-acetylglucosaminyltransferase v (Mgat5)-mediated N-glycosylation negatively regulates Th1 cytokine production by T cells. *J. Immunol.* 173, 7200-7208 (2004).
6. Ebers, G. C. et al. A population-based study of multiple sclerosis in twins. *N Engl. J. Med.* 315, 1638-1642 (1986).
7. Ebers, G. C., Sadovnick, A. D. & Risch, N. J. A genetic basis for familial aggregation in multiple sclerosis. Canadian Collaborative Study Group. *Nature* 377, 150-151 (1995).
8. Dyment, D. A. et al. An extended genome scan in 442 Canadian multiple sclerosis-affected sibships: a report from the Canadian Collaborative Study Group. *Hum. Mol. Genet.* 13, 1005-1015 (2004).
9. Butterfield, R. J. et al. New genetic loci that control susceptibility and symptoms of experimental allergic encephalomyelitis in inbred mice. *J. Immunol.* 161, 1860-1867 (1998).
10. Encinas, J. A. et al. Genetic analysis of susceptibility to experimental autoimmune encephalomyelitis in a cross between SJL/J and B10.S mice. *J. Immunol.* 157, 2186-2192 (1996).
11. Goverman, J. et al. Transgenic mice that express a myelin basic protein-specific T cell receptor develop spontaneous autoimmunity. *Cell* 72, 551-560 (1993).
12. Lafaille, J. J., Nagashima, K., Katsuki, M. & Tonegawa, S. High incidence of spontaneous autoimmune encephalomyelitis in immunodeficient anti-myelin basic protein T cell receptor transgenic mice. *Cell* 78, 399-408 (1994).
13. Waldner, H., Whitters, M. J., Sobel, R. A., Collins, M. & Kuchroo, V. K. Fulminant spontaneous autoimmunity of the central nervous system in mice transgenic for the myelin proteolipid protein-specific T cell receptor. *Proc. Natl. Acad. Sci. U. S. A* 97, 3412-3417 (2000).
14. Bettelli, E. et al. Myelin oligodendrocyte glycoprotein-specific T cell receptor transgenic mice develop spontaneous autoimmune optic neuritis. *J. Exp. Med.* 197, 1073-1081 (2003).
15. Tranchant, C., Bhatia, K. P. & Marsden, C. D. Movement disorders in multiple sclerosis. *Mov Disord.* 10, 418-423 (1995).
16. Baker, D. et al. Cannabinoids control spasticity and tremor in a multiple sclerosis model. *Nature* 404, 84-87 (2000).
17. Kornek, B, & Lassmann, H. Axonal pathology in multiple sclerosis. A historical note. *Brain Pathol.* 9, 651-656 (1999).
18. Bjartmar, C., Wujek, J. R. & Trapp, B. D. Axonal loss in the pathology of MS: consequences for understanding the progressive phase of the disease. *J. Neurol. Sci.* 206, 165-171 (2003).
19. Penninger, J. M., Irie-Sasaki, J., Sasaki, T. & Oliveira-dos-Santos, A. J. CD45: new jobs for an old acquaintance. *Nat. Immunol.* 2, 389-396 (2001).
20. Sarova-Pinhas, I., Achiron, A., Gilad, R. & Lampl, Y. Peripheral neuropathy in multiple sclerosis: a clinical and electrophysiologic study. *Acta Neurol. Scand.* 91, 234-238 (1995).
21. Grana, E. A. & Kraft, G. H. Electrodiagnostic abnormalities in patients with multiple sclerosis. *Arch. Phys. Med. Rehabil.* 75, 778-782 (1994).
22. Ormerod, I. E., Waddy, H. M., Kermode, A. G., Murray, N. M. & Thomas, P. K. Involvement of the central nervous system in chronic inflammatory demyelinating polyneuropathy: a clinical, electrophysiological and magnetic resonance imaging study. *J. Neurol. Neurosurg. Psychiatry* 53, 789-793 (1990).
23. Jabs, C. et al. Genetic background determines the requirement for B7 costimulation in induction of autoimmunity. *Eur. J. Immunol.* 32, 2687-2697 (2002).
24. Demetriou, M., Nabi, I. R., Coppolino, M., Dedhar, S. & Dennis, J. W. Reduced contact-inhibition and substratum adhesion in epithelial cells expressing GlcNAc-transferase V. *J. Cell Biol.* 130, 383-392 (1995).
25. Korczak, B., Le, T., Elowe, S., Datti, A. & Dennis, J. W. Minimal catalytic domain of N-acetylglucosaminyltransferase V. *Glycobiology* 10, 595-599 (2000).
26. Sasai, K., Ikeda, Y., Fujii, T., Tsuda, T. & Taniguchi, N. UDP-GlcNAc concentration is an important factor in the biosynthesis of beta1,6-branched oligosaccharides: regulation based on the kinetic properties of N-acetylglucosaminyltransferase V. *Glycobiology* 12, 119-127 (2002).

27. Viola, A. & Lanzavecchia, A. T cell activation determined by T cell receptor number and tunable thresholds. *Science* 273, 104-106 (1996).
28. Granovsky, M. et al. Suppression of tumor growth and metastasis in Mgat5-deficient mice. *Nat. Med.* 6, 306-312 (2000).
29. Partridge, E. A. et al. Regulation of cytokine receptors by Golgi N-glycan processing and endocytosis. *Science* 306, 120-124 (2004).
30. Scott, R. S. et al. Phagocytosis and clearance of apoptotic cells is mediated by MER. *Nature* 411, 207-211 (2001).
31. Ebers, G. C. et al. A full genome search in multiple sclerosis. *Nat. Genet.* 13, 472-476 (1996).
32. Haines, J. L. et al. A complete genomic screen for multiple sclerosis underscores a role for the major histocompatability complex. The Multiple Sclerosis Genetics Group. *Nat. Genet.* 13, 469-471 (1996).
33. Sawcer, S. et al. A genome screen in multiple sclerosis reveals susceptibility loci on chromosome 6p21 and 17q22. *Nat. Genet.* 13, 464-468 (1996).
34. Sawcer, S. et al. A whole genome screen for linkage disequilibrium in multiple sclerosis confirms disease associations with regions previously linked to susceptibility. *Brain* 125, 1337-1347 (2002).
35. Akesson, E. et al. A genome-wide screen for linkage in Nordic sib-pairs with multiple sclerosis. *Genes Immun.* 3, 279-285 (2002).
36. Ban, M. et al. A genome screen for linkage in Australian sibling-pairs with multiple sclerosis. *Genes Immun.* 3, 464-469 (2002).
37. Broadley, S. et al. A genome screen for multiple sclerosis in Italian families. *Genes Immun.* 2, 205-210 (2001).
38. Coraddu, F. et al. A genome screen for multiple sclerosis in Sardinian multiplex families. *Eur. J. Hum. Genet.* 9, 621-626 (2001).
39. Kuokkanen, S. et al. Genomewide scan of multiple sclerosis in Finnish multiplex families. *Am. J. Hum. Genet.* 61, 1379-1387 (1997).
40. Pericak-Vance, M. A. et al. Investigation of seven proposed regions of linkage in multiple sclerosis: an American and French collaborative study. *Neurogenetics.* 5, 45-48 (2004).
41. Becker, K. G. et al. Clustering of non-major histocompatibility complex susceptibility candidate loci in human autoimmune diseases. *Proc. Natl. Acad. Sci. U.S.A* 95, 9979-9984 (1998).
42. Jacobsen, M. et al. A point mutation in PTPRC is associated with the development of multiple sclerosis. *Nat. Genet.* 26, 495-499 (2000).
43. Barcellos, L. F. et al. PTPRC (CD45) is not associated with the development of multiple sclerosis in U.S. patients. *Nat. Genet.* 29, 23-24 (2001).
44. Kornfeld, R. & Kornfeld, S. Assembly of asparagine-linked oligosaccharides. *Annu. Rev. Biochem.* 54, 631-664 (1985).
45. Helms, C. et al. A putative RUNX1 binding site variant between SLC9A3R1 and NAT9 is associated with susceptibility to psoriasis. *Nat. Genet.* 35, 349-356 (2003).
46. Onengut-Gumuscu, S. & Concannon, P. Mapping genes for autoimmunity in humans: type 1 diabetes as a model. *Immunol. Rev.* 190, 182-194 (2002).
47. Bowcock, A. M. & Cookson, W. O. The genetics of psoriasis, psoriatic arthritis and atopic dermatitis. *Hum. Mol. Genet.* 13 Spec No 1, R43-R55 (2004).
48. Mathew, C. G. & Lewis, C. M. Genetics of inflammatory bowel disease: progress and prospects. *Hum. Mol. Genet.* 13 Spec No 1, R161-R168 (2004).
49. Prokunina, L. & Alarcon-Riquelme, M. The genetic basis of systemic lupus erythematosus—knowledge of today and thoughts for tomorrow. *Hum. Mol. Genet.* 13 Spec No 1, R143-R148 (2004).
50. Ayadi, H., Hadj, K. H., Rebai, A. & Farid, N. R. The genetics of autoimmune thyroid disease. *Trends Endocrinol. Metab* 15, 234-239 (2004).
51. Dell, A. & Morris, H. R. Glycoprotein structure determination by mass spectrometry. *Science* 291, 2351-2356 (2001).
52. Kim, C. H. Increased expression of N-acetylglucosaminyltransferase-V in human hepatoma cells by retinoic acid and 1alpha,25-dihydroxyvitamin D3. *Int. J. Biochem. Cell Biol.* 36, 2307-2319 (2004).
53. Tsoukas, C. D., Provvedini, D. M. & Manolagas, S. C. 1,25-dihydroxyvitamin D3: a novel immunoregulatory hormone. *Science* 224, 1438-1440 (1984).
54. Lemire, J. M. & Archer, D. C. 1,25-dihydroxyvitamin D3 prevents the in vivo induction of murine experimental autoimmune encephalomyelitis. *J. Clin. Invest* 87, 1103-1107 (1991).
55. Munger, K. L. et al. Vitamin D intake and incidence of multiple sclerosis. *Neurology* 62, 60-65 (2004).
56. McDonald, W. I. et al. Recommended diagnostic criteria for multiple sclerosis: guidelines from the International Panel on the diagnosis of multiple sclerosis. *Ann. Neurol.* 50, 121-127 (2001).
57. Tejada-Simon, M. V., Hong, J., Rivera, V. M. & Zhang, J. Z. Reactivity pattern and cytokine profile of T cells primed by myelin peptides in multiple sclerosis and healthy individuals. *Eur. J. Immunol.* 31, 907-917 (2001).
58. Tremblay, L. O. & Herscovics, A. Characterization of a cDNA encoding a novel human Golgi alpha 1, 2-mannosidase (IC) involved in N-glycan biosynthesis. *J. Biol. Chem.* 275, 31655-31660 (2000).
59. H. Schachter, Glycobiology 1, 453-461 (1991)
60. K. A. Frauwirth and C. B. Thompson, J. Immunol. 172, 4661-4665 (2004).
61. C. J. Harrington et al., Immunity. 8, 571-580 (1998).
62. G. Y. Liu et al., Immunity. 3, 407-415 (1995).
63. H. Ueda et al., Nature 423, 506-511 (2003).
64. V. Suppiah et al., J. Neuroimmunol. 164, 148-153 (2005).
65. R. Niehues et al., J. Clin. Invest 101, 1414-1420 (1998).
66. Z. Ye and J. D. Marth, Glycobiology 14, 547-558 (2004).
67. Y. Hong, S. Sundaram, D. J. Shin, P. Stanley, J. Biol. Chem. 279, 49894-49901 (2004).
68. W. A. Lubas and R. G. Spiro, J. Biol. Chem. 262, 3775-3781 (1987).
69. S. E. Moore and R. G. Spiro, J. Biol. Chem. 265, 13104-13112 (1990).
70. C. M. De Praeter et al., Am. J. Hum. Genet. 66, 1744-1756 (2000).
71. H. H. Freeze, Biochim. Biophys. Acta 1573, 388-393 (2002).
72. Voit, E. O. Computational Analysis of biochemical systems: a practical guide for biochemists and molecular biologists. (Cambridge University Press, 2000).
73. U. S. Bhalla and R. Iyengar, *Science* 283, 381-387 (1999).
74. R. A. Freitas Jr, Nanomedicine, volume 1: basic capabilities (Landes Bioscience, Georgetown, Tex., 1999).
75. B. C. Waldman and G. Rudnick, *Biochemistry* 29, 44-52 (1990).
76. B. Bendiak and H. Schachter, *J. Biol. Chem.* 262, 5784-5790 (1987).

What is claimed:

1. A method for treating insulin-dependent diabetes mellitus comprising administering to a subject having insulin-dependent diabetes mellitus a pharmaceutical composition comprising N-acetylglucosamine (GlcNAc) and a pharmaceutically acceptable carrier,
    wherein the level of Mgat5 modified glycans is increased in the subject, thereby treating the subject's insulin-dependent diabetes mellitus.

2. The method of claim 1, further comprising administering a hexosamine pathway metabolite.

3. The method of claim 2, wherein GlcNAc and the hexosamine pathway metabolite are administered in synergistic quantities.

4. The method of claim 2, further comprising administering uridine, uridine 5' diphosphate (UDP), uridine 5' monophosphate (UMP), uridine 5' triphosphate (UTP), glutamine or uracil.

5. The method of claim 4, further comprising administering Vitamin D3.

6. The method of claim 2, wherein the composition is administered orally.

7. The method of claim 1, further comprising administering uridine, uridine 5' diphosphate (UDP), uridine 5' monophosphate (UMP), uridine 5' triphosphate (UTP), glutamine or uracil.

8. The method of claim 7, further comprising administering Vitamin D3.

9. The method of claim 1, wherein the composition is administered orally.

10. A method for treating insulin-dependent diabetes mellitus comprising administering to a subject having insulin-dependent diabetes mellitus a pharmaceutical composition comprising N-acetylglucosamine (GlcNAc) and a compound selected from uridine, uridine 5' diphosphate (UDP), uridine 5' monophosphate (UMP), uridine 5' triphosphate (UTP), glutamine or uracil, and a pharmaceutically acceptable carrier,
    wherein the level of Mgat5 modified glycans is increased in the subject, thereby treating the subject's insulin-dependent diabetes mellitus.

11. The method of claim 10, further comprising administering Vitamin D3.

12. The method of claim 11, wherein the composition is administered orally.

13. The method of claim 10, wherein the composition is administered orally.

* * * * *